(12) United States Patent
Simpson et al.

(10) Patent No.: US 10,980,452 B2
(45) Date of Patent: *Apr. 20, 2021

(54) ANALYTE SENSOR

(71) Applicant: DexCom, Inc., San Diego, CA (US)

(72) Inventors: Peter C. Simpson, Cardiff, CA (US); James H. Brauker, Coldwater, MI (US); Mark C. Brister, Encinitas, CA (US); Paul V. Goode, Jr., Round Rock, TX (US); Apurv Ullas Kamath, San Diego, CA (US); Steve Masterson, Encinitas, CA (US); Aarthi Mahalingam, San Diego, CA (US); John Nolting, San Diego, CA (US); James R. Petisce, San Diego, CA (US); Jack Pryor, Ladera Ranch, CA (US); Sean Saint, San Diego, CA (US); Vance Swanson, San Diego, CA (US); Matthew D. Wightlin, San Diego, CA (US)

(73) Assignee: DexCom, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/088,396

(22) Filed: Nov. 3, 2020

(65) Prior Publication Data

US 2021/0068726 A1 Mar. 11, 2021

Related U.S. Application Data

(63) Continuation of application No. 16/924,117, filed on Jul. 8, 2020, now Pat. No. 10,918,315, which is a
(Continued)

(51) Int. Cl.
*A61B 5/1468* (2006.01)
*A61B 5/1486* (2006.01)
(Continued)

(52) U.S. Cl.
CPC ........ *A61B 5/14532* (2013.01); *A61B 5/0002* (2013.01); *A61B 5/0004* (2013.01);
(Continued)

(58) Field of Classification Search
CPC ............ A61B 5/14532; A61B 5/68335; A61B 5/0002; A61B 5/0004; A61B 5/05;
(Continued)

(56) References Cited

U.S. PATENT DOCUMENTS 52,641 A 2/1866 Gregg et al.
62,334 A 2/1867 Berner et al.
(Continued)

FOREIGN PATENT DOCUMENTS

CA 2127172 C 7/1998
DE 2658734 A1 6/1978
(Continued)

OTHER PUBLICATIONS

US 7,530,950 B2, 05/2009, Brister et al. (withdrawn)
(Continued)

*Primary Examiner* — Navin Natnithithadha
(74) *Attorney, Agent, or Firm* — Knobbe, Martens, Olson & Bear, LLP

(57) ABSTRACT

The present invention relates generally to systems and methods for measuring an analyte in a host. More particularly, the present invention relates to systems and methods for transcutaneous measurement of glucose in a host.

86 Claims, 50 Drawing Sheets

Related U.S. Application Data continuation of application No. 16/691,358, filed on Nov. 21, 2019, now Pat. No. 10,709,362, which is a continuation of application No. 16/674,610, filed on Nov. 5, 2019, now Pat. No. 10,722,152, which is a continuation of application No. 16/392,521, filed on Apr. 23, 2019, which is a continuation of application No. 14/590,483, filed on Jan. 6, 2015, now Pat. No. 10,314,525, which is a continuation of application No. 13/909,962, filed on Jun. 4, 2013, now Pat. No. 9,247,900, which is a continuation of application No. 11/360,262, filed on Feb. 22, 2006, now Pat. No. 8,615,282.

(51) Int. Cl.

| | |
|---|---|
| *A61B 5/1495* | (2006.01) |
| *A61B 5/1473* | (2006.01) |
| *A61B 5/145* | (2006.01) |
| *A61B 5/05* | (2021.01) |
| *A61B 5/00* | (2006.01) |
| *A61B 5/15* | (2006.01) |
| *A61B 17/34* | (2006.01) |
| *A61M 5/172* | (2006.01) |
| *A61M 5/158* | (2006.01) |
| *A61M 5/142* | (2006.01) |

(52) U.S. Cl.
CPC .............. *A61B 5/05* (2013.01); *A61B 5/1411* (2013.01); *A61B 5/1473* (2013.01); *A61B 5/1486* (2013.01); *A61B 5/1495* (2013.01); *A61B 5/14503* (2013.01); *A61B 5/14507* (2013.01); *A61B 5/14514* (2013.01); *A61B 5/14546* (2013.01); *A61B 5/14735* (2013.01); *A61B 5/14865* (2013.01); *A61B 5/6801* (2013.01); *A61B 5/6833* (2013.01); *A61B 5/6848* (2013.01); *A61B 5/6849* (2013.01); *A61B 5/68335* (2017.08); *A61B 5/72* (2013.01); *A61B 17/3468* (2013.01); *A61B 5/14* (2013.01); *A61B 5/145* (2013.01); *A61B 5/1468* (2013.01); *A61B 5/150022* (2013.01); *A61B 2017/3492* (2013.01); *A61B 2560/0223* (2013.01); *A61B 2560/045* (2013.01); *A61B 2562/18* (2013.01); *A61M 5/14244* (2013.01); *A61M 5/1723* (2013.01); *A61M 2005/1585* (2013.01); *Y02A 90/10* (2018.01)

(58) Field of Classification Search
CPC .............. A61B 5/1411; A61B 5/14503; A61B 5/14507; A61B 5/14514; A61B 5/14546; A61B 5/1473; A61B 5/14735; A61B 5/1486; A61B 5/14865; A61B 5/1495; A61B 5/6801; A61B 5/6833; A61B 5/6848; A61B 5/6849; A61B 5/72; A61B 17/3468; A61B 5/14; A61B 5/145; A61B 5/1468; A61B 5/150022; A61B 2017/3492; A61B 2560/0223; A61B 2560/045; A61B 2562/18; Y02A 90/26; A61M 5/14244; A61M 5/1723; A61M 2005/1585
USPC .......................................... 600/309, 345–366
See application file for complete search history.

(56) References Cited

U.S. PATENT DOCUMENTS

| | | |
|---|---|---|
| 65,604 A | 6/1867 | Heller et al. |
| 1,498,738 A | 6/1924 | Gustave et al. |
| 1,564,641 A | 12/1925 | St. James |
| 1,726,766 A | 9/1929 | Rector |
| 2,057,029 A | 10/1936 | McC. Johnstone |
| 2,402,306 A | 6/1946 | Henry et al. |
| 2,497,894 A | 2/1950 | Clare et al. |
| 2,719,797 A | 10/1955 | Rosenblatt et al. |
| 2,882,696 A | 4/1959 | Herrmann et al. |
| 2,910,256 A | 10/1959 | Richard et al. |
| 3,022,639 A | 2/1962 | Brown et al. |
| 3,210,578 A | 10/1965 | Sherer |
| 3,218,819 A | 11/1965 | Crotser |
| 3,219,533 A | 11/1965 | Mullins |
| 3,381,371 A | 5/1968 | Russell |
| 3,506,032 A | 4/1970 | Eveleigh et al. |
| 3,539,455 A | 11/1970 | Clark, Jr. |
| 3,556,950 A | 1/1971 | Dahms et al. |
| 3,562,352 A | 2/1971 | Nyilas et al. |
| 3,607,329 A | 9/1971 | Manjikian |
| 3,610,226 A | 10/1971 | Albisser |
| 3,652,475 A | 3/1972 | Wada et al. |
| 3,728,678 A | 4/1973 | Tong |
| 3,775,182 A | 11/1973 | Patton et al. |
| 3,780,727 A | 12/1973 | King |
| 3,791,871 A | 2/1974 | Rowley |
| 3,826,244 A | 7/1974 | Salcman et al. |
| 3,837,339 A | 9/1974 | Aisenberg et al. |
| 3,838,033 A | 9/1974 | Mindt et al. |
| 3,838,682 A | 10/1974 | Clark et al. |
| 3,872,455 A | 3/1975 | Fuller et al. |
| 3,874,850 A | 4/1975 | Sorensen et al. |
| 3,882,011 A | 5/1975 | Hines et al. |
| 3,898,984 A | 8/1975 | Mandel et al. |
| 3,910,256 A | 10/1975 | Clark et al. |
| 3,926,760 A | 12/1975 | Allen et al. |
| 3,929,971 A | 12/1975 | Roy |
| 3,930,462 A | 1/1976 | Day |
| 3,933,593 A | 1/1976 | Sternberg |
| 3,943,918 A | 3/1976 | Lewis |
| 3,957,613 A | 5/1976 | Macur |
| 3,957,651 A | 5/1976 | Kesting |
| 3,964,974 A | 6/1976 | Banauch et al. |
| 3,966,580 A | 6/1976 | Janata et al. |
| 3,978,684 A | 9/1976 | Taylor |
| 3,979,274 A | 9/1976 | Newman |
| 3,982,530 A | 9/1976 | Storch |
| 4,003,621 A | 1/1977 | Lamp |
| 4,008,717 A | 2/1977 | Kowarski |
| 4,016,866 A | 4/1977 | Lawton |
| 4,024,312 A | 5/1977 | Korpman |
| 4,036,749 A | 7/1977 | Anderson |
| 4,037,563 A | 7/1977 | Pflueger et al. |
| 4,040,908 A | 8/1977 | Clark, Jr. |
| 4,052,754 A | 10/1977 | Homsy |
| 4,055,175 A | 10/1977 | Clemens et al. |
| 4,067,322 A | 1/1978 | Johnson |
| 4,068,660 A | 1/1978 | Beck |
| 4,073,713 A | 2/1978 | Newman |
| 4,076,656 A | 2/1978 | White et al. |
| 4,101,395 A | 7/1978 | Motani et al. |
| 4,109,505 A | 8/1978 | Clark et al. |
| 4,110,997 A | 9/1978 | Klotz et al. |
| 4,116,920 A | 9/1978 | Honma et al. |
| 4,119,406 A | 10/1978 | Clemens |
| 4,151,845 A | 5/1979 | Clemens |
| 4,172,770 A | 10/1979 | Semersky et al. |
| 4,176,659 A | 12/1979 | Rolfe |
| 4,187,390 A | 2/1980 | Gore |
| 4,197,840 A | 4/1980 | Beck et al. |
| 4,197,852 A | 4/1980 | Schindler et al. |
| 4,206,755 A | 6/1980 | Klein |
| 4,215,703 A | 8/1980 | Willson |
| 4,225,410 A | 9/1980 | Pace |
| 4,230,118 A | 10/1980 | Holman et al. |
| 4,240,438 A | 12/1980 | Updike et al. |
| 4,240,889 A | 12/1980 | Yoda et al. |
| 4,245,634 A | 1/1981 | Albisser et al. |
| 4,248,246 A | 2/1981 | Ikeda |
| 4,253,469 A | 3/1981 | Aslan |
| 4,255,500 A | 3/1981 | Hooke |

(56) References Cited

U.S. PATENT DOCUMENTS

| | | |
|---|---|---|
| 4,259,540 A | 3/1981 | Sabia |
| 4,260,725 A | 4/1981 | Keogh et al. |
| 4,260,726 A | 4/1981 | Deubzer et al. |
| 4,265,249 A | 5/1981 | Schindler et al. |
| 4,286,039 A | 8/1981 | Landa et al. |
| 4,319,578 A | 3/1982 | Enger |
| 4,324,256 A | 4/1982 | Vesterager |
| 4,324,257 A | 4/1982 | Albarda et al. |
| 4,327,725 A | 5/1982 | Cortese et al. |
| 4,353,368 A | 10/1982 | Slovak et al. |
| 4,353,888 A | 10/1982 | Sefton |
| 4,366,040 A | 12/1982 | Marsoner et al. |
| 4,369,785 A | 1/1983 | Rehkopf et al. |
| 4,374,013 A | 2/1983 | Enfors |
| 4,378,016 A | 3/1983 | Loeb |
| 4,388,166 A | 6/1983 | Suzuki et al. |
| 4,402,694 A | 9/1983 | Ash et al. |
| 4,403,847 A | 9/1983 | Chrestensen |
| 4,403,984 A | 9/1983 | Ash et al. |
| 4,415,666 A | 11/1983 | D'Orazio et al. |
| 4,418,148 A | 11/1983 | Oberhardt |
| 4,419,535 A | 12/1983 | O'Hara |
| 4,431,004 A | 2/1984 | Bessman et al. |
| 4,431,507 A | 2/1984 | Nankai et al. |
| 4,432,366 A | 2/1984 | Margules |
| 4,436,094 A | 3/1984 | Cerami |
| 4,442,841 A | 4/1984 | Uehara et al. |
| 4,453,537 A | 6/1984 | Spitzer |
| 4,454,295 A | 6/1984 | Wittmann et al. |
| 4,457,339 A | 7/1984 | Juan et al. |
| 4,469,110 A | 9/1984 | Slama |
| 4,477,314 A | 10/1984 | Richter et al. |
| 4,478,222 A | 10/1984 | Koning et al. |
| 4,484,987 A | 11/1984 | Gough |
| 4,486,290 A | 12/1984 | Cahalan et al. |
| 4,492,575 A | 1/1985 | Mabille |
| 4,493,714 A | 1/1985 | Ueda et al. |
| 4,494,950 A | 1/1985 | Fischell |
| 4,506,680 A | 3/1985 | Stokes |
| 4,519,973 A | 5/1985 | Cahalan et al. |
| RE31,916 E | 6/1985 | Oswin et al. |
| 4,526,569 A | 7/1985 | Bernardi |
| 4,527,999 A | 7/1985 | Lee |
| 4,534,355 A | 8/1985 | Potter |
| 4,534,825 A | 8/1985 | Koning et al. |
| 4,535,786 A | 8/1985 | Kater |
| 4,538,616 A | 9/1985 | Rogoff |
| 4,545,382 A | 10/1985 | Higgins et al. |
| 4,554,927 A | 11/1985 | Fussell |
| 4,561,963 A | 12/1985 | Owen et al. |
| 4,565,665 A | 1/1986 | Fogt |
| 4,565,666 A | 1/1986 | Cahalan et al. |
| 4,568,444 A | 2/1986 | Nakamura et al. |
| 4,571,292 A | 2/1986 | Liu et al. |
| 4,573,968 A | 3/1986 | Parker |
| 4,577,642 A | 3/1986 | Stokes |
| 4,578,215 A | 3/1986 | Bradley |
| 4,579,120 A | 4/1986 | MacGregor |
| 4,583,976 A | 4/1986 | Ferguson |
| 4,592,824 A | 6/1986 | Smith et al. |
| 4,600,495 A | 7/1986 | Fogt |
| 4,602,922 A | 7/1986 | Cabasso et al. |
| 4,603,152 A | 7/1986 | Laurin et al. |
| 4,614,514 A | 9/1986 | Carr et al. |
| 4,619,793 A | 10/1986 | Lee |
| 4,625,730 A | 12/1986 | Fountain et al. |
| 4,626,104 A | 12/1986 | Pointon et al. |
| RE32,361 E | 2/1987 | Duggan |
| 4,647,643 A | 3/1987 | Zdrahala et al. |
| 4,650,547 A | 3/1987 | Gough |
| 4,655,880 A | 4/1987 | Liu |
| 4,663,824 A | 5/1987 | Kenmochi |
| 4,671,288 A | 6/1987 | Gough |
| 4,672,970 A | 6/1987 | Uchida et al. |
| 4,675,346 A | 6/1987 | Lin et al. |
| 4,680,268 A | 7/1987 | Clark, Jr. |
| 4,684,538 A | 8/1987 | Klemarczyk |
| 4,684,558 A | 8/1987 | Keusch et al. |
| 4,685,463 A | 8/1987 | Williams |
| 4,685,903 A | 8/1987 | Cable et al. |
| 4,686,137 A | 8/1987 | Ward, Jr. et al. |
| 4,689,149 A | 8/1987 | Kanno et al. |
| 4,689,309 A | 8/1987 | Jones |
| 4,694,861 A | 9/1987 | Goodale et al. |
| 4,703,756 A | 11/1987 | Gough et al. |
| 4,703,989 A | 11/1987 | Price et al. |
| 4,705,503 A | 11/1987 | Dorman et al. |
| 4,711,245 A | 12/1987 | Higgins et al. |
| 4,711,251 A | 12/1987 | Stokes |
| 4,721,677 A | 1/1988 | Clark, Jr. |
| 4,726,381 A | 2/1988 | Jones |
| 4,731,726 A | 3/1988 | Allen, III |
| 4,734,092 A | 3/1988 | Millerd |
| 4,736,748 A | 4/1988 | Nakamura et al. |
| 4,739,380 A | 4/1988 | Lauks et al. |
| 4,747,822 A | 5/1988 | Peabody |
| 4,750,496 A | 6/1988 | Reinhart et al. |
| 4,752,935 A | 6/1988 | Beck |
| 4,753,652 A | 6/1988 | Langer et al. |
| 4,755,168 A | 7/1988 | Romanelli et al. |
| 4,757,022 A | 7/1988 | Shults et al. |
| 4,759,828 A | 7/1988 | Young et al. |
| 4,761,748 A | 8/1988 | Le Rat et al. |
| 4,763,648 A | 8/1988 | Wyatt |
| 4,763,658 A | 8/1988 | Jones |
| 4,776,343 A | 10/1988 | Hubbard et al. |
| 4,777,953 A | 10/1988 | Ash et al. |
| 4,781,680 A | 11/1988 | Redmond et al. |
| 4,781,798 A | 11/1988 | Gough |
| 4,784,157 A | 11/1988 | Halls et al. |
| 4,786,394 A | 11/1988 | Enzer et al. |
| 4,787,398 A | 11/1988 | Garcia et al. |
| 4,789,467 A | 12/1988 | Lindsay et al. |
| 4,791,932 A | 12/1988 | Margules |
| 4,793,555 A | 12/1988 | Lee et al. |
| 4,795,435 A | 1/1989 | Steer |
| 4,795,542 A | 1/1989 | Ross et al. |
| 4,803,243 A | 2/1989 | Fujimoto et al. |
| 4,805,624 A | 2/1989 | Yao et al. |
| 4,805,625 A | 2/1989 | Wyler |
| 4,807,632 A | 2/1989 | Liess et al. |
| 4,808,089 A | 2/1989 | Buchholtz et al. |
| 4,808,292 A | 2/1989 | Kessler et al. |
| 4,809,704 A | 3/1989 | Sogawa et al. |
| 4,810,243 A | 3/1989 | Howson |
| 4,810,470 A | 3/1989 | Burkhardt et al. |
| 4,813,424 A | 3/1989 | Wilkins |
| 4,815,471 A | 3/1989 | Stobie |
| 4,820,281 A | 4/1989 | Lawler, Jr. |
| 4,822,336 A | 4/1989 | DiTraglia |
| 4,826,706 A | 5/1989 | Hilker et al. |
| 4,828,544 A | 5/1989 | Lane et al. |
| 4,830,013 A | 5/1989 | Maxwell |
| 4,831,070 A | 5/1989 | McInally et al. |
| 4,832,005 A | 5/1989 | Takamiya et al. |
| 4,832,034 A | 5/1989 | Pizziconi et al. |
| 4,834,101 A | 5/1989 | Collison et al. |
| 4,838,281 A | 6/1989 | Rogers et al. |
| 4,841,974 A | 6/1989 | Gumbrecht et al. |
| 4,849,458 A | 7/1989 | Reed et al. |
| 4,852,573 A | 8/1989 | Kennedy |
| 4,852,604 A | 8/1989 | Wales et al. |
| 4,854,322 A | 8/1989 | Ash et al. |
| 4,858,615 A | 8/1989 | Meinema |
| 4,861,454 A | 8/1989 | Ushizawa et al. |
| 4,867,741 A | 9/1989 | Portnoy |
| 4,871,440 A | 10/1989 | Nagata et al. |
| 4,874,363 A | 10/1989 | Abell |
| 4,883,057 A | 11/1989 | Broderick |
| 4,883,467 A | 11/1989 | Franetzki et al. |
| 4,886,070 A | 12/1989 | Demarest |
| 4,886,562 A | 12/1989 | Pinson |
| 4,889,528 A | 12/1989 | Nadai et al. |
| 4,889,744 A | 12/1989 | Quaid |

(56) References Cited

U.S. PATENT DOCUMENTS

| | | |
|---|---|---|
| 4,890,620 A | 1/1990 | Gough |
| 4,890,621 A | 1/1990 | Hakky |
| 4,894,339 A | 1/1990 | Hanazato et al. |
| 4,900,305 A | 2/1990 | Smith et al. |
| 4,902,294 A | 2/1990 | Gosserez |
| 4,907,857 A | 3/1990 | Giuliani et al. |
| 4,909,786 A | 3/1990 | Gijselhart et al. |
| 4,909,908 A | 3/1990 | Ross et al. |
| 4,919,114 A | 4/1990 | Miyazaki |
| 4,919,141 A | 4/1990 | Zier et al. |
| 4,919,649 A | 4/1990 | Timothy et al. |
| 4,921,477 A | 5/1990 | Davis |
| 4,921,480 A | 5/1990 | Sealfon |
| 4,925,444 A | 5/1990 | Orkin et al. |
| 4,927,407 A | 5/1990 | Dorman |
| 4,927,516 A | 5/1990 | Yamaguchi et al. |
| 4,928,694 A | 5/1990 | Maxwell |
| 4,934,369 A | 6/1990 | Maxwell |
| 4,934,375 A | 6/1990 | Cole et al. |
| 4,935,345 A | 6/1990 | Guilbeau et al. |
| 4,940,065 A | 7/1990 | Tanagho et al. |
| 4,944,299 A | 7/1990 | Silvian |
| 4,946,439 A | 8/1990 | Eggers |
| 4,951,657 A | 8/1990 | Pfister et al. |
| 4,951,669 A | 8/1990 | Maxwell et al. |
| 4,952,618 A | 8/1990 | Olsen |
| 4,953,552 A | 9/1990 | DeMarzo |
| 4,955,861 A | 9/1990 | Enegren et al. |
| 4,957,483 A | 9/1990 | Gonser et al. |
| 4,958,148 A | 9/1990 | Olson |
| 4,960,594 A | 10/1990 | Honeycutt |
| 4,961,434 A | 10/1990 | Stypulkowski |
| 4,963,595 A | 10/1990 | Ward et al. |
| 4,966,579 A | 10/1990 | Polaschegg |
| 4,967,940 A | 11/1990 | Blette et al. |
| 4,970,145 A | 11/1990 | Bennetto et al. |
| 4,974,592 A | 12/1990 | Branco |
| 4,974,929 A | 12/1990 | Curry |
| 4,975,175 A | 12/1990 | Karube et al. |
| 4,975,636 A | 12/1990 | Desautels |
| 4,976,687 A | 12/1990 | Martin |
| 4,979,509 A | 12/1990 | Hakky |
| 4,984,929 A | 1/1991 | Rock et al. |
| 4,986,271 A | 1/1991 | Wilkins |
| 4,986,671 A | 1/1991 | Sun et al. |
| 4,988,341 A | 1/1991 | Columbus et al. |
| 4,988,758 A | 1/1991 | Fukuda et al. |
| 4,989,607 A | 2/1991 | Keusch et al. |
| 4,990,231 A | 2/1991 | Stewart et al. |
| 4,992,794 A | 2/1991 | Brouwers |
| 4,994,026 A | 2/1991 | Fecondini |
| 4,994,167 A | 2/1991 | Shults et al. |
| 4,997,627 A | 3/1991 | Bergkuist et al. |
| 5,000,194 A | 3/1991 | Van Den Honert et al. |
| 5,002,055 A | 3/1991 | Merki et al. |
| 5,002,572 A | 3/1991 | Picha |
| 5,002,590 A | 3/1991 | Friesen et al. |
| 5,006,050 A | 4/1991 | Cooke et al. |
| 5,006,111 A | 4/1991 | Inokuchi et al. |
| 5,007,929 A | 4/1991 | Quaid |
| 5,009,251 A | 4/1991 | Pike et al. |
| 5,019,096 A | 5/1991 | Fox, Jr. et al. |
| 5,026,348 A | 6/1991 | Venegas |
| 5,030,199 A | 7/1991 | Barwick et al. |
| 5,030,310 A | 7/1991 | Wogoman |
| 5,030,333 A | 7/1991 | Clark, Jr. |
| 5,034,112 A | 7/1991 | Murase et al. |
| 5,035,711 A | 7/1991 | Aoki et al. |
| 5,037,497 A | 8/1991 | Stypulkowski |
| 5,041,092 A | 8/1991 | Barwick |
| 5,045,057 A | 9/1991 | Van Driessche et al. |
| 5,045,601 A | 9/1991 | Capelli et al. |
| 5,046,496 A | 9/1991 | Betts et al. |
| 5,048,525 A | 9/1991 | Maxwell |
| 5,050,612 A | 9/1991 | Matsumura |
| 5,055,171 A | 10/1991 | Peck |
| 5,055,198 A | 10/1991 | Shettigar |
| 5,059,654 A | 10/1991 | Hou et al. |
| 5,063,081 A | 11/1991 | Cozzette et al. |
| 5,067,491 A | 11/1991 | Taylor, II et al. |
| 5,068,536 A | 11/1991 | Rosenthal |
| 5,077,476 A | 12/1991 | Rosenthal |
| 5,082,550 A | 1/1992 | Rishpon et al. |
| 5,088,981 A | 2/1992 | Howson et al. |
| 5,089,112 A | 2/1992 | Skotheim et al. |
| 5,089,421 A | 2/1992 | Dieffenbach |
| 5,096,669 A | 3/1992 | Lauks et al. |
| 5,097,834 A | 3/1992 | Skrabal |
| 5,098,377 A | 3/1992 | Borsanyi et al. |
| 5,101,814 A | 4/1992 | Palti |
| 5,108,819 A | 4/1992 | Heller et al. |
| 5,109,850 A | 5/1992 | Blanco et al. |
| 5,112,301 A | 5/1992 | Fenton, Jr. et al. |
| 5,116,313 A | 5/1992 | McGregor |
| 5,120,813 A | 6/1992 | Ward, Jr. |
| 5,127,405 A | 7/1992 | Alcala et al. |
| 5,130,009 A | 7/1992 | Marsoner et al. |
| 5,130,231 A | 7/1992 | Kennedy et al. |
| 5,135,297 A | 8/1992 | Valint, Jr. |
| 5,137,028 A | 8/1992 | Nishimura |
| 5,140,985 A | 8/1992 | Schroeder et al. |
| 5,145,565 A | 9/1992 | Kater et al. |
| 5,147,725 A | 9/1992 | Pinchuk |
| 5,152,746 A | 10/1992 | Atkinson et al. |
| 5,160,418 A | 11/1992 | Mullen |
| 5,161,532 A | 11/1992 | Joseph |
| 5,162,407 A | 11/1992 | Turner |
| 5,165,406 A | 11/1992 | Wong |
| 5,165,407 A | 11/1992 | Wilson et al. |
| 5,171,689 A | 12/1992 | Kawaguri et al. |
| 5,174,123 A | 12/1992 | Erickson |
| 5,174,291 A | 12/1992 | Schoonen et al. |
| 5,176,632 A | 1/1993 | Bernardi |
| 5,176,658 A | 1/1993 | Ranford |
| 5,176,662 A | 1/1993 | Bartholomew et al. |
| 5,178,142 A | 1/1993 | Harjunmaa et al. |
| 5,178,957 A | 1/1993 | Kolpe et al. |
| 5,182,004 A | 1/1993 | Kohno |
| 5,183,549 A | 2/1993 | Joseph et al. |
| 5,188,591 A | 2/1993 | Dorsey, III |
| 5,190,038 A | 3/1993 | Polson et al. |
| 5,190,041 A | 3/1993 | Palti |
| 5,195,963 A | 3/1993 | Yafuso et al. |
| 5,198,771 A | 3/1993 | Fidler et al. |
| 5,200,051 A | 4/1993 | Cozzette et al. |
| 5,202,261 A | 4/1993 | Musho et al. |
| 5,207,218 A | 5/1993 | Carpentier et al. |
| 5,208,147 A | 5/1993 | Kagenow et al. |
| 5,208,313 A | 5/1993 | Krishnan |
| 5,212,050 A | 5/1993 | Mier et al. |
| 5,220,917 A | 6/1993 | Cammilli et al. |
| 5,220,920 A | 6/1993 | Gharib |
| 5,222,980 A | 6/1993 | Gealow |
| 5,224,929 A | 7/1993 | Remiszewski |
| 5,225,063 A | 7/1993 | Gumbrecht et al. |
| 5,232,434 A | 8/1993 | Inagaki et al. |
| 5,235,003 A | 8/1993 | Ward et al. |
| 5,243,696 A | 9/1993 | Carr et al. |
| 5,243,982 A | 9/1993 | Mostl et al. |
| 5,243,983 A | 9/1993 | Tarr et al. |
| 5,249,576 A | 10/1993 | Goldberger et al. |
| 5,250,439 A | 10/1993 | Musho et al. |
| 5,254,102 A | 10/1993 | Ogawa |
| 5,261,892 A | 11/1993 | Bertaud et al. |
| 5,262,305 A | 11/1993 | Heller et al. |
| 5,264,104 A | 11/1993 | Gregg et al. |
| 5,265,594 A | 11/1993 | Olsson et al. |
| 5,265,999 A | 11/1993 | Wenschhof et al. |
| 5,266,179 A | 11/1993 | Nankai et al. |
| 5,269,891 A | 12/1993 | Colin |
| 5,271,736 A | 12/1993 | Picha |
| 5,271,815 A | 12/1993 | Wong |
| 5,279,294 A | 1/1994 | Anderson et al. |
| 5,281,319 A | 1/1994 | Kaneko et al. |

(56) References Cited

U.S. PATENT DOCUMENTS

| | | |
|---|---|---|
| 5,282,844 A | 2/1994 | Stokes et al. |
| 5,282,848 A | 2/1994 | Schmitt |
| 5,284,140 A | 2/1994 | Allen et al. |
| 5,284,570 A | 2/1994 | Savage et al. |
| 5,285,513 A | 2/1994 | Kaufman et al. |
| 5,286,364 A | 2/1994 | Yacynych et al. |
| 5,287,753 A | 2/1994 | Routh et al. |
| 5,296,144 A | 3/1994 | Sternina et al. |
| 5,298,022 A | 3/1994 | Bernardi |
| 5,298,144 A | 3/1994 | Spokane |
| 5,299,571 A | 4/1994 | Mastrototaro |
| 5,302,093 A | 4/1994 | Owens et al. |
| 5,302,440 A | 4/1994 | Davis |
| 5,304,468 A | 4/1994 | Phillips et al. |
| 5,307,263 A | 4/1994 | Brown |
| 5,310,469 A | 5/1994 | Cunningham et al. |
| 5,311,908 A | 5/1994 | Barone et al. |
| 5,312,361 A | 5/1994 | Zadini et al. |
| 5,314,471 A | 5/1994 | Brauker et al. |
| 5,316,008 A | 5/1994 | Suga et al. |
| 5,316,452 A | 5/1994 | Bogen et al. |
| 5,318,511 A | 6/1994 | Riquier et al. |
| 5,322,063 A | 6/1994 | Allen et al. |
| 5,324,322 A | 6/1994 | Grill, Jr. et al. |
| 5,326,356 A | 7/1994 | Della Valle et al. |
| 5,326,449 A | 7/1994 | Cunningham |
| 5,328,451 A | 7/1994 | Davis et al. |
| 5,330,521 A | 7/1994 | Cohen |
| 5,330,634 A | 7/1994 | Wong et al. |
| 5,331,555 A | 7/1994 | Hashimoto et al. |
| 5,335,658 A | 8/1994 | Bedingham |
| 5,336,102 A | 8/1994 | Cairns et al. |
| 5,337,747 A | 8/1994 | Neftel |
| 5,340,352 A | 8/1994 | Nakanishi et al. |
| 5,342,348 A | 8/1994 | Kaplan |
| 5,342,409 A | 8/1994 | Mullett |
| 5,342,789 A | 8/1994 | Chick et al. |
| 5,343,869 A | 9/1994 | Pross et al. |
| 5,344,451 A | 9/1994 | Dayton |
| 5,344,454 A | 9/1994 | Clarke et al. |
| 5,345,932 A | 9/1994 | Yafuso et al. |
| 5,348,788 A | 9/1994 | White |
| 5,352,348 A | 10/1994 | Young et al. |
| 5,352,351 A | 10/1994 | White et al. |
| 5,354,272 A | 10/1994 | Swendson et al. |
| 5,354,449 A | 10/1994 | Band et al. |
| 5,356,375 A | 10/1994 | Higley |
| 5,356,378 A | 10/1994 | Doan |
| 5,356,786 A | 10/1994 | Heller et al. |
| 5,358,409 A | 10/1994 | Obara |
| 5,362,761 A | 11/1994 | Uragami et al. |
| 5,368,028 A | 11/1994 | Palti |
| 5,368,224 A | 11/1994 | Richardson et al. |
| 5,368,562 A | 11/1994 | Blomquist et al. |
| 5,372,133 A | 12/1994 | Hogen Esch |
| 5,372,135 A | 12/1994 | Mendelson et al. |
| 5,372,709 A | 12/1994 | Hood |
| 5,372,719 A | 12/1994 | Afeyan et al. |
| 5,376,070 A | 12/1994 | Purvis et al. |
| 5,378,229 A | 1/1995 | Layer et al. |
| 5,380,268 A | 1/1995 | Wheeler |
| 5,380,422 A | 1/1995 | Negishi et al. |
| 5,380,491 A | 1/1995 | Carver, Jr. et al. |
| 5,380,536 A | 1/1995 | Hubbell et al. |
| 5,380,665 A | 1/1995 | Cusack et al. |
| 5,382,514 A | 1/1995 | Passaniti et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,393,401 A | 2/1995 | Knoll |
| 5,397,848 A | 3/1995 | Yang et al. |
| 5,400,267 A | 3/1995 | Denen et al. |
| 5,404,877 A | 4/1995 | Nolan et al. |
| 5,405,510 A | 4/1995 | Betts et al. |
| 5,411,052 A | 5/1995 | Murray |
| 5,411,647 A | 5/1995 | Johnson et al. |
| 5,411,866 A | 5/1995 | Luong et al. |
| 5,417,115 A | 5/1995 | Burns |
| 5,417,206 A | 5/1995 | Kaneyoshi |
| 5,417,395 A | 5/1995 | Fowler et al. |
| 5,418,142 A | 5/1995 | Kiser et al. |
| 5,421,328 A | 6/1995 | Bedingham |
| 5,421,923 A | 6/1995 | Clarke et al. |
| 5,423,738 A | 6/1995 | Robinson et al. |
| 5,423,749 A | 6/1995 | Merte et al. |
| 5,425,717 A | 6/1995 | Mohiuddin |
| 5,426,032 A | 6/1995 | Phillips et al. |
| 5,428,123 A | 6/1995 | Ward et al. |
| 5,429,129 A | 7/1995 | Lovejoy et al. |
| 5,429,485 A | 7/1995 | Dodge |
| 5,429,602 A | 7/1995 | Hauser |
| 5,429,735 A | 7/1995 | Johnson et al. |
| 5,431,160 A | 7/1995 | Wilkins |
| 5,431,174 A | 7/1995 | Knute |
| 5,431,921 A | 7/1995 | Thombre |
| 5,434,412 A | 7/1995 | Sodickson et al. |
| 5,437,635 A | 8/1995 | Fields et al. |
| 5,437,999 A | 8/1995 | Diebold et al. |
| 5,438,984 A | 8/1995 | Schoendorfer |
| 5,445,610 A | 8/1995 | Evert |
| 5,448,992 A | 9/1995 | Kupershmidt |
| 5,451,260 A | 9/1995 | Versteeg et al. |
| 5,453,199 A | 9/1995 | Afeyan et al. |
| 5,453,278 A | 9/1995 | Chan et al. |
| 5,458,631 A | 10/1995 | Xavier |
| 5,462,051 A | 10/1995 | Oka et al. |
| 5,462,064 A | 10/1995 | D'Angelo et al. |
| 5,462,645 A | 10/1995 | Albery et al. |
| 5,466,356 A | 11/1995 | Schneider et al. |
| 5,466,575 A | 11/1995 | Cozzette et al. |
| 5,469,846 A | 11/1995 | Khan |
| 5,474,552 A | 12/1995 | Palti |
| 5,476,094 A | 12/1995 | Allen et al. |
| 5,476,776 A | 12/1995 | Wilkins |
| 5,480,711 A | 1/1996 | Ruefer |
| 5,482,008 A | 1/1996 | Stafford et al. |
| 5,482,446 A | 1/1996 | Williamson et al. |
| 5,482,473 A | 1/1996 | Lord et al. |
| 5,484,404 A | 1/1996 | Schulman et al. |
| 5,486,776 A | 1/1996 | Chiang |
| 5,490,323 A | 2/1996 | Thacker et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,502,396 A | 3/1996 | Desarzens et al. |
| 5,505,828 A | 4/1996 | Wong et al. |
| 5,507,288 A | 4/1996 | Bocker et al. |
| 5,508,203 A | 4/1996 | Fuller et al. |
| 5,508,509 A | 4/1996 | Yafuso et al. |
| 5,509,888 A | 4/1996 | Miller |
| 5,512,046 A | 4/1996 | Pusinelli et al. |
| 5,512,248 A | 4/1996 | Van |
| 5,513,636 A | 5/1996 | Palti |
| 5,514,253 A | 5/1996 | Davis et al. |
| 5,515,170 A | 5/1996 | Matzinger et al. |
| 5,515,851 A | 5/1996 | Goldstein |
| 5,516,832 A | 5/1996 | Kennan et al. |
| 5,518,601 A | 5/1996 | Foos et al. |
| 5,526,120 A | 6/1996 | Jina et al. |
| 5,527,288 A | 6/1996 | Gross et al. |
| 5,529,066 A | 6/1996 | Palti |
| 5,529,676 A | 6/1996 | Maley et al. |
| 5,531,679 A | 7/1996 | Schulman et al. |
| 5,531,878 A | 7/1996 | Vadgama et al. |
| 5,540,828 A | 7/1996 | Yacynych |
| 5,545,200 A | 8/1996 | West et al. |
| 5,545,220 A | 8/1996 | Andrews et al. |
| 5,545,223 A | 8/1996 | Neuenfeldt et al. |
| 5,549,547 A | 8/1996 | Cohen et al. |
| 5,549,548 A | 8/1996 | Larsson |
| 5,549,569 A | 8/1996 | Lynn et al. |
| 5,549,651 A | 8/1996 | Lynn |

(56) References Cited

U.S. PATENT DOCUMENTS

| | | |
|---|---|---|
| 5,549,675 A | 8/1996 | Neuenfeldt et al. |
| 5,551,850 A | 9/1996 | Williamson et al. |
| 5,552,112 A | 9/1996 | Schiffmann et al. |
| 5,553,616 A | 9/1996 | Ham et al. |
| 5,554,339 A | 9/1996 | Cozzette et al. |
| 5,558,957 A | 9/1996 | Datta et al. |
| 5,562,614 A | 10/1996 | O'Donnell |
| 5,562,615 A | 10/1996 | Nassif |
| 5,564,439 A | 10/1996 | Picha |
| 5,568,806 A | 10/1996 | Cheney, II et al. |
| 5,569,186 A | 10/1996 | Lord et al. |
| 5,569,188 A | 10/1996 | Mackool |
| 5,569,219 A | 10/1996 | Hakki et al. |
| 5,569,462 A | 10/1996 | Martinson et al. |
| 5,571,395 A | 11/1996 | Park et al. |
| 5,575,293 A | 11/1996 | Miller et al. |
| 5,575,930 A | 11/1996 | Tietje-Girault et al. |
| 5,577,499 A | 11/1996 | Teves |
| 5,582,184 A | 12/1996 | Erickson et al. |
| 5,582,497 A | 12/1996 | Noguchi |
| 5,582,593 A | 12/1996 | Hultman |
| 5,582,697 A | 12/1996 | Ikeda et al. |
| 5,584,813 A | 12/1996 | Livingston et al. |
| 5,584,876 A | 12/1996 | Bruchman et al. |
| 5,586,553 A | 12/1996 | Halili et al. |
| 5,587,273 A | 12/1996 | Yan et al. |
| 5,588,560 A | 12/1996 | Benedict et al. |
| 5,589,133 A | 12/1996 | Suzuki |
| 5,589,563 A | 12/1996 | Ward et al. |
| 5,590,651 A | 1/1997 | Shaffer et al. |
| 5,593,440 A | 1/1997 | Brauker et al. |
| 5,593,852 A | 1/1997 | Heller et al. |
| 5,607,565 A | 3/1997 | Azarnia et al. |
| 5,609,572 A | 3/1997 | Lang |
| 5,611,900 A | 3/1997 | Worden et al. |
| 5,624,409 A | 4/1997 | Seale |
| 5,624,537 A | 4/1997 | Turner et al. |
| 5,626,561 A | 5/1997 | Butler et al. |
| 5,626,563 A | 5/1997 | Dodge et al. |
| 5,628,619 A | 5/1997 | Wilson |
| 5,628,890 A | 5/1997 | Carter et al. |
| 5,630,978 A | 5/1997 | Domb |
| 5,637,083 A | 6/1997 | Bertrand et al. |
| 5,637,135 A | 6/1997 | Ottenstein et al. |
| 5,640,470 A | 6/1997 | Iyer et al. |
| 5,640,954 A | 6/1997 | Pfeiffer et al. |
| 5,643,195 A | 7/1997 | Drevet et al. |
| 5,651,767 A | 7/1997 | Schulman et al. |
| 5,653,756 A | 8/1997 | Clarke et al. |
| 5,653,863 A | 8/1997 | Genshaw et al. |
| 5,658,247 A | 8/1997 | Henley |
| 5,658,250 A | 8/1997 | Blomquist et al. |
| 5,658,330 A | 8/1997 | Carlisle et al. |
| 5,658,802 A | 8/1997 | Hayes et al. |
| 5,660,163 A | 8/1997 | Schulman et al. |
| 5,660,177 A | 8/1997 | Faupel et al. |
| 5,662,616 A | 9/1997 | Bousquet |
| 5,665,061 A | 9/1997 | Antwiler |
| 5,665,065 A | 9/1997 | Colman et al. |
| 5,665,215 A | 9/1997 | Bussmann et al. |
| 5,667,504 A | 9/1997 | Baumann et al. |
| 5,673,694 A | 10/1997 | Rivers |
| 5,676,651 A | 10/1997 | Larson, Jr. et al. |
| 5,676,820 A | 10/1997 | Wang et al. |
| 5,681,572 A | 10/1997 | Seare, Jr. |
| 5,682,884 A | 11/1997 | Hill et al. |
| 5,683,562 A | 11/1997 | Schaffar et al. |
| 5,686,829 A | 11/1997 | Girault |
| 5,688,239 A | 11/1997 | Walker |
| 5,688,244 A | 11/1997 | Lang |
| 5,690,119 A | 11/1997 | Rytky et al. |
| 5,695,623 A | 12/1997 | Michel et al. |
| 5,696,314 A | 12/1997 | McCaffrey et al. |
| 5,697,366 A | 12/1997 | Kimball et al. |
| 5,697,899 A | 12/1997 | Hillman et al. |
| 5,697,976 A | 12/1997 | Chesterfield et al. |
| 5,703,359 A | 12/1997 | Wampler, III |
| 5,704,354 A | 1/1998 | Preidel et al. |
| 5,706,807 A | 1/1998 | Picha |
| 5,707,502 A | 1/1998 | McCaffrey et al. |
| 5,711,302 A | 1/1998 | Lampropoulos et al. |
| 5,711,685 A | 1/1998 | Wood |
| 5,711,861 A | 1/1998 | Ward et al. |
| 5,713,842 A | 2/1998 | Kay |
| 5,713,888 A | 2/1998 | Neuenfeldt et al. |
| 5,714,123 A | 2/1998 | Sohrab |
| 5,714,391 A | 2/1998 | Omura et al. |
| 5,720,293 A | 2/1998 | Quinn et al. |
| 5,730,654 A | 3/1998 | Brown |
| 5,733,336 A | 3/1998 | Neuenfeldt et al. |
| 5,735,273 A | 4/1998 | Kurnik et al. |
| 5,741,319 A | 4/1998 | Woloszko et al. |
| 5,741,330 A | 4/1998 | Brauker et al. |
| 5,741,634 A | 4/1998 | Nozoe et al. |
| 5,743,262 A | 4/1998 | Lepper, Jr. et al. |
| 5,746,898 A | 5/1998 | Preidel |
| 5,749,832 A | 5/1998 | Vadgama et al. |
| 5,749,907 A | 5/1998 | Mann |
| 5,755,692 A | 5/1998 | Manicom |
| 5,756,632 A | 5/1998 | Ward et al. |
| 5,758,643 A | 6/1998 | Wong et al. |
| 5,763,760 A | 6/1998 | Gumbrecht et al. |
| 5,763,787 A | 6/1998 | Gravel et al. |
| 5,766,151 A | 6/1998 | Valley et al. |
| 5,770,028 A | 6/1998 | Maley et al. |
| 5,770,208 A | 6/1998 | Fattom et al. |
| 5,771,890 A | 6/1998 | Tamada |
| 5,773,270 A | 6/1998 | D'Orazio et al. |
| 5,773,286 A | 6/1998 | Dionne et al. |
| 5,776,324 A | 7/1998 | Usala |
| 5,777,060 A | 7/1998 | Van Antwerp |
| 5,779,665 A | 7/1998 | Mastrototaro et al. |
| 5,781,455 A | 7/1998 | Hyodo |
| 5,782,880 A | 7/1998 | Lahtinen et al. |
| 5,782,912 A | 7/1998 | Brauker et al. |
| 5,783,054 A | 7/1998 | Raguse et al. |
| 5,786,439 A | 7/1998 | Van Antwerp et al. |
| 5,787,900 A | 8/1998 | Butler et al. |
| 5,791,344 A | 8/1998 | Schulman et al. |
| 5,791,880 A | 8/1998 | Wilson |
| 5,795,453 A | 8/1998 | Gilmartin |
| 5,795,774 A | 8/1998 | Matsumoto et al. |
| 5,798,065 A | 8/1998 | Picha |
| 5,798,085 A | 8/1998 | Seaton et al. |
| 5,800,383 A | 9/1998 | Chandler et al. |
| 5,800,420 A | 9/1998 | Gross et al. |
| 5,800,529 A | 9/1998 | Brauker et al. |
| 5,804,048 A | 9/1998 | Wong et al. |
| 5,806,517 A | 9/1998 | Gerhardt et al. |
| 5,807,274 A | 9/1998 | Henning et al. |
| 5,807,312 A | 9/1998 | Dzwonkiewicz |
| 5,807,375 A | 9/1998 | Gross et al. |
| 5,807,406 A | 9/1998 | Brauker et al. |
| 5,810,736 A | 9/1998 | Pail |
| 5,810,770 A | 9/1998 | Chin et al. |
| 5,811,487 A | 9/1998 | Schulz, Jr. et al. |
| 5,814,599 A | 9/1998 | Mitragotri et al. |
| 5,820,570 A | 10/1998 | Erickson et al. |
| 5,820,589 A | 10/1998 | Torgerson et al. |
| 5,820,622 A | 10/1998 | Gross et al. |
| 5,822,715 A | 10/1998 | Worthington et al. |
| 5,823,802 A | 10/1998 | Bartley |
| 5,824,651 A | 10/1998 | Nanci et al. |
| 5,827,183 A | 10/1998 | Kurnik et al. |
| 5,833,603 A | 11/1998 | Kovacs et al. |
| 5,836,886 A | 11/1998 | Itoigawa et al. |
| 5,836,887 A | 11/1998 | Oka et al. |
| 5,836,989 A | 11/1998 | Shelton |
| 5,837,454 A | 11/1998 | Cozzette et al. |
| 5,837,728 A | 11/1998 | Purcell |
| 5,840,026 A | 11/1998 | Uber, III et al. |
| 5,840,148 A | 11/1998 | Campbell et al. |
| 5,840,240 A | 11/1998 | Stenoien et al. |
| 5,843,069 A | 12/1998 | Butler et al. |

(56) References Cited

U.S. PATENT DOCUMENTS

| | | |
|---|---|---|
| 5,848,991 A | 12/1998 | Gross et al. |
| 5,851,197 A | 12/1998 | Marano et al. |
| 5,857,983 A | 1/1999 | Douglas et al. |
| 5,858,296 A | 1/1999 | Domb |
| 5,858,365 A | 1/1999 | Faller |
| 5,858,747 A | 1/1999 | Schinstine et al. |
| 5,861,019 A | 1/1999 | Sun et al. |
| 5,863,400 A | 1/1999 | Drummond et al. |
| 5,863,460 A | 1/1999 | Slovacek et al. |
| 5,871,499 A | 2/1999 | Hahn et al. |
| 5,871,514 A | 2/1999 | Wiklund et al. |
| 5,872,198 A | 2/1999 | Mosbach et al. |
| 5,872,499 A | 2/1999 | Poulsen |
| 5,873,862 A | 2/1999 | Lopez |
| 5,874,500 A | 2/1999 | Rhee et al. |
| 5,879,294 A | 3/1999 | Anderson et al. |
| 5,879,373 A | 3/1999 | Roper et al. |
| 5,879,713 A | 3/1999 | Roth et al. |
| 5,879,828 A | 3/1999 | Debe et al. |
| 5,882,354 A | 3/1999 | Brauker et al. |
| 5,882,494 A | 3/1999 | Van Antwerp |
| 5,895,235 A | 4/1999 | Droz |
| 5,897,525 A | 4/1999 | Dey et al. |
| 5,897,578 A | 4/1999 | Wiklund et al. |
| 5,897,955 A | 4/1999 | Drumheller |
| 5,899,855 A | 5/1999 | Brown |
| 5,904,666 A | 5/1999 | DeDecker et al. |
| 5,904,708 A | 5/1999 | Goedeke |
| 5,910,554 A | 6/1999 | Kempe et al. |
| 5,911,219 A | 6/1999 | Aylsworth et al. |
| 5,913,998 A | 6/1999 | Butler et al. |
| 5,914,026 A | 6/1999 | Blubaugh, Jr. et al. |
| 5,914,182 A | 6/1999 | Drumheller |
| 5,916,445 A | 6/1999 | Hjerten et al. |
| 5,917,346 A | 6/1999 | Gord |
| 5,919,215 A | 7/1999 | Wiklund et al. |
| 5,921,951 A | 7/1999 | Morris |
| 5,922,530 A | 7/1999 | Yu |
| 5,928,130 A | 7/1999 | Schmidt |
| 5,928,155 A | 7/1999 | Eggers et al. |
| 5,928,182 A | 7/1999 | Kraus et al. |
| 5,928,189 A | 7/1999 | Phillips et al. |
| 5,928,195 A | 7/1999 | Malamud et al. |
| 5,931,814 A | 8/1999 | Alex et al. |
| 5,932,175 A | 8/1999 | Knute et al. |
| 5,933,136 A | 8/1999 | Brown |
| 5,935,785 A | 8/1999 | Reber et al. |
| 5,938,636 A | 8/1999 | Kramer et al. |
| 5,938,679 A | 8/1999 | Freeman et al. |
| 5,944,661 A | 8/1999 | Swette et al. |
| 5,945,498 A | 8/1999 | Hopken et al. |
| 5,947,911 A | 9/1999 | Wong et al. |
| 5,951,521 A | 9/1999 | Mastrototaro et al. |
| 5,954,643 A | 9/1999 | VanAntwerp et al. |
| 5,954,685 A | 9/1999 | Tierney |
| 5,954,954 A | 9/1999 | Houck et al. |
| 5,957,854 A | 9/1999 | Besson et al. |
| 5,957,903 A | 9/1999 | Mirzaee et al. |
| 5,959,050 A | 9/1999 | Mosbach et al. |
| 5,961,451 A | 10/1999 | Reber et al. |
| 5,963,132 A | 10/1999 | Yoakum |
| 5,964,261 A | 10/1999 | Neuenfeldt et al. |
| 5,964,745 A | 10/1999 | Lyles et al. |
| 5,964,804 A | 10/1999 | Brauker et al. |
| 5,964,993 A | 10/1999 | Blubaugh, Jr. et al. |
| 5,965,125 A | 10/1999 | Mineau-Hanschke |
| 5,965,380 A | 10/1999 | Heller et al. |
| 5,967,986 A | 10/1999 | Cimochowski et al. |
| 5,968,836 A | 10/1999 | Matzinger et al. |
| 5,971,922 A | 10/1999 | Arita et al. |
| 5,972,199 A | 10/1999 | Heller et al. |
| 5,976,085 A | 11/1999 | Kimball et al. |
| 5,977,241 A | 11/1999 | Koloski et al. |
| 5,985,129 A | 11/1999 | Gough et al. |
| 5,985,693 A | 11/1999 | Leedy |
| 5,987,352 A | 11/1999 | Klein et al. |
| 5,989,409 A | 11/1999 | Kurnik et al. |
| 5,995,208 A | 11/1999 | Sarge et al. |
| 5,995,860 A | 11/1999 | Sun et al. |
| 5,997,501 A | 12/1999 | Gross et al. |
| 5,998,247 A | 12/1999 | Wu |
| 5,999,848 A | 12/1999 | Gord et al. |
| 5,999,849 A | 12/1999 | Gord et al. |
| 6,001,067 A | 12/1999 | Shults et al. |
| 6,001,471 A | 12/1999 | Bries et al. |
| 6,007,845 A | 12/1999 | Domb et al. |
| 6,011,984 A | 1/2000 | Van Antwerp et al. |
| 6,013,113 A | 1/2000 | Mika |
| 6,014,577 A | 1/2000 | Henning et al. |
| 6,015,392 A | 1/2000 | Douglas et al. |
| 6,015,572 A | 1/2000 | Lin et al. |
| 6,016,448 A | 1/2000 | Busacker et al. |
| 6,017,435 A | 1/2000 | Hassard et al. |
| 6,018,033 A | 1/2000 | Chen et al. |
| 6,023,629 A | 2/2000 | Tamada |
| 6,024,720 A | 2/2000 | Chandler et al. |
| 6,027,445 A | 2/2000 | Von Bahr |
| 6,027,479 A | 2/2000 | Alei et al. |
| 6,032,059 A | 2/2000 | Henning et al. |
| 6,032,667 A | 3/2000 | Heinonen |
| 6,036,924 A | 3/2000 | Simons et al. |
| 6,043,328 A | 3/2000 | Domschke et al. |
| 6,045,567 A | 4/2000 | Taylor et al. |
| 6,045,671 A | 4/2000 | Wu et al. |
| 6,048,691 A | 4/2000 | Maracas |
| 6,049,727 A | 4/2000 | Crothall |
| 6,051,372 A | 4/2000 | Bayerl et al. |
| 6,051,389 A | 4/2000 | Ahl et al. |
| 6,057,377 A | 5/2000 | Sasaki et al. |
| 6,059,946 A | 5/2000 | Yukawa et al. |
| 6,060,640 A | 5/2000 | Pauley et al. |
| 6,063,637 A | 5/2000 | Arnold et al. |
| 6,065,154 A | 5/2000 | Hulings et al. |
| 6,066,083 A | 5/2000 | Slater et al. |
| 6,066,088 A | 5/2000 | Davis |
| 6,066,448 A | 5/2000 | Wohlstadter et al. |
| 6,068,668 A | 5/2000 | Mastroianni |
| 6,071,391 A | 6/2000 | Gotoh et al. |
| 6,071,406 A | 6/2000 | Tsou |
| 6,074,775 A | 6/2000 | Gartstein et al. |
| 6,077,299 A | 6/2000 | Adelberg et al. |
| 6,080,583 A | 6/2000 | Von Bahr |
| 6,081,735 A | 6/2000 | Diab et al. |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,090,087 A | 7/2000 | Tsukada et al. |
| 6,091,975 A | 7/2000 | Daddona et al. |
| 6,093,156 A | 7/2000 | Cunningham et al. |
| 6,093,172 A | 7/2000 | Funderburk et al. |
| 6,099,511 A | 8/2000 | Devos et al. |
| 6,101,404 A | 8/2000 | Yoon et al. |
| 6,103,033 A | 8/2000 | Say et al. |
| 6,103,533 A | 8/2000 | Hassard et al. |
| 6,106,486 A | 8/2000 | Tenerz et al. |
| 6,107,083 A | 8/2000 | Collins et al. |
| 6,115,622 A | 9/2000 | Minoz |
| 6,115,634 A | 9/2000 | Donders et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,122,536 A | 9/2000 | Sun et al. |
| 6,123,827 A | 9/2000 | Wong et al. |
| 6,127,154 A | 10/2000 | Mosbach et al. |
| 6,128,519 A | 10/2000 | Say |
| 6,134,461 A | 10/2000 | Say et al. |
| 6,135,978 A | 10/2000 | Houben et al. |
| 6,139,718 A | 10/2000 | Kurnik et al. |
| 6,141,573 A | 10/2000 | Kurnik et al. |
| D433,755 S | 11/2000 | Mastrototaro et al. |
| 6,142,939 A | 11/2000 | Eppstein et al. |
| 6,144,869 A | 11/2000 | Berner et al. |

(56) References Cited

U.S. PATENT DOCUMENTS

| | | |
|---|---|---|
| 6,144,871 A | 11/2000 | Saito et al. |
| RE36,991 E | 12/2000 | Yamamoto et al. |
| 6,156,051 A | 12/2000 | Schraga |
| 6,157,860 A | 12/2000 | Hauser et al. |
| 6,159,186 A | 12/2000 | Wickham et al. |
| 6,159,497 A | 12/2000 | LaPrade et al. |
| 6,162,201 A | 12/2000 | Cohen et al. |
| 6,162,611 A | 12/2000 | Heller et al. |
| 6,164,921 A | 12/2000 | Moubayed et al. |
| 6,165,154 A | 12/2000 | Gray et al. |
| 6,165,156 A | 12/2000 | Cesarczyk et al. |
| 6,167,614 B1 | 1/2001 | Tuttle et al. |
| 6,168,568 B1 | 1/2001 | Gavriely |
| 6,169,155 B1 | 1/2001 | Alvarez et al. |
| 6,171,276 B1 | 1/2001 | Lippe et al. |
| 6,175,752 B1 | 1/2001 | Say et al. |
| 6,175,767 B1 | 1/2001 | Doyle, Sr. |
| 6,180,221 B1 | 1/2001 | Crotzer et al. |
| 6,180,416 B1 | 1/2001 | Kurnik et al. |
| 6,183,437 B1 | 2/2001 | Walker |
| 6,187,062 B1 | 2/2001 | Oweis et al. |
| 6,189,536 B1 | 2/2001 | Martinez et al. |
| 6,191,860 B1 | 2/2001 | Klinger et al. |
| 6,192,891 B1 | 2/2001 | Gravel et al. |
| 6,197,040 B1 | 3/2001 | LeVaughn et al. |
| 6,198,969 B1 | 3/2001 | Kuzma |
| 6,200,772 B1 | 3/2001 | Vadgama et al. |
| 6,201,979 B1 | 3/2001 | Kurnik et al. |
| 6,201,980 B1 | 3/2001 | Darrow et al. |
| 6,201,993 B1 | 3/2001 | Kruse et al. |
| 6,206,856 B1 | 3/2001 | Mahurkar |
| 6,208,894 B1 | 3/2001 | Schulman et al. |
| 6,212,416 B1 | 4/2001 | Ward et al. |
| 6,212,424 B1 | 4/2001 | Robinson |
| 6,213,739 B1 | 4/2001 | Phallen et al. |
| 6,214,185 B1 | 4/2001 | Offenbacher et al. |
| 6,214,901 B1 | 4/2001 | Chudzik et al. |
| 6,219,574 B1 | 4/2001 | Cormier et al. |
| 6,223,080 B1 | 4/2001 | Thompson |
| 6,223,083 B1 | 4/2001 | Rosar |
| 6,230,059 B1 | 5/2001 | Duffin |
| 6,231,879 B1 | 5/2001 | Li et al. |
| 6,232,783 B1 | 5/2001 | Merrill |
| 6,233,080 B1 | 5/2001 | Brenner et al. |
| 6,233,471 B1 | 5/2001 | Berner et al. |
| 6,241,663 B1 | 6/2001 | Wu et al. |
| 6,241,863 B1 | 6/2001 | Monbouquette |
| 6,248,067 B1 | 6/2001 | Causey, III et al. |
| 6,248,077 B1 | 6/2001 | Elson et al. |
| 6,248,093 B1 | 6/2001 | Moberg |
| 6,251,280 B1 | 6/2001 | Dai et al. |
| 6,254,586 B1 | 7/2001 | Mann et al. |
| 6,255,592 B1 | 7/2001 | Pennington et al. |
| 6,256,522 B1 | 7/2001 | Schultz |
| 6,259,937 B1 | 7/2001 | Schulman et al. |
| 6,261,280 B1 | 7/2001 | Houben et al. |
| 6,263,222 B1 | 7/2001 | Diab et al. |
| 6,264,825 B1 | 7/2001 | Blackburn et al. |
| 6,266,551 B1 | 7/2001 | Osadchy et al. |
| 6,268,161 B1 | 7/2001 | Han et al. |
| 6,270,478 B1 | 8/2001 | Mernøe |
| 6,271,332 B1 | 8/2001 | Lohmann et al. |
| 6,272,364 B1 | 8/2001 | Kurnik |
| 6,272,382 B1 | 8/2001 | Faltys et al. |
| 6,272,480 B1 | 8/2001 | Tresp et al. |
| 6,274,285 B1 | 8/2001 | Gries et al. |
| 6,274,686 B1 | 8/2001 | Mosbach et al. |
| 6,275,717 B1 | 8/2001 | Gross et al. |
| 6,280,408 B1 | 8/2001 | Sipin |
| 6,284,125 B1 | 9/2001 | Hodges et al. |
| 6,284,126 B1 | 9/2001 | Kurnik et al. |
| 6,284,478 B1 | 9/2001 | Heller et al. |
| 6,285,897 B1 | 9/2001 | Kilcoyne et al. |
| 6,293,925 B1 | 9/2001 | Safabash et al. |
| 6,294,281 B1 | 9/2001 | Heller |
| 6,295,506 B1 | 9/2001 | Heinonen et al. |
| 6,296,615 B1 | 10/2001 | Brockway et al. |
| 6,298,254 B2 | 10/2001 | Tamada |
| 6,298,255 B1 | 10/2001 | Cordero et al. |
| 6,299,578 B1 | 10/2001 | Kurnik et al. |
| 6,299,583 B1 | 10/2001 | Eggers et al. |
| 6,300,002 B1 | 10/2001 | Webb et al. |
| 6,300,884 B1 | 10/2001 | Wilson |
| 6,302,855 B1 | 10/2001 | Lav et al. |
| 6,306,424 B1 | 10/2001 | Vyakarnam et al. |
| 6,306,594 B1 | 10/2001 | Cozzette et al. |
| 6,308,089 B1 | 10/2001 | Von Der Ruhr et al. |
| 6,309,351 B1 | 10/2001 | Kurnik et al. |
| 6,309,384 B1 | 10/2001 | Harrington et al. |
| 6,309,526 B1 | 10/2001 | Fujiwara et al. |
| 6,309,884 B1 | 10/2001 | Cooper et al. |
| 6,310,110 B1 | 10/2001 | Markowitz et al. |
| 6,315,738 B1 | 11/2001 | Nishikawa et al. |
| 6,319,566 B1 | 11/2001 | Polanyi et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,488 B1 | 12/2001 | Terry et al. |
| 6,329,929 B1 | 12/2001 | Weijand et al. |
| 6,330,464 B1 | 12/2001 | Colvin, Jr. et al. |
| 6,335,203 B1 | 1/2002 | Patel et al. |
| 6,336,269 B1 | 1/2002 | Eldridge et al. |
| 6,340,588 B1 | 1/2002 | Nova et al. |
| 6,341,232 B1 | 1/2002 | Conn et al. |
| 6,343,225 B1 | 1/2002 | Clark, Jr. |
| 6,344,021 B1 | 2/2002 | Juster et al. |
| 6,346,114 B1 | 2/2002 | Schraga |
| 6,355,000 B1 | 3/2002 | Ogura |
| 6,356,776 B1 | 3/2002 | Berner et al. |
| 6,358,225 B1 | 3/2002 | Butterfield |
| 6,360,888 B1 | 3/2002 | McIvor et al. |
| 6,365,670 B1 | 4/2002 | Fry |
| 6,366,794 B1 | 4/2002 | Moussy et al. |
| 6,368,141 B1 | 4/2002 | VanAntwerp et al. |
| 6,368,274 B1 | 4/2002 | Van Antwerp et al. |
| 6,368,658 B1 | 4/2002 | Schwarz et al. |
| 6,370,410 B2 | 4/2002 | Kurnik et al. |
| 6,370,941 B2 | 4/2002 | Nakamura et al. |
| 6,371,963 B1 | 4/2002 | Nishtala et al. |
| 6,372,244 B1 | 4/2002 | Antanavich et al. |
| 6,379,201 B1 | 4/2002 | Biggs et al. |
| 6,379,301 B1 | 4/2002 | Worthington et al. |
| 6,379,317 B1 | 4/2002 | Kintzig et al. |
| 6,379,883 B2 | 4/2002 | Davis et al. |
| 6,387,709 B1 | 5/2002 | Mason et al. |
| 6,391,019 B1 | 5/2002 | Ito |
| 6,393,318 B1 | 5/2002 | Conn et al. |
| 6,398,562 B1 | 6/2002 | Butler et al. |
| 6,400,974 B1 | 6/2002 | Lesho |
| 6,402,703 B1 | 6/2002 | Kensey et al. |
| 6,403,944 B1 | 6/2002 | MacKenzie et al. |
| 6,405,066 B1 | 6/2002 | Essenpreis et al. |
| 6,406,066 B1 | 6/2002 | Uegane |
| 6,406,426 B1 | 6/2002 | Reuss et al. |
| 6,407,195 B2 | 6/2002 | Sherman et al. |
| 6,409,674 B1 | 6/2002 | Brockway et al. |
| 6,413,393 B1 | 7/2002 | Van Antwerp et al. |
| 6,413,410 B1 | 7/2002 | Hodges et al. |
| 6,416,651 B1 | 7/2002 | Millar |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,430,437 B1 | 8/2002 | Marro |
| 6,432,050 B1 | 8/2002 | Porat et al. |
| 6,438,414 B1 | 8/2002 | Conn et al. |
| 6,442,413 B1 | 8/2002 | Silver |
| 6,447,448 B1 | 9/2002 | Ishikawa et al. |
| 6,447,542 B1 | 9/2002 | Weadock |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,464,849 B1 | 10/2002 | Say et al. |
| 6,465,066 B1 | 10/2002 | Rule et al. |

(56) References Cited

U.S. PATENT DOCUMENTS

| | | |
|---|---|---|
| 6,466,810 B1 | 10/2002 | Ward et al. |
| 6,467,480 B1 | 10/2002 | Meier et al. |
| 6,468,287 B1 | 10/2002 | Baugh |
| 6,471,689 B1 | 10/2002 | Joseph et al. |
| 6,471,993 B1 | 10/2002 | Shastri et al. |
| 6,474,360 B1 | 11/2002 | Ito |
| 6,475,372 B1 | 11/2002 | Ohara et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,484,045 B1 | 11/2002 | Holker et al. |
| 6,484,046 B1 | 11/2002 | Say et al. |
| 6,484,132 B1 | 11/2002 | Hively et al. |
| 6,485,449 B2 | 11/2002 | Ito |
| 6,487,429 B2 | 11/2002 | Hockersmith et al. |
| 6,488,652 B1 | 12/2002 | Weijand et al. |
| 6,494,830 B1 | 12/2002 | Wessel |
| 6,494,879 B2 | 12/2002 | Lennox et al. |
| 6,497,729 B1 | 12/2002 | Moussy et al. |
| 6,498,043 B1 | 12/2002 | Schulman et al. |
| 6,498,941 B1 | 12/2002 | Jackson |
| 6,501,976 B1 | 12/2002 | Sohrab |
| 6,510,239 B1 | 1/2003 | Wieres et al. |
| 6,510,329 B2 | 1/2003 | Heckel |
| 6,512,939 B1 | 1/2003 | Colvin et al. |
| 6,514,718 B2 | 2/2003 | Heller et al. |
| 6,517,508 B1 | 2/2003 | Utterberg et al. |
| 6,520,326 B2 | 2/2003 | McIvor et al. |
| 6,520,477 B2 | 2/2003 | Trimmer |
| 6,520,937 B2 | 2/2003 | Hart et al. |
| 6,520,938 B1 | 2/2003 | Funderburk et al. |
| 6,520,997 B1 | 2/2003 | Pekkarinen et al. |
| 6,522,903 B1 | 2/2003 | Berman et al. |
| 6,524,861 B1 | 2/2003 | Anderson |
| 6,526,298 B1 | 2/2003 | Khalil et al. |
| 6,527,729 B1 | 3/2003 | Turcott |
| 6,528,584 B2 | 3/2003 | Kennedy et al. |
| 6,529,755 B2 | 3/2003 | Kurnik et al. |
| 6,534,711 B1 | 3/2003 | Pollack |
| 6,536,433 B1 | 3/2003 | Cewers |
| 6,537,318 B1 | 3/2003 | Ita et al. |
| 6,541,107 B1 | 4/2003 | Zhong et al. |
| 6,541,266 B2 | 4/2003 | Modzelewski et al. |
| 6,542,765 B1 | 4/2003 | Guy et al. |
| 6,544,212 B2 | 4/2003 | Galley et al. |
| 6,545,085 B2 | 4/2003 | Kilgour et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,551,494 B1 | 4/2003 | Heller et al. |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,554,805 B2 | 4/2003 | Hiejima |
| 6,554,822 B1 | 4/2003 | Holschneider et al. |
| 6,558,320 B1 | 5/2003 | Causey, III et al. |
| 6,558,321 B1 | 5/2003 | Burd et al. |
| 6,558,347 B1 | 5/2003 | Jhuboo et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,565,535 B2 | 5/2003 | Zaias et al. |
| 6,565,807 B1 | 5/2003 | Patterson et al. |
| 6,569,309 B2 | 5/2003 | Otsuka et al. |
| 6,569,521 B1 | 5/2003 | Sheridan et al. |
| 6,572,542 B1 | 6/2003 | Houben et al. |
| 6,572,545 B2 | 6/2003 | Knobbe et al. |
| 6,572,579 B1 | 6/2003 | Raghavan et al. |
| 6,572,745 B2 | 6/2003 | Rappin et al. |
| 6,574,490 B2 | 6/2003 | Abbink et al. |
| 6,575,905 B2 | 6/2003 | Knobbe et al. |
| 6,579,257 B1 | 6/2003 | Elgas et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,585,675 B1 | 7/2003 | O'Mahony et al. |
| 6,585,763 B1 | 7/2003 | Keilman et al. |
| 6,587,704 B1 | 7/2003 | Fine et al. |
| 6,587,705 B1 | 7/2003 | Kim et al. |
| 6,589,229 B1 | 7/2003 | Connelly et al. |
| 6,591,123 B2 | 7/2003 | Fein et al. |
| 6,591,125 B1 | 7/2003 | Buse et al. |
| 6,592,745 B1 | 7/2003 | Feldman et al. |
| 6,594,514 B2 | 7/2003 | Berner et al. |
| 6,595,756 B2 | 7/2003 | Gray et al. |
| 6,595,919 B2 | 7/2003 | Berner et al. |
| 6,602,221 B1 | 8/2003 | Saravia et al. |
| 6,603,995 B1 | 8/2003 | Carter |
| 6,605,072 B2 | 8/2003 | Struys et al. |
| 6,607,509 B2 | 8/2003 | Bobroff et al. |
| 6,607,658 B1 | 8/2003 | Heller et al. |
| 6,609,071 B2 | 8/2003 | Shapiro et al. |
| 6,612,984 B1 | 9/2003 | Kerr, II |
| 6,613,379 B2 | 9/2003 | Ward et al. |
| 6,615,061 B1 | 9/2003 | Khalil et al. |
| 6,615,078 B1 | 9/2003 | Burson et al. |
| 6,618,603 B2 | 9/2003 | Varalli et al. |
| 6,618,934 B1 | 9/2003 | Feldman et al. |
| 6,628,975 B1 | 9/2003 | Fein et al. |
| 6,633,772 B2 | 10/2003 | Ford et al. |
| 6,641,533 B2 | 11/2003 | Causey, III et al. |
| 6,642,015 B2 | 11/2003 | Vachon et al. |
| 6,645,181 B1 | 11/2003 | Lavi et al. |
| 6,645,219 B2 | 11/2003 | Roe |
| 6,648,821 B2 | 11/2003 | Lebel et al. |
| 6,653,091 B1 | 11/2003 | Dunn et al. |
| 6,654,625 B1 | 11/2003 | Say et al. |
| 6,656,157 B1 | 12/2003 | Duchon et al. |
| 6,663,615 B1 | 12/2003 | Madou et al. |
| 6,666,821 B2 | 12/2003 | Keimel |
| 6,673,022 B1 | 1/2004 | Bobo et al. |
| 6,673,596 B1 | 1/2004 | Sayler et al. |
| 6,679,865 B2 | 1/2004 | Shekalim |
| 6,683,535 B1 | 1/2004 | Utke |
| 6,684,904 B2 | 2/2004 | Ito |
| 6,685,668 B1 | 2/2004 | Cho et al. |
| 6,687,522 B2 | 2/2004 | Tamada |
| 6,689,056 B1 | 2/2004 | Kilcoyne et al. |
| 6,689,089 B1 | 2/2004 | Tiedtke et al. |
| 6,689,265 B2 | 2/2004 | Heller et al. |
| 6,692,456 B1 | 2/2004 | Eppstein et al. |
| 6,694,191 B2 | 2/2004 | Starkweather et al. |
| 6,695,860 B1 | 2/2004 | Ward et al. |
| 6,699,188 B2 | 3/2004 | Wessel |
| 6,699,218 B2 | 3/2004 | Flaherty et al. |
| 6,699,383 B2 | 3/2004 | Lemire et al. |
| 6,702,249 B2 | 3/2004 | Ito |
| 6,702,857 B2 | 3/2004 | Brauker et al. |
| 6,702,972 B1 | 3/2004 | Markle |
| 6,705,833 B2 | 3/2004 | Tam et al. |
| 6,711,424 B1 | 3/2004 | Fine et al. |
| 6,712,796 B2 | 3/2004 | Fentis et al. |
| 6,721,586 B2 | 4/2004 | Kiser et al. |
| 6,721,587 B2 | 4/2004 | Gough |
| 6,723,077 B2 | 4/2004 | Pickup et al. |
| 6,723,086 B2 | 4/2004 | Bassuk et al. |
| 6,730,072 B2 | 5/2004 | Shawgo et al. |
| 6,730,200 B1 | 5/2004 | Stewart et al. |
| 6,731,976 B2 | 5/2004 | Penn et al. |
| 6,733,655 B1 | 5/2004 | Davies et al. |
| 6,736,777 B2 | 5/2004 | Kim et al. |
| 6,736,783 B2 | 5/2004 | Blake et al. |
| 6,737,158 B1 | 5/2004 | Thompson |
| 6,740,059 B2 | 5/2004 | Flaherty |
| 6,740,075 B2 | 5/2004 | Lebel et al. |
| 6,741,877 B1 | 5/2004 | Shults et al. |
| 6,742,635 B2 | 6/2004 | Hirshberg |
| 6,743,635 B2 | 6/2004 | Neel et al. |
| 6,749,587 B2 | 6/2004 | Flaherty |
| 6,767,632 B2 | 7/2004 | Axelgaard et al. |
| 6,770,030 B1 | 8/2004 | Schaupp et al. |

(56) References Cited

U.S. PATENT DOCUMENTS

| | | |
|---|---|---|
| 6,770,067 B2 | 8/2004 | Lorenzen et al. |
| 6,773,565 B2 | 8/2004 | Kunimoto et al. |
| 6,780,297 B2 | 8/2004 | Matsumoto et al. |
| 6,782,343 B2 | 8/2004 | Hasper |
| 6,784,274 B2 | 8/2004 | Van Antwerp et al. |
| 6,789,634 B1 | 9/2004 | Denton |
| 6,793,632 B2 | 9/2004 | Sohrab |
| 6,793,802 B2 | 9/2004 | Lee et al. |
| 6,801,041 B2 | 10/2004 | Karinka et al. |
| 6,802,957 B2 | 10/2004 | Jung et al. |
| 6,804,002 B2 | 10/2004 | Fine et al. |
| 6,804,544 B2 | 10/2004 | Van Antwerp et al. |
| 6,805,693 B2 | 10/2004 | Gray et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,810,736 B2 | 11/2004 | Ikezawa et al. |
| 6,811,548 B2 | 11/2004 | Jeffrey |
| 6,813,519 B2 | 11/2004 | Lebel et al. |
| 6,814,845 B2 | 11/2004 | Wilson et al. |
| 6,815,186 B2 | 11/2004 | Clark, Jr. |
| 6,830,551 B1 | 12/2004 | Uchigaki et al. |
| 6,835,553 B2 | 12/2004 | Han et al. |
| 6,849,052 B2 | 2/2005 | Uchigaki et al. |
| 6,849,463 B2 | 2/2005 | Santini, Jr. et al. |
| 6,850,790 B2 | 2/2005 | Berner et al. |
| 6,858,020 B2 | 2/2005 | Rusnak |
| 6,862,465 B2 | 3/2005 | Shults et al. |
| 6,863,800 B2 | 3/2005 | Karinka et al. |
| 6,867,262 B1 | 3/2005 | Angel et al. |
| 6,869,413 B2 | 3/2005 | Langley et al. |
| 6,875,386 B1 | 4/2005 | Ward et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,887,228 B2 | 5/2005 | McKay |
| 6,891,317 B2 | 5/2005 | Pei et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,895,265 B2 | 5/2005 | Silver |
| 6,902,544 B2 | 6/2005 | Ludin et al. |
| 6,908,681 B2 | 6/2005 | Terry et al. |
| 6,919,566 B1 | 7/2005 | Cadell |
| 6,923,763 B1 | 8/2005 | Kovatchev et al. |
| 6,925,393 B1 | 8/2005 | Kalatz et al. |
| 6,926,691 B2 | 8/2005 | Miethke |
| 6,931,327 B2 | 8/2005 | Goode, Jr. et al. |
| 6,932,584 B2 | 8/2005 | Gray et al. |
| 6,932,894 B2 | 8/2005 | Mao et al. |
| 6,936,006 B2 | 8/2005 | Sabra |
| 6,945,965 B2 | 9/2005 | Whiting |
| 6,948,492 B2 | 9/2005 | Wermeling et al. |
| 6,952,604 B2 | 10/2005 | DeNuzzio et al. |
| 6,954,662 B2 | 10/2005 | Freger et al. |
| 6,960,192 B1 | 11/2005 | Flaherty et al. |
| 6,965,791 B1 | 11/2005 | Hitchcock et al. |
| 6,966,325 B2 | 11/2005 | Erickson |
| 6,972,080 B1 | 12/2005 | Tomioka et al. |
| 6,973,706 B2 | 12/2005 | Say et al. |
| 6,974,437 B2 | 12/2005 | Lebel et al. |
| 6,975,893 B2 | 12/2005 | Say et al. |
| 6,979,315 B2 | 12/2005 | Rogers et al. |
| 6,989,891 B2 | 1/2006 | Braig et al. |
| 6,990,366 B2 | 1/2006 | Say et al. |
| 6,991,643 B2 | 1/2006 | Saadat |
| 6,997,921 B2 | 2/2006 | Gray et al. |
| 6,998,247 B2 | 2/2006 | Monfre et al. |
| 7,003,336 B2 | 2/2006 | Holker et al. |
| 7,003,341 B2 | 2/2006 | Say et al. |
| 7,008,979 B2 | 3/2006 | Schottman et al. |
| 7,011,630 B2 | 3/2006 | Desai et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,025,425 B2 | 4/2006 | Kovatchev et al. |
| 7,025,727 B2 | 4/2006 | Brockway et al. |
| 7,025,743 B2 | 4/2006 | Mann et al. |
| 7,027,848 B2 | 4/2006 | Robinson et al. |
| 7,029,444 B2 | 4/2006 | Shin et al. |
| 7,033,322 B2 | 4/2006 | Silver |
| 7,039,446 B2 | 5/2006 | Ruchti et al. |
| 7,048,687 B1 | 5/2006 | Reuss et al. |
| 7,048,727 B1 | 5/2006 | Moss |
| 7,058,437 B2 | 6/2006 | Buse et al. |
| 7,060,059 B2 | 6/2006 | Keith et al. |
| 7,061,593 B2 | 6/2006 | Braig et al. |
| 7,063,086 B2 | 6/2006 | Shahbazpour et al. |
| 7,066,884 B2 | 6/2006 | Custer et al. |
| 7,070,577 B1 | 7/2006 | Haller et al. |
| 7,070,580 B2 | 7/2006 | Nielsen |
| 7,074,307 B2 | 7/2006 | Simpson et al. |
| 7,078,582 B2 | 7/2006 | Stebbings et al. |
| 7,081,195 B2 | 7/2006 | Simpson et al. |
| 7,097,775 B2 | 8/2006 | Greenberg et al. |
| 7,098,803 B2 | 8/2006 | Mann et al. |
| 7,100,628 B1 | 9/2006 | Izenson et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,115,884 B1 | 10/2006 | Walt et al. |
| 7,120,483 B2 | 10/2006 | Russell et al. |
| 7,131,967 B2 | 11/2006 | Gray et al. |
| 7,134,999 B2 | 11/2006 | Brauker et al. |
| 7,136,689 B2 | 11/2006 | Shults et al. |
| 7,141,034 B2 | 11/2006 | Eppstein et al. |
| 7,144,496 B2 | 12/2006 | Meserol et al. |
| 7,146,202 B2 | 12/2006 | Ward et al. |
| 7,150,741 B2 | 12/2006 | Erickson et al. |
| 7,153,265 B2 | 12/2006 | Vachon |
| 7,162,290 B1 | 1/2007 | Levin |
| 7,163,511 B2 | 1/2007 | Conn et al. |
| 7,166,074 B2 | 1/2007 | Reghabi et al. |
| 7,168,597 B1 | 1/2007 | Jones et al. |
| 7,169,289 B2 | 1/2007 | Schulein et al. |
| 7,172,075 B1 | 2/2007 | Ji |
| 7,183,102 B2 | 2/2007 | Monfre et al. |
| 7,184,810 B2 | 2/2007 | Caduff et al. |
| 7,190,988 B2 | 3/2007 | Say et al. |
| 7,192,450 B2 | 3/2007 | Brauker et al. |
| 7,207,968 B1 | 4/2007 | Harcinske |
| 7,207,974 B2 | 4/2007 | Safabash et al. |
| 7,211,074 B2 | 5/2007 | Sansoucy |
| 7,221,970 B2 | 5/2007 | Parker |
| 7,223,253 B2 | 5/2007 | Hogendijk |
| 7,225,535 B2 | 6/2007 | Feldman et al. |
| 7,226,978 B2 | 6/2007 | Tapsak et al. |
| 7,228,162 B2 | 6/2007 | Ward et al. |
| 7,229,288 B2 | 6/2007 | Stuart et al. |
| 7,238,165 B2 | 7/2007 | Vincent et al. |
| 7,241,266 B2 | 7/2007 | Zhou et al. |
| 7,241,586 B2 | 7/2007 | Gulati et al. |
| 7,247,138 B2 | 7/2007 | Reghabi et al. |
| 7,248,906 B2 | 7/2007 | Dirac et al. |
| 7,254,450 B2 | 8/2007 | Christopherson et al. |
| 7,255,690 B2 | 8/2007 | Gray et al. |
| 7,258,681 B2 | 8/2007 | Houde |
| 7,261,690 B2 | 8/2007 | Teller et al. |
| 7,266,400 B2 | 9/2007 | Fine et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,288,085 B2 | 10/2007 | Olsen |
| 7,295,867 B2 | 11/2007 | Berner et al. |
| 7,299,082 B2 | 11/2007 | Feldman et al. |
| 7,310,544 B2 | 12/2007 | Brister et al. |
| 7,311,690 B2 | 12/2007 | Burnett |
| 7,313,425 B2 | 12/2007 | Finarov et al. |
| 7,314,452 B2 | 1/2008 | Madonia |
| 7,315,767 B2 | 1/2008 | Caduff et al. |
| 7,316,662 B2 | 1/2008 | Delnevo et al. |
| 7,317,939 B2 | 1/2008 | Fine et al. |
| 7,318,814 B2 | 1/2008 | Levine et al. |
| 7,324,012 B2 | 1/2008 | Mann et al. |

(56) References Cited

U.S. PATENT DOCUMENTS

| | | |
|---|---|---|
| 7,327,273 B2 | 2/2008 | Hung et al. |
| 7,329,234 B2 | 2/2008 | Sansoucy |
| 7,329,239 B2 | 2/2008 | Safabash et al. |
| 7,334,594 B2 | 2/2008 | Ludin |
| 7,335,179 B2 | 2/2008 | Burnett |
| 7,335,195 B2 | 2/2008 | Mehier |
| 7,335,286 B2 | 2/2008 | Abel et al. |
| 7,338,464 B2 | 3/2008 | Blischak et al. |
| 7,344,499 B1 | 3/2008 | Prausnitz et al. |
| 7,344,500 B2 | 3/2008 | Talbot et al. |
| 7,354,420 B2 | 4/2008 | Steil et al. |
| 7,359,723 B2 | 4/2008 | Jones |
| 7,361,155 B2 | 4/2008 | Sage, Jr. et al. |
| 7,364,562 B2 | 4/2008 | Braig et al. |
| 7,364,592 B2 | 4/2008 | Carr-Brendel et al. |
| 7,366,556 B2 | 4/2008 | Brister et al. |
| 7,366,566 B2 | 4/2008 | Henry et al. |
| 7,367,942 B2 | 5/2008 | Grage et al. |
| 7,381,184 B2 | 6/2008 | Funderburk et al. |
| 7,392,080 B2 | 6/2008 | Eppstein et al. |
| 7,395,158 B2 | 7/2008 | Monfre et al. |
| 7,396,353 B2 | 7/2008 | Lorenzen et al. |
| 7,399,277 B2 | 7/2008 | Saidara et al. |
| 7,402,153 B2 | 7/2008 | Steil et al. |
| 7,404,819 B1 | 7/2008 | Darios et al. |
| 7,405,055 B2 | 7/2008 | Dunn et al. |
| 7,417,164 B2 | 8/2008 | Suri |
| 7,424,318 B2 | 9/2008 | Brister et al. |
| 7,426,408 B2 | 9/2008 | Denuzzio et al. |
| 7,433,727 B2 | 10/2008 | Ward et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,525,298 B2 | 4/2009 | Morgan et al. |
| 7,582,059 B2 | 9/2009 | Funderburk et al. |
| 7,583,990 B2 | 9/2009 | Goode, Jr. et al. |
| 7,587,287 B2 | 9/2009 | Connolly et al. |
| 7,591,801 B2 | 9/2009 | Brauker et al. |
| 7,599,726 B2 | 10/2009 | Goode, Jr. et al. |
| 7,604,593 B2 | 10/2009 | Parris et al. |
| 7,615,007 B2 | 11/2009 | Shults et al. |
| 7,618,368 B2 | 11/2009 | Brown |
| 7,618,369 B2 | 11/2009 | Hayter et al. |
| 7,624,028 B1 | 11/2009 | Brown |
| 7,632,228 B2 | 12/2009 | Brauker et al. |
| 7,636,602 B2 | 12/2009 | Baru Fassio et al. |
| 7,637,868 B2 | 12/2009 | Saint et al. |
| 7,640,032 B2 | 12/2009 | Jones |
| 7,640,048 B2 | 12/2009 | Dobbles et al. |
| 7,647,237 B2 | 1/2010 | Malave et al. |
| 7,654,956 B2 | 2/2010 | Brister et al. |
| 7,657,297 B2 | 2/2010 | Simpson et al. |
| 7,687,586 B2 | 3/2010 | Ward et al. |
| 7,695,434 B2 | 4/2010 | Malecha |
| 7,697,967 B2 | 4/2010 | Stafford |
| 7,699,775 B2 | 4/2010 | Desai et al. |
| 7,711,402 B2 | 5/2010 | Shults et al. |
| 7,711,493 B2 | 5/2010 | Bartkowiak et al. |
| 7,713,574 B2 | 5/2010 | Brister et al. |
| 7,725,148 B2 | 5/2010 | Shah et al. |
| 7,727,148 B2 | 6/2010 | Talbot et al. |
| 7,731,659 B2 | 6/2010 | Malecha |
| 7,736,322 B2 | 6/2010 | Roe et al. |
| 7,761,126 B2 | 7/2010 | Gardner et al. |
| 7,766,830 B2 | 8/2010 | Fox et al. |
| 7,771,352 B2 | 8/2010 | Shults et al. |
| 7,774,145 B2 | 8/2010 | Brauker et al. |
| 7,778,680 B2 | 8/2010 | Goode, Jr. et al. |
| 7,792,562 B2 | 9/2010 | Shults et al. |
| 7,811,231 B2 | 10/2010 | Jin et al. |
| 7,826,981 B2 | 11/2010 | Goode, Jr. et al. |
| 7,857,760 B2 | 12/2010 | Brister et al. |
| 7,860,545 B2 | 12/2010 | Shults et al. |
| 7,862,622 B2 | 1/2011 | Dunlap et al. |
| 7,874,985 B2 | 1/2011 | Kovatchev et al. |
| 7,875,293 B2 | 1/2011 | Shults et al. |
| 7,879,010 B2 | 2/2011 | Hunn et al. |
| 7,881,763 B2 | 2/2011 | Brauker et al. |
| 7,885,697 B2 | 2/2011 | Brister et al. |
| 7,885,698 B2 | 2/2011 | Feldman |
| 7,890,295 B2 | 2/2011 | Shin et al. |
| 7,896,809 B2 | 3/2011 | Simpson et al. |
| 7,899,511 B2 | 3/2011 | Shults et al. |
| 7,901,354 B2 | 3/2011 | Shults et al. |
| 7,905,833 B2 | 3/2011 | Brister et al. |
| 7,917,186 B2 | 3/2011 | Kamath et al. |
| 7,310,544 C1 | 4/2011 | Brister et al. |
| 7,920,906 B2 | 4/2011 | Goode, Jr. et al. |
| 7,925,321 B2 | 4/2011 | Goode et al. |
| 7,927,274 B2 | 4/2011 | Rasdal et al. |
| 7,935,499 B2 | 5/2011 | Dunn et al. |
| 7,946,984 B2 | 5/2011 | Brister et al. |
| 7,946,985 B2 | 5/2011 | Mastrototaro et al. |
| 7,949,381 B2 | 5/2011 | Brister et al. |
| 7,640,048 C1 | 7/2011 | Dobbles et al. |
| 7,986,986 B2 | 7/2011 | Goode et al. |
| 7,998,071 B2 | 8/2011 | Goode, Jr. et al. |
| 8,000,901 B2 | 8/2011 | Brauker et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,019,421 B2 | 9/2011 | Darvish et al. |
| 7,497,827 C1 | 10/2011 | Brister et al. |
| 7,905,833 C1 | 11/2011 | Brister et al. |
| 8,060,173 B2 | 11/2011 | Goode, Jr. et al. |
| RE43,039 E | 12/2011 | Brister et al. |
| 8,073,520 B2 | 12/2011 | Kamath et al. |
| 8,095,197 B2 | 1/2012 | Santini, Jr. et al. |
| 8,118,877 B2 | 2/2012 | Brauker et al. |
| 7,774,145 C1 | 3/2012 | Brauker et al. |
| 8,133,178 B2 | 3/2012 | Brauker et al. |
| 8,152,789 B2 | 4/2012 | Starkweather et al. |
| 8,160,669 B2 | 4/2012 | Brauker et al. |
| 8,160,671 B2 | 4/2012 | Kamath et al. |
| 8,167,801 B2 | 5/2012 | Goode, Jr. et al. |
| 8,170,803 B2 | 5/2012 | Kamath et al. |
| 7,713,574 C1 | 6/2012 | Brister et al. |
| 8,192,395 B2 | 6/2012 | Estes et al. |
| 8,216,139 B2 | 7/2012 | Brauker et al. |
| 8,229,534 B2 | 7/2012 | Brister et al. |
| 8,231,531 B2 | 7/2012 | Brister et al. |
| 8,233,958 B2 | 7/2012 | Brauker et al. |
| 8,251,906 B2 | 8/2012 | Brauker et al. |
| 8,257,259 B2 | 9/2012 | Brauker et al. |
| 8,265,725 B2 | 9/2012 | Brauker et al. |
| 8,275,438 B2 | 9/2012 | Simpson et al. |
| 8,277,713 B2 | 10/2012 | Petisce et al. |
| 8,280,475 B2 | 10/2012 | Brister et al. |
| 8,282,549 B2 | 10/2012 | Brauker et al. |
| 8,290,559 B2 | 10/2012 | Shariati et al. |
| 8,290,560 B2 | 10/2012 | Kamath et al. |
| 8,290,561 B2 | 10/2012 | Brauker et al. |
| 8,298,142 B2 | 10/2012 | Simpson et al. |
| 7,310,544 C2 | 11/2012 | Brister et al. |
| 8,311,749 B2 | 11/2012 | Brauker et al. |
| 8,313,434 B2 | 11/2012 | Brister et al. |
| 8,321,149 B2 | 11/2012 | Brauker et al. |
| 8,353,881 B2 | 1/2013 | Jennewine |
| 8,355,753 B2 | 1/2013 | Bochenko et al. |
| 8,364,229 B2 | 1/2013 | Simpson et al. |
| 8,366,614 B2 | 2/2013 | Say et al. |
| 8,374,667 B2 | 2/2013 | Brauker et al. |
| 8,452,368 B2 | 5/2013 | Brister et al. |
| 8,457,708 B2 | 6/2013 | Brister et al. |
| 8,463,350 B2 | 6/2013 | Kamath et al. |
| 8,469,886 B2 | 6/2013 | Brauker et al. |
| 8,474,397 B2 | 7/2013 | Brister et al. |
| 8,475,373 B2 | 7/2013 | Brister et al. |
| 8,483,791 B2 | 7/2013 | Brister et al. |

(56) References Cited

U.S. PATENT DOCUMENTS

| | | |
|---|---|---|
| 8,506,482 B2 | 8/2013 | Feldman |
| 8,512,276 B2 | 8/2013 | Talbot et al. |
| 8,515,516 B2 | 8/2013 | Kamath et al. |
| 8,515,519 B2 | 8/2013 | Brister et al. |
| 8,548,551 B2 | 10/2013 | Kamath et al. |
| 8,560,037 B2 | 10/2013 | Goode, Jr. et al. |
| 8,565,848 B2 | 10/2013 | Brister et al. |
| 8,565,849 B2 | 10/2013 | Kamath et al. |
| 8,571,625 B2 | 10/2013 | Kamath et al. |
| 8,579,816 B2 | 11/2013 | Kamath et al. |
| 8,611,978 B2 | 12/2013 | Kamath et al. |
| 8,615,282 B2 | 12/2013 | Brister et al. |
| 7,713,574 C2 | 3/2014 | Brister et al. |
| 8,663,109 B2 | 3/2014 | Brister et al. |
| 8,668,645 B2 | 3/2014 | Drucker et al. |
| 8,690,775 B2 | 4/2014 | Brister et al. |
| 8,731,630 B2 | 5/2014 | Kamath et al. |
| 8,750,955 B2 | 6/2014 | Brister et al. |
| 8,788,007 B2 | 7/2014 | Brauker et al. |
| 8,792,953 B2 | 7/2014 | Brister et al. |
| 8,792,954 B2 | 7/2014 | Brister et al. |
| 8,792,955 B2 | 7/2014 | Brister et al. |
| 8,825,127 B2 | 9/2014 | Kamath et al. |
| 8,858,434 B2 | 10/2014 | Kamath et al. |
| 8,886,272 B2 | 11/2014 | Brister et al. |
| 8,915,849 B2 | 12/2014 | Brauker et al. |
| 8,968,198 B2 | 3/2015 | Brauker et al. |
| 8,986,209 B2 | 3/2015 | Brauker et al. |
| 8,989,833 B2 | 3/2015 | Brauker et al. |
| 9,044,199 B2 | 6/2015 | Brister et al. |
| 9,055,901 B2 | 6/2015 | Brister et al. |
| 9,060,742 B2 | 6/2015 | Brister et al. |
| 9,078,608 B2 | 7/2015 | Kamath et al. |
| 9,078,626 B2 | 7/2015 | Brister et al. |
| 9,155,496 B2 | 10/2015 | Shults et al. |
| 9,220,449 B2 | 12/2015 | Pryor et al. |
| 9,247,900 B2 | 2/2016 | Brister et al. |
| 9,314,196 B2 | 4/2016 | Pryor et al. |
| 9,414,777 B2 | 8/2016 | Brister et al. |
| 9,603,557 B2 | 3/2017 | Brister et al. |
| 9,610,031 B2 | 4/2017 | Brister et al. |
| 9,668,677 B2 | 6/2017 | Brister et al. |
| 9,669,156 B2 | 6/2017 | Jennewine |
| 9,724,028 B2 | 8/2017 | Brauker et al. |
| 9,775,543 B2 | 10/2017 | Brister et al. |
| 9,801,572 B2 | 10/2017 | Brister et al. |
| 9,814,414 B2 | 11/2017 | Brister et al. |
| 9,833,176 B2 | 12/2017 | Brister et al. |
| 9,918,668 B2 | 3/2018 | Pryor et al. |
| 10,022,078 B2 | 7/2018 | Brauker et al. |
| 10,314,525 B2 | 6/2019 | Simpson et al. |
| 10,376,188 B2 | 8/2019 | Simpson et al. |
| 10,524,703 B2 | 1/2020 | Brister et al. |
| 10,610,135 B2 | 4/2020 | Kamath et al. |
| 10,610,136 B2 | 4/2020 | Kamath et al. |
| 10,610,137 B2 | 4/2020 | Kamath et al. |
| 10,617,336 B2 | 4/2020 | Kamath et al. |
| 10,709,362 B2 | 7/2020 | Simpson et al. |
| 10,709,363 B2 | 7/2020 | Brister et al. |
| 10,709,364 B2 | 7/2020 | Kamath et al. |
| 10,716,498 B2 | 7/2020 | Kamath et al. |
| 10,722,152 B2 | 7/2020 | Brister et al. |
| 10,743,801 B2 | 8/2020 | Kamath et al. |
| 10,799,158 B2 * | 10/2020 | Brister ............... A61B 5/14735 |
| 10,813,577 B2 * | 10/2020 | Brister ............... A61B 5/1473 |
| 10,827,956 B2 | 11/2020 | Brister et al. |
| 10,918,313 B2 * | 2/2021 | Brister ............... A61B 5/6801 |
| 10,918,314 B2 * | 2/2021 | Brister ............... A61B 5/6849 |
| 10,918,315 B2 * | 2/2021 | Brister ............... A61B 5/14503 |
| 2001/0008187 A1 | 7/2001 | Hanssen et al. |
| 2001/0016682 A1 | 8/2001 | Berner et al. |
| 2001/0020546 A1 | 9/2001 | Eldridge et al. |
| 2001/0021817 A1 | 9/2001 | Brugger et al. |
| 2001/0027327 A1 | 10/2001 | Schraga |
| 2001/0039053 A1 | 11/2001 | Liseo et al. |
| 2001/0039387 A1 | 11/2001 | Rutynowski et al. |
| 2001/0041830 A1 | 11/2001 | Varalli et al. |
| 2001/0044413 A1 | 11/2001 | Pierce et al. |
| 2001/0044588 A1 | 11/2001 | Mault |
| 2001/0051766 A1 | 12/2001 | Gazdzinski |
| 2001/0051768 A1 | 12/2001 | Schulman et al. |
| 2001/0053933 A1 | 12/2001 | Phaneuf et al. |
| 2002/0009810 A1 | 1/2002 | O'Connor et al. |
| 2002/0016535 A1 | 2/2002 | Martin et al. |
| 2002/0019022 A1 | 2/2002 | Dunn et al. |
| 2002/0019330 A1 | 2/2002 | Murray et al. |
| 2002/0022883 A1 | 2/2002 | Burg |
| 2002/0022884 A1 | 2/2002 | Mansmann |
| 2002/0023852 A1 | 2/2002 | McIvor et al. |
| 2002/0026110 A1 | 2/2002 | Parris et al. |
| 2002/0026111 A1 | 2/2002 | Ackerman |
| 2002/0032531 A1 | 3/2002 | Mansky et al. |
| 2002/0038081 A1 | 3/2002 | Fein et al. |
| 2002/0042090 A1 | 4/2002 | Heller et al. |
| 2002/0042561 A1 | 4/2002 | Schulman et al. |
| 2002/0043471 A1 | 4/2002 | Ikeda et al. |
| 2002/0043651 A1 | 4/2002 | Darrow et al. |
| 2002/0045808 A1 | 4/2002 | Ford et al. |
| 2002/0055673 A1 | 5/2002 | Van Antwerp et al. |
| 2002/0065453 A1 | 5/2002 | Lesho et al. |
| 2002/0068860 A1 | 6/2002 | Clark, Jr. |
| 2002/0071776 A1 | 6/2002 | Bandis et al. |
| 2002/0072720 A1 | 6/2002 | Hague et al. |
| 2002/0077599 A1 | 6/2002 | Wojcik |
| 2002/0084196 A1 | 7/2002 | Liamos et al. |
| 2002/0099282 A1 | 7/2002 | Knobbe et al. |
| 2002/0099997 A1 | 7/2002 | Piret |
| 2002/0100474 A1 | 8/2002 | Kellner et al. |
| 2002/0100725 A1 | 8/2002 | Lee et al. |
| 2002/0111547 A1 | 8/2002 | Knobbe et al. |
| 2002/0119711 A1 | 8/2002 | VanAntwerp et al. |
| 2002/0123048 A1 | 9/2002 | Gau, Jr. |
| 2002/0128419 A1 | 9/2002 | Terry et al. |
| 2002/0128546 A1 | 9/2002 | Silver |
| 2002/0132279 A1 | 9/2002 | Hockersmith |
| 2002/0133063 A1 | 9/2002 | Hockersmith et al. |
| 2002/0133224 A1 | 9/2002 | Bajgar et al. |
| 2002/0137991 A1 | 9/2002 | Scarantino et al. |
| 2002/0151796 A1 | 10/2002 | Koulik |
| 2002/0151816 A1 | 10/2002 | Rich et al. |
| 2002/0155615 A1 | 10/2002 | Novikov et al. |
| 2002/0160722 A1 | 10/2002 | Terranova et al. |
| 2002/0161288 A1 | 10/2002 | Shin et al. |
| 2002/0169369 A1 | 11/2002 | Ward et al. |
| 2002/0169405 A1 | 11/2002 | Roberts |
| 2002/0177763 A1 | 11/2002 | Burns et al. |
| 2002/0177764 A1 | 11/2002 | Sohrab |
| 2002/0182241 A1 | 12/2002 | Borenstein et al. |
| 2002/0185384 A1 | 12/2002 | Leong et al. |
| 2002/0186185 A1 | 12/2002 | Ide et al. |
| 2002/0188185 A1 | 12/2002 | Sohrab |
| 2002/0188216 A1 | 12/2002 | Kayyali et al. |
| 2002/0188252 A1 | 12/2002 | Bardy |
| 2002/0193679 A1 | 12/2002 | Malave et al. |
| 2002/0193885 A1 | 12/2002 | Legeay et al. |
| 2002/0198513 A1 | 12/2002 | Lebel et al. |
| 2003/0003524 A1 | 1/2003 | Taniike et al. |
| 2003/0004432 A1 | 1/2003 | Assenheimer |
| 2003/0004457 A1 | 1/2003 | Andersson |
| 2003/0006669 A1 | 1/2003 | Pei et al. |
| 2003/0009093 A1 | 1/2003 | Silver |
| 2003/0021729 A1 | 1/2003 | Moller et al. |
| 2003/0023171 A1 | 1/2003 | Sato et al. |
| 2003/0023317 A1 | 1/2003 | Brauker et al. |
| 2003/0024811 A1 | 2/2003 | Davies et al. |
| 2003/0028089 A1 | 2/2003 | Galley et al. |
| 2003/0032874 A1 | 2/2003 | Rhodes et al. |
| 2003/0036773 A1 | 2/2003 | Whitehurst et al. |
| 2003/0049166 A1 | 3/2003 | Pendo et al. |
| 2003/0050537 A1 | 3/2003 | Wessel |
| 2003/0050546 A1 | 3/2003 | Desai et al. |
| 2003/0054428 A1 | 3/2003 | Monfre et al. |
| 2003/0055464 A1 | 3/2003 | Darvish et al. |
| 2003/0059631 A1 | 3/2003 | Al-Lamee |

(56) References Cited

U.S. PATENT DOCUMENTS

| | | |
|---|---|---|
| 2003/0060765 A1 | 3/2003 | Campbell et al. |
| 2003/0065254 A1 | 4/2003 | Schulman et al. |
| 2003/0070548 A1 | 4/2003 | Clausen |
| 2003/0072741 A1 | 4/2003 | Berglund et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0088166 A1 | 5/2003 | Say et al. |
| 2003/0091433 A1 | 5/2003 | Tam et al. |
| 2003/0096424 A1 | 5/2003 | Mao et al. |
| 2003/0097082 A1 | 5/2003 | Purdy et al. |
| 2003/0099682 A1 | 5/2003 | Moussy et al. |
| 2003/0100040 A1 | 5/2003 | Bonnecaze et al. |
| 2003/0100821 A1 | 5/2003 | Heller et al. |
| 2003/0104119 A1 | 6/2003 | Wilson et al. |
| 2003/0114735 A1 | 6/2003 | Silver et al. |
| 2003/0117296 A1 | 6/2003 | Seely |
| 2003/0119208 A1 | 6/2003 | Yoon et al. |
| 2003/0120152 A1 | 6/2003 | Omiya |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0132227 A1 | 7/2003 | Geisler et al. |
| 2003/0134100 A1 | 7/2003 | Mao et al. |
| 2003/0134347 A1 | 7/2003 | Heller et al. |
| 2003/0138674 A1 | 7/2003 | Zeikus et al. |
| 2003/0143746 A1 | 7/2003 | Sage, Jr. |
| 2003/0146110 A1 | 8/2003 | Karinka et al. |
| 2003/0153821 A1 | 8/2003 | Berner et al. |
| 2003/0157409 A1 | 8/2003 | Huang |
| 2003/0158520 A1 | 8/2003 | Safabash et al. |
| 2003/0176183 A1 | 9/2003 | Drucker et al. |
| 2003/0181794 A1 | 9/2003 | Rini et al. |
| 2003/0186457 A1 | 10/2003 | Iwaki et al. |
| 2003/0187338 A1 | 10/2003 | Say et al. |
| 2003/0188427 A1 | 10/2003 | Say et al. |
| 2003/0190383 A1 | 10/2003 | Kim |
| 2003/0191377 A1 | 10/2003 | Robinson et al. |
| 2003/0199744 A1 | 10/2003 | Buse et al. |
| 2003/0199745 A1 | 10/2003 | Burson et al. |
| 2003/0199878 A1 | 10/2003 | Pohjonen et al. |
| 2003/0200040 A1 | 10/2003 | Trygg et al. |
| 2003/0203498 A1 | 10/2003 | Neel et al. |
| 2003/0203991 A1 | 10/2003 | Schottman et al. |
| 2003/0208113 A1 | 11/2003 | Mault et al. |
| 2003/0211625 A1 | 11/2003 | Cohan et al. |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0217966 A1 | 11/2003 | Tapsak et al. |
| 2003/0225324 A1 | 12/2003 | Anderson et al. |
| 2003/0225360 A1 | 12/2003 | Eppstein et al. |
| 2003/0225361 A1 | 12/2003 | Sabra |
| 2003/0225437 A1 | 12/2003 | Ferguson |
| 2003/0228681 A1 | 12/2003 | Ritts et al. |
| 2003/0231550 A1 | 12/2003 | MacFarlane |
| 2003/0235817 A1 | 12/2003 | Bartkowiak et al. |
| 2004/0002682 A1 | 1/2004 | Kovelman et al. |
| 2004/0006263 A1 | 1/2004 | Anderson et al. |
| 2004/0008761 A1 | 1/2004 | Kelliher et al. |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0018486 A1 | 1/2004 | Dunn et al. |
| 2004/0023253 A1 | 2/2004 | Kunwar et al. |
| 2004/0023317 A1 | 2/2004 | Motamedi et al. |
| 2004/0024327 A1 | 2/2004 | Brodnick |
| 2004/0024553 A1 | 2/2004 | Monfre et al. |
| 2004/0030285 A1 | 2/2004 | Lavi et al. |
| 2004/0030294 A1 | 2/2004 | Mahurkar |
| 2004/0039298 A1 | 2/2004 | Abreu |
| 2004/0039342 A1 | 2/2004 | Eppstein et al. |
| 2004/0039343 A1 | 2/2004 | Eppstein et al. |
| 2004/0039406 A1 | 2/2004 | Jessen |
| 2004/0040840 A1 | 3/2004 | Mao et al. |
| 2004/0045879 A1 | 3/2004 | Shults et al. |
| 2004/0052689 A1 | 3/2004 | Yao |
| 2004/0054352 A1 | 3/2004 | Adams et al. |
| 2004/0064156 A1 | 4/2004 | Shah et al. |
| 2004/0068230 A1 | 4/2004 | Estes et al. |
| 2004/0074785 A1 | 4/2004 | Holker et al. |
| 2004/0078219 A1 | 4/2004 | Kaylor et al. |
| 2004/0087671 A1 | 5/2004 | Tamada et al. |
| 2004/0088023 A1 | 5/2004 | Imran et al. |
| 2004/0106741 A1 | 6/2004 | Kriesel et al. |
| 2004/0106857 A1 | 6/2004 | Gough |
| 2004/0106858 A1 | 6/2004 | Say et al. |
| 2004/0106859 A1 | 6/2004 | Say et al. |
| 2004/0106860 A1 | 6/2004 | Say et al. |
| 2004/0111017 A1 | 6/2004 | Say et al. |
| 2004/0120848 A1 | 6/2004 | Teodorczyk |
| 2004/0122353 A1 | 6/2004 | Shahmirian et al. |
| 2004/0127777 A1 | 7/2004 | Ruchti et al. |
| 2004/0127818 A1 | 7/2004 | Roe et al. |
| 2004/0133131 A1 | 7/2004 | Kuhn et al. |
| 2004/0133164 A1 | 7/2004 | Funderburk et al. |
| 2004/0138543 A1 | 7/2004 | Russell et al. |
| 2004/0143173 A1 | 7/2004 | Reghabi et al. |
| 2004/0146909 A1 | 7/2004 | Duong et al. |
| 2004/0147872 A1 | 7/2004 | Thompson |
| 2004/0152187 A1 | 8/2004 | Haight et al. |
| 2004/0152622 A1 | 8/2004 | Keith et al. |
| 2004/0158138 A1 | 8/2004 | Kilcoyne et al. |
| 2004/0158207 A1 | 8/2004 | Hunn et al. |
| 2004/0167382 A1 | 8/2004 | Gardner et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0204744 A1 | 10/2004 | Penner et al. |
| 2004/0219664 A1 | 11/2004 | Heller et al. |
| 2004/0220517 A1 | 11/2004 | Starkweather et al. |
| 2004/0225199 A1 | 11/2004 | Evanyk et al. |
| 2004/0228902 A1 | 11/2004 | Benz |
| 2004/0234575 A1 | 11/2004 | Horres et al. |
| 2004/0236200 A1 | 11/2004 | Say et al. |
| 2004/0236251 A1 | 11/2004 | Roe et al. |
| 2004/0242982 A1 | 12/2004 | Sakata et al. |
| 2004/0244151 A1 | 12/2004 | Sakata et al. |
| 2004/0249421 A1 | 12/2004 | Harel et al. |
| 2004/0253365 A1 | 12/2004 | Warren et al. |
| 2004/0254433 A1 | 12/2004 | Bandis et al. |
| 2004/0260164 A1 | 12/2004 | Kilcoyne et al. |
| 2004/0260234 A1 | 12/2004 | Srinivasan et al. |
| 2004/0263354 A1 | 12/2004 | Mann et al. |
| 2004/0265940 A1 | 12/2004 | Slater et al. |
| 2005/0000829 A1 | 1/2005 | Morita et al. |
| 2005/0003399 A1 | 1/2005 | Blackburn et al. |
| 2005/0004438 A1 | 1/2005 | Ward et al. |
| 2005/0004439 A1 | 1/2005 | Shin et al. |
| 2005/0006122 A1 | 1/2005 | Burnette |
| 2005/0008671 A1 | 1/2005 | Van Antwerp |
| 2005/0010265 A1 | 1/2005 | Baru Fassio et al. |
| 2005/0013842 A1 | 1/2005 | Qiu et al. |
| 2005/0016325 A1 | 1/2005 | Enokido |
| 2005/0023137 A1 | 2/2005 | Bhullar et al. |
| 2005/0026689 A1 | 2/2005 | Marks |
| 2005/0027180 A1 | 2/2005 | Goode, Jr. et al. |
| 2005/0027181 A1 | 2/2005 | Goode, Jr. et al. |
| 2005/0027182 A1 | 2/2005 | Siddiqui et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode, Jr. et al. |
| 2005/0049472 A1 | 3/2005 | Manda et al. |

(56) References Cited

U.S. PATENT DOCUMENTS

| | | |
|---|---|---|
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056551 A1 | 3/2005 | White et al. |
| 2005/0056552 A1 | 3/2005 | Simpson et al. |
| 2005/0059871 A1 | 3/2005 | Gough et al. |
| 2005/0065464 A1 | 3/2005 | Talbot et al. |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0080345 A1 | 4/2005 | Finburgh et al. |
| 2005/0085839 A1 | 4/2005 | Allen et al. |
| 2005/0090607 A1 | 4/2005 | Tapsak et al. |
| 2005/0096512 A1 | 5/2005 | Fox et al. |
| 2005/0096519 A1 | 5/2005 | DeNuzzio et al. |
| 2005/0101847 A1 | 5/2005 | Routt et al. |
| 2005/0103625 A1 | 5/2005 | Rhodes et al. |
| 2005/0106713 A1 | 5/2005 | Phan et al. |
| 2005/0107677 A1 | 5/2005 | Ward et al. |
| 2005/0112169 A1 | 5/2005 | Brauker et al. |
| 2005/0113653 A1 | 5/2005 | Fox et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0121322 A1 | 6/2005 | Say et al. |
| 2005/0124873 A1 | 6/2005 | Shults et al. |
| 2005/0131305 A1 | 6/2005 | Danielson et al. |
| 2005/0133368 A1 | 6/2005 | Davies et al. |
| 2005/0139489 A1 | 6/2005 | Davies et al. |
| 2005/0143635 A1 | 6/2005 | Kamath et al. |
| 2005/0143636 A1 | 6/2005 | Zhang et al. |
| 2005/0143675 A1 | 6/2005 | Neel et al. |
| 2005/0154264 A1 | 7/2005 | Lecompte et al. |
| 2005/0154271 A1 | 7/2005 | Rasdal et al. |
| 2005/0154272 A1 | 7/2005 | Dirac et al. |
| 2005/0161346 A1 | 7/2005 | Simpson et al. |
| 2005/0173245 A1 | 8/2005 | Feldman et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0177398 A1 | 8/2005 | Watanabe et al. |
| 2005/0181012 A1 | 8/2005 | Saint et al. |
| 2005/0182451 A1 | 8/2005 | Griffin et al. |
| 2005/0183954 A1 | 8/2005 | Hitchcock et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0196747 A1 | 9/2005 | Stiene |
| 2005/0197554 A1 | 9/2005 | Polcha |
| 2005/0203360 A1 | 9/2005 | Brauker et al. |
| 2005/0203364 A1 | 9/2005 | Monfre et al. |
| 2005/0209665 A1 | 9/2005 | Hunter et al. |
| 2005/0211571 A1 | 9/2005 | Schulein et al. |
| 2005/0215871 A1 | 9/2005 | Feldman et al. |
| 2005/0215872 A1 | 9/2005 | Berner et al. |
| 2005/0215979 A1 | 9/2005 | Kornerup et al. |
| 2005/0225361 A1 | 10/2005 | Rhee |
| 2005/0228238 A1 | 10/2005 | Monitzer |
| 2005/0233407 A1 | 10/2005 | Pamidi et al. |
| 2005/0239154 A1 | 10/2005 | Feldman et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0251083 A1 | 11/2005 | Carr-Brendel et al. |
| 2005/0258037 A1 | 11/2005 | Hajizadeh et al. |
| 2005/0261563 A1 | 11/2005 | Zhou et al. |
| 2005/0267325 A1 | 12/2005 | Bouchier et al. |
| 2005/0267440 A1 | 12/2005 | Herman et al. |
| 2005/0271546 A1 | 12/2005 | Gerber et al. |
| 2005/0272989 A1 | 12/2005 | Shah et al. |
| 2005/0282997 A1 | 12/2005 | Ward et al. |
| 2005/0288596 A1 | 12/2005 | Eigler et al. |
| 2006/0001550 A1 | 1/2006 | Mann et al. |
| 2006/0003398 A1 | 1/2006 | Heller et al. |
| 2006/0007017 A1 | 1/2006 | Mann et al. |
| 2006/0008370 A1 | 1/2006 | Massaro et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0047215 A1 | 3/2006 | Newman et al. |
| 2006/0052745 A1 | 3/2006 | Van Antwerp et al. |
| 2006/0065527 A1 | 3/2006 | Samproni |
| 2006/0068208 A1 | 3/2006 | Tapsak et al. |
| 2006/0074564 A1 | 4/2006 | Bartkowiak et al. |
| 2006/0079740 A1 | 4/2006 | Silver et al. |
| 2006/0079809 A1 | 4/2006 | Goldberger et al. |
| 2006/0086624 A1 | 4/2006 | Tapsak et al. |
| 2006/0094946 A1 | 5/2006 | Kellogg et al. |
| 2006/0100588 A1 | 5/2006 | Brunnberg et al. |
| 2006/0118415 A1 | 6/2006 | Say et al. |
| 2006/0142651 A1 | 6/2006 | Brister et al. |
| 2006/0155180 A1 | 7/2006 | Brister et al. |
| 2006/0159718 A1 | 7/2006 | Rathenow et al. |
| 2006/0159981 A1 | 7/2006 | Heller |
| 2006/0171980 A1 | 8/2006 | Helmus et al. |
| 2006/0173444 A1 | 8/2006 | Choy et al. |
| 2006/0183178 A1 | 8/2006 | Gulati et al. |
| 2006/0183871 A1 | 8/2006 | Ward et al. |
| 2006/0183984 A1 | 8/2006 | Dobbles et al. |
| 2006/0183985 A1 | 8/2006 | Brister et al. |
| 2006/0189856 A1 | 8/2006 | Petisce et al. |
| 2006/0189863 A1 | 8/2006 | Peyser et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0204536 A1 | 9/2006 | Shults et al. |
| 2006/0211921 A1 | 9/2006 | Brauker et al. |
| 2006/0222566 A1 | 10/2006 | Brauker et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0235285 A1 | 10/2006 | Brister et al. |
| 2006/0253085 A1 | 11/2006 | Geismar et al. |
| 2006/0257995 A1 | 11/2006 | Simpson et al. |
| 2006/0257996 A1 | 11/2006 | Simpson et al. |
| 2006/0258761 A1 | 11/2006 | Boock et al. |
| 2006/0258929 A1 | 11/2006 | Goode, Jr. et al. |
| 2006/0263673 A1 | 11/2006 | Kim et al. |
| 2006/0263763 A1 | 11/2006 | Simpson et al. |
| 2006/0263839 A1 | 11/2006 | Ward et al. |
| 2006/0270922 A1 | 11/2006 | Brauker et al. |
| 2006/0270923 A1 | 11/2006 | Brauker et al. |
| 2006/0275859 A1 | 12/2006 | Kjaer |
| 2006/0281985 A1 | 12/2006 | Ward et al. |
| 2006/0289307 A1 | 12/2006 | Yu et al. |
| 2006/0290496 A1 | 12/2006 | Peeters |
| 2006/0293576 A1 | 12/2006 | Van Antwerp et al. |
| 2007/0003588 A1 | 1/2007 | Chinn et al. |
| 2007/0007133 A1 | 1/2007 | Mang et al. |
| 2007/0016381 A1 | 1/2007 | Kamath et al. |
| 2007/0017805 A1 | 1/2007 | Hodges et al. |
| 2007/0027370 A1 | 2/2007 | Brauker et al. |
| 2007/0027381 A1 | 2/2007 | Stafford |

(56) References Cited

U.S. PATENT DOCUMENTS

| | | |
|---|---|---|
| 2007/0027384 A1 | 2/2007 | Brister et al. |
| 2007/0027385 A1 | 2/2007 | Brister et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |
| 2007/0045902 A1 | 3/2007 | Brauker et al. |
| 2007/0049865 A1 | 3/2007 | Radmer et al. |
| 2007/0049873 A1 | 3/2007 | Hansen et al. |
| 2007/0059196 A1 | 3/2007 | Brister et al. |
| 2007/0066873 A1 | 3/2007 | Kamath et al. |
| 2007/0073129 A1 | 3/2007 | Shah et al. |
| 2007/0085995 A1 | 4/2007 | Pesach et al. |
| 2007/0093704 A1 | 4/2007 | Brister et al. |
| 2007/0100222 A1 | 5/2007 | Mastrototaro et al. |
| 2007/0116600 A1 | 5/2007 | Kochar et al. |
| 2007/0129524 A1 | 6/2007 | Sunkara |
| 2007/0129619 A1 | 6/2007 | Ward et al. |
| 2007/0129621 A1 | 6/2007 | Kellogg et al. |
| 2007/0135698 A1 | 6/2007 | Shah et al. |
| 2007/0135699 A1 | 6/2007 | Ward et al. |
| 2007/0142584 A1 | 6/2007 | Schorzman et al. |
| 2007/0151869 A1 | 7/2007 | Heller et al. |
| 2007/0163880 A1 | 7/2007 | Woo et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |
| 2007/0173761 A1 | 7/2007 | Kanderian, Jr. et al. |
| 2007/0179436 A1 | 8/2007 | Braig et al. |
| 2007/0197889 A1 | 8/2007 | Brister et al. |
| 2007/0197890 A1 | 8/2007 | Boock et al. |
| 2007/0200254 A1 | 8/2007 | Curry |
| 2007/0200267 A1 | 8/2007 | Tsai |
| 2007/0202562 A1 | 8/2007 | Curry |
| 2007/0202672 A1 | 8/2007 | Curry |
| 2007/0203407 A1 | 8/2007 | Hoss et al. |
| 2007/0203410 A1 | 8/2007 | Say et al. |
| 2007/0203966 A1 | 8/2007 | Brauker et al. |
| 2007/0206193 A1 | 9/2007 | Pesach |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0219441 A1 | 9/2007 | Carlin et al. |
| 2007/0225579 A1 | 9/2007 | Lucassen et al. |
| 2007/0225675 A1 | 9/2007 | Robinson et al. |
| 2007/0227907 A1 | 10/2007 | Shah et al. |
| 2007/0232876 A1 | 10/2007 | Otto et al. |
| 2007/0232879 A1 | 10/2007 | Brister et al. |
| 2007/0233013 A1 | 10/2007 | Schoenberg |
| 2007/0235331 A1 | 10/2007 | Simpson et al. |
| 2007/0240497 A1 | 10/2007 | Robinson et al. |
| 2007/0244381 A1 | 10/2007 | Robinson et al. |
| 2007/0244382 A1 | 10/2007 | Robinson et al. |
| 2007/0249916 A1 | 10/2007 | Pesach et al. |
| 2007/0255114 A1 | 11/2007 | Ackermann et al. |
| 2007/0255126 A1 | 11/2007 | Moberg et al. |
| 2007/0259217 A1 | 11/2007 | Logan |
| 2007/0275193 A1 | 11/2007 | DeSimone et al. |
| 2007/0276211 A1 | 11/2007 | Mir et al. |
| 2007/0282180 A1 | 12/2007 | Caduff et al. |
| 2007/0299385 A1 | 12/2007 | Santini, Jr. et al. |
| 2007/0299409 A1 | 12/2007 | Whitbourne et al. |
| 2008/0001318 A1 | 1/2008 | Schorzman et al. |
| 2008/0021666 A1 | 1/2008 | Goode, Jr. et al. |
| 2008/0027245 A1 | 1/2008 | Suri |
| 2008/0029390 A1 | 2/2008 | Roche et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0033269 A1 | 2/2008 | Zhang |
| 2008/0034972 A1 | 2/2008 | Gough et al. |
| 2008/0045824 A1 | 2/2008 | Tapsak et al. |
| 2008/0064941 A1 | 3/2008 | Funderburk et al. |
| 2008/0064944 A1 | 3/2008 | VanAntwerp et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0072663 A1 | 3/2008 | Keenan et al. |
| 2008/0081969 A1 | 4/2008 | Feldman et al. |
| 2008/0086040 A1 | 4/2008 | Heller et al. |
| 2008/0086041 A1 | 4/2008 | Heller et al. |
| 2008/0086042 A1 | 4/2008 | Brister et al. |
| 2008/0086043 A1 | 4/2008 | Heller et al. |
| 2008/0086044 A1 | 4/2008 | Brister et al. |
| 2008/0086273 A1 | 4/2008 | Shults et al. |
| 2008/0091094 A1 | 4/2008 | Heller et al. |
| 2008/0091095 A1 | 4/2008 | Heller et al. |
| 2008/0108942 A1 | 5/2008 | Brister et al. |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0119707 A1 | 5/2008 | Stafford |
| 2008/0125751 A1 | 5/2008 | Fjield et al. |
| 2008/0139910 A1 | 6/2008 | Mastrototaro et al. |
| 2008/0154101 A1 | 6/2008 | Jain et al. |
| 2008/0161666 A1 | 7/2008 | Feldman et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0193936 A1 | 8/2008 | Squirrell |
| 2008/0194837 A1 | 8/2008 | Kim et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0210557 A1 | 9/2008 | Heller et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262334 A1 | 10/2008 | Dunn et al. |
| 2008/0262469 A1 | 10/2008 | Brister et al. |
| 2008/0275313 A1 | 11/2008 | Brister et al. |
| 2008/0275326 A1 | 11/2008 | Kasielke et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2008/0306368 A1 | 12/2008 | Goode, Jr. et al. |
| 2008/0306433 A1 | 12/2008 | Cesaroni |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312397 A1 | 12/2008 | Lai et al. |
| 2008/0312859 A1 | 12/2008 | Skyggebjerg et al. |
| 2008/0313896 A1 | 12/2008 | Shah et al. |
| 2009/0005666 A1 | 1/2009 | Shin et al. |
| 2009/0012379 A1 | 1/2009 | Goode, Jr. et al. |
| 2009/0018418 A1 | 1/2009 | Markle et al. |
| 2009/0018424 A1 | 1/2009 | Kamath et al. |
| 2009/0018426 A1 | 1/2009 | Markle et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |

(56) References Cited

U.S. PATENT DOCUMENTS

| | | |
|---|---|---|
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054748 A1 | 2/2009 | Feldman |
| 2009/0054812 A1 | 2/2009 | Mace |
| 2009/0061528 A1 | 3/2009 | Suri |
| 2009/0062633 A1 | 3/2009 | Brauker et al. |
| 2009/0062635 A1 | 3/2009 | Brauker et al. |
| 2009/0062645 A1 | 3/2009 | Fehre et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0081803 A1 | 3/2009 | Gamsey et al. |
| 2009/0099434 A1 | 4/2009 | Liu et al. |
| 2009/0099436 A1 | 4/2009 | Brister et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156924 A1 | 6/2009 | Shariati et al. |
| 2009/0163790 A1 | 6/2009 | Brister et al. |
| 2009/0177059 A1 | 7/2009 | Say et al. |
| 2009/0177060 A1 | 7/2009 | Say et al. |
| 2009/0177143 A1 | 7/2009 | Markle et al. |
| 2009/0178459 A1 | 7/2009 | Li et al. |
| 2009/0182217 A1 | 7/2009 | Li et al. |
| 2009/0187090 A1 | 7/2009 | Say et al. |
| 2009/0187091 A1 | 7/2009 | Say et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247857 A1 | 10/2009 | Harper et al. |
| 2009/0264719 A1 | 10/2009 | Markle et al. |
| 2009/0264856 A1 | 10/2009 | Lebel et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010330 A1 | 1/2010 | Rankers et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087721 A1 | 4/2010 | Stafford |
| 2010/0087724 A1 | 4/2010 | Brauker et al. |
| 2010/0113897 A1 | 5/2010 | Brenneman et al. |
| 2010/0161269 A1 | 6/2010 | Kamath et al. |
| 2010/0168543 A1 | 7/2010 | Kamath et al. |
| 2010/0168545 A1 | 7/2010 | Kamath et al. |
| 2010/0168546 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0179399 A1 | 7/2010 | Goode, Jr. et al. |
| 2010/0179400 A1 | 7/2010 | Brauker et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179405 A1 | 7/2010 | Goode, Jr. et al. |
| 2010/0179406 A1 | 7/2010 | Goode, Jr. et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0191082 A1 | 7/2010 | Brister et al. |
| 2010/0198035 A1 | 8/2010 | Kamath et al. |
| 2010/0204555 A1 | 8/2010 | Shults et al. |
| 2010/0212583 A1 | 8/2010 | Brister et al. |
| 2010/0214104 A1 | 8/2010 | Goode, Jr. et al. |
| 2010/0217106 A1 | 8/2010 | Goode, Jr. et al. |
| 2010/0217555 A1 | 8/2010 | Kamath et al. |
| 2010/0234707 A1 | 9/2010 | Goode, Jr. et al. |
| 2010/0234796 A1 | 9/2010 | Kamath et al. |
| 2010/0235106 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0256779 A1 | 10/2010 | Brauker et al. |
| 2010/0286496 A1 | 11/2010 | Simpson et al. |
| 2010/0305869 A1 | 12/2010 | Brauker et al. |
| 2010/0331648 A1 | 12/2010 | Kamath et al. |
| 2010/0331655 A1 | 12/2010 | Kamath et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0027127 A1 | 2/2011 | Simpson et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0087196 A1 | 4/2011 | Hunn et al. |
| 2011/0118579 A1 | 5/2011 | Goode, Jr. et al. |
| 2011/0124992 A1 | 5/2011 | Brauker et al. |
| 2011/0124997 A1 | 5/2011 | Goode, Jr. et al. |
| 2011/0128052 A1 | 6/2011 | Fujibe et al. |
| 2011/0130639 A1 | 6/2011 | Feldman |
| 2011/0130970 A1 | 6/2011 | Goode, Jr. et al. |
| 2011/0136249 A1 | 6/2011 | Stiene |
| 2011/0137601 A1 | 6/2011 | Goode, Jr. et al. |
| 2011/0144465 A1 | 6/2011 | Shults et al. |
| 2011/0178378 A1 | 7/2011 | Brister et al. |
| 2011/0190614 A1 | 8/2011 | Brister et al. |

(56) References Cited

U.S. PATENT DOCUMENTS

| | | |
|---|---|---|
| 2011/0201910 A1 | 8/2011 | Rasdal et al. |
| 2011/0218414 A1 | 9/2011 | Kamath et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257895 A1 | 10/2011 | Brauker et al. |
| 2011/0263958 A1 | 10/2011 | Brauker et al. |
| 2011/0270158 A1 | 11/2011 | Brauker et al. |
| 2011/0290645 A1 | 12/2011 | Brister et al. |
| 2011/0313543 A1 | 12/2011 | Brauker et al. |
| 2011/0319739 A1 | 12/2011 | Kamath et al. |
| 2012/0130214 A1 | 5/2012 | Brister et al. |
| 2012/0172691 A1 | 7/2012 | Brauker et al. |
| 2012/0265042 A1 | 10/2012 | Neinast et al. |
| 2012/0277562 A1 | 11/2012 | Brister et al. |
| 2012/0277566 A1 | 11/2012 | Kamath et al. |
| 2013/0012798 A1 | 1/2013 | Brister et al. |
| 2013/0060112 A1 | 3/2013 | Pryor et al. |
| 2013/0131478 A1 | 5/2013 | Simpson et al. |
| 2013/0255570 A1 | 10/2013 | Brister et al. |
| 2013/0267808 A1 | 10/2013 | Brister et al. |
| 2013/0281931 A1 | 10/2013 | Hunn et al. |
| 2013/0296677 A1 | 11/2013 | Pryor et al. |
| 2014/0128704 A1 | 5/2014 | Simpson et al. |
| 2014/0142405 A1 | 5/2014 | Brister et al. |
| 2014/0257065 A1 | 9/2014 | Brister et al. |
| 2014/0288402 A1 | 9/2014 | Brister et al. |
| 2016/0008029 A1 | 1/2016 | Brister et al. |
| 2016/0051173 A1 | 2/2016 | Brister et al. |
| 2016/0310051 A1 | 10/2016 | Brister et al. |
| 2017/0196491 A1 | 7/2017 | Brister et al. |
| 2017/0367627 A1 | 12/2017 | Brister et al. |
| 2018/0014762 A1 | 1/2018 | Brister et al. |
| 2018/0049682 A1 | 2/2018 | Brister et al. |
| 2018/0055423 A1 | 3/2018 | Pryor et al. |
| 2018/0140236 A1 | 5/2018 | Brister et al. |
| 2018/0160949 A1 | 6/2018 | Brister et al. |
| 2018/0242894 A1 | 8/2018 | Brauker et al. |
| 2018/0303394 A1 | 10/2018 | Brauker et al. |
| 2019/0015020 A1 | 1/2019 | Brister et al. |
| 2019/0069817 A1 | 3/2019 | Brister et al. |
| 2019/0076071 A1 | 3/2019 | Brister et al. |
| 2019/0246965 A1 | 8/2019 | Simpson et al. |
| 2019/0320951 A1 | 10/2019 | Pryor et al. |
| 2019/0320952 A1 | 10/2019 | Pryor et al. |
| 2019/0320953 A1 | 10/2019 | Pryor et al. |
| 2019/0320954 A1 | 10/2019 | Pryor et al. |
| 2019/0320955 A1 | 10/2019 | Pryor et al. |
| 2019/0320956 A1 | 10/2019 | Pryor et al. |
| 2019/0320957 A1 | 10/2019 | Pryor et al. |
| 2019/0343436 A1 | 11/2019 | Pryor et al. |
| 2019/0350503 A1 | 11/2019 | Pryor et al. |
| 2019/0350504 A1 | 11/2019 | Pryor et al. |
| 2019/0357821 A1 | 11/2019 | Brister et al. |
| 2019/0357822 A1 | 11/2019 | Pryor et al. |
| 2020/0077928 A1 | 3/2020 | Brister et al. |
| 2020/0077932 A1 | 3/2020 | Simpson et al. |
| 2020/0085350 A1 | 3/2020 | Simpson et al. |
| 2020/0085351 A1 | 3/2020 | Simpson et al. |
| 2020/0085354 A1 | 3/2020 | Pryor et al. |
| 2020/0085355 A1 | 3/2020 | Pryor et al. |
| 2020/0085356 A1 | 3/2020 | Pryor et al. |
| 2020/0100713 A1 | 4/2020 | Simpson et al. |
| 2020/0100714 A1 | 4/2020 | Simpson et al. |
| 2020/0100715 A1 | 4/2020 | Kamath et al. |
| 2020/0138346 A1 | 5/2020 | Brister et al. |
| 2020/0155049 A1 | 5/2020 | Pryor et al. |
| 2020/0155050 A1 | 5/2020 | Pryor et al. |
| 2020/0178861 A1 | 6/2020 | Brister |
| 2020/0178862 A1 | 6/2020 | Brister |
| 2020/0178863 A1 | 6/2020 | Brister |
| 2020/0196924 A1 | 6/2020 | Brister |
| 2020/0405203 A1 | 12/2020 | Brister et al. |

FOREIGN PATENT DOCUMENTS

| | | |
|---|---|---|
| DE | 3144459 A1 | 10/1982 |
| DE | 4105222 A1 | 8/1992 |
| DE | 3933373 C2 | 9/1992 |
| DE | 20110059 U1 | 8/2002 |
| DE | 10117285 A1 | 11/2002 |
| EP | 0098592 A2 | 1/1984 |
| EP | 0107634 A2 | 5/1984 |
| EP | 0127958 A2 | 12/1984 |
| EP | 0143517 A1 | 6/1985 |
| EP | 0139277 B1 | 6/1988 |
| EP | 0282349 A2 | 9/1988 |
| EP | 0284518 A2 | 9/1988 |
| EP | 0286039 A2 | 10/1988 |
| EP | 0286118 A2 | 10/1988 |
| EP | 0288793 A2 | 11/1988 |
| EP | 0143517 B1 | 4/1989 |
| EP | 0314027 A1 | 5/1989 |
| EP | 0319277 A1 | 6/1989 |
| EP | 0320109 A1 | 6/1989 |
| EP | 0351892 A2 | 1/1990 |
| EP | 0352138 A2 | 1/1990 |
| EP | 0352610 A2 | 1/1990 |
| EP | 0352631 A2 | 1/1990 |
| EP | 0352708 A2 | 1/1990 |
| EP | 0353328 A1 | 2/1990 |
| EP | 0390390 A1 | 10/1990 |
| EP | 0396788 A1 | 11/1990 |
| EP | 0406473 A1 | 1/1991 |
| EP | 0420021 A2 | 4/1991 |
| EP | 0440044 A1 | 8/1991 |
| EP | 0441252 A2 | 8/1991 |
| EP | 0441394 A2 | 8/1991 |
| EP | 0457292 A2 | 11/1991 |
| EP | 0467078 A2 | 1/1992 |
| EP | 0471391 A2 | 2/1992 |
| EP | 0473065 A2 | 3/1992 |
| EP | 0476980 A2 | 3/1992 |
| EP | 0275139 B1 | 4/1992 |
| EP | 0477501 A2 | 4/1992 |
| EP | 0494704 A3 | 9/1992 |
| EP | 0494705 A3 | 9/1992 |
| EP | 0508388 A1 | 10/1992 |
| EP | 0512122 A1 | 11/1992 |
| EP | 0520430 A2 | 12/1992 |
| EP | 0520443 A2 | 12/1992 |
| EP | 0262328 B1 | 1/1993 |
| EP | 0319277 B1 | 3/1993 |
| EP | 0534074 A1 | 3/1993 |
| EP | 0535898 A1 | 4/1993 |
| EP | 0539625 A1 | 5/1993 |
| EP | 0264036 B1 | 6/1993 |
| EP | 0351891 B1 | 9/1993 |
| EP | 0563795 A1 | 10/1993 |
| EP | 0567725 A1 | 11/1993 |
| EP | 0323605 B1 | 1/1994 |
| EP | 0279069 B1 | 7/1994 |
| EP | 0595474 A3 | 7/1994 |
| EP | 0561966 B1 | 10/1994 |
| EP | 0286118 B1 | 1/1995 |
| EP | 0478550 B1 | 1/1995 |
| EP | 0647849 A2 | 4/1995 |
| EP | 0424634 B1 | 6/1995 |
| EP | 0677743 A2 | 10/1995 |
| EP | 0191640 B2 | 11/1995 |
| EP | 0424633 B1 | 1/1996 |
| EP | 0690134 A1 | 1/1996 |
| EP | 0534074 B1 | 3/1996 |
| EP | 0709677 A2 | 5/1996 |
| EP | 0532187 B1 | 10/1996 |
| EP | 0470652 B1 | 12/1996 |
| EP | 0476715 B1 | 12/1996 |
| EP | 0747069 A2 | 12/1996 |
| EP | 0776628 A2 | 6/1997 |
| EP | 0387696 B1 | 8/1997 |
| EP | 0593096 A3 | 12/1997 |
| EP | 0817809 A1 | 1/1998 |
| EP | 0838230 A2 | 4/1998 |

(56) References Cited

FOREIGN PATENT DOCUMENTS

| | | |
|---|---|---|
| EP | 0880936 A2 | 12/1998 |
| EP | 0885932 A2 | 12/1998 |
| EP | 0587008 B1 | 2/1999 |
| EP | 0967788 A2 | 12/1999 |
| EP | 0995805 A1 | 4/2000 |
| EP | 0678308 B1 | 5/2000 |
| EP | 1077634 A1 | 2/2001 |
| EP | 1078258 A1 | 2/2001 |
| EP | 1028320 A3 | 3/2001 |
| EP | 1111378 A2 | 6/2001 |
| EP | 1112717 A1 | 7/2001 |
| EP | 1112718 A1 | 7/2001 |
| EP | 1120084 A1 | 8/2001 |
| EP | 1120085 A1 | 8/2001 |
| EP | 1120650 A2 | 8/2001 |
| EP | 1130386 A1 | 9/2001 |
| EP | 1153571 A1 | 11/2001 |
| EP | 0777122 B1 | 4/2002 |
| EP | 0817809 B1 | 7/2002 |
| EP | 1251137 A2 | 10/2002 |
| EP | 0958495 B1 | 11/2002 |
| EP | 1258728 A2 | 11/2002 |
| EP | 1266607 A2 | 12/2002 |
| EP | 1281351 A2 | 2/2003 |
| EP | 0824900 B1 | 4/2003 |
| EP | 1340980 A1 | 9/2003 |
| EP | 1340981 A2 | 9/2003 |
| EP | 1077636 B1 | 1/2004 |
| EP | 0674176 B1 | 2/2004 |
| EP | 1391728 A1 | 2/2004 |
| EP | 0846776 B1 | 3/2004 |
| EP | 1413245 A2 | 4/2004 |
| EP | 1498067 A1 | 1/2005 |
| EP | 1498428 A1 | 1/2005 |
| EP | 1614464 A1 | 1/2006 |
| EP | 0922959 B1 | 10/2006 |
| EP | 1717924 A2 | 11/2006 |
| EP | 0877252 B1 | 1/2007 |
| EP | 1234053 B1 | 4/2007 |
| EP | 1798542 A1 | 6/2007 |
| EP | 1286164 B1 | 7/2007 |
| EP | 1804650 A1 | 7/2007 |
| EP | 1612560 B1 | 10/2007 |
| EP | 1905514 A1 | 4/2008 |
| EP | 1582874 B1 | 7/2008 |
| EP | 1977829 A1 | 10/2008 |
| EP | 1982644 A1 | 10/2008 |
| EP | 1457913 B1 | 12/2008 |
| EP | 2223710 A1 | 9/2010 |
| EP | 2226086 A1 | 9/2010 |
| EP | 2228642 A1 | 9/2010 |
| EP | 2236077 A1 | 10/2010 |
| EP | 2327362 A1 | 6/2011 |
| EP | 2329770 B1 | 9/2014 |
| EP | 2407094 B1 | 10/2014 |
| EP | 2335584 B1 | 6/2015 |
| FR | 2656423 A1 | 6/1991 |
| FR | 2760962 A1 | 9/1998 |
| GB | 1442303 A | 7/1976 |
| GB | 1556969 A | 12/1979 |
| GB | 2149918 A | 6/1985 |
| GB | 2230865 A | 10/1990 |
| JP | S5441190 A | 4/1979 |
| JP | S57156004 A | 9/1982 |
| JP | S58124912 A | 7/1983 |
| JP | S59211459 A | 11/1984 |
| JP | S61271418 A | 12/1986 |
| JP | S6283649 A | 4/1987 |
| JP | S6283849 A | 4/1987 |
| JP | H022913 A | 1/1990 |
| JP | H03293556 A | 12/1991 |
| JP | H06288853 A | 10/1994 |
| JP | H06307898 A | 11/1994 |
| JP | H0783871 A | 3/1995 |
| JP | H11258381 A | 9/1999 |
| JP | 2000060826 A | 2/2000 |
| JP | 2000149072 A | 5/2000 |
| JP | 2002513602 A | 5/2002 |
| JP | 2002189015 A | 7/2002 |
| JP | 2003108679 A | 4/2003 |
| JP | 2003297163 A | 10/2003 |
| WO | WO-8103614 A1 | 12/1981 |
| WO | WO-8706342 A1 | 10/1987 |
| WO | WO-8706706 A1 | 11/1987 |
| WO | WO-8808137 A1 | 10/1988 |
| WO | WO-8902720 A1 | 4/1989 |
| WO | WO-8904302 A1 | 5/1989 |
| WO | WO-8907263 A1 | 8/1989 |
| WO | WO-9000738 A1 | 1/1990 |
| WO | WO-9002938 A1 | 3/1990 |
| WO | WO-9005296 A1 | 5/1990 |
| WO | WO-9005301 A1 | 5/1990 |
| WO | WO-9005302 A1 | 5/1990 |
| WO | WO-9005910 A1 | 5/1990 |
| WO | WO-9007525 A1 | 7/1990 |
| WO | WO-9007575 A1 | 7/1990 |
| WO | WO-9010716 A1 | 9/1990 |
| WO | WO-9010861 A1 | 9/1990 |
| WO | WO-9013021 A1 | 11/1990 |
| WO | WO-9109302 A1 | 6/1991 |
| WO | WO-9115993 A1 | 10/1991 |
| WO | WO-9116416 A1 | 10/1991 |
| WO | WO-9117259 A1 | 11/1991 |
| WO | WO-9201315 A1 | 1/1992 |
| WO | WO-9201928 A1 | 2/1992 |
| WO | WO-9207525 A1 | 5/1992 |
| WO | WO-9208985 A2 | 5/1992 |
| WO | WO-9210584 A1 | 6/1992 |
| WO | WO-9212255 A1 | 7/1992 |
| WO | WO-9213271 A1 | 8/1992 |
| WO | WO-9214138 A1 | 8/1992 |
| WO | WO-9214139 A1 | 8/1992 |
| WO | WO-9218887 A1 | 10/1992 |
| WO | WO-9221772 A1 | 12/1992 |
| WO | WO-9301308 A1 | 1/1993 |
| WO | WO-9302703 A1 | 2/1993 |
| WO | WO-9303362 A1 | 2/1993 |
| WO | WO-9305701 A1 | 4/1993 |
| WO | WO-9312256 A1 | 6/1993 |
| WO | WO-9313048 A1 | 7/1993 |
| WO | WO-9313408 A1 | 7/1993 |
| WO | WO-9314185 A1 | 7/1993 |
| WO | WO-9314693 A1 | 8/1993 |
| WO | WO-9319370 A1 | 9/1993 |
| WO | WO-9319701 A1 | 10/1993 |
| WO | WO-9320240 A1 | 10/1993 |
| WO | WO-9320440 A1 | 10/1993 |
| WO | WO-9320441 A1 | 10/1993 |
| WO | WO-9320443 A1 | 10/1993 |
| WO | WO-9320444 A1 | 10/1993 |
| WO | WO-9320450 A1 | 10/1993 |
| WO | WO-9323744 A1 | 11/1993 |
| WO | WO-9406011 A1 | 3/1994 |
| WO | WO-9406012 A1 | 3/1994 |
| WO | WO-9408236 A1 | 4/1994 |
| WO | WO-9409506 A1 | 4/1994 |
| WO | WO-9409507 A1 | 4/1994 |
| WO | WO-9419695 A1 | 9/1994 |
| WO | WO-9421642 A1 | 9/1994 |
| WO | WO-9421643 A1 | 9/1994 |
| WO | WO-9421644 A1 | 9/1994 |
| WO | WO-9422367 A1 | 10/1994 |
| WO | WO-9426414 A1 | 11/1994 |
| WO | WO-9502357 A1 | 1/1995 |
| WO | WO-9507109 A1 | 3/1995 |
| WO | WO-9508774 A2 | 3/1995 |
| WO | WO-9510044 A1 | 4/1995 |
| WO | WO-9511454 A1 | 4/1995 |
| WO | WO-9513838 A1 | 5/1995 |
| WO | WO-9517966 A1 | 7/1995 |
| WO | WO-9522597 A1 | 8/1995 |
| WO | WO-9528878 A1 | 11/1995 |
| WO | WO-9534814 A1 | 12/1995 |
| WO | WO-9601611 A1 | 1/1996 |

(56) References Cited

FOREIGN PATENT DOCUMENTS

| | | |
|---|---|---|
| WO | WO-9603117 A1 | 2/1996 |
| WO | WO-9605501 A1 | 2/1996 |
| WO | WO-9606947 A1 | 3/1996 |
| WO | WO-9614026 A1 | 5/1996 |
| WO | WO-9622991 A1 | 8/1996 |
| WO | WO-9622992 A1 | 8/1996 |
| WO | WO-9624690 A1 | 8/1996 |
| WO | WO-9625088 A1 | 8/1996 |
| WO | WO-9625089 A1 | 8/1996 |
| WO | WO-9630431 A1 | 10/1996 |
| WO | WO-9632076 A1 | 10/1996 |
| WO | WO-9636296 A1 | 11/1996 |
| WO | WO-9636870 A1 | 11/1996 |
| WO | WO-9641179 A1 | 12/1996 |
| WO | WO-9701986 A1 | 1/1997 |
| WO | WO-9702811 A1 | 1/1997 |
| WO | WO-9706727 A1 | 2/1997 |
| WO | WO-9711080 A1 | 3/1997 |
| WO | WO-9713874 A1 | 4/1997 |
| WO | WO-9717884 A2 | 5/1997 |
| WO | WO-9719188 A1 | 5/1997 |
| WO | WO-9719344 A1 | 5/1997 |
| WO | WO-9728737 A1 | 8/1997 |
| WO | WO-9730628 A1 | 8/1997 |
| WO | WO-9733176 A1 | 9/1997 |
| WO | WO-9738625 A1 | 10/1997 |
| WO | WO-9743633 A1 | 11/1997 |
| WO | WO-9801071 A1 | 1/1998 |
| WO | WO-9806423 A1 | 2/1998 |
| WO | WO-9819159 A1 | 5/1998 |
| WO | WO-9824358 A2 | 6/1998 |
| WO | WO-9824366 A2 | 6/1998 |
| WO | WO-9833549 A1 | 8/1998 |
| WO | WO-9834541 A1 | 8/1998 |
| WO | WO-9838904 A1 | 9/1998 |
| WO | WO-9838906 A1 | 9/1998 |
| WO | WO-9841854 A1 | 9/1998 |
| WO | WO-9842249 A1 | 10/1998 |
| WO | WO-9844347 A1 | 10/1998 |
| WO | WO-9844348 A1 | 10/1998 |
| WO | WO-9845331 A2 | 10/1998 |
| WO | WO-9845427 A2 | 10/1998 |
| WO | WO-9852043 A1 | 11/1998 |
| WO | WO-9856293 A1 | 12/1998 |
| WO | WO-9856923 A1 | 12/1998 |
| WO | WO-9858250 A2 | 12/1998 |
| WO | WO-9904043 A1 | 1/1999 |
| WO | WO-9912607 A1 | 3/1999 |
| WO | WO-9913101 A1 | 3/1999 |
| WO | WO-9913574 A1 | 3/1999 |
| WO | WO-9927848 A1 | 6/1999 |
| WO | WO-9927852 A1 | 6/1999 |
| WO | WO-9929230 A1 | 6/1999 |
| WO | WO-9929429 A1 | 6/1999 |
| WO | WO-9929892 A1 | 6/1999 |
| WO | WO-9933504 A1 | 7/1999 |
| WO | WO-9940848 A1 | 8/1999 |
| WO | WO-9948419 A1 | 9/1999 |
| WO | WO-9949856 A2 | 10/1999 |
| WO | WO-9956613 A1 | 11/1999 |
| WO | WO-9958051 A1 | 11/1999 |
| WO | WO-9958709 A1 | 11/1999 |
| WO | WO-9958973 A1 | 11/1999 |
| WO | WO-9959657 A1 | 11/1999 |
| WO | WO-9964620 A2 | 12/1999 |
| WO | WO-0007013 A2 | 2/2000 |
| WO | WO-0012720 A2 | 3/2000 |
| WO | WO-0013002 A2 | 3/2000 |
| WO | WO-0013003 A1 | 3/2000 |
| WO | WO-0018449 A2 | 4/2000 |
| WO | WO-0019887 A1 | 4/2000 |
| WO | WO-0020626 A1 | 4/2000 |
| WO | WO-0030530 A1 | 6/2000 |
| WO | WO-0032098 A1 | 6/2000 |
| WO | WO-0033065 A1 | 6/2000 |
| WO | WO-0035530 A1 | 6/2000 |
| WO | WO-0045696 A1 | 8/2000 |
| WO | WO-0049940 A2 | 8/2000 |
| WO | WO-0049941 A1 | 8/2000 |
| WO | WO-0049942 A2 | 8/2000 |
| WO | WO-0059373 A1 | 10/2000 |
| WO | WO-0074753 A1 | 12/2000 |
| WO | WO-0078210 A1 | 12/2000 |
| WO | WO-0078992 A2 | 12/2000 |
| WO | WO-0079258 A1 | 12/2000 |
| WO | WO-0100865 A2 | 1/2001 |
| WO | WO-0109096 A2 | 2/2001 |
| WO | WO-0112158 A1 | 2/2001 |
| WO | WO-0116579 A1 | 3/2001 |
| WO | WO-0120019 A2 | 3/2001 |
| WO | WO-0120334 A1 | 3/2001 |
| WO | WO-0121827 A1 | 3/2001 |
| WO | WO-0134243 A1 | 5/2001 |
| WO | WO-0136666 A1 | 5/2001 |
| WO | WO-0143660 A2 | 6/2001 |
| WO | WO-0152727 A1 | 7/2001 |
| WO | WO-0152935 A1 | 7/2001 |
| WO | WO-0154753 A2 | 8/2001 |
| WO | WO-0158347 A1 | 8/2001 |
| WO | WO-0158348 A1 | 8/2001 |
| WO | WO-0159425 A1 | 8/2001 |
| WO | WO-0164105 A1 | 9/2001 |
| WO | WO-0168901 A2 | 9/2001 |
| WO | WO-0169222 A2 | 9/2001 |
| WO | WO-0173109 A2 | 10/2001 |
| WO | WO-0188524 A1 | 11/2001 |
| WO | WO-0188534 A2 | 11/2001 |
| WO | WO-0191634 A2 | 12/2001 |
| WO | WO-0202755 A2 | 1/2002 |
| WO | WO-0205702 A2 | 1/2002 |
| WO | WO-0207596 A1 | 1/2002 |
| WO | WO-0207617 A2 | 1/2002 |
| WO | WO-0216535 A2 | 2/2002 |
| WO | WO-0217780 A1 | 3/2002 |
| WO | WO-0224065 A1 | 3/2002 |
| WO | WO-0233407 A1 | 4/2002 |
| WO | WO-0243585 A1 | 6/2002 |
| WO | WO-02056751 A2 | 7/2002 |
| WO | WO-02058537 A2 | 8/2002 |
| WO | WO-02062210 A1 | 8/2002 |
| WO | WO-02066509 A2 | 8/2002 |
| WO | WO-02066986 A2 | 8/2002 |
| WO | WO-02074161 A2 | 9/2002 |
| WO | WO-02082989 A1 | 10/2002 |
| WO | WO-02087681 A2 | 11/2002 |
| WO | WO-02089666 A2 | 11/2002 |
| WO | WO-02097414 A2 | 12/2002 |
| WO | WO-02099097 A2 | 12/2002 |
| WO | WO-02099428 A1 | 12/2002 |
| WO | WO-02100266 A1 | 12/2002 |
| WO | WO-02100457 A2 | 12/2002 |
| WO | WO-02100474 A2 | 12/2002 |
| WO | WO-03000127 A2 | 1/2003 |
| WO | WO-03008013 A2 | 1/2003 |
| WO | WO-03008014 A2 | 1/2003 |
| WO | WO-03009207 A1 | 1/2003 |
| WO | WO-03009208 A1 | 1/2003 |
| WO | WO-03011131 A2 | 2/2003 |
| WO | WO-03012422 A1 | 2/2003 |
| WO | WO-03022327 A2 | 3/2003 |
| WO | WO-03028797 A1 | 4/2003 |
| WO | WO-03032411 A2 | 4/2003 |
| WO | WO-03033726 A1 | 4/2003 |
| WO | WO-03035117 A1 | 5/2003 |
| WO | WO-03036310 A1 | 5/2003 |
| WO | WO-03044511 A2 | 5/2003 |
| WO | WO-03053498 A2 | 7/2003 |
| WO | WO-03057028 A2 | 7/2003 |
| WO | WO-03063700 A1 | 8/2003 |
| WO | WO-03072164 A2 | 9/2003 |
| WO | WO-03072269 A1 | 9/2003 |
| WO | WO-03076937 A2 | 9/2003 |
| WO | WO-03082091 A2 | 10/2003 |
| WO | WO-03088832 A1 | 10/2003 |

(56) References Cited

FOREIGN PATENT DOCUMENTS

| | | |
|---|---|---|
| WO | WO-03094714 A1 | 11/2003 |
| WO | WO-03097866 A1 | 11/2003 |
| WO | WO-03101862 A1 | 12/2003 |
| WO | WO-03106031 A1 | 12/2003 |
| WO | WO-03106966 A2 | 12/2003 |
| WO | WO-2004004905 A2 | 1/2004 |
| WO | WO-2004010844 A2 | 2/2004 |
| WO | WO-2004030726 A1 | 4/2004 |
| WO | WO-2004036183 A2 | 4/2004 |
| WO | WO-2004039265 A2 | 5/2004 |
| WO | WO-2004052190 A1 | 6/2004 |
| WO | WO-2004060455 A1 | 7/2004 |
| WO | WO-2004061420 A2 | 7/2004 |
| WO | WO-2004063718 A2 | 7/2004 |
| WO | WO-2004071291 A2 | 8/2004 |
| WO | WO-2004073138 A1 | 8/2004 |
| WO | WO-2004086970 A1 | 10/2004 |
| WO | WO-2004098685 A1 | 11/2004 |
| WO | WO-2004105641 A2 | 12/2004 |
| WO | WO-2004110256 A2 | 12/2004 |
| WO | WO-2004113901 A1 | 12/2004 |
| WO | WO-2005011489 A1 | 2/2005 |
| WO | WO-2005012873 A2 | 2/2005 |
| WO | WO-2005013824 A1 | 2/2005 |
| WO | WO-2005018443 A1 | 3/2005 |
| WO | WO-2005026178 A2 | 3/2005 |
| WO | WO-2005026689 A2 | 3/2005 |
| WO | WO-2005026690 A2 | 3/2005 |
| WO | WO-2005032362 A2 | 4/2005 |
| WO | WO-2005032400 A2 | 4/2005 |
| WO | WO-2005041766 A1 | 5/2005 |
| WO | WO-2005048834 A1 | 6/2005 |
| WO | WO-2005051440 A1 | 6/2005 |
| WO | WO-2005057168 A2 | 6/2005 |
| WO | WO-2005057173 A2 | 6/2005 |
| WO | WO-2005057175 A2 | 6/2005 |
| WO | WO-2005063115 A1 | 7/2005 |
| WO | WO-2005065542 A2 | 7/2005 |
| WO | WO-2005067797 A1 | 7/2005 |
| WO | WO-2005070287 A1 | 8/2005 |
| WO | WO-2005074811 A1 | 8/2005 |
| WO | WO-2005078424 A1 | 8/2005 |
| WO | WO-2005084530 A2 | 9/2005 |
| WO | WO-2005084545 A1 | 9/2005 |
| WO | WO-2005084546 A2 | 9/2005 |
| WO | WO-2005089103 A2 | 9/2005 |
| WO | WO-2005026689 A9 | 10/2005 |
| WO | WO-2005094714 A1 | 10/2005 |
| WO | WO-2005098431 A1 | 10/2005 |
| WO | WO-2005107594 A2 | 11/2005 |
| WO | WO-2005114218 A2 | 12/2005 |
| WO | WO-2005121355 A1 | 12/2005 |
| WO | WO-2005121785 A2 | 12/2005 |
| WO | WO-2005122296 A2 | 12/2005 |
| WO | WO-2006001929 A1 | 1/2006 |
| WO | WO-2006001973 A2 | 1/2006 |
| WO | WO-2006002960 A1 | 1/2006 |
| WO | WO-2006005503 A1 | 1/2006 |
| WO | WO-2006010533 A2 | 2/2006 |
| WO | WO-2006017358 A1 | 2/2006 |
| WO | WO-2006018425 A2 | 2/2006 |
| WO | WO-2006019665 A1 | 2/2006 |
| WO | WO-2006021430 A2 | 3/2006 |
| WO | WO-2006024671 A1 | 3/2006 |
| WO | WO-2006029293 A1 | 3/2006 |
| WO | WO-2006023241 A9 | 5/2006 |
| WO | WO-2006050405 A1 | 5/2006 |
| WO | WO-2006050843 A1 | 5/2006 |
| WO | WO-2006060806 A2 | 6/2006 |
| WO | WO-2006071770 A2 | 7/2006 |
| WO | WO-2006072089 A1 | 7/2006 |
| WO | WO-2006076412 A1 | 7/2006 |
| WO | WO-2006088576 A2 | 8/2006 |
| WO | WO-2006098887 A2 | 9/2006 |
| WO | WO-2006099151 A2 | 9/2006 |
| WO | WO-2006102359 A2 | 9/2006 |
| WO | WO-2006102412 A2 | 9/2006 |
| WO | WO-2006104843 A1 | 10/2006 |
| WO | WO-2006105146 A2 | 10/2006 |
| WO | WO-2006108811 A1 | 10/2006 |
| WO | WO-2006118713 A1 | 11/2006 |
| WO | WO-2006122048 A1 | 11/2006 |
| WO | WO-2006122553 A1 | 11/2006 |
| WO | WO-2006124759 A2 | 11/2006 |
| WO | WO-2006130268 A1 | 12/2006 |
| WO | WO-2006131288 A1 | 12/2006 |
| WO | WO-2006132884 A2 | 12/2006 |
| WO | WO-2006133171 A2 | 12/2006 |
| WO | WO-2007002209 A2 | 1/2007 |
| WO | WO-2007002579 A2 | 1/2007 |
| WO | WO-2007005170 A2 | 1/2007 |
| WO | WO-2007006454 A1 | 1/2007 |
| WO | WO-2007009911 A1 | 1/2007 |
| WO | WO-2007011587 A2 | 1/2007 |
| WO | WO-2007016399 A2 | 2/2007 |
| WO | WO-2007021892 A1 | 2/2007 |
| WO | WO-2007021894 A2 | 2/2007 |
| WO | WO-2007025088 A2 | 3/2007 |
| WO | WO-2007028138 A2 | 3/2007 |
| WO | WO-2007028271 A2 | 3/2007 |
| WO | WO-2007033010 A1 | 3/2007 |
| WO | WO-2007037970 A1 | 4/2007 |
| WO | WO-2007037989 A2 | 4/2007 |
| WO | WO-2007040559 A2 | 4/2007 |
| WO | WO-2007041070 A2 | 4/2007 |
| WO | WO-2007041072 A2 | 4/2007 |
| WO | WO-2007041248 A2 | 4/2007 |
| WO | WO-2007053832 A2 | 5/2007 |
| WO | WO-2007056638 A2 | 5/2007 |
| WO | WO-2007058921 A2 | 5/2007 |
| WO | WO-2007059476 A2 | 5/2007 |
| WO | WO-2007059478 A1 | 5/2007 |
| WO | WO-2007061992 A2 | 5/2007 |
| WO | WO-2007065285 A2 | 6/2007 |
| WO | WO-2007070486 A2 | 6/2007 |
| WO | WO-2007076303 A1 | 7/2007 |
| WO | WO-2007079015 A2 | 7/2007 |
| WO | WO-2007079025 A2 | 7/2007 |
| WO | WO-2007081811 A2 | 7/2007 |
| WO | WO-2007090037 A2 | 8/2007 |
| WO | WO-2007097754 A1 | 8/2007 |
| WO | WO-2007101223 A2 | 9/2007 |
| WO | WO-2007101260 A2 | 9/2007 |
| WO | WO-2007109372 A2 | 9/2007 |
| WO | WO-2007111885 A2 | 10/2007 |
| WO | WO-2007112006 A2 | 10/2007 |
| WO | WO-2007114943 A2 | 10/2007 |
| WO | WO-2007115094 A2 | 10/2007 |
| WO | WO-2007120363 A2 | 10/2007 |
| WO | WO-2007127606 A1 | 11/2007 |
| WO | WO-2007127622 A2 | 11/2007 |
| WO | WO-2007127879 A2 | 11/2007 |
| WO | WO-2007127880 A2 | 11/2007 |
| WO | WO-2007130239 A1 | 11/2007 |
| WO | WO-2007137286 A2 | 11/2007 |
| WO | WO-2007143225 A2 | 12/2007 |
| WO | WO-2008001091 A1 | 1/2008 |
| WO | WO-2008003003 A2 | 1/2008 |
| WO | WO-2008005780 A2 | 1/2008 |
| WO | WO-2008013849 A2 | 1/2008 |
| WO | WO-2008016486 A2 | 2/2008 |
| WO | WO-2008021913 A2 | 2/2008 |
| WO | WO-2008022021 A2 | 2/2008 |
| WO | WO-2008028644 A1 | 3/2008 |
| WO | WO-2008031106 A2 | 3/2008 |
| WO | WO-2008031110 A2 | 3/2008 |
| WO | WO-2008037485 A1 | 4/2008 |
| WO | WO-2008039944 A2 | 4/2008 |
| WO | WO-2008039946 A2 | 4/2008 |
| WO | WO-2008039949 A2 | 4/2008 |
| WO | WO-2008042760 A2 | 4/2008 |
| WO | WO-2008048709 A1 | 4/2008 |
| WO | WO-2008051407 A2 | 5/2008 |
| WO | WO-2008051924 A2 | 5/2008 |

(56) References Cited

FOREIGN PATENT DOCUMENTS

| | | |
|---|---|---|
| WO | WO-2008052199 A2 | 5/2008 |
| WO | WO-2008055037 A2 | 5/2008 |
| WO | WO-2008055128 A1 | 5/2008 |
| WO | WO-2008055199 A1 | 5/2008 |
| WO | WO-2008067314 A2 | 6/2008 |
| WO | WO-2008069931 A1 | 6/2008 |
| WO | WO-2008069932 A1 | 6/2008 |
| WO | WO-2008073813 A1 | 6/2008 |
| WO | WO-2008076868 A2 | 6/2008 |
| WO | WO-2008079616 A1 | 7/2008 |
| WO | WO-2008080591 A1 | 7/2008 |
| WO | WO-2008083379 A1 | 7/2008 |
| WO | WO-2008088490 A1 | 7/2008 |
| WO | WO-2008094249 A1 | 8/2008 |
| WO | WO-2008101211 A2 | 8/2008 |
| WO | WO-2008101217 A2 | 8/2008 |
| WO | WO-2008103620 A2 | 8/2008 |
| WO | WO-2008116329 A1 | 10/2008 |
| WO | WO-2008118257 A1 | 10/2008 |
| WO | WO-2008119470 A1 | 10/2008 |
| WO | WO-2008124597 A1 | 10/2008 |
| WO | WO-2008134441 A1 | 11/2008 |
| WO | WO-2008135453 A1 | 11/2008 |
| WO | WO-2008137405 A1 | 11/2008 |
| WO | WO-2008138006 A2 | 11/2008 |
| WO | WO-2008150280 A1 | 12/2008 |
| WO | WO-2008150917 A1 | 12/2008 |
| WO | WO-2008150946 A1 | 12/2008 |
| WO | WO-2008150949 A1 | 12/2008 |
| WO | WO-2009006139 A2 | 1/2009 |
| WO | WO-2009105709 A1 | 8/2009 |

OTHER PUBLICATIONS

Aalders, et al., "Development of a Wearable Glucose Sensor; Studies in Healthy Volunteers and in Diabetic Patients," The International Journal of Artificial Organs, 1991, vol. 14, No. 2, pp. 102-108.
Abe, et al., "Characterization of Glucose Microsensors for Intracellular Measurements," Analytical Chemistry, 1992, vol. 64, No. 18, pp. 2160-2163.
Abel, et al., "Biosensors for in Vivo Glucose Measurements: Can We Cross the Experimental Stage," Biosensors & Bioelectronics, 2002, vol. 17, pp. 1059-1070.
Abel, et al., "Experience With an Implantable Glucose Sensor as a Prerequisite of an Artificial Beta Cell," Biomed. Biochim. Actan, 1984, vol. 43, No. 5, pp. 577-584.
Adilman, et al., "Videogames: Knowing the Score, Creative Computing," Dec. 1983, Dialog: File 148; IAC Trade & Industry Database, vol. 9, p. 224(5) (9 pages).
Alberts B., et al., "Molecular Biology of the Cell," 3rd edition, 1994, p. G19 (3 pages).
Alcock S.J., et al., "Continuous Analyte Monitoring to Aid Clinical Practice," IEEE Engineering in Medicine & Biology, 1994, vol. 13, pp. 319-325.
Amato, et al., "Experience with the Polytetrafluoroethylene Surgical Membrane for Pericardial Closure in Operations for Congenital Cardiac Defects," Journal of Thoracic and Cardiovascular Surgery, 1989, vol. 97, pp. 929-934.
Amer M.M.B., "An Accurate Amperometric Glucose Sensor Based Glucometer with Eliminated Cross-Sensitivity," Journal of Medical Engineering & Technology, vol. 26 (5), Sep./Oct. 2002, pp. 208-213.
Amin R., et al., "Hypoglycemia Prevalence in Prepubertal Children With Type 1 Diabetes on Standard Insulin Regimen: Use of Continuous Glucose Monitoring System," Diabetes Care, 2003, vol. 26, No. 3, pp. 662-667.
Armour J.C., et al., "Application of Chronic Intravascular Blood Glucose Sensor in Dogs," Diabetes, Dec. 1990, vol. 39, pp. 1519-1526.
Asberg P., et al., "Hydrogels of a Conducting Conjugated Polymer as 3-D Enzyme Electrode," Biosensors Bioelectronics, 2003, vol. 19, pp. 199-207.
Asker.Co.JP, "What is durometer?," /Product/, Kobunshi Keiki Co., Ltd. retrieved from http://www.asker.co.jp/en/products/durometer/analog/about/index.html on May 9, 2018, 2 pages.
Assolant-Vinet C.H., et al., "New Immobilized Enzyme Membranes for Tailor-Made Biosensors," Analytical Letters, 1986, vol. 19(7 &8), pp. 875-885.
ASTM International, Inc., "ASTM, Designation: D2240-05, Standard Test Method for Rubber Property-Durometer Hardness," 2005, 13 pages.
Atanasov P., et al., "Biosensor for Continuous Glucose Monitoring," Biotechnology and Bioengineering, John Wiley & sons Inc, 1994, vol. 43, pp. 262-266.
Atanasov P., et al., "Implantation of a Refillable Glucose Monitoring-Telemetry Device," Biosensors and Bioelectronics, vol. 12 (7), 1997, pp. 669-680.
Aussedat B., et al., "A User-Friendly Method for Calibrating a Subcutaneous Glucose Sensor-Based Hypoglycaemic Alarm," Elsevier Science Limited, Biosensors & Bioelectronic, 1997, vol. 12, No. 11, pp. 1061-1071.
Bailey T.S., et al., "Reduction in Hemoglobin A1C with Real-Time Continuous Glucose Monitoring: Results from a 12-Week Observational Study," Diabetes Technology & Therapeutics, vol. 9 (3), 2007, pp. 203-210.
Baker D.A., et al., "Dynamic Concentration Challenges for Biosensor Characterization," Biosensors & Bioelectronics, vol. 8, 1993, pp. 433-441.
Baker D.A., et al., "Dynamic Delay and Maximal Dynamic Error in Continuous Biosensors," Analytical Chemistry, vol. 68 (8), Apr. 15, 1996, pp. 1292-1297.
Bard A.J., et al., "Electrochemical Methods," Fundamentals and Applications, John Wiley & Sons, New York, 1980, pp. 173-175.
Bardeletti G., et al., "A Reliable L-Lactate Electrode with a New Membrane for Enzyme Immobilization for Amperometric Assay of Lactate," Analytica Chemica Acta, vol. 187, 1986, pp. 47-54.
Beach R.D., et al., "Subminiature Implantable Potentiostat and Modified Commercial Telemetry Device for Remote Glucose Monitoring," IEEE Transactions on Instrumentation and Measurement, vol. 48 (6), Dec. 1999, pp. 1239-1245.
Bellucci F., et al., "Electrochemical Behaviour of Graphite-Epoxy Composite Materials (GECM) in Aqueous Salt Solutions," Journal of Applied Electrochemistry, vol. 16 (1), Jan. 1986, pp. 15-22.
Bergveld, et al., "Fabrication and Mass Production," Advances in Biosensors, Supplement 1, Chapter 6, 1993, pp. 165-186.
Bertrand C., et al., "Multipurpose Electrode with Different Enzyme Systems Bound to Collagen Films," Analytica Chemica Acta, 1981, vol. 126, pp. 23-34.
Bessman S.P., et al., "Progress toward a Glucose Sensor for the Artificial Pancreas," Proceedings of a Workshop on Ion-Selective Microelectrodes, Jun. 4-5, 1973, Boston University, 1973, pp. 189-197.
Biermann E., et al., "How Would Patients Behave if they were Continually Informed of their Blood Glucose Levels? a Simulation Study Using A "Virtual" Patient," Diabetes Technology & Therapeutics, vol. 10 (3), 2008, pp. 178-187.
Bindra D.S., et al., "Design and in Vitro Studies of a Needle-Type Glucose Sensor for Subcutaneous Monitoring," Analytical Chemistry, vol. 63, Sep. 1, 1991, pp. 1692-1696.
Bindra D.S., et al., "Pulsed Amperometric Detection of Glucose in Biological Fluids at a Surface-Modified Gold Electrode," Analytical Chemistry, vol. 61 (22), Nov. 15, 1989, pp. 2566-2570.
Bisenberger M., et al., "A Triple-Step Potential Waveform at Enzyme Multisensors with Thick-Film Gold Electrodes for Detection of Glucose and Sucrose," Sensors and Actuators B, vol. 28, 1995, pp. 181-189.
Bland J.M., et al., "A Note on the Use of the Intraclass Correlation Coefficient in the Evaluation of Agreement between Two Methods of Measurement," Computers in Biology and Medicine, vol. 20 (5), 1990, pp. 337-340.
Bland J.M., et al., "Statistical Methods for Assessing Agreement Between Two Methods of Clinical Measurement," The Lancet, Feb. 8, 1986, pp. 307-310.

(56) References Cited

OTHER PUBLICATIONS

Bobbioni-Harsch E., et al., "Lifespan of Subcutaneous Glucose Sensors and their Performances during Dynamic Glycaemia Changes in Rats," J. Biomed. Eng., vol. 15, 1993, pp. 457-463.

Bode B.W., "Clinical Utility of the Continuous Glucose Monitoring System," Diabetes Technology & Therapeutics, vol. 2, Supplement 1, 2000, pp. S35-S41.

Bode B.W., et al., "Continuous Glucose Monitoring Used to Adjust Diabetes Therapy Improves Glycosylated Hemoglobin: A Pilot Study," Diabetes Research and Clinical Practice, vol. 46, 1999, pp. 183-190.

Bode B.W., et al., "Using the Continuous Glucose Monitoring System to Improve the Management of Type 1 Diabetes," Diabetes Technology & Therapeutics, vol. 2, Supplement 1, 2000, pp. S43-S48.

Boedeker Plastics Inc, "Polyethylene Specifications," Polyethylene Data Sheet, Retrieved from http://www.boedeker.com/polye.sub.--p.htm on Aug. 19, 2009, 4 pages.

Boland E., et al., "Limitations of Conventional Methods of Self-Monitoring of Blood Glucose," Diabetes Care, vol. 24 (11), Nov. 2001, pp. 1858-1862.

Bolinder J., et al., "Self-Monitoring of Blood Glucose in Type I Diabetic Patients: Comparison with Continuous Microdialysis Measurements of Glucose in Subcutaneous Adipose Tissue during Ordinary Life Conditions," Diabetes Care, vol. 20 (1), Jan. 1997, pp. 64-70.

Bolinder J., et al., "Microdialysis Measurement of the Absolute Glucose Concentration in Subcutaneous Adipose Tissue Allowing Glucose Monitoring in Diabetic Patients," Rapid Communication, Diabetologia, vol. 35, 1992, pp. 1177-1180.

Bott A.W., "A Comparison of Cyclic Voltammetry and Cyclic Staircase Voltammetry," Current Separations, vol. 16 (1), 1997, pp. 23-26.

Bott A.W., "Electrochemical Methods for the Determination of Glucose," Current Separations, vol. 17 (1), 1998, pp. 25-31.

Bowman L., et al., "The Packaging of Implantable Integrated Sensors," IEEE Transactions in Biomedical Engineering, vol. BME-33 (2), Feb. 1986, pp. 248-255.

Brauker, et al., "Sustained Expression of High Levels of Human Factor IX from Human Cells Implanted within an Immunoisolation Device into Athymic Rodents," Human Gene Therapy, Apr. 10, 1998, vol. 9, pp. 879-888.

Brauker J., et al., "Local Inflammatory Response Around Diffusion Chambers Containing Xenografts," Transplantation, vol. 61 (12), Jun. 27, 1996, pp. 1671-1677.

Brauker J H., et al., "Neovascularization of Synthetic Membranes Directed by Membrane Microarchitecture," Journal of Biomedical Material Research, 1995, vol. 29, pp. 1517-1524.

Brauker J., "Unraveling Mysteries at the Biointerface: Molecular Mediator of Inhibition of Blood Vessel Formation in the Foreign Body Capsule Revealed," SurFACTS in Biomaterials, vol. 6 (3), 2001, pp. 1,5.

Braunwald E., "Biomarkers in Heart Failure," Medical Progress, The New England Journal of Medicine, vol. 358, May 15, 2008, pp. 2148-2159.

Bremer T., et al., "Is Blood Glucose Predictable from Previous Values? A Solicitation for Data," Perspectives in Diabetes, vol. 48, Mar. 1999, pp. 445-451.

Bremer T.M., et al., "Benchmark Data from the Literature for Evaluation of New Glucose Sensing Technologies," Diabetes Technology & Therapeutics, vol. 3 (3), 2001, pp. 409-418.

Brooks S.L., et al., "Development of an On-line Glucose Sensor for Fermentation Monitoring," Biosensors, vol. 3, 1987/1988, pp. 45-56.

Bruckel J., et al., "In Vivo Measurement of Subcutaneous Glucose Concentrations with an Enzymatic Glucose Sensor and a Wick Method," Klin Wochenschr, vol. 67, 1989, pp. 491-495.

Brunner G.A., et al., "Validation of Home Blood Glucose Meters with Respect to Clinical and Analytical Approaches," Diabetes Care, vol. 21, No. 4, Apr. 1998, pp. 585-590.

Brunstein E., et al., "Preparation and Validation of Implantable Electrodes for the Measurement of Oxygen and Glucose," Biomed Biochim. Acta, vol. 48 (11/12), 1989, pp. 911-917.

Cai Q., et al., "A Wireless, Remote Query Glucose Biosensor Based on a pH-Sensitive Polymer," Analytical Chemistry, vol. 76 (14), Jul. 15, 2004, pp. 4038-4043.

Cameron T., et al., "Micromodular Implants to Provide Electrical Stimulation of Paralyzed Muscles and Limbs," IEEE Transactions on Biomedical Engineering, vol. 44 (9), Sep. 1997, pp. 781-790.

Campanella L., et al., "Biosensor for Direct Determination of Glucose and Lactate in Undiluted Biological Fluids," Biosensors & Bioelectronics, vol. 8, 1993, pp. 307-314.

Candas B., et al., "An Adaptive Plasma Glucose Controller Based on a Nonlinear Insulin/Glucose Model," IEEE Transactions on Biomedical Engineering, vol. 41 (2), Feb. 1994, pp. 116-124.

Cass A.E.G., et al., "Ferrocene-Mediated Enzyme Electrodes for Amperometric Determination of Glucose," Analytical Chemistry, vol. 56 (4), Apr. 1984, pp. 667-671.

Cassidy J.F., et al., "Novel Electrochemical Device for the Detection of Cholesterol or Glucose," Analyst, vol. 118, Apr. 1993, pp. 415-418.

Chase H.P., et al., "Continuous Subcutaneous Glucose Monitoring in Children with Type 1 Diabetes," Pediatrics, vol. 107 (2), Feb. 2001, pp. 222-226.

Chatterjee G., et al., "Poly(ether urethane) and Poly(ether urethane urea) Membranes with High H2S/CH4 Selectivity," Journal of Membrane Science, vol. 135, 1997, pp. 99-106.

Chen C., et al., "A Noninterference Polypyrrole Glucose Biosensor," Biosensors and Bioelectronics, vol. 22, 2006, pp. 639-643.

Chen T., et al., "Defining the Period of Recovery of the Glucose Concentration after its Local Perturbation by the Implantation of a Miniature Sensor," Clinical Chemistry and Laboratory Medicine, vol. 40 (8), 2002, pp. 786-789.

Chia C.W., et al., "Glucose Sensors: Toward Closed Loop Insulin Delivery," Endocrinology and Metabolism Clinics of North America, vol. 33, 2004, pp. 175-195.

Choleau C., et al., "Calibration of a Subcutaneous Amperometric Glucose Sensor Implanted for 7 Days in Diabetic Patients Part 2. Superiority of the One-point Calibration Method," Biosensors and Bioelectronics, vol. 17 (8), 2002, pp. 647-654.

Choleau C., et al., "Calibration of a Subcutaneous Amperometric Glucose Sensor Part 1. Effect of Measurement Uncertainties on the Determination of Sensor Sensitivity and Background Current," Biosensors and Bioelectronics, vol. 17, 2002, pp. 641-646.

CIBA Specialty Chemicals, "Ciba® IRGACURE® 2959," Coating Effects Segment, Photoinitiator Product Description, Basel Switzerland, Apr. 2, 1998, 3 pages.

Claremont D.J., et al., "Potentially-Implantable, Ferrocene-Mediated Glucose Sensor," Journal of Biomedical Engineering, vol. 8, Jul. 1986, pp. 272-274.

Claremont D.J., et al., "Subcutaneous Implantation of a Ferrocene-Mediated Glucose Sensor in Pigs," Diabetologia, vol. 29, 1986, pp. 817-821.

Clark L.C., et al., "Configurational Cyclic Voltammetry: Increasing the Specificity and Reliability of Implanted Electrodes," IEEE/Ninth Annual Conference of the Engineering in Medicine and Biology Society, 1987, pp. 0782-0783.

Clark L.C., et al., "Long-Term Stability of Electroenzymatic Glucose Sensors Implanted in Mice," vol. XXXIV, Transactions—American Society for Artificial Internal Organs, 1988, vol. 34, pp. 259-265.

Clark L.C., et al., "One-Minute Electrochemical Enzymic Assay for Cholesterol in Biological Materials," Clinical Chemistry, vol. 27 (12), 1981, pp. 1978-1982.

Clarke W.L., et al., "Evaluating Clinical Accuracy of Systems for Self Monitoring of Blood Glucose," Technical Articles, Diabetes Care, vol. 10 (5), Sep.-Oct. 1987, pp. 622-628.

Clarke W.L., et al., "Evaluating the Clinical Accuracy of Two Continuous Glucose Sensors Using Continuous Glucose-Error Grid Analysis," Emerging Treatment and Technologies, Diabetes Care, vol. 28(10), Oct. 2005, pp. 2412-2417.

(56) References Cited

OTHER PUBLICATIONS

Colangelo V.J., et al., "Corrosion Rate Measurements in Vivo," Journal of Biomedical Materials Research, vol. 1, 1967, pp. 405-414.
Colowick S.P., et al., "Methods in Enzymology," vol. XLIV, Immobilized Enzymes, Edited by Mosbach K, New York Academic Press, 1976, 11 pages.
Copeland J.G., et al., "Synthetic Membrane Neo-Pericardium Facilitates Total Artificial Heart Explanation," The Journal of Heart Lung Transplantation, vol. 20(6), Jun. 2001, pp. 654-656.
Coulet P.R., et al., "Enzymes Immobilized on Collagen Membranes: A Tool for Fundamental Research and Enzyme Engineering," Journal of Chromatography, vol. 215, 1981, pp. 65-72.
Coulet P.R., "Polymeric Membranes and Coupled Enzymes in the Design of Biosensors," Journal of Membrane Science, 1992, vol. 68, pp. 217-228.
Cox D.J., et al., "Accuracy of Perceiving Blood Glucose in IDDM," Diabetes Care, vol. 8 (6), Nov.-Dec. 1985, pp. 529-536.
Csoregi E., et al., "Amperometric Microbiosensors for Detection of Hydrogen Peroxide and Glucose Based on Peroxidase-Modified Carbon Fibers," Electroanalysis, vol. 6, 1994, pp. 925-933.
Csoregi E., et al., "Design, Characterization and One-Point in Vivo Calibration of a Subcutaneously Implanted Glucose Electrode," American Chemical Society, Analytical Chemistry, vol. 66 (19), Oct. 1, 1994, pp. 3131-3138.
Currie J.F., et al., "Novel Non-Intrusive Trans-Dermal Remote Wireless Micro-Fluidic Monitoring System Applied to Continuous Glucose and Lactate Assays for Casualty Care and Combat Readiness Assessment," RTO HFM Symposium, RTO-MP-HFM-109, Aug. 16-18, 2004, pp. '24-1'-'24-18'.
Dai W.S., et al., "Hydrogel Membranes with Mesh Size Asymmetry based on the Gradient Crosslinking of Poly(Vinyl Alcohol)," Journal of Membrane Science, 1999, vol. 156, pp. 67-79.
Danielsson B., et al., "Enzyme Thermistors," Methods in Enzymology, vol. 137, 1988, pp. 181-197.
D'Arrigo G., et al., "Porous-Si Based Bio Reactors for Glucose Monitoring and Drugs Production," Proceedings of SPIE, 2003, vol. 4982, pp. 178-184.
Dassau E., et al., "In Silico Evaluation Platform for Artificial Pancreatic β-Cell Development—A Dynamic Simulator for Closed-Loop Control with Hardware-in-the-loop," Diabetes Technology & Therapeutics, vol. 11 (3), 2009, pp. 1-8.
Dassau E., et al., "Real-Time Hypoglycemia Prediction Suite Using Continuous Glucose Monitoring," Emerging Treatment and Technologies, Diabetes Care, vol. 33 (6), Jun. 2010, pp. 1249-1254.
Davies M.L., et al., "Polymer Membranes in Clinical Sensor Applications," An overview of membrane function, Biomaterials, vol. 13 (14), 1992, pp. 971-978.
Davis G., et al., "Bioelectrochemical Fuel Cell and Sensor Based on a Quinoprotein, Alcohol Dehydrogenase," Enzyme and Microbial Technology, vol. 5 (5), Sep. 1983, pp. 383-388.
Declaration presented during Opposition proceedings EP2407094, Pace L., Nov. 13, 2015, 6 pages.
Declaration presented during Opposition proceedings EP2407094, Schoonmaker R., Dec. 14, 2015, 10 pages.
Definition of plunger: https://www.merriam-webster.com/dictionary/plunger, dated Nov. 7, 2016, 2 pages.
Deutsch T., et al., "Time Series Analysis and Control of Blood Glucose Levels in Diabetic Patients," Computer Methods and Programs in Biomedicine, Elsevier Scientific Publishers, vol. 41, 1994, pp. 167-182.
Dixon B.M., et al., "Characterization in Vitro and in Vivo of the Oxygen Dependence of an Enzyme/Polymer Biosensor for Monitoring Brain Glucose," Journal of Neuroscience Methods, vol. 119, 2002, pp. 135-142.
Dobson D.E., et al.,"1-Butyrul-Glycerol: A Novel Angiogenesis Factor Secreted by Differentiating Adipocytes," Cell, Apr. 20, 1990, vol. 61 (2), pp. 223-230.
DuPont, "Dimension® AR Clinical Chemistry System," The Chemistry Analyzer that Makes the most of your Time, Money and Effort, Dade International, Chemistry Systems, Newark, 1998, 18 pages.
Durliat H., et al., "Spectrophotometric and Electrochemical Determinations of L( +)-Lactate in Blood by Use of Lactate Dehydrogenase from Yeast," Clinical Chemistry, vol. 22 (11), 1976, pp. 1802-1805.
Edwards Lifesciences, "Accuracy for You and Your Patients," Marketing materials, 2002, 4 pages.
El Degheidy M.M., et al., "Optimization of an Implantable Coated Wire Glucose Sensor," Journal of Biomedical Engineering, vol. 8, Apr. 1986, pp. 121-129.
Elco Diagnostics Company, "Direct 30/30® Blood Glucose Sensor," Markwell Medical Catalog, 1990, 1 page.
El-Khatib F.H., et al., "Adaptive Closed-Loop Control Provides Blood-Glucose Regulation Using Dual Subcutaneous Insulin and Glucagon Infusion in Diabetic Swine," Journal of Diabetes Science and Technology, Diabetes Technology Society, vol. 1 (2), 2007, pp. 181-192.
El-Sa'ad L., et al., "Moisture Absorption by Epoxy Resins: The Reverse Thermal Effect," Journal of Materials Science, vol. 25, 1990, pp. 3577-3582.
English D., et al., "Platelet-Released Phospholipids Link Haemostasis and Angiogenesis," Cardiovascular Research, 2001, vol. 49, pp. 588-599.
Ernst H., et al., "Reliable Glucose Monitoring Through the Use of Microsystem Technology," Analytical Bioanalytical Chemistry, vol. 373, 2002, pp. 758-761.
European Electronic File History for EP Application No. 10195447.7, filed Jul. 13, 2005—withdrawn, 200 pages.
European Electronic File History for EP Application No. 10195504.5, filed Jul. 13, 2005, 184 pages—withdrawn.
European Electronic File History for EP Application No. 11182615.2, filed Feb. 22, 2006, 344 pages.
European Electronic File History for EP Application No. 11182630.1, filed Sep. 23, 2011, 336 pages.
European Electronic File History for EP Application No. 14184330.0, filed Sep. 10, 2014, 377 pages.
European Electronic File History for EP Application No. 17198022.0, filed Oct. 24, 2017, 339 pages.
European Electronic File History for EP Patent Application No. 06773682.7 filed Jun. 20, 2006, 1697 pages.
European Electronic File History for EP Patent No. 1804650 (05771643.3) granted Mar. 14, 2012, 3733 pages.
European Electronic File History for EP Patent No. 1855588 (06748336.2), granted Nov. 21, 2007, 862 pages.
European Electronic File History for EP Patent No. 1986543 (06736006.5) granted Dec. 14, 2011, 1895 pages.
European Electronic File History for EP Patent No. 2322094 (10195496.4) granted Mar. 5, 2014, 1778 pages.
European Electronic File History for EP Patent No. 2327362 (10195517.7) granted Nov. 13, 2013, 423 pages.
European Electronic File History for EP Patent No. 2327984 (10195521.9) granted Feb. 25, 2015, 394 pages.
European Electronic File History for EP Patent No. 2329770 (10195509.4) granted Sep. 10, 2014, 1274 pages.
European Electronic File History for EP Patent No. 2332466 (10195483.2) granted Apr. 9, 2014, 484 pages.
European Electronic File History for EP Patent No. 2335582 (10195511.0) granted Sep. 10, 2014, 608 pages.
European Electronic File History for EP Patent No. 2335583 (10195520.1) granted Mar. 18, 2015, 677 pages.
European Electronic File History for EP Patent No. 2335584 (10195519.3) granted Jun. 17, 2015, 796 pages.
European Electronic File History for EP Patent No. 2335585 (10195508.6) granted Sep. 7, 2016, 722 pages.
European Electronic File History for EP Patent No. 2335586 (10195514.4) granted Feb. 19, 2014, 526 pages.
European Electronic File History for EP Patent No. 2335587 (10195518.5) granted Feb. 19, 2014, 5531 pages.
European Electronic File History for EP Patent No. 2407094 (11182622.8) granted Oct. 22, 2014, 2417 pages.
European Electronic File History for EP Patent No. 2499969 (12151826.0) granted Jun. 4, 2014, 814 pages.

(56) References Cited

OTHER PUBLICATIONS

European Electronic File History for EP Patent No. 2517623 (12151823.7) granted Mar. 2, 2016, 864 pages.
European Electronic File History for EP Patent No. 2532302 (12151819.5) granted Nov. 18, 2015, 845 pages.
European Electronic File History for EP Patent No. 2532305 (12171365.5) granted Aug. 13, 2014, 504 pages.
European Electronic File History for EP Patent No. 2561807 (12193934.2) granted Oct. 5, 2016, revoked Jan. 31, 2019, 2496 pages.
European Electronic File History for EP Patent No. 2596747 (13156245.6) granted Oct. 25, 2017, 1091 pages.
European Electronic File History for EP Publication No. 3001952 (15195173.8), published Apr. 16, 2016, 237 pages.
European Electronic File History for EP Publication No. 3111832 (16179208.0), published Jan. 4, 2017—pending, 191 pages.
European Search Report for Application No. 98908875.2 dated Apr. 29, 2004, 5 pages.
Extended European Search Report for Application No. 20174073.5 dated Sep. 4, 2020, 8 pages.
Extended European Search Report for Application No. 20174075.0 dated Sep. 4, 2020, 8 pages.
Extended European Search Report for Application No. 06718980.3 dated Mar. 9, 2010, 8 pages.
Extended European Search Report for Application No. 19185160.9 dated Sep. 23, 2019, 8 pages.
Extended European Search Report for Application No. 20156336.8 dated Apr. 23, 2020, 7 pages.
Fabietti P.G., et al., "Clinical Validation of a New Control-Oriented Model of Insulin and Glucose Dynamics in Subjects with Type 1 Diabetes," Diabetes Technology & Therapeutics, vol. 9 (4), 2007, pp. 327-338.
Fahy B.G., et al., "An Analysis: Hyperglycemic Intensive Care Patients Need Continuous Glucose Monitoring-Easier Said Than Done," Journal of Diabetes Science and Technology, Diabetes Technology Society, vol. 2 (2), Mar. 2008, pp. 201-204.
Fare T.L., et al., "Functional Characterization of a Conducting Polymer-Based Immunoassay System," Biosensors & Bioelectronics, vol. 13 (3-4), 1998, pp. 459-470.
Farlex, Inc., "Statistical Distribution—Definition of Statistical Distribution by the Free Dictionary—Thesaurus," 2003-2016, 2 pages.
Farlex, Inc, Definition of term "elastomeric", Free Dictionary, Copyright 2008, retrieved from http://www.thefreedictionary.com/elastomeric, 3 pages.
Feldman B., et al., "A Continuous Glucose Sensor Based on Wired EnzymeTM Technology—Results from a 3-Day Trial in Patients with Type 1 Diabetes," Diabetes Technology & Therapeutics, vol. 5 (5), 2003, pp. 769-779.
File History of U.S. Appl. No. 11/334,107, filed Jan. 17, 2006, 191 pages.
File History of U.S. Appl. No. 11/842,139, filed Aug. 21, 2007, 274 pages.
File History of U.S. Appl. No. 11/842,142, filed Aug. 21, 2007, 163 pages.
File History of U.S. Appl. No. 11/842,146, filed Aug. 21, 2007, 252 pages.
File History of U.S. Appl. No. 11/842,148, filed Aug. 21, 2007, 166 pages.
File History of U.S. Appl. No. 11/842,154, filed Aug. 21, 2007, 199 pages.
File History of European Patent Application No. 19185160.9, filed on Mar. 10, 2006, 541 pages.
File History of U.S. Appl. No. 09/334,996, filed Jun. 17, 1999, 36 pages.
File History of U.S. Appl. No. 09/447,227, filed Nov. 22, 1999, 1184 pages.
File History of U.S. Appl. No. 09/489,588, filed Jan. 21, 2000, 412 pages.
File History of U.S. Appl. No. 09/636,369, filed Aug. 11, 2000, 91 pages.
File History of U.S. Appl. No. 09/916,711, filed Jul. 27, 2001, 400 pages.
File History of U.S. Appl. No. 09/916,858, filed Jul. 27, 2001, 243 pages.
File History of U.S. Appl. No. 10/153,356, filed May 22, 2002, 326 pages.
File History of U.S. Appl. No. 10/632,537, filed Aug. 1, 2003, 211 pages.
File History of U.S. Appl. No. 10/633,329, filed Aug. 1, 2003, 711 pages.
File History of U.S. Appl. No. 10/633,367, filed Aug. 1, 2003, 432 pages.
File History of U.S. Appl. No. 10/633,404, filed Aug. 1, 2003, 270 pages.
File History of U.S. Appl. No. 10/646,333, filed Aug. 22, 2003, 303 pages.
File History of U.S. Appl. No. 10/647,065, filed Aug. 22, 2003, 203 pages.
File History of U.S. Appl. No. 10/648,849, filed Aug. 22, 2003, 803 pages.
File History of U.S. Appl. No. 10/695,636, filed Oct. 28, 2003, 194 pages.
File History of U.S. Appl. No. 10/789,359, filed Feb. 26, 2004, 361 pages.
File History of U.S. Appl. No. 10/838,658, filed May 3, 2004, 748 pages.
File History of U.S. Appl. No. 10/838,909, filed May 3, 2004, 356 pages.
File History of U.S. Appl. No. 10/838,912, filed May 3, 2004, 1288 pages.
File History of U.S. Appl. No. 10/842,716, filed May 10, 2004, 670 pages.
File History of U.S. Appl. No. 10/846,150, filed May 14, 2004, 382 pages.
File History of U.S. Appl. No. 10/885,476, filed Jul. 6, 2004, 226 pages.
File History of U.S. Appl. No. 10/896,637, filed Jul. 21, 2004, 295 pages.
File History of U.S. Appl. No. 10/896,639, filed Jul. 21, 2004, 337 pages.
File History of U.S. Appl. No. 10/896,772, filed Jul. 21, 2004, 210 pages.
File History of U.S. Appl. No. 10/897,312, filed Jul. 21, 2004, 139 pages.
File History of U.S. Appl. No. 10/897,377, filed Jul. 21, 2004, 178 pages.
File History of U.S. Appl. No. 11/039,269, filed Jan. 19, 2005, 209 pages.
File History of U.S. Appl. No. 11/077,643, filed Mar. 10, 2005, 253 pages.
File History of U.S. Appl. No. 11/077,693, filed Mar. 10, 2005, 755 pages.
File History of U.S. Appl. No. 11/077,713, filed Mar. 10, 2005, 1025 pages.
File History of U.S. Appl. No. 11/077,714, filed Mar. 10, 2005, 320 pages.
File History of U.S. Appl. No. 11/077,715, filed Mar. 10, 2005, 717 pages.
File History of U.S. Appl. No. 11/077,739, filed Mar. 10, 2005, 778 pages.
File History of U.S. Appl. No. 11/077,740, filed Mar. 10, 2005, 921 pages.
File History of U.S. Appl. No. 11/077,763, filed Mar. 10, 2005, 515 pages.
File History of U.S. Appl. No. 11/077,765, filed Mar. 10, 2005, 932 pages.
File History of U.S. Appl. No. 11/077,883, filed Mar. 10, 2005, 1159 pages.
File History of U.S. Appl. No. 11/078,072, filed Mar. 10, 2005, 1334 pages.
File History of U.S. Appl. No. 11/078,230, filed Mar. 10, 2005, 535 pages.

(56) References Cited

OTHER PUBLICATIONS

File History of U.S. Appl. No. 11/078,232, filed Mar. 10, 2005, 256 pages.
File History of U.S. Appl. No. 11/157,365, filed Jun. 21, 2005, 977 pages.
File History of U.S. Appl. No. 11/157,746, filed Jun. 21, 2005, 603 pages.
File History of U.S. Appl. No. 11/158,227, filed Jun. 21, 2005, 474 pages.
File History of U.S. Appl. No. 11/201,445, filed Aug. 10, 2005, 120 pages.
File History of U.S. Appl. No. 11/280,102, filed Nov. 16, 2005, 109 pages.
File History of U.S. Appl. No. 11/280,672, filed Nov. 16, 2005, 572 pages.
File History of U.S. Appl. No. 11/333,837, filed Jan. 17, 2006, 672 pages.
File History of U.S. Appl. No. 11/335,879, filed Jan. 18, 2006, 499 pages.
File History of U.S. Appl. No. 11/360,262, filed Feb. 22, 2006, 766 pages.
File History of U.S. Appl. No. 11/360,299, filed Feb. 22, 2006, 676 pages.
File History of U.S. Appl. No. 11/360,819, filed Feb. 22, 2006, 778 pages.
File History of U.S. Appl. No. 11/373,628, filed Mar. 9, 2006, 532 pages.
File History of U.S. Appl. No. 11/411,656, filed Apr. 26, 2006, 285 pages.
File History of U.S. Appl. No. 11/415,593, filed May 2, 2006, 160 pages.
File History of U.S. Appl. No. 11/415,999, filed May 2, 2006, 154 pages.
File History of U.S. Appl. No. 11/416,375, filed May 2, 2006, 153 pages.
File History of U.S. Appl. No. 11/439,559, filed May 23, 2006, 155 pages.
File History of U.S. Appl. No. 11/439,630, filed May 23, 2006, 1237 pages.
File History of U.S. Appl. No. 11/439,800, filed May 23, 2006, 157 pages.
File History of U.S. Appl. No. 11/445,792, filed Jun. 1, 2006, 811 pages.
File History of U.S. Appl. No. 11/503,367, filed Aug. 10, 2006, 1169 pages.
File History of U.S. Appl. No. 11/618,706, filed Dec. 29, 2006, 288 pages.
File History of U.S. Appl. No. 11/681,145, filed Mar. 1, 2007, 684 pages.
File History of U.S. Appl. No. 11/690,752, filed Mar. 23, 2007, 528 pages.
File History of U.S. Appl. No. 11/695,607, filed Apr. 3, 2007, 615 pages.
File History of U.S. Appl. No. 11/734,178, filed Apr. 11, 2007, 512 pages.
File History of U.S. Appl. No. 11/734,184, filed Apr. 11, 2007, 531 pages.
File History of U.S. Appl. No. 11/734,203, filed Apr. 11, 2007, 606 pages.
File History of U.S. Appl. No. 11/742,546, filed Apr. 30, 2007, 348 pages.
File History of U.S. Appl. No. 11/766,747, filed Jun. 21, 2007, 789 pages.
File History of U.S. Appl. No. 11/797,520, filed May 3, 2007, 406 pages.
File History of U.S. Appl. No. 11/797,521, filed May 3, 2007, 374 pages.
File History of U.S. Appl. No. 11/842,143, filed Aug. 21, 2007, 235 pages.
File History of U.S. Appl. No. 11/842,149, filed Aug. 21, 2007, 256 pages.
File History of U.S. Appl. No. 11/842,151 filed Aug. 21, 2007, 252 pages.
File History of U.S. Appl. No. 11/842,157, filed Aug. 21, 2007, 167 pages.
File History of U.S. Appl. No. 11/925,603, filed Oct. 26, 2007, 453 pages.
File History of U.S. Appl. No. 11/928,968, filed Oct. 30, 2007, 741 pages.
File History of U.S. Appl. No. 12/101,790, filed Apr. 11, 2008, 431 pages.
File History of U.S. Appl. No. 12/101,806, filed Apr. 11, 2008, 611 pages.
File History of U.S. Appl. No. 12/101,810, filed Apr. 11, 2008, 569 pages.
File History of U.S. Appl. No. 12/137,396, filed Jun. 11, 2008, 278 pages.
File History of U.S. Appl. No. 12/175,391, filed Jul. 17, 2008, 564 pages.
File History of U.S. Appl. No. 12/245,618, filed Oct. 3, 2008, 214 pages.
File History of U.S. Appl. No. 12/250,918, filed Oct. 14, 2008, 333 pages.
File History of U.S. Appl. No. 12/273,359, filed Nov. 18, 2008, 312 pages.
File History of U.S. Appl. No. 12/329,496, filed Dec. 5, 2008, 438 pages.
File History of U.S. Appl. No. 12/353,870, filed Jan. 14, 2009, 425 pages.
File History of U.S. Appl. No. 12/359,207, filed Jan. 23, 2009, 456 pages.
File History of U.S. Appl. No. 12/364,786, filed Feb. 3, 2009, 1230 pages.
File History of U.S. Appl. No. 12/391,148, filed Feb. 23, 2009, 484 pages.
File History of U.S. Appl. No. 12/393,887, filed Feb. 26, 2009, 502 pages.
File History of U.S. Appl. No. 12/405,883, filed Mar. 17, 2009, 215 pages.
File History of U.S. Appl. No. 12/437,436, filed May 7, 2009, 524 pages.
File History of U.S. Appl. No. 12/537,245, filed Aug. 6, 2009, 107 pages.
File History of U.S. Appl. No. 12/610,866, filed Nov. 2, 2009, 682 pages.
File History of U.S. Appl. No. 12/683,724, filed Jan. 7, 2010, 497 pages.
File History of U.S. Appl. No. 12/683,755, filed Jan. 7, 2010, 694 pages.
File History of U.S. Appl. No. 12/728,032, filed Mar. 19, 2010, 819 pages.
File History of U.S. Appl. No. 12/728,060, filed Mar. 19, 2010, 323 pages.
File History of U.S. Appl. No. 12/728,061, filed Mar. 19, 2010, 437 pages.
File History of U.S. Appl. No. 12/728,082, filed Mar. 19, 2010, 802 pages.
File History of U.S. Appl. No. 12/729,035, filed Mar. 22, 2010, 466 pages.
File History of U.S. Appl. No. 12/729,048, filed Mar. 22, 2010, 488 pages.
File History of U.S. Appl. No. 12/729,058, filed Mar. 22, 2010, 502 pages.
File History of U.S. Appl. No. 12/730,072, filed Mar. 23, 2010, 278 pages.
File History of U.S. Appl. No. 12/748,154, filed Mar. 26, 2010, 419 pages.
File History of U.S. Appl. No. 12/749,139, filed Mar. 29, 2010, 489 pages.
File History of U.S. Appl. No. 12/749,981, filed Mar. 30, 2010, 662 pages.

(56) References Cited

OTHER PUBLICATIONS

File History of U.S. Appl. No. 12/775,315, filed May 6, 2010, 447 pages.
File History of U.S. Appl. No. 12/780,606, filed May 14, 2010, 372 pages.
File History of U.S. Appl. No. 12/780,723, filed May 14, 2010, 519 pages.
File History of U.S. Appl. No. 12/780,725, filed May 14, 2010, 415 pages.
File History of U.S. Appl. No. 12/780,739, filed May 14, 2010, 346 pages.
File History of U.S. Appl. No. 12/780,759, filed May 14, 2010, 348 pages.
File History of U.S. Appl. No. 12/853,235, filed Aug. 9, 2010, 374 pages.
File History of U.S. Appl. No. 13/077,884, filed Mar. 31, 2011, 635 pages.
File History of U.S. Appl. No. 13/086,160, filed Apr. 13, 2011, 967 pages.
File History of U.S. Appl. No. 13/116,871, filed May 26, 2011, 475 pages.
File History of U.S. Appl. No. 13/157,031, filed Jun. 9, 2011, 514 pages.
File History of U.S. Appl. No. 13/172,640, filed Jun. 29, 2011, 436 pages.
File History of U.S. Appl. No. 13/361,820, filed Jan. 30, 2012, 383 pages.
File History of U.S. Appl. No. 13/415,721, filed Mar. 8, 2012, 473 pages.
File History of U.S. Appl. No. 13/547,952, filed Jul. 12, 2012, 539 pages.
File History of U.S. Appl. No. 13/548,627, filed Jul. 13, 2012, 361 pages.
File History of U.S. Appl. No. 13/549,313, filed Jul. 13, 2012, 354 pages.
File History of U.S. Appl. No. 13/607,162, filed Sep. 7, 2012, 420 pages.
File History of U.S. Appl. No. 13/620,574, filed Sep. 14, 2012, 318 pages.
File History of U.S. Appl. No. 13/893,237, filed May 13, 2013, 569 pages.
File History of U.S. Appl. No. 13/903,609, filed May 28, 2013, 401 pages.
File History of U.S. Appl. No. 13/909,962, filed Jun. 4, 2013, 723 pages.
File History of U.S. Appl. No. 13/938,103, filed Jul. 9, 2013, 393 pages.
File History of U.S. Appl. No. 14/144,523, filed Dec. 30, 2013, 405 pages.
File History of U.S. Appl. No. 14/163,346, filed Jan. 24, 2014, 583 pages.
File History of U.S. Appl. No. 14/283,153, filed May 20, 2014, 568 pages.
File History of U.S. Appl. No. 14/293,298, filed Jun. 2, 2014, 565 pages.
File History of U.S. Appl. No. 14/296,735, filed Jun. 5, 2014, 637 pages.
File History of U.S. Appl. No. 14/552,398, filed Nov. 24, 2014, 422 pages.
File History of U.S. Appl. No. 14/590,483, filed Jan. 6, 2015, 556 pages.
File History of U.S. Appl. No. 14/743,777, filed Jun. 18, 2015, 392 pages.
File History of U.S. Appl. No. 14/860,602, filed Sep. 21, 2015, 429 pages.
File History of U.S. Appl. No. 14/923,350, filed Oct. 26, 2015, 476 pages.
File History of U.S. Appl. No. 14/924,030, filed Oct. 27, 2015, 403 pages.
File History of U.S. Appl. No. 15/065,623, filed Mar. 9, 2016, 401 pages.
File History of U.S. Appl. No. 15/201,313, filed Jul. 1, 2016, 800 pages.
File History of U.S. Appl. No. 15/470,766, filed Mar. 27, 2017, 336 pages.
File History of U.S. Appl. No. 15/686,650, filed Aug. 25, 2017, 296 pages.
File History of U.S. Appl. No. 15/719,298, filed Sep. 28, 2017, 258 pages.
File History of U.S. Appl. No. 15/787,595, filed Oct. 18, 2017, 230 pages.
File History of U.S. Appl. No. 15/797,986, filed Oct. 30, 2017, 342 pages.
File History of U.S. Appl. No. 15/798,097, filed Oct. 30, 2017, 323 pages.
File History of U.S. Appl. No. 15/877,311, filed Jan. 22, 2018, 208 pages.
File History of U.S. Appl. No. 15/891,201, filed Feb. 7, 2018, 364 pages.
File History of U.S. Appl. No. 15/967,338, filed Apr. 30, 2018, 191 pages.
File History of U.S. Appl. No. 16/017,668, filed Jun. 25, 2018, 308 pages.
File History of U.S. Appl. No. 16/133,469, filed Sep. 17, 2018, 178 pages.
File History of U.S. Appl. No. 16/137,411, filed Sep. 20, 2018, 174 pages.
File History of U.S. Appl. No. 16/179,662, filed Nov. 2, 2018, 272 pages.
File History of U.S. Appl. No. 16/181,678, filed Nov. 6, 2018, 155 pages.
File History of U.S. Appl. No. 60/362,899, filed Mar. 8, 2002, 67 pages.
File History of U.S. Appl. No. 60/527,892, filed Dec. 8, 2003, 25 pages.
File History of U.S. Appl. No. 60/528,382, filed Dec. 9, 2003, 182 pages.
File History of U.S. Appl. No. 60/587,787, filed Jul. 13, 2004, 70 pages.
File History of U.S. Appl. No. 60/587,800, filed Jul. 13, 2004, 29 pages.
File History of U.S. Appl. No. 60/614,683, filed Sep. 30, 2004, 465 pages.
File History of U.S. Appl. No. 60/614,764, filed Sep. 30, 2004, 657 pages.
File History of U.S. Appl. No. 60/660,743, filed Mar. 10, 2005, 104 pages.
File History of U.S. Appl. No. 90/011,086, filed Jul. 8, 2010, 169 pages.
File History of U.S. Appl. No. 90/011,351, filed Nov. 22, 2010, 260 pages.
File History of U.S. Appl. No. 90/011,663, filed Apr. 29, 2011, 306 pages.
File History of U.S. Appl. No. 90/011,720, filed May 31, 2011, 361 pages.
File History of U.S. Appl. No. 90/011,887, filed Oct. 7, 2011, 769 pages.
File History of U.S. Appl. No. 90/012,558, filed Sep. 13, 2012, 294 pages.
File History of U.S. Appl. No. 95/001,038, filed Apr. 17, 2008, 1332 pages.
File History of U.S. Appl. No. 95/001,039, filed Apr. 17, 2008, 1409 pages.
File History of U.S. Appl. No. 95/002,333, filed Sep. 14, 2012, 556 pages.
File History of U.S. Appl. No. 11/334,876, filed Jan. 18, 2006, 751 pages.
File History of U.S. Appl. No. 11/360,250, filed Feb. 22, 2006, 950 pages.
File History of U.S. Appl. No. 11/360,252, filed Feb. 22, 2006, 594 pages.

(56) References Cited

OTHER PUBLICATIONS

File History of U.S. Appl. No. 90/011,333, filed Nov. 15, 2010, 315 pages.
Fischer U., et al., "Assessment of Subcutaneous Glucose Concentration: Validation of the Wick Technique as a Reference for Implanted Electrochemical Sensors in Normal and Diabetic Dogs," Diabetologia, vol. 30, 1987, pp. 940-945.
Fischer U., et al., "Hypoglycaemia-Warning by Means of Subcutaneous Electrochemical Glucose Sensors: an Animal Study," Horm. Metab. Res, vol. 27, 1995, p. 53. (Abstract Only).
Fischer U., et al., "Oxygen Tension at the Subcutaneous Implantation Site of Glucose Sensors," Biomed. Biochim. Acta, vol. 48 (11/12), 1989, pp. 965-971.
Freedman D., et al., "Statistics," Second Edition, W.W. Norton & Company, New York & London, 1991, p. 74 (3 pages).
Freiberger P., "Video Game Takes on Diabetes Superhero 'Captain Novolin' Offers Treatment Tips," Fourth Edition, Jun. 26, 1992, Business Section, 2 pages.
Frohnauer M.K., et al., "Graphical Human Insulin Time-Activity Profiles Using Standardized Definitions," Diabetes Technology & Therapeutics, vol. 3 (3), 2001, pp. 419-429.
Frost M.C., et al., "Implantable Chemical Sensors for Real-Time Clinical Monitoring: Progress and Challenges," Current Opinion in Chemical Biology, Analytical Techniques, vol. 6, 2002, pp. 633-641.
Gabby R.A., et al., "Optical Coherence Tomography-Based Continuous Noninvasive Glucose Monitoring in Patients with Diabetes," Diabetes Technology & Therapeutics, vol. 10, Nov. 3, 2008, pp. 188-193.
Ganesan N., et al., "Gold Layer-Based Dual Crosslinking Procedure of Glucose Oxidase with Ferrocene Monocarboxylic Acid Provides a Stable Biosensor," Analytical Biochemistry, Notes & Tips, vol. 343, 2005, pp. 188-191.
Ganesh A., et al., "Evaluation of the VIA® Blood Chemistry Monitor for Glucose in Healthy and Diabetic Volunteers," Journal of Diabetes Science and Technology, vol. 2 (2), Mar. 2008, pp. 182-193.
Gao S., et al., "Determination of Interfacial Parameters of Cellulose Acetate Membrane Materials by HPLC," Journal of Liquid Chromatography, 1989, vol. 12(11), pp. 2083-2092.
Garg S.K., et al., "Correlation of Fingerstick Blood Glucose Measurements With GlucoWatch Biographer Glucose Results in Young Subjects With Type 1 Diabetes," Emerging Treatments and Technologies, Diabetes Care, vol. 22 (10), Oct. 1999, pp. 1708-1714.
Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.
Geller R.I., et al., "Use of an Immunoisolation Device for Cell Transplantation and Tumor Immunotherapy," Annals of the New York Academy of Science, 1997, vol. 831, pp. 438-451.
Gerritsen M., et al., "Influence of Inflammatory Cells and Serum on the Performance of Implantable Glucose Sensors," Journal of Biomedical Material Research, 2001, vol. 54, pp. 69-75.
Gerritsen M., et al., "Performance of Subcutaneously Implanted Glucose Sensors for Continuous Monitoring," The Netherlands Journal of Medicine, vol. 54, 1999, pp. 167-179.
Gerritsen M., et al., "Problems Associated with Subcutaneously Implanted Glucose Sensors," Diabetes Care, vol. 23 (2), Feb. 2000, pp. 143-145.
Gilligan B.J., et al., "Evaluation of a Subcutaneous Glucose Sensor Out to 3 Months in a Dog Model" Diabetes Care, vol. 17 (8), Aug. 1994, pp. 882-887.
Gilligan B.J., et al., "Feasibility of Continuous Long-Term Glucose Monitoring from a Subcutaneous Glucose Sensor in Humans," Diabetes Technology & Therapeutics, vol. 6 (3), 2004, pp. 378-386.
Godsland I.F., et al., "Maximizing the Success Rate of Minimal Model Insulin Sensitivity Measurement in Humans: The Importance of Basal Glucose Levels," The Biochemical Society and the Medical Research Society, Clinical Science, vol. 101, 2001, pp. 1-9.
Gore Preclude®, Pericardial Membrane Brochure, Jun. 2009. W.L. Gore & Associates Inc., Flagstaff, AZ 86004.
Gore Preclude®, Pericardial Membrane Brochure, Nov. 2001, W.L. Gore & Associates Inc., Flagstaff, AZ—86004, 4 pages.
Gouda M.D., et al., "Thermal Inactivation of Glucose Oxidase," The Journal of Biological Chemistry, vol. 278 (27), Issue of Jul. 4, 2003, pp. 24324-24333.
Gough D.A., et al., "Frequency Characterization of Blood Glucose Dynamics," Annals of Biomedical Engineering, vol. 31, 2003, pp. 91-97.
Gough D.A., et al., "Immobilized Glucose Oxidase in Implantable Glucose Sensor Technology," Diabetes Technology & Therapeutics, vol. 2 (3), 2000, pp. 377-380.
Gough D.A., "The implantable Glucose Sensor: An Example of Bioengineering Design," Introduction to Bioengineering, 2001, Chapter 3, pp. 57-66.
Gregg B A., et al., "Cross-Linked Redox Gels Containing Glucose Oxidase for Amperometric Biosensor Applications," Anal Chem, 1990, vol. 62, pp. 258-263.
Gross, et al., "Diabetes Technology & Therapeutics," Letters to the Editor, Diabetes Technology & Therapeutics, vol. 3 (1), 2001, pp. 129-131.
Gross T.M., et al., "Efficacy and Reliability of the Continuous Glucose Monitoring System," Diabetes Technology & Therapeutics, vol. 2, Supplement 1, 2000, pp. S19-S26.
Gross T.M., et al., "Performance Evaluation of the Minimed® Continuous Glucose Monitoring System During Patient Home Use," Diabetes Technology & Therapeutics, vol. 2(1), 2000, pp. 49-56.
Guerci B., et al., "Clinical Performance of CGMS in Type 1 Diabetic Patients Treated by Continuous Subcutaneous Insulin Infusion Using Insulin Analogs," Diabetes Care, vol. 26, 2003, pp. 582-589.
Guerra S., et al., "Enhancing the Accuracy of Subcutaneous Glucose Sensors: A Real-Time Deconvolution-Based Approach," IEEE Transactions on Biomedical Engineering, vol. 59(6), Jun. 2012, pp. 1658-1669.
Guo M., et al., "Modification of Cellulose Acetate Ultrafiltration Membrane by Gamma Ray Radiation," Shuichuli Jishi Bianji Weiyuanhui, 1998, vol. 23(6), pp. 315-318. (Abstract only).
Hall S.B., et al., "Electrochemical Oxidation of Hydrogen Peroxide at Platinum Electrodes. Part 1. An Adsorption-controlled Mechanism," Electrochimica Acta, vol. 43, Nos. 5/6, 1998, pp. 579-588.
Hall S.B., et al., "Electrochemical Oxidation of Hydrogen Peroxide at Platinum Electrodes. Part II: Effect of potential," Electrochimica Acta, vol. 43 (14-15), 1998, pp. 2015-2024.
Hall S.B., et al., "Electrochemical Oxidation of Hydrogen Peroxide at Platinum Electrodes. Part III: Effect of Temperature," Electrochimica Acta, vol. 44, 1999, pp. 2455-2462.
Hall S.B., et al., "Electrochemical Oxidation of Hydrogen Peroxide at Platinum Electrodes. Part IV: Phosphate Buffer Dependence," Electrochimica Acta, vol. 44, 1999, pp. 4573-4582.
Hall S.B., et al., "Electrochemical Oxidation of Hydrogen Peroxide at Platinum Electrodes. Part V: Inhibition by Chloride," Electrochimica Acta, vol. 45, 2000, pp. 3573-3579.
Halvorsen C., et al., "Vasodilation of Rat Retinal Microvessels Induced by Monobutyrin," Journal of Clinical Investigation, Dec. 1993, vol. 92, pp. 2872-2876.
Hamilton, "Complete Guide to Selecting the Right Hamilton GASTIGHT, MICROLITER, and Specialty Syringe for your Application," Syringe Selection, http://www.hamiltoncompany.com 2006, 20 pages.
Harada, et al., "Long-Term Results of the Clinical Use of an Expanded Polytetrafluoroethylene Surgical Membrane as a Pericardial Substitute," Journal of Thoracic and Cardiovascular Surgery, 1988, vol. 96(5), pp. 811-815.
Harrison, et al., "Characterization of Perfluorosulfonic Acid Polymer Coated Enzyme Electrodes and a Miniaturized Integrated Potentiostat for Glucose Analysis in Whole Blood," Analytical Chemistry, 1988, vol. 60, pp. 2002-2007.
Hashiguchi Y., et al., "Development of a Miniaturized Glucose Monitoring System by Combining a Needle-Type Glucose Sensor with Microdialysis Sampling Method: Long-term subcutaneous

(56) References Cited

OTHER PUBLICATIONS tissue glucose monitoring in ambulatory diabetic patients," Diabetes Care, vol. 17, No. 5, May 1994, pp. 387-396.
Heise T., et al., "Hypoglycemia warning signal and glucose sensors: Requirements and concepts," Diabetes Technology & Therapeutics, vol. 5, No. 4, 2003, pp. 563-571.
Heller A., "Electrical Connection of Enzyme Redox Centers to Electrodes," J. Phys. Chem., vol. 96, 1992, pp. 3579-3587.
Heller A., "Electrical Wiring of Redox Enzymes," Ace. Chem. Res., vol. 23, 1990, pp. 128-134.
Heller A., "Implanted Electrochemical Glucose Sensors for the Management of Diabetes," Annu. Rev., Biomed Eng., vol. 1, 1999, pp. 153-175.
Heller A., "Plugging Metal Connectors into Enzymes," Nature Biotechnology, vol. 21, No. 6, Jun. 2003, pp. 631-632.
Heller, et al., "In vivo Glucose Monitoring with Miniature "Wired" Glucose Oxidase Electrodes," Analytical Sciences, 2001, vol. 17 Supplement, pp. i297-i300.
Heydron W H., et al., "A New Look at Pericardial Substitutes", Journal of Thoracic and Cardiovascular Surgery, 1987, vol. 94(2), pp. 291-296.
Hicks J.M., "In Situ Monitoring," Clinical Chemistry, vol. 31 (12), 1985, pp. 1931-1935.
Hitchman M.L., "Measurement of Dissolved Oxygen," Edited by Elving P.J et al., Chemical Analysis, New York, John Wiley & Sons, vol. 49, Chapter 3, 1978, pp. 34-49 and 59-123.
Hoel P.G., "Elementary Statistics," Fourth Edition, John Wiley & Sons, Inc., 1976, pp. 113-114.
Houghton Mifflin Company, "American Heritage Dictionary," 4th Edition, 2000, pp. 82.
Houghton Mifflin Company, "Xenogenic, the American Heritage Stedman's Medical Dictionary," 2002, Answers.Com, retrieved from http://www.answers.com/topic/xenogenic, on Nov. 7, 2006, 2 pages.
Hrapovic S., et al., "Picoamperometric Detection of Glucose at Ultrasmall Platinum-Based Biosensors Preparation and Characterization," Anal. Chem, vol. 75, 2003, pp. 3308-3315.
Hu Y., et al., "A Needle-Type Enzyme-Based Lactate Sensor for In Vivo Monitoring," Analytica Chimica Acta, vol. 281, 1993, pp. 503-511.
Huang C., et al., "Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode," U.S. Department of Commence/NTIS, 1975, 126 pages.
Huang Q., et al., "A 0.5mW Passive Telemetry IC for Biomedical Applications," Proceedings of the 23rd European Solid-State Circuits Conference (ESSCIRC '97), Southampton, UK, Sep. 16-18, 1997, pp. 172-175.
Hunter I., et al., "Minimally Invasive Glucose Sensor and Insulin Delivery System," MIT Home Automation and Healthcare Consortium, Mar. 31, 2000, Progress Report No. 25, 17 pages.
International Preliminary Examination Report for Application No. PCT/US2002/023903 dated Apr. 20, 2005, 5 pages.
International Preliminary Report on Patentability for Application No. PCT/US2004/023455 dated Jan. 23, 2006, 7 pages.
International Preliminary Report on Patentability for Application No. PCT/US2004/040476 dated Dec. 8, 2006, 4 pages.
International Preliminary Report on Patentability for Application No. PCT/US2005/014696 dated Nov. 7, 2006, 6 pages.
International Preliminary Report on Patentability for Application No. PCT/US2005/024993, dated Jan. 16, 2007, 7 pages.
International Preliminary Report on Patentability for Application No. PCT/US2005/024994 dated Jan. 16, 2007, 8 pages.
International Preliminary Report on Patentability for Application No. PCT/US2006/006574 dated Aug. 26, 2008, 10 pages.
International Preliminary Report on Patentability for Application No. PCT/US2006/008616 dated Mar. 3, 2009, 7 pages.
International Preliminary Report on Patentability for Application No. PCT/US2006/024132, dated Dec. 24, 2007, 6 pages.
International Preliminary Report on Patentability for Application No. PCT/US2006/031496 dated Nov. 27, 2008, 8 pages.
International Preliminary Report on Patentability for Application No. PCT/US2007/005422 dated Sep. 1, 2009, 5 pages.
International Preliminary Report on Patentability for Application No. PCT/US2008/058158, dated Sep. 29, 2009, 9 pages.
International Search Report and Written Opinion for Application No. PCT/US2003/15816 dated Sep. 22, 2003, 4 pages.
International Search Report and Written Opinion for Application No. PCT/US2004/023455 dated Dec. 23, 2004, 8 pages.
International Search Report and Written Opinion for Application No. PCT/US2004/040476 dated Nov. 16, 2006, 4 pages.
International Search Report and Written Opinion for Application No. PCT/US2005/014696 dated Jun. 29, 2006, 8 pages.
International Search Report and Written Opinion for Application No. PCT/US2005/024993, dated Nov. 4, 2005, 12 pages.
International Search Report and Written Opinion for Application No. PCT/US2005/024994 dated Nov. 15, 2005, 11 pages.
International Search Report and Written Opinion for Application No. PCT/US2006/001998 dated Jul. 25, 2006, 5 pages.
International Search Report and Written Opinion for Application No. PCT/US2006/006574 dated Aug. 4, 2006, 13 pages.
International Search Report and Written Opinion for Application No. PCT/US2006/008616 dated Mar. 13, 2008, 9 pages.
International Search Report and Written Opinion for Application No. PCT/US2006/019889 dated Feb. 20, 2007, 6 pages.
International Search Report and Written Opinion for Application No. PCT/US2006/024132, dated Jul. 20, 2007, 6 pages.
International Search Report and Written Opinion for Application No. PCT/US2006/031496 dated Sep. 20, 2007, 9 pages.
International Search Report and Written Opinion for Application No. PCT/US2006/038820 dated Jun. 20, 2007, 7 pages.
International Search Report and Written Opinion for Application No. PCT/US2007/005422 dated May 20, 2008, 5 pages.
International Search Report and Written Opinion for Application No. PCT/US2008/058158, dated Aug. 8, 2008, 10 pages.
International Search Report for Application No. PCT/US2001/023850 dated Jan. 16, 2002, 3 pages.
International Search Report for Application No. PCT/US2002/023903 dated Feb. 27, 2003, 4 pages.
Ishikawa M., et al., "Initial Evaluation of a 290-Mm Diameter Subcutaneous Glucose Sensor: Glucose Monitoring With a Biocompatible, Flexible-Wire, Enzyme-Based Amperometric Microsensor in Diabetic and Nondiabetic Humans," Journal of Diabetes and Its Complications, vol. 12, 1998, pp. 295-301.
Jablecki M., et al., "Simulations of the Frequency Response of Implantable Glucose Sensors," Analytical Chemistry, vol. 72, 2000, 1853-1859.
Jaffari S.A., et al., "Recent Advances in Amperometric Glucose Biosensors for In Vivo Monitoring," Physiological Measurement, 1995, vol. 16, pp. 1-15.
Jaremko J., et al., "Advances Toward the Implantable Artificial Pancreas for Treatment of Diabetes," Diabetes Care, vol. 21 (3), Mar. 1998, pp. 444-450.
Jensen M.B., et al., "Fast Wave Forms for Pulsed Electrochemical Detection of Glucose by Incorporation of Reductive Desorption of Oxidation Products,"Analytical Chemistry, vol. 69 (9), May 1997, pp. 1776-1781.
Jeong R.A., et al., "In Vivo Calibration of the Subcutaneous Amperometric Glucose Sensors Using a Non-Enzyme Electrode," Biosensors and Bioelectronics, Elsevier, vol. 19, 2003, pp. 313-319.
Jeutter D.C., "A Transcutaneous Implanted Battery Recharging and Biotelemeter Power Switching System," IEEE Transactions on Biomedical Engineering, vol. BME-29 (5), May 1982, pp. 314-321.
Jeutter D.C., et al., "Design of a Radio-Linked Implantable Cochlear Prosthesis Using Surface Acoustic Wave Devices," IEEE Transactions on Ultrasonics, Ferroelectrics and Frequency Control, vol. 40 (5), Sep. 1993, pp. 469-477.
Jobst G., et al., "Thin-Film Microbiosensors for Glucose-Lactate Monitoring," Anal Chem, Sep. 15, 1996, vol. 68(18), pp. 3173-3179.

(56) References Cited

OTHER PUBLICATIONS

Johnson K.W., et al., "In Vivo Evaluation of an Electroenzymatic Glucose Sensor Implanted in Subcutaneous Tissue," Biosensors and Bioelectronics, 1992, vol. 7, pp. 709-714.
Johnson K.W., "Reproducible Electrodeposition of Biomolecules for the Fabrication of Miniature Electroenzymatic Biosensors," Sensors and Actuators B, vol. 5, 1991, pp. 85-89.
Johnson R.C., et al., "Abstract: Neovascularization of Cell Transplantation Devices: Role of Membrane Architecture and Encapsulated Tissue," Abstracts of Papers, American Chemical Society, Sep. 7-11, 1997, 214th ACS National Meeting, Part 2, 305-PMSE, 2 pages.
Joung G.B., et al., "An Energy Transmission System for an Artificial Heart Using Leakage Inductance Compensation of Transcutaneous Transformer," IEEE Transactions on Power Electronics, vol. 13 (6), Nov. 1998, pp. 1013-1022.
Jovanovic L.M.D., "The Role of Continuous Glucose Monitoring in Gestational Diabetes Mellitus," Diabetes Technology and Therapeutics, vol. 2 (1), 2000, pp. S67-S71.
Kacaniklic V., et al., "Amperometric Biosensors for Detection of L- and D-Amino Acids Based on Coimmoblized Peroxidase and L- and D-Amino Acid Oxidases in Carbon Paste Electrodes," Electroanalysis, vol. 6, May-Jun. 1994, pp. 381-390.
Kamath A., et al., "Analysis of Time Lags and Other Sources of Error of the DexCom Seven Continuous Glucose Monitor," Diabetics Technology and Therapeutic, Nov. 2009, vol. 11, No. 11, pp. 689-695.
Kamath A., et al., "Calibration of a Continuous Glucose Monitor: Effect of Glucose Rate of Change," Eighth Annual Diabetes Technology Meeting, Nov. 13-15, 2008, pp. A88 (2 pages).
Kang S.K., et al., "In Vitro and Short-Term in Vivo Characteristics of a Kel-F Thin Film Modified Glucose Sensor," Analytical Sciences, vol. 19, Nov. 2003, pp. 1481-1486.
Kaplan S.M., "Wiley Electrical and Electronics Engineering Dictionary," IEEE Press, John Wiley & Sons, Inc., 2004, pp. 141, 142, 548 & 549.
Kargol M., et al., "Studies on the Structural Properties of Porous Membranes: Measurement of Linear Dimensions of Solutes," Biophysical Chemistry, 2001, vol. 91, pp. 263-271.
Karube I., et al., "Microbiosensors for Acetylcholine and Glucose," Biosensors & Bioelectronics, 1993, vol. 8, pp. 219-228.
Kaufman F.R., et al., "A Pilot Study of the Continuous Glucose Monitoring System," Diabetes Care, vol. 24 (12), Dec. 2001, pp. 2030-2034.
Kaufman F.R., "Role of the Continuous Glucose Monitoring System in Pediatric Patients," Diabetes Technology and Therapeutics, vol. 2 (1), 2000, S49-S52.
Kawagoe J.L., et al., "Enzyme-Modified Organic Conducting Salt Microelectrode," Analytical Chemistry, vol. 63, 1991, pp. 2961-2965.
Keedy F.H., et al., "Determination of Urate in Undiluted Whole Blood by Enzyme Electrode," Biosensors and Bioelectronics, vol. 6, 1991, pp. 491-499.
Kerner, et al., "A Potentially Implantable Enzyme Electrode for Amperometric Measurement of Glucose," Hormone and Metabolic Research Supplement, vol. 20, 1988, pp. 8-13.
Kerner W., et al., "The Function of a Hydrogen Peroxide-Detecting Electroenzymatic Glucose Electrode is Markedly Impaired in Human Sub-Cutaneous Tissue and Plasma," Biosensors and Bioelectronics, vol. 8, 1993, pp. 473-482.
Kerner W., "Implantable Glucose Sensors: Present Status and Future Developments," Experimental and Clinical Endocrinol Diabetes, vol. 109 (2), 2001, pp. S341-S346.
Kidd K R., et al., "Angiogenesis and Neovascularization Associated with Extracellular Matrix Modified Porous Implants," Journal of Biomedical Materials Research, 2001, vol. 59(2), pp. 366-377.
Kiechle F.L., "The Impact of Continuous Glucose Monitoring on Hospital Point-of-Care Testing Programs," Diabetes Technology and Therapeutics, vol. 3 (4), 2001, pp. 647-649.
Klonoff D., et al., "Performance Metrics for Continuous Interstitial Glucose Monitoring; Approved Guideline," Clinical and Laboratory Standards Institute, POCT05-A, vol. 28 (33), 2008, 72 pages.
Klueh U., et al., "Inflammation and Glucose Sensors: Use of Dexamethasone to Extend Glucose Sensor Function and Life Span in Vivo," Journal of Diabetes Science and Technology, vol. 1 (4), Jul. 2007, pp. 496-504.
Klueh U., et al., "Use of Vascular Endothelial Cell Growth Factor Gene Transfer to Enhance Implantable Sensor Function in Vivo," Biosensor Function and VEGF-Gene Transfer, vol. 67 (4), 2003, pp. 1072-1086.
Kondo T., et al., "A Miniature Glucose Sensor, Implantable in the Blood Stream," Diabetes Care, vol. 5 (3), May-Jun. 1982, 218-221.
Koschinsky T., et al., "Sensors for Glucose Monitoring: Technical and Clinical Aspects," Diabetes Metabolism Research and Reviews, vol. 17, No. 2, Jan. 1, 2001, pp. 113-123.
Koschinsky T., et al., "New Approach to Technical and Clinical Evaluation of Devices for Self-Monitoring of Blood Glucose," Diabetes Care, vol. 11 (8), Sep. 1988, pp. 619-629.
Kost J., et al., "Glucose-Sensitive Membranes Containing Glucose Oxidase: Activity, Swelling, and Permeability Studies," Journal of Biomedical Materials Research, vol. 19, 1985, pp. 1117-1133.
Koudelka M., et al., "In Vivo Response of Microfabricated Glucose Sensors to Glycemia Changes in Normal Rats," Biomed. Biochim. Acta, vol. 48 (11/12), Nov.-Dec. 1989, pp. 953-956.
Koudelka M., et al., "In-Vivo Behaviour of Hypodermically Implanted Microfabricated Glucose Sensors," Biosensors and Bioelectronics, vol. 6, 1991, pp. 31-36.
Kovatchev B.P., et al., "Evaluating the Accuracy of Continuous Glucose-Monitoring Sensors: Continuous Glucose-Error Grid Analysis Illustrated by TheraSense Freestyle Navigator Data," Diabetes Care, vol. 27 (8), Aug. 2004, pp. 1922-1928.
Kraver., et al., "A Mixed-Signal Sensor Interface Microinstrument," Sensors and Actuators A, Physical 2001, vol. 91, pp. 266-277.
Krouwer J.S., "Setting Performance Goals and Evaluating Total Analytical Error for Diagnostic Assays," Clinical Chemistry, vol. 48 (6), 2002, pp. 919-927.
Kruger D., et al., "Psychological Motivation and Patient Education: A Role for Continuous Glucose Monitoring," Diabetes Technology and Therapeutics, vol. 2 (1), 2000, pp. S93-S97.
Kugler J D., et al., "A New Steroid-Eluting Epicardial Lead: Experience with Atrial and Ventricular Implantation in the Immature Swine," PACE, Aug. 1990, vol. 13, pp. 976-981.
Kulys J., et al., "Carbon-Paste Biosensors Array for Long-Term Glucose Measurement," Biosensors & Bioelectronics, vol. 9, 1994, pp. 491-500.
Kunjan K., et al., "Automated Blood Sampling and Glucose Sensing in Critical Care Settings," Journal of Diabetes Science and Technology, vol. 2 (2), Mar. 2008, pp. 194-200.
Kunzler J., et al.,"Hydrogels based on Hydrophilic Side Chain Siloxanes," Poly Mat Sci and Eng, 1993, vol. 69, pp. 226-227.
Kunzler J F., et al., "Contact Lens Materials," Chemistry & Industry, Aug. 21, 1995, pp. 651-655.
Kurnik R.T., et al., "Application of the Mixtures of Experts Algorithm for Signal Processing in a Noninvasive Glucose Monitoring System," Sensors and Actuators B, vol. 60, 1999, pp. 19-26.
Kurtz T.W., et al., "Recommendations for Blood Pressure Measurement in Humans and Experimental Animals, Part 2: Blood Pressure Measurement in Experimental Animals: A Statement for Professionals From the Subcommittee of Professional and Public Education of the American Heart Association Council on High Blood Pressure Research," Hypertension, Feb. 2005, vol. 45, pp. 299-310.
Kusano H., "Glucose Enzyme Electrode with Percutaneous Interface which Operates Independently of Dissolved Oxygen," Clinical Physics and Physiological Measurement, 1989, vol. 10, No. 1, pp. 1-9.
Lacourse W.R., et al., "Optimization of Waveforms for Pulsed Amperometric Detection of Carbohydrates Based on Pulsed Voltammetry," Analytical Chemistry, vol. 65, 1993, pp. 50-52.
Ladd M.F.C., et al., "Structure Determination by X-Ray Crystallography," 3rd Edition, Plenum Press, 1994, Ch. 1, pp. xxi-xxiv and 1-58.

(56) References Cited

OTHER PUBLICATIONS

Lee E., et al., "Effects of Pore Size, Void Volume, and Pore Connectivity on Tissue Responses to Porous Silicone Implants," Society for Biomaterials, 25th Annual Meeting, 1999, p. 171.
Lehmann E.D., et al., Retrospective Validation of a Physiological Model of Glucose-Insulin Interaction in Type 1 Diabetes Mellitus. Medical Engineering & Physics, vol. 16, May 1994, pp. 193-202.
Leprince P., et al., "Expanded Polytetrafluoroethylene Membranes to Wrap Surfaces of Circulatory Support Devices in Patients Undergoing Bridge to Heart Transplantation," European Journal of Cardiothoracic Surgery, 2001, vol. 19, pp. 302-306.
Lerner., et al., "An Implantable Electrochemical Glucose Sensor," Ann. N. Y. Acad. Sci., vol. 428, May 1984, pp. 263-278.
Lewandowski J.J., et al., "Evaluation of a Miniature Blood Glucose Sensor," Transactions—American Society for Artificial Internal Organs, vol. 34, 1988, pp. 255-258.
Leypoldt J.K., et al., "Model of a Two-Substrate Enzyme Electrode for Glucose," Analytical Chemistry, vol. 56, 1984, pp. 2896-2904.
Linke B., et al., "Amperometric Biosensor for In Vivo Glucose Sensing Based on Glucose Oxidase Immobilized in a Redox Hydrogel," Biosensors and Bioelectronics, vol. 9, 1994, pp. 151-158.
Loebe M., et al., "Use of Polytetrafluoroethylene Surgical Membranes as a Pericardial Substitute," PTFE Membrane in Correction of Congenital Heart Defects, Texas Heart Institute Journal, 1993, vol. 20, No. 3, pp. 213-217.
Loffler P., et al., "Separation and Determination of Traces of Ammonia in Air by Means of Chromatomembrane Cells," Fresenius Journal of Analytical Chemistry, 1995, vol. 352, pp. 613-614.
Lohn A., et al., "A Knowledge-Based System for Real-Time Validation of Calibrations and Measurements," Chemometrics and Intelligent Laboratory Systems, vol. 46, 1999, pp. 57-66.
Lowe C.R., "Biosensors," Trends in Biotechnology, vol. 2 (3), 1984, pp. 59-65.
Luong J.H.T., et al., "Solubilization of Multiwall Carbon Nanotubes by 3-Aminopropyltriethoxysilane towards the Fabrication of Electrochemical Biosensors with Promoted Electron Transfer," Electroanalysis, vol. 16 (1-2), 2004, pp. 132-139.
Lyandres O., et al. "Progress toward an In Vivo Surface-Enhanced Raman Spectroscopy Glucose Sensor," Diabetes Technology and Therapeutics, vol. 10 (4), 2008, pp. 257-265.
Lyman D J., "Polyurethanes. I. The Solution Polymerization of Diisocyanates with Ethylene Glycol," Journal of Polymer Science, 1960, vol. XLV, pp. 49-59.
Lynch S.M., et al., "Estimation-Based Model Predictive Control of Blood Glucose in Type I Diabetics: A Simulation Study," Proceedings of the IEEE 27th Annual Northeast Bioengineering Conference, 2001, pp. 79-80.
Lynn P.A., "Recursive Digital Filters for Biological Signals," Med. & Biol. Engineering, vol. 9, 1971, pp. 37-43.
Madaras M B., et al., "Microfabricated Amperometric Creatine and Creatinine Biosensors," Analytica Chimica Acta, 1996, vol. 319, pp. 335-345.
Maidan R., et al., "Elimination of Electrooxidizable Interferent-Produced Currents in Amperometric Biosensors," Analytical Chemistry, vol. 64, 1992, pp. 2889-2896.
Makale M.T., et al., "Tissue Window Chamber System for Validation of Implanted Oxygen Sensors," American Journal of Physiology—Heart and Circulatory Physiology, vol. 284, Feb. 21, 2003, pp. 1-27.
Malin S.F., et al., "Noninvasive Prediction of Glucose by Near-Infrared Diffuse Reflectance Spectroscopy," Clinical Chemistry, vol. 45 (9), 1999, pp. 1651-1658.
Mancy K.H., et al., "A Galvanic Cell Oxygen Analyzer," Journal of Electroanalytical Chemistry, vol. 4, 1962, pp. 65-92.
Maran A., et al., "Continuous Subcutaneous Glucose Monitoring in Diabetic Patients," A Multicenter Analysis, Diabetes Care, vol. 25 (2), Feb. 2002, pp. 347-352.
March W.F., "Dealing with the Delay," Diabetes Technology & Therapeutics, vol. 4 (1), 2002, pp. 49-50.

Marena S., et al., "The Artificial Endocrine Pancreas in Clinical Practice and Research," Panminerva Medica, vol. 35 (2), 1993, pp. 67-74.
Martin R.F., "General Deming Regression for Estimating Systematic Bias and its Confidence Interval in Method-Comparison Studies," Clinical Chemistry, vol. 46 (1), 2000, pp. 100-104.
Mascini M., et al., "Glucose Electrochemical Probe with Extended Linearity for Whole Blood," Journal Pharmaceutical and Biomedical Analysis, vol. 7 (12), 1989, pp. 1507-1512.
Mastrototaro J.J., et al., "An Electroenzymatic Glucose Sensor Fabricated on a Flexible Substrate," Sensors and Actuators B, vol. 5, 1991, pp. 139-144.
Mastrototaro J.J., et al., "Reproducibility of the Continuous Glucose Monitoring System Matches Previous Reports and the Intended Use of the Product," Diabetes Care, vol. 26 (1), Jan. 2003, pp. 256-257.
Mastrototaro J.J., "The MiniMed Continuous Glucose Monitoring System," Diabetes Technology & Therapeutics, vol. 2, Supplement 1, 2000, pp. S13-S18.
Mathivanar R., et al., "In Vivo Elution Rate of Drug Eluting Ceramic Leads with a Reduced Dose of Dexamethasone Sodium Phosphate," PACE, vol. 13, Part II, Dec. 1990, pp. 1883-1886.
Matsuki H., "Energy Transfer System Utilizing Amorphous Wires for Implantable Medical Devices," IEEE Transactions on Magnetics, vol. 31 (2), 1994, pp. 1276-1282.
Matsumoto T., et al., "A Micro-Planar Amperometric Glucose Sensor Unsusceptible to Interference Species," Sensors and Actuators B, 49, 1998, pp. 68-72.
Matthews D.R., et al., "An Amperometric Needle-Type Glucose Sensor Testing in Rats and Man," Diabetic Medicine, vol. 5, 1988, pp. 248-252.
Mazze R.S., et al., "Characterizing Glucose Exposure for Individuals with Normal Glucose Tolerance Using Continuous Glucose Monitoring and Ambulatory Glucose Profile Analysis," Diabetes Technology & Therapeutics, vol. 10 (3), 2008, pp. 149-159.
Mazzola F., et al., "Video Diabetes: A Teaching Tool for Children with Insulin-Dependent Diabetes," IEEE, Proceedings 7th Annual Symposium on Computer Applications in Medical Care, Oct. 1983, 1 page Abstract.
McCartney L.J., et al., "Near-Infrared Fluorescence Lifetime Assay for Serum Glucose Based on Allophycocyanin-Labeled Concanavalin A," Analytical Biochemistry, vol. 292, 2001, pp. 216-221.
McGrath M.J., et al., "The Use of Differential Measurements with a Glucose Biosensor for Interference Compensation During Glucose Determinations by Flow Injection Analysis," Biosens Bioelectron, vol. 10, 1995, pp. 937-943.
McKean B.D., et al., "A Telemetry Instrumentation System for Chronically Implanted Glucose and Oxygen Sensors," IEEE Transactions on Biomedical Engineering, vol. 35 (7), Jul. 1988, pp. 526-532.
Memoli A., et al., "A Comparison between Different Immobilised Glucoseoxidase-Based Electrodes," Journal of Pharmaceutical and Biomedical Analysis, vol. 29, 2002, pp. 1045-1052.
Merriam Webster Online Dictionary, Definition for "Aberrant," retrieved from https://www.merriam-webster.com/dictionary/aberrant Aug. 19, 2008, 1 page.
Merriam-Webster Online Dictionary, Definition of "Acceleration" retrieved from http://www.merriam-webster.com/dictionary/Acceleration Jan. 11, 2010, 1 page.
Merriam-Webster Online Dictionary, Definition of "Nominal" retrieved from http://www.merriam-webster.com/dictionary/nominal Apr. 23, 2007, 1 page.
Merriam-Webster Online Dictionary, Definition of "System". http://www.merriamwebster.com/dictionary/System Jan. 11, 2010, 2 pages.
Metzger M., et al., "Reproducibility of Glucose Measurements using the Glucose Sensor," Diabetes Care, vol. 25 (6), Jul. 2002, pp. 1185-1191.
Meyerhoff C., et al., "On Line Continuous Monitoring of Subcutaneous Tissue Glucose in Men by Combining Portable Glucosensor With Microdialysis," Diabetologia, vol. 35 (11), 1992, pp. 1087-1092.
Mid-West Innovators, Inc., "Durometer Product Description," 2014, 1 page.

(56) References Cited

OTHER PUBLICATIONS

Miller J.A., et al., "Development of an Autotuned Transcutaneous Energy Transfer System," ASAIO Journal, vol. 39, 1993, pp. M706-M710.
Miller K.M., et al., "Generation of IL-1 like Activity in Response to Biomedical Polymer Implants: a Comparison of in Vitro and in Vivo Models," Journal of Biomedical Materials Research, vol. 23(9), 1989, pp. 1007-1026.
Miller K.M., et al., "Human monocyte/macrophage activation and interleukin 1 generation by biomedical polymers," Journal of Biomedical Materials Research, vol. 22 (8), 1988, pp. 713-731.
Miller K.M., et al., "In Vitro Stimulation of Fibroblast Activity by Factors Generated from Human Monocytes Activated by Biomedical Polymers," Journal of Biomedical Materials Research, vol. 23(8), 1989, pp. 911-930.
Minale C., et al., "Clinical Experience with Expanded Polytetrafluoroethylene Gore-Tex Surgical Membrane for Pericardial Closer: A Study of 110 Cases," Journal of Cardiac Surgery, vol. 3, Sep. 1988, pp. 193-201.
Moatti-Sirat D., et al., "Evaluating In Vitro and In Vivo the Interference of Ascorbate and Acetaminophen on Glucose Detection by a Needle-Type Glucose Sensor," Biosensors and Bioelectronics, vol. 7, 1992, pp. 345-352.
Moatti-Sirat D., et al., "Reduction of Acetaminophen Interference in Glucose Sensors by a Composite Nafion Membrane: Demonstration in Rats and Man," Diabetologia, vol. 37 (6), Jun. 1994, pp. 610-616.
Moatti-Sirat., et al., "Towards Continuous Glucose Monitoring: In Vivo Evaluation of a Miniaturized Glucose Sensor Implanted for Several Days in Rat Subcutaneous Tissue," Diabetologia, vol. 35, 1992, pp. 224-230.
Mond H.G., et al., "The Electrode-Tissue Interface: The Revolutionary Role of Steroid Elution," PACE, vol. 15, Jan. 1992, pp. 95-107.
Monsod T.P., et al., "Do Sensor Glucose Levels Accurately Predict Plasma Glucose Concentrations During Hypoglycemia and Hyperinsulinemia?," Diabetes Care, vol. 25 (5), 2002, pp. 889-893.
Morff R.J., et al., "Microfabrication of Reproducible, Economical, Electroenzymatic Glucose Sensors," Annual International Conference of the IEEE Engineering in Medicine and Biology Society, vol. 12 (2), 1990, pp. 0483-0484.
Mosbach K., et al., "Determination of Heat Changes in the Proximity of Immobilized Enzymes with an Enzyme Thermistor and its Use for the Assay of Metabolites," Biochimica Biophysica Acta, vol. 403, 1975, pp. 256-265.
Motonaka J., et al., "Determination of Cholesterol and Cholesterol Ester with Novel enzyme Microsensors," Anal. Chem., vol. 65, 1993, pp. 3258-3261.
Moussy F., et al., "A Miniaturized Nafion-Based Glucose Sensor: In Vitro and In Vivo Evaluation in Dogs," International Journals of Artificial Organs, vol. 17 (2), 1994, pp. 88-94.
Moussy F., et al., "Biomaterials community examines biosensor biocompatibility," Diabetes Technology & Therapeutics, vol. 2(3), 2000, pp. 473-477.
Moussy F., et al., "Performance of Subcutaneously Implanted Needle-Type Glucose Sensors Employing a Novel Trilayer Coating," Analytical Chemistry, vol. 65, Aug. 1, 1993, pp. 2072-2077.
Moussy F., "Implantable Glucose Sensor: Progress and Problems," IEEE, Nov. 2002, pp. 270-273.
Mowery K.A., et al., "Preparation and Characterization by Hydrophobic Polymeric Films that are Thromboresistant via Nitric Oxide Release," Biomaterials, vol. 21, 2000, pp. 9-21.
Murphy S.M., et al., "Polymer Membranes in Clinical Sensor Applications, II. The Design and Fabrication of Permselective Hydrogels for Electrochemical Devices," Biomaterials, 1992, vol. 13 (14), pp. 979-990.
Muslu, "Trickling Filter Performance," Applied Biochemistry and Biotechnology, vol. 37, 1992, pp. 211-224.
Myler S., et al., "Ultra-Thin-Polysiloxane-Film-Composite Membranes for the Optimisation of Amperometric Oxidase Enzyme Electrodes," Biosensors & Bioelectronics, vol. 17, 2002, pp. 35-43.
Nakayama Y., et al., "Surface Fixation of Hydrogels: Heparin and Glucose Oxidase Hydrogelated Surfaces" ASAIO Journal, 1992, pp. M421-M424.
Nam Y.S., et al., "A Novel Fabrication Method of Macroporous Biodegradable Polymer Scaffolds Using Gas Foaming Salt as a Porogen Additive," J Biomed Mater Res, 2000, vol. 53, pp. 1-7.
Neuburger G.G., et al., "Pulsed Amperometric Detection of Carbohydrates at Gold Electrodes with a Two-Step Potential Waveform," Anal. Chem., vol. 59, 1987, pp. 150-154.
Nintendo Healthcare, Wired, Dec. 1993, 1 page.
Novo Nordisk Pharmaceuticals Inc., "Diabetes Educational Video Game Recognized by Software Publishers Association," Press Release, Mar. 14, 1994, 4 pages.
Office Action for European Application No. 10193214.3, dated May 2, 2013, and Applicant Response filed Aug. 28, 2013, 12 pages.
Office Action for Japanese Application No. 10-538680, dated Nov. 20, 2007, 6 pages.
Office Action for U.S. Appl. No. 08/811,473, dated Dec. 7, 1998, 5 pages.
Office Action for U.S. Appl. No. 09/916,386, dated Apr. 9, 2003, 8 pages.
Office Action for U.S. Appl. No. 10/657,843, dated Sep. 21, 2004, 8 pages.
Office Action for U.S. Appl. No. 10/768,889, dated Feb. 4, 2009, 9 pages.
Office Action for U.S. Appl. No. 10/991,966, dated Jul. 22, 2008, 12 pages.
Office Action for U.S. Appl. No. 10/991,966, dated Nov. 28, 2007, 13 pages.
Office Action for U.S. Appl. No. 11/007,635, dated Jan. 27, 2006, 9 pages.
Office Action for U.S. Appl. No. 11/007,920, dated Jun. 24, 2008, 10 pages.
Office Action for U.S. Appl. No. 11/021,046, dated Aug. 19, 2009, 6 pages.
Office Action for U.S. Appl. No. 11/021,046, dated Dec. 26, 2007, 6 pages.
Office Action for U.S. Appl. No. 11/021,046, dated Feb. 4, 2009, 7 pages.
Office Action for U.S. Appl. No. 11/021,046, dated Jun. 23, 2008, 6 pages.
Office Action for U.S. Appl. No. 11/021,162, dated Jun. 19, 2008, 8 pages.
Office Action for U.S. Appl. No. 11/034,343, dated Dec. 30, 2008, 4 pages.
Office Action for U.S. Appl. No. 11/034,343, dated Jul. 10, 2008, 6 pages.
Office Action for U.S. Appl. No. 11/034,343, dated Nov. 1, 2007, 5 pages.
Office Action for U.S. Appl. No. 11/034,344, dated Jan. 15, 2008, 5 pages.
Office Action for U.S. Appl. No. 11/038,340, dated Feb. 2, 2010, 18 pages.
Office Action for U.S. Appl. No. 11/038,340, dated Jan. 5, 2009, 13 pages.
Office Action for U.S. Appl. No. 11/038,340, dated Jun. 7, 2010, 18 pages.
Office Action for U.S. Appl. No. 11/038,340, dated Jun. 17, 2008, 11 pages.
Office Action for U.S. Appl. No. 11/038,340, dated May 19, 2009, 14 pages.
Office Action for U.S. Appl. No. 11/038,340, dated Nov. 9, 2009, 16 pages.
Office Action for U.S. Appl. No. 11/055,779, dated May 23, 2007, 13 pages.
Office Action for U.S. Appl. No. 11/055,779, dated Oct. 24, 2007, 15 pages.
Office Action for U.S. Appl. No. 11/077,759, dated Jul. 10, 2008, 10 pages.
Office Action for U.S. Appl. No. 11/077,759, dated Mar. 31, 2008, 16 pages.
Office Action for U.S. Appl. No. 11/077,759, dated May 17, 2007, 13 pages.

(56) References Cited

OTHER PUBLICATIONS

Office Action for U.S. Appl. No. 11/077,759, dated May 26, 2009, 8 pages.
Office Action for U.S. Appl. No. 11/415,631, dated Mar. 4, 2010, 6 pages.
Office Action for U.S. Appl. No. 11/416,058, dated Mar. 5, 2010, 6 pages.
Office Action for U.S. Appl. No. 11/416,346, dated Mar. 4, 2010, 7 pages.
Office Action for U.S. Appl. No. 11/416,734, dated May 17, 2010, 10 pages.
Office Action for U.S. Appl. No. 11/416,734, dated Oct. 14, 2009, 11 pages.
Office Action for U.S. Appl. No. 11/416,825, dated Oct. 22, 2009, 11 pages.
Office Action for U.S. Appl. No. 11/543,539, dated Dec. 12, 2007, 8 pages.
Office Action for U.S. Appl. No. 11/543,539, dated May 23, 2007, 6 pages.
Office Action for U.S. Appl. No. 11/543,683, dated Dec. 12, 2007, 8 pages.
Office Action for U.S. Appl. No. 11/543,683, dated May 18, 2007, 7 pages.
Office Action for U.S. Appl. No. 11/543,707, dated Dec. 12, 2007, 8 pages.
Office Action for U.S. Appl. No. 11/543,707, dated May 18, 2007, 6 pages.
Office Action for U.S. Appl. No. 11/543,734, dated Dec. 17, 2007, 11 pages.
Office Action for U.S. Appl. No. 11/543,734, dated Jun. 5, 2007, 7 pages.
Office Action for U.S. Appl. No. 11/546,157, dated Feb. 26, 2010, 6 pages.
Office Action for U.S. Appl. No. 11/691,424, dated Dec. 8, 2009, 10 pages.
Office Action for U.S. Appl. No. 11/691,424, dated Jun. 11, 2009, 21 pages.
Office Action for U.S. Appl. No. 11/691,424, dated Nov. 12, 2009, 18 pages.
Office Action for U.S. Appl. No. 11/691,424, dated Sep. 25, 2008, 15 pages.
Office Action for U.S. Appl. No. 11/691,432, dated Feb. 18, 2010, 11 pages.
Office Action for U.S. Appl. No. 11/691,432, dated Jun. 10, 2009, 17 pages.
Office Action for U.S. Appl. No. 11/691,432, dated Nov. 30, 2009, 15 pages.
Office Action for U.S. Appl. No. 11/691,432, dated Sep. 19, 2008, 11 pages.
Office Action for U.S. Appl. No. 11/691,466, dated Oct. 3, 2008, 15 pages.
Office Action for U.S. Appl. No. 11/692,154, dated Jan. 22, 2009, 9 pages.
Office Action for U.S. Appl. No. 11/692,154, dated Jul. 8, 2009, 6 pages.
Office Action for U.S. Appl. No. 12/037,812, dated Apr. 1, 2009, 5 pages.
Office Action for U.S. Appl. No. 12/037,812, dated Jul. 24, 2009, 6 pages.
Office Action for U.S. Appl. No. 12/037,812, dated Sep. 29, 2008, 7 pages.
Office Action for U.S. Appl. No. 12/037,830, dated Aug. 7, 2009, 7 pages.
Office Action for U.S. Appl. No. 12/037,830, dated Feb. 23, 2010, 7 pages.
Office Action for U.S. Appl. No. 12/037,830, dated Feb. 26, 2009, 7 pages.
Office Action for U.S. Appl. No. 12/037,830, dated Sep. 29, 2008, 6 pages.
Office Action for U.S. Appl. No. 12/052,489, dated Aug. 25, 2010, 12 pages.
Office Action for U.S. Appl. No. 12/055,098, dated Oct. 5, 2010, 12 pages.
Office Action for U.S. Appl. No. 12/098,359, dated Jul. 7, 2010, 18 pages.
Office Action for U.S. Appl. No. 12/102,654, dated Jul. 30, 2009, 9 pages.
Office Action for U.S. Appl. No. 12/102,654, dated Mar. 10, 2010, 6 pages.
Office Action for U.S. Appl. No. 12/102,729, dated Jul. 7, 2009, 7 pages.
Office Action for U.S. Appl. No. 12/102,745, dated Dec. 23, 2008, 4 pages.
Office Action for U.S. Appl. No. 12/111,062, dated Mar. 3, 2010, 8 pages.
Office Action for U.S. Appl. No. 12/113,508, dated Feb. 23, 2010, 9 pages.
Office Action for U.S. Appl. No. 12/113,724, dated Jun. 24, 2010, 12 pages.
Office Action for U.S. Appl. No. 12/133,738, dated Sep. 10, 2010, 11 pages.
Office Action for U.S. Appl. No. 12/133,761, dated Sep. 7, 2010, 11 pages.
Office Action for U.S. Appl. No. 12/139,305, dated Jan. 13, 2010, 12 pages.
Office Action for U.S. Appl. No. 12/182,073, dated Jun. 28, 2010, 20 pages.
Office Action for U.S. Appl. No. 12/182,083, dated Jun. 24, 2010, 8 pages.
Office Action for U.S. Appl. No. 12/264,160, dated Jun. 3, 2010, 5 pages.
Office Action for U.S. Appl. No. 12/536,852, dated Jun. 25, 2010, 8 pages.
Office Action for U.S. Appl. No. 12/536,852, dated Oct. 18, 2010, 10 pages.
Office Action for U.S. Appl. No. 12/619,502, dated Sep. 7, 2010, 6 pages.
Office Action for U.S. Appl. No. 12/829,337, dated Oct. 5, 2012, 10 pages.
Office Action from European Patent Application No. 05771646.6, dated Aug. 16, 2011, 3 pages.
Office Action from European Patent Application No. 05771646.6, dated Aug. 19, 2009, 4 pages.
Office Action from European Patent Application No. 05771646.6, dated Jun. 2, 2010, 5 pages.
Office Action from European Patent Application No. 05856669.6, dated Aug. 4, 2011, 7 pages.
Office Action from European Patent Application No. 05856669.6, dated Jun. 7, 2010, 5 pages.
Office Action from European Patent Application No. 05856669.6, dated Nov. 8, 2010, 6 pages.
Office Action from Japanese Patent Application No. 2007-521636 dated Mar. 1, 2011, 4 pages.
Office Action from Japanese Patent Application No. 2011-121598 dated May 22, 2012, 5 pages.
Office Action from Japanese Patent Application No. 2011-121598 dated Oct. 18, 2011, 9 pages.
Office Action from Japanese Patent Application No. 2012-006893 dated May 22, 2012, 4 pages.
Office Action from Japanese Patent Application No. 2012-169323 dated Oct. 16, 2012, 4 pages.
Office Action from Japanese Patent Application No. 2013-000959 dated Jan. 31, 2014, 6 pages.
Ohara T.J., et al., "Glucose Electrodes Based on Cross-Linked [Os(bpy)2Cl](+/2+) Complexed Poly(1-Vinylimidazole) Films," Analytical Chemistry, vol. 65, Dec. 1993, pp. 3512-3517.
Ohara T.J., et al., ""Wired" Enzyme Electrodes for Amperometric Determination of Glucose or Lactate in the Presence of Interfering Substances," Anal Chem, vol. 66, 1994, pp. 2451-2457.
Okuda, et al., "Mutarotase Effect on Micro Determinations of D-Glucose and its Anomers with β D-Glucose Oxidase," Anal Biochem, vol. 43 (1), 1971, pp. 312-315.

(56) References Cited

OTHER PUBLICATIONS

Oxford English Dictionary Online, Definition of "Impending," http://www.askoxford.com/results/?view=devdict&field-12668446_Impending&branch Jan. 11, 2010, 1 page.
Palmisano F., et al., "Simultaneous Monitoring of Glucose and Lactate by an Interference and Cross-Talk Free Dual Electrode Amperometric Biosensor Based on Electropolymerized Thin Films," Biosensors & Bioelectronics, vol. 15, 2000, pp. 531-539.
Panetti T.S., "Differential Effects of Sphingosine 1-Phosphate and Lysophosphatidic Acid on Endothelial Cells," Biochimica et Biophysica Acta, vol. 1582, 2002, pp. 190-196.
Panteleon A.E., et al., "The Role of the Independent Variable to Glucose Sensor Calibration," Diabetes Technology & Therapeutics, vol. 5 (3), 2003, pp. 401-410.
Paramount PDS., "Durometer Made Easy (R) / Durometer Hardness Scales—General Reference Guide," Paramount Industries Inc., 2008, 1 page.
Park I.B., et al., "Gas Separation Properties of Polysiloxane/Polyether Mixed Soft Segment Urethane Urea Membranes," Journal of Membrane science, vol. 204, 2002, pp. 257-269.
Parker R.S., et al., "A Model-Based Algorithm for Blood Glucose Control in Type I Diabetic Patients," IEEE Trans Biomed Engg (BME), vol. 46(2), 1999, pp. 148-157.
Patel H., et al., "Amperometric Glucose Sensors Based on Ferrocene Containing Polymeric Electron Transfer Systems—A Preliminary Report," Biosensors & Bioelectronics, vol. 18, 2003, pp. 1073-1076.
Peacock W.F., et al., "Cardiac Troponin and Outcome in Acute Heart Failure," N. Engl. J. Med., vol. 358, 2008, pp. 2117-2126.
Pegoraro M., et al., "Gas Transport Properties of Siloxane Polyurethanes," Journal of Applied Polymer Science, vol. 57, 1995, pp. 421-429.
Peguin S., et al., "Pyruvate Oxidase and Oxaloacetate Decarboxylase Enzyme Electrodes—Simultaneous Determination of Transaminases with a Two-electrode-based Analyzer," Analytica Chimica Acta, vol. 222, 1989, pp. 83-93.
Pfeiffer E.F., et al., "On Line Continuous Monitoring of Subcutaneous Tissue Glucose is Feasible by Combining Portable Glucosensor with Microdialysis," Horm. Metab. Res., vol. 25, 1993, pp. 121-124.
Pfeiffer E.F., "The Glucose Sensor: The Missing Link in Diabetes Therapy," Horm Metab Res Suppl., vol. 24, 1990, pp. 154-164.
Phillips R.E., et al., "Biomedical Applications of Polyurethanes: Implications of Failure Mechanisms," Journal of Biomedical application, vol. 3, Oct. 1988, pp. 206-227.
Phillips R.P., "A High Capacity Transcutaneous Energy Transmission System," ASAIO Journal, vol. 41, 1995, pp. M259-M262.
Pichert J.W., et al., "Issues for the Coming Age of Continuous Glucose Monitoring," Diabetes Educator, vol. 26 (6), Nov.-Dec. 2000, pp. 969-980.
Pickup J.C., et al., "Developing Glucose Sensors for In Vivo Use," Elsevier Science Publishers Ltd (UK), TIBTECH, vol. 11, 1993, pp. 285-291.
Pickup J.C., et al., "Implantable Glucose Sensors: Choosing the Appropriate Sensor Strategy," Biosensors, vol. 3, (1987/1988), pp. 335-346.
Pickup J.C., et al., "In Vivo Molecular Sensing in Diabetes Mellitus: An Implantable Glucose Sensor with Direct Electron Transfer," Diabetologia, vol. 32, 1989, pp. 213-217.
Pickup J.C., et al., "Potentially-Implantable, Amperometric Glucose Sensors with Mediated Electron Transfer: Improving the Operating Stability," Biosensors, vol. 4, 1989, pp. 109-119.
Pickup J.C., et al., "Progress Towards in Vivo Glucose Sensing with a Ferrocene-Mediated Amperometric Enzyme Electrode," Horm Metab Res Suppl, vol. 20, 1988, pp. 34-36.
Pickup J.C., et al., "Responses and Calibration of Amperometric Glucose Sensors Implanted in the Subcutaneous Tissue of Man," ACTA Diabetol, vol. 30, 1993, pp. 143-148.
Pineda L.M., et al., "Bone Regeneration with Resorbable Polymeric Membranes. III. Effect of Poly(L-lactide) Membrane Pore Size on the Bone Healing Process in Large Defects," Journal of Biomedical Materials Research, vol. 31, 1996, pp. 385-394.
Pinner S.H., et al., "Cross-Linking of Cellulose Acetate by Ionizing Radiation," Nature, vol. 184, Oct. 24, 1959, pp. 1303-1304.
Pishko M.V., et al., "Amperometric Glucose Microelectrodes Prepared Through Immobilization of Glucose Oxidase in Redox Hydrogels," Analytical Chemistry, vol. 63 (20), 1991, pp. 2268-2272.
Pitzer K.R., et al., "Detection of Hypoglycemia with the Glucowatch Biographer," Diabetes Care, vol. 24 (5), 2001, pp. 881-885.
Poirier J.Y., et al., "Clinical and Statistical Evaluation of Self-Monitoring Blood Glucose Meters," Diabetes Care, vol. 21 (11), Nov. 1998, pp. 1919-1924.
Poitout V., et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, vol. 36, 1993, pp. 658-663.
Poitout V., et al., "Development of a Glucose Sensor for Glucose Monitoring in Man: The Disposable Implant Concept," Clinical Materials, vol. 15, 1994, pp. 241-246.
Poitout V., et al., "In Vitro and In Vivo Evaluation in Dogs of a Miniaturized Glucose Sensor," ASAIO Transactions, vol. 37, 1991, pp. M298-M300.
Postlethwaite T.A., et al., "Interdigitated Array Electrode as an Alternative to the Rotated Ring-Disk Electrode for Determination of the Reaction Products of Dioxygen Reduction," Analytical Chemistry, vol. 68 (17), Sep. 1996, pp. 2951-2958.
Prabhu V.G., et al., "Electrochemical Studies of Hydrogen Peroxide at a Platinum Disc Electrode," Electrochimica Acta, vol. 26 (6), 1981, pp. 725-729.
Preliminary Amendment for U.S. Appl. No. 12/052,489, filed Mar. 20, 2008, 8 pages.
Quinn C.A.P., et al., "Biocompatible, Glucose-Permeable Hydrogel for in situ Coating of Implantable Biosensors," Biomaterials, vol. 18 (24), 1997, pp. 1665-1670.
Quinn C.P., et al., "Kinetics of Glucose Delivery to Subcutaneous Tissue in Rats Measured with 0.3-mm Amperometric Microsensors," The American Physiological Society, vol. 269, 1995, pp. E155-E161.
Rabah M.A., et al., "Electrochemical Wear of Graphite Anodes During Electrolysis of Brine," Carbon, vol. 29 (2), 1991, pp. 165-171.
Radovsky A.N., et al., "Effects of Dexamethasone Elution on Tissue Reaction Around Stimulating Electrodes of Endocardial Pacing Leads in Dogs," American Heart Journal, vol. 117 (6), Jun. 1989, pp. 1288-1298.
Rafael E., "Cell Transplantation and Immunoisolation: Studies on a Macroencapsulation Device," Departments of Transplantation Surgery and Pathology, Karolinska Institutet, Huddinge Hospital, Stockholm, Sweden, 1999, pp. 1-83.
Ratner B.D., "Reducing Capsular Thickness and Enhancing Angiogenesis around Implant Drug Release Systems," Journal of Controlled Release, vol. 78, 2002, pp. 211-218.
Rawlings R.A., et al., "Translating Glucose Variability Metrics into the Clinic via Continuous Glucose Monitoring: A Graphical User Interface for Diabetes Evaluation (CGM-Guide)," Diabetes Technology & Therapeutics, vol. 13 (12), 2011, pp. 1241-1248.
Raya Systems Pioneers, "Raya Systems Pioneers Healthy Video Games," PlayRight, Nov. 1993, pp. 14-15.
Reach, et al., "Clinical Sensors for In Vivo Monitoring," Advances in Biosensors, COMAC Biomedical Engineering Concerted Action on Chemical Sensors for In Vivo Monitoring, Supplement 1: Chapter 1, 1993, pp. 7-28.
Reach G., "A Method for Evaluating in vivo the Functional Characteristics of Glucose Sensors," Biosensors, vol. 2, 1986, pp. 211-220.
Reach G., et al., "Can Continuous Glucose Monitoring Be Used for the Treatment of Diabetes?," Analytical Chemistry, vol. 64 (6), Mar. 15, 1992, pp. 381A-386A.
Reach G., "Which Threshold to Detect Hypoglycemia? Value of Receiver-Operator Curve Analysis to Find a Compromise Between Sensitivity and Specificity," Diabetes Care, vol. 24 (5), May 2001, pp. 803-804.

(56) References Cited

OTHER PUBLICATIONS

Rebrin K., et al., "Automated Feedback Control of Subcutaneous Glucose Concentration in Diabetic Dogs," Diabetologia, vol. 32, 1989, pp. 573-576.
Rebrin K., et al., "Subcutaneous Glucose Monitoring by Means of Electrochemical Sensors: Fiction or Reality?," Journal of Biomedical Engineering, vol. 14, Jan. 1992, pp. 33-40.
Rebrin K., et al., "Subcutaneous Glucose Predicts Plasma Glucose Independent of Insulin: Implications for Continuous Monitoring," The American Physiological Society, vol. 277, 1999, pp. E561-E571.
Reush, "Organometallic Compounds," Chemical Reactivity, Virtual Textbook of Organic Chemistry, Retrieved from http://www.cem.msu.edu/-reuschlVirtualText/orgmetal.htm 2004, pp. 1-16.
Revuelta J.M., et al., "Expanded Polytetrafluoroethylene Surgical Membrane for Pericardial Closure," The Journal of Thoracic and cardiovascular Surgery, vol. 89 (3), Mar. 1985, pp. 451-455.
Rhodes R.K., et al., "Prediction of Pocket-Portable and Implantable Glucose Enzyme Electrode Performance from Combined Species Permeability and Digital Simulation Analysis," Analytical Chemistry, vol. 66 (9), May 1, 1994, pp. 1520-1529.
Rigla M., et al., "Real-Time Continuous Glucose Monitoring Together with Telemedical Assistance Improves Glycemic Control and Glucose Stability in Pump-Treated Patients," Diabetes Technology & Therapeutics, vol. 10 (3), 2008, pp. 194-199.
Rinken T., et al., "Calibration of Glucose Biosensors by Using Pre-Steady State Kinetic Data," Biosensors & Bioelectronics, vol. 13, 1998, pp. 801-807.
Rivers E.P., et al., "Central Venous Oxygen Saturation Monitoring in the Critically Ill Patient," Current Opinion in Critical Care, 2001, vol. 7, pp. 204-211.
Sachlos E., et al., "Making Tissue Engineering Scaffolds Work Review on the Application of Solid Freeform Fabrication Technology to the Production of Tissue Engineering Scaffolds," European Cells and Materials, vol. 5, 2003, pp. 29-40.
Sakakida M., et al., "Development of Ferrocene-Mediated Needle-Type Glucose Sensor as a Measure of True Subcutaneous Tissue Glucose Concentrations," Artif. Organs Today, vol. 2 (2), 1992, pp. 145-158.
Sakakida M., et al., "Ferrocene-Mediated Needle Type Glucose Sensor Covered with Newly Designed Biocompatible Membrane," Sensors and Actuators B, vol. 13-14, 1993, pp. 319-322.
Salardi S., et al., "The Glucose Area Under the Profiles Obtained with Continuous Glucose Monitoring System Relationships with HbA1C in Pediatric Type 1 Diabetic Patients," Diabetes Care, vol. 25 (10), Oct. 2002, pp. 1840-1844.
Samuels M.P., "The Effects of Flight and Altitude," Arch Dis Child, vol. 89, 2004, pp. 448-455.
San Diego Plastics Inc, "Polyethylene," Datasheet, Retrieved from http://www.sdplastics.com/polyeth.html on Aug. 19, 2009, 7 pages.
Sanders E., et al., "Fibrous Encapsulation of Single Polymer Microfibers Depends on their Vertical Dimension in Subcutaneous Tissue Polymer Microfibers," Journal of Biomedical Material Research, vol. 67A, 2003, pp. 1181-1187.
Sansen W., et al., "A Smart Sensor for the Voltammetric Measurement of Oxygen or Glucose Concentrations," Sensors and Actuators B1, 1990, pp. 298-302.
Sansen W., et al., "Glucose Sensor with Telemetry System," In Implantable Sensors for Closed Loop Prosthetic Systems edited by Ko W.H, Chapter 12, 1985, pp. 167-175.
Schaffar B.P.H., "Thick Film Biosensors for Metabolites in Undiluted Whole Blood and Plasma Samples," Analytical Bioanalytical Chemistry, Dec. 2001, vol. 372, pp. 254-260.
Schmidt F.J., et al., "Calibration of a Wearable Glucose Sensor," The International Journal of Artificial Organs, Wichtig Publishing, IT, vol. 15 (1), Jan. 1, 1992, pp. 55-61.
Schmidt F.J., et al., "Glucose Concentration in Subcutaneous Extracellular Space," Diabetes Care, vol. 16 (5), May 1993, pp. 695-700.
Schmidtke D.W., et al., "Accuracy of the One-Point in Vivo Calibration of "Wired" Glucose Oxidase Electrodes Implanted in Jugular Veins of Rats in Periods of Rapid Rise and Decline of the Glucose Concentration," Analytical Chemistry, vol. 70 (10), May 15, 1998, pp. 2149-2155.
Schmidtke D.W., et al., "Measurement and Modeling of the Transient Difference Between Blood and Subcutaneous Glucose Concentrations in the Rat After Injection of Insulin," Proceedings of the National Academy of Sciences, vol. 95, Jan. 1998, pp. 294-299.
Schoemaker M., et al., "The SCGMI System: Subcutaneous Continuous Glucose Monitoring Based on Microdialysis Technique," Diabetes Technology & Therapeutics, vol. 5 (4), 2003, pp. 599-608.
Schoonen A.J.M., et al., "Development of a Potentially Wearable Glucose Sensor for Patients with Diabetes Mellitus: Design and In-vitro Evaluation," Biosensors & Bioelectronics, vol. 5, 1990, pp. 37-46.
Schuler, et al., "Modified Gas-Permeable Silicone Rubber Membranes for Covalent Immobilisation of Enzymes and their Use in Biosensor Development," Analyst, 1999, vol. 124, pp. 1181-1184.
Selam J.L., "Management of Diabetes with Glucose Sensors and Implantable Insulin Pumps," From the Dream of the 60s to the Realities of the 90s, ASAIO Journal 1997, vol. 43, pp. 137-142.
Service F.J., et al., "Mean Amplitude of Glycemic Excursions, A Measure of Diabetic Instability," Diabetes, vol. 19 (9), Sep. 1970, pp. 644-655.
Service F.J., et al., "Measurements of Glucose Control," Diabetes Care, vol. 10 (2), Mar.-Apr. 1987, pp. 225-237.
Service R.F., "Can Sensors Make a Home in the Body?," Science, Materials Science: Soft Surface, vol. 297, Aug. 9, 2002, pp. 962-963.
Sharkawy A.A., et al., "Engineering the Tissue Which Encapsulates Subcutaneous Implants. I. Diffusion Properties," Journal of Biomedical Materials Research, vol. 37, 1996, pp. 401-412.
Shaw G.W., et al., "In Vitro Testing of a Simply Constructed, Highly Stable Glucose Sensor Suitable for Implantation in Diabetic Patients," Biosensors & Bioelectronics, vol. 6, 1991, pp. 401-406.
Shichiri, et al., "In Vivo Characteristics of Needle-Type Glucose Sensor-Measurements of Subcutaneous Glucose Concentrations in Human Volunteers," Implantable Glucose Sensors—The State of the Art, Hormone and Metabolic Research Supplement Series, 1988, vol. 20, pp. 17-20.
Shichiri M., et al., "Glycaemic Control in Pancreatectomized Dogs with a Wearable Artificial Endocrine Pancreas," Diabetologia, vol. 24, 1983, pp. 179-184.
Shichiri M., et al., "Membrane Design for Extending the Long-Life of an Implantable Glucose Sensor," Diabetes Nutrition & Metabolism, vol. 2 (4), 1989, pp. 309-313.
Shichiri M., et al., "Needle Type Glucose Sensor for Wearable Artificial Endocrine Pancreas," In Implantable Sensors for Closed-Loop Prosthetic Systems edited by Ko W.H, Chapter 15, 1985, pp. 197-210.
Shichiri M., et al., "Telemetry Glucose Monitoring Device with Needle-Type Glucose Sensor: A Useful Tool for Blood Glucose Monitoring in Diabetic Individuals," Diabetes Care, vol. 9 (3), May-Jun. 1986, pp. 298-301.
Shichiri M., et al., "Wearable Artificial Endocrine Pancreas with Needle-Type Glucose Sensor," Preliminary Communication, Lancet, vol. 2, Nov. 20, 1982, pp. 1129-1131.
Shults M.C., et al., "A Telemetry-Instrumentation System for Monitoring Multiple Subcutaneously Implanted Glucose Sensors," IEEE Transactions on Biomedical Engineering, vol. 41 (10), Oct. 1994, pp. 937-942.
Sieminski, et al., "Biomaterial-Microvasculature Interactions," Biomaterials, 2000, vol. 21, pp. 2233-2241.
Sigma-Aldrich Corp., "Cellulose Acetate," Product Description, Product No. 419028, St. Louis, MO, 2005, 1 page.
Sigma-Aldrich Corp. "Nafion® 117 Solution Product Description, Product No. 70160," retrieved from https//:http://www.sigmaaldrich.com/cgi-bin/hsrun/Suite7/Suite/HAHTpage/Suite.HsExternalProd on Apr. 7, 2005, 1 page.
Skyler J.S., "The Economic Burden of Diabetes and the Benefits of Improved Glycemic Control: The Potential Role of a Continuous Glucose Monitoring System," Diabetes Technology & Therapeutics, vol. 2, Supplement 1, 2000, pp. S7-S12.

(56) References Cited

OTHER PUBLICATIONS

Slater-Maclean L., et al., "Accuracy of Glycemic Measurements in the Critically Ill," Diabetes Technology and Therapeutics, vol. 10 (3), 2008, pp. 169-177.
Smith B., et al., "An Externally Powered, Multichannel, Implantable Stimulator-Telemeter for Control of Paralyzed Muscle," IEEE Transactions on Biomedical Engineering, vol. 45 (4), Apr. 1998, pp. 463-475.
Smith, et al.,"A Comparison of Islet Transplantation and Subcutaneous Insulin Injections for the Treatment of Diabetes Mellitus," Computers in Biology and Medicine, 1991, vol. 21 (6), pp. 417-427.
Smith, "The Scientist and Engineer's Guide to Digital Signal Processing," California Technical Publishing, 1997-2007, retrieved from http://www.dspguide.com/ch19.htm on Jan. 1, 2009, 2 Pages.
Smooth-On, "Durometer Shore Hardness Scale," downloaded from https://www.smooth-on.com/page/durometer-shore-hardness-scale/ on May 19, 2016, 1 page.
Sokol L., et al., "Immobilized-Enzyme Rate-Determination Method for Glucose Analysis," Clinical Chemistry, vol. 26 (1), 1980, pp. 89-92.
Sokolov S., et al., "Metrological Opportunities of the Dynamic Mode of Operating an Enzyme Amperometric Biosensor," Medical Engineering & Physics, vol. 17 (6), 1995, pp. 471-476.
Sparacino G., et al., "Continuous Glucose Monitoring Time Series and Hypo-Hyperglycemia Prevention: Requirements, Methods, Open Problems," Current Diabetes Reviews, vol. 4 (3), 2008, pp. 181-192.
Sproule B.A., et al., "Fuzzy Pharmacology: Theory and Applications," Trends in Pharmacological Sciences, vol. 23 (9), Sep. 2002, pp. 412-417.
Sriyudthsak M., et al., "Enzyme-Epoxy Membrane Based Glucose Analyzing System and Medical Applications," Biosensors & Bioelectronics, vol. 11 (8), 1996, pp. 735-742.
Steil G.M., et al., "Determination of Plasma Glucose During Rapid Glucose Excursions with a Subcutaneous Glucose Sensor," Diabetes Technology & Therapeutics, vol. 5 (1), 2003, pp. 27-31.
Stern M., et al., "Electrochemical Polarization: I. A Theoretical Analysis of the Shape of Polarization Curves," Journal of the Electrochemical Society, vol. 104 (1), Jan. 1957, pp. 56-63.
Sternberg, et al., "Covalent Enzyme Coupling on Cellulose Acetate Membranes for Glucose Sensor Development," Anal Chem, Dec. 1988, vol. 60(24), pp. 2781-2786.
Sternberg F., et al., "Does Fall in Tissue Glucose Precede Fall in Blood Glucose?," Diabetologia, vol. 39, 1996, pp. 609-612.
Sternberg R., et al., "Study and Development of Multilayer Needle-type Enzyme Based Glucose Microsensors," Biosensors, vol. 4, 1988, pp. 27-40.
Stokes, "Polyether Polyurethanes: Biostable or Not," Journal of Biomaterials Applications, Oct. 1988, vol. 3, pp. 228-259.
Street, et al., "Islet Graft Assessment in the Edmonton Protocol: Implications for Predicting Long-Term Clinical Outcome," Diabetes, 2004, vol. 53, pp. 3107-3114.
Street J.O., et al., "A Note on Computing Robust Regression Estimates Via Iteratively Reweighted Least Squares," The American Statistician, vol. 42 (2), May 1988, pp. 152-154.
Suh, et al., "Behavior of Fibroblasts on a Porous Hyaluronic Acid Incorporated Collagen Matrix," Yonsei Medical Journal, 2002, vol. 43 (2), pp. 193-202.
Sumino T., et al., "Preliminary Study of Continuous Glucose Monitoring with a Microdialysis Technique," Proceedings of the 20th Annual International Conference of the IEEE Engineering in Medicine and Biology Society, vol. 20 (4), 1998, pp. 1775-1778.
Takatsu I., et al., "Solid State Biosensors Using Thin-Film Electrodes," Sensors and Actuators, 1987, vol. 11, pp. 309-317.
Takegami S., et al., "Pervaporation of Ethanol/Water Mixtures Using Novel Hydrophobic Membranes Containing Polydimethylsiloxane," Journal of Membrane Science, vol. 75, 1992, pp. 93-105.
Tamura T., et al., "Preliminary Study of Continuous Glucose Monitoring with a Microdialysis Technique and a Null Method—A Numerical Analysis," Frontiers of Medical & Biological Engineering, vol. 10 (2), 2000, pp. 147-156.
Tanenberg R.J., et al., "Continuous Glucose Monitoring System: A New Approach to the Diagnosis of Diabetic Gastroparesis," Diabetes Technology & Therapeutics, vol. 2, Supplement 1, 2000, pp. S73-S80.
Tang, et al., "Fibrin(ogen) Mediates Acute Inflammatory Responses to Biomaterials," J.Exp.Med, 1993, vol. 178, pp. 2147-2156.
Tang, et al., "Inflammatory Responses to Biomaterials," Am J Clin Pathol, 1995, vol. 103, pp. 466-471.
Tang, et al., "Mast Cells Mediate Acute Inflammatory Responses to Implanted Biomaterials," Proceedings of the National Academy of Sciences of the USA, 1998, vol. 95, pp. 8841-8846.
Tang, et al., "Molecular Determinants of Acute Inflammatory Responses to Biomaterials," J Clin Invest, 1996, vol. 97, pp. 1329-1334.
Tatsuma T., et al., "Oxidase/Peroxidase Bilayer-Modified Electrodes as Sensors for Lactate, Pyruvate, Cholesterol and Uric Acid," Analytica Chimica Acta, vol. 242, 1991, pp. 85-89.
Taub M.B., et al., "Numerical Simulation of the Effect of Rate of Change of Glucose on Measurement Error of Continuous Glucose Monitors," Journal of Diabetes Science and Technology, vol. 1 (5), Sep. 2007, pp. 685-694.
Thijssen, et al., "A Kalman Filter for Calibration, Evaluation of Unknown Samples and Quality Control in Drifting Systems," Part 1,Theory and Simulations, Analytica chimica Acta, 1984, vol. 156, pp. 87-101.
Thijssen, et al., "A Kalman Filter for Calibration, Evaluation of Unknown Samples and Quality Control in Drifting Systems," Part 3,Variance Reduction ,Analytica chimica Acta, 1985, vol. 173, pp. 265-272.
Thijssen, et al., "A Kalman Filter for Calibration, Evaluation of Unknown Samples and Quality Control in Drifting Systems," Part 4,Flow Injection Analysis, Analytica chimica Acta, 1985, vol. 174, pp. 27-40.
Thijssen P.C.,"A Kalman Filter for Calibration, Evaluation of Unknown Samples and Quality Control in Drifting Systems," Part 2,Optimal Designs, Analytica chimica Acta, vol. 162, 1984, pp. 253-262.
Thome V., et al., "(Abstract) Can the Decrease in Subcutaneous Glucose Concentration Precede the Decrease in Blood Glucose Level? Proposition for a Push-Pull Kinetics Hypothesis," Horm. metab. Res., vol. 27, 1995, p. 53.
Thome-Duret V., et al., "Continuous Glucose Monitoring in the Free-Moving Rat," Metabolism, vol. 47 (7), Jul. 1998, pp. 799-803.
Thome-Duret V., et al., "Modification of the Sensitivity of Glucose Sensor Implanted into Subcutaneous Tissue," Diabetes & Metabolism, vol. 22, 1996, pp. 174-178.
Thome-Duret V., et al., "Use of a Subcutaneous Glucose Sensor to Detect Decreases in Glucose Concentration Prior to Observation in Blood," Analytical Chemistry, vol. 68 (21), Nov. 1, 1996, pp. 3822-3826.
Thompson M., et al., "In Vivo Probes: Problems and Perspectives," Clinical Biochemistry, vol. 19 (5), Oct. 1986, pp. 255-261.
Tibell, et al., "Survival of Macroencapsulated Allogeneic Parathyroid Tissue One Year after Transplantation in Nonimmunosuppressed Humans," Cell Transplantation, 2001, vol. 10, pp. 591-599.
Tierney M.J., et al., "Effect of Acetaminophen on the Accuracy of Glucose Measurements Obtained with the GlucoWatch Biographer," Diabetes Technology & Therapeutics, vol. 2 (2), 2000, pp. 199-207.
Tierney M.J., et al., "The Gluco Watch® Biographer: A Frequent, Automatic and Noninvasive Glucose Monitor," Annals of Medicine, vol. 32, 2000, pp. 632-641.
Tilbury J.B., et al., "Receiver Operating Characteristic Analysis for Intelligent Medical Systems—A New Approach for Finding Confidence Intervals," IEEE Transactions on Biomedical Engineering, vol. 47 (7), Jul. 2000, pp. 952-963.
Torjman M.C., et al., "Glucose Monitoring in Acute Care: Technologies on the Horizon," Journal of Diabetes Science and Technology, vol. 2 (2), Mar. 2008, pp. 178-181.
Trajanoski Z., et al., "Neural Predictive Controller for Insulin Delivery Using the Subcutaneous Route," IEEE Transactions on Biomedical Engineering, vol. 45(9), 1998, pp. 1122-1134.

(56) References Cited

OTHER PUBLICATIONS

Trecroci D., "A Glimpse into the Future-Continuous Monitoring of Glucose with a Microfiber," Diabetes Interview, Jul. 2002, pp. 42-43.
Tse P.S.H., et al., "Time-Dependent Inactivation of Immobilized Glucose Oxidase and Catalase," Biotechnology & Bioengineering, vol. 29, 1987, pp. 705-713.
Turner A.P.F., "Amperometric Biosensor based on Mediator-Modified Electrodes," Methods in Enzymology, 1988, vol. 137, pp. 90-103.
Turner A.P.F., et al., "Carbon Monoxide: Acceptor Oxidoreductase from Pseudomonas Thermocarboxydovorans Strain C2 and its Use in a Carbon Monoxide Sensor," Analytica Chimica Acta, vol. 163, 1984, pp. 161-174.
Turner A.P.F., et al., "Diabetes Mellitus: Biosensors for Research and Management," Biosensors, vol. 1, 1985, pp. 85-115.
Unger J., et al., "Glucose Control in the Hospitalized Patient," Emergency Medicine, vol. 36 (9), 2004, pp. 12-18.
Updike S.J., et al., "A Subcutaneous Glucose Sensor with Improved Longevity, Dynamic Range, and Stability of Calibration," Diabetes Care, vol. 23 (2), Feb. 2000, pp. 208-214.
Updike S.J., et al., "Continuous Glucose Monitor Based on an Immobilized Enzyme Electrode Detector," Journal of Laboratory and Clinical Medicine, vol. 93(4), 1979, pp. 518-527.
Updike S.J., et al., "Enzymatic Glucose Sensor: Improved Long-Term Performance in Vitro and In Vivo," ASAIO Journal, vol. 40 (2), Apr.-Jun. 1994, pp. 157-163.
Updike S.J., et al., "Implanting the Glucose Enzyme Electrode: Problems, Progress, and Alternative Solutions," Diabetes Care, vol. 5 (3), May-Jun. 1982, pp. 207-212.
Updike S.J., et al., "Laboratory Evaluation of New Reusable Blood Glucose Sensor," Diabetes Care, vol. 11 (10), Nov.-Dec. 1988, pp. 801-807.
Updike S.J., et al., "Principles of Long-Term Fully Implanted Sensors with Emphasis on Radiotelemetric Monitoring of Blood Glucose Form Inside a Subcutaneous Foreign Body Capsule (FBC)," Edited by Fraser D M, Biosensors in the Body: Continuous in vivo Monitoring, John Wiley & Sons Ltd., New York, 1997, Chapter 4, pp. 117-137.
Updike S.J., et al., "The Enzyme Electrode," Nature, vol. 214, Jun. 3, 1967, pp. 986-988.
Utah Medical Products Inc., "Deltran—Disposable Blood Pressure Transducers," Product Specifications, 2003-2006, 6 pages.
Vadgama P., "Diffusion Limited Enzyme Electrodes," NATO ASI Series: Series C, Math and Phys. Sci, vol. 226, 1988, pp. 359-377.
Vadgama P., "Enzyme Electrodes as Practical Biosensors," Journal of Medical Engineering & Technology, vol. 5 (6), Nov. 1981, pp. 293-298.
Valdes T.I., et al., "In Vitro and In Vivo Degradation of Glucose Oxidase Enzyme used for an Implantable Glucose Biosensor," Diabetes Technology & Therapeutics, vol. 2 (3), 2000, pp. 367-376.
Van Den Berghe, "Tight Blood Glucose Control with Insulin in "Real-Life" Intensive Care," Mayo Clinic Proceedings, vol. 79 (8), Aug. 2004, pp. 977-978.
Velho G., et al., "In Vitro and In Vivo Stability of Electrode Potentials in Needle-Type Glucose Sensors," Influence of Needle Material, Diabetes, vol. 38, Feb. 1989, pp. 164-171.
Velho G., et al., "Strategies for Calibrating a Subcutaneous Glucose Sensor," Biomed Biochim Acta, vol. 48 (11/12), 1989, pp. 957-964.
Vig, et al., "A Review of Sensor Sensitivity and Stability," IEEE/EIA International Frequency Control Symposium and Exhibition, 2000, pp. 30-33.
Von Woedtke T., et al., "In Situ Calibration of Implanted Electro-chemical Glucose Sensors," Biomed. Biochim. Acta 48 vol. 11/12, 1989, pp. 943-952.
Wade L.G., "Reactions of Aromatic Compounds," Organic Chemistry, Chapter 17, 5th edition, 2003, pp. 762-763.
Wagner, et al., "Continuous Amperometric Monitoring of Glucose in a Brittle Diabetic Chimpanzee with a Miniature Subcutaneous Electrode," Proc. Natl. Acad. Sci. USA, vol. 95, May 1998, pp. 6379-6382.
Wang J., "Electrochemical Glucose Biosensors," American Chemical Society, Chemical Reviews, Published on Web, Dec. 23, 2007, pp. 1-12.
Wang J., et al., "Highly Selective Membrane-Free Mediator-Free Glucose Biosensor," Analytical Chemistry, vol. 66 (21), Nov. 1, 1994, pp. 3600-3603.
Wang X., et al., "Improved Ruggedness for Membrane-Based Amperometric Sensors using a Pulsed Amperometric Method," Analytical Chemistry, vol. 69 (21), Nov. 1, 1997, pp. 4482-4489.
Ward, et al., "A Wire-Based Dual-Analyte Sensor for Glucose and Lactate: In Vitro and In Vivo Evaluation," Diabetes Technology and Therapeutics, 2004, vol. 6 (3), pp. 389-401.
Ward W.K., et al., "A New Amperometric Glucose Microsensor: In Vitro and Short-Term In Vivo Evaluation," Biosensors & Bioelectronics, vol. 17, 2002, pp. 181-189.
Ward W.K., et al., "Assessment of Chronically Subcutaneous Glucose Sensors in Dogs: The Effect of Surrounding Fluid Masses," ASAIO Journal, 1999, vol. 45 (6), pp. 555-561.
Ward W.K., et al., "Rise in Background Current Over Time in a Subcutaneous Glucose Sensor in the Rabbit," Relevance to Calibration and Accuracy, Biosensors & Bioelectronics, vol. 15, 2000, pp. 53-61.
Ward W.K., et al., "Understanding Spontaneous Output Fluctuations of an Amperometric Glucose Sensor: Effect of Inhalation Anesthesia and Use of a Nonenzyme Containing Electrode," ASAIO Journal, 2000, pp. 540-546.
Wientjes K.J.C., "Development of a Glucose Sensor for Diabetic Patients," (Ph.D. Thesis), 2000, 212 pages.
Wikipedia., "Intravenous Therapy," http://en.wikipedia.org/wiki/Intravenous_therapy, Aug. 15, 2006, 6 pages.
Wilkins E., et al., "Glucose Monitoring: State of the Art and Future Possibilities," Med. Eng. Phys., vol. 18 (4), 1996, pp. 273-288.
Wilkins E., et al., "Integrated Implantable Device for Long-Term Glucose Monitoring," Biosensors & Bioelectronics, vol. 10, 1995, pp. 485-494.
Wilkins E.S., et al., "The Coated Wire Electrode Glucose Sensor," Horm Metab Res Suppl., vol. 20, 1988, pp. 50-55.
Wilson G., et al., "Biosensors for Real-time in Vivo Measurements," Biosensors and Bioelectronics, Elsevier Science Ltd, vol. 20, No. 12, Jan. 15, 2005, pp. 2388-2403.
Wilson G.S., et al., "Enzyme-Based Biosensors for In Vivo Measurements," Chem. Rev., vol. 100, 2000, pp. 2693-2704.
Wilson G.S., et al., "Progress Toward the Development of an Implantable Sensor for Glucose," Clinical Chemistry, vol. 38 (9), 1992, pp. 1613-1617.
Wolpert H., "Establishing a Continuous Glucose Monitoring Program," Journal of Diabetes Science and Technology, Mar. 2008, vol. 2 (2), pp. 307-310.
Wood W D., et al., "Hermetic Sealing with Epoxy," Pave Technology—Mechanical Engineering, Mar. 1990, 3 pages.
Woodward S.C., "How Fibroblasts and Giant Cells Encapsulate Implants: Considerations in Design of Glucose Sensors," Diabetes Care, vol. 5 (3) May-Jun. 1982, pp. 278-281.
Worsley G.J et al., "Measurement of Glucose in Blood with a Phenylboronic Acid Optical Sensor," Journal of Diabetes Science and Technology, vol. 2 (2), Mar. 2008, pp. 213-220.
Wright M., et al., "Bioelectrochemical Dehalogenations Via Direct Electrochemistry of Poly(ethylene oxide)-Modified Myoglobin," Electrochemistry Communications, vol. 1, 1999, pp. 609-613.
Written Opinion for Application No. PCT/US2002/023903 dated Nov. 15, 2004, 5 pages.
Wu H., et al., "In Situ Electrochemical Oxygen Generation with an Immunoisolation Device," Annals New York Academy of Sciences, vol. 875, 1999, pp. 105-125.
Yamasaki Y., et al., "Direct Measurement of Whole Blood Glucose by a Needle-Type Sensor," Clinica Chimica Acta. 93, 1989, pp. 93-98.

(56) References Cited

OTHER PUBLICATIONS

Yamasaki Y., "The Development of a Needle-Type Glucose Sensor for Wearable Artificial Endocrine Pancreas," Medical Journal of Osaka University, vol. 35 (1-2), Sep. 1984, pp. 25-34.
Yang C., et al., "A Comparison of Physical Properties and Fuel Cell Performance of Nafion and Zirconium Phosphate/Nation Composite Membranes," Journal of Membrane Science, vol. 237, 2004, pp. 145-161.
Yang Q., et al., "Development of Needle-Type Glucose Sensor with High Selectivity," Science and Actuators B, vol. 46, 1998, pp. 249-256.
Yang S., et al., "A Glucose Biosensor Based on an Oxygen Electrode: In-Vitro Performances in a Model Buffer Solution and in Blood Plasma," Biomedical Instrumentation & Technology, vol. 30 (1), 1996, pp. 55-61.
Yang S., et al., "Glucose Biosensors with Enzyme Entrapped in Polymer Coating," Biomedical Instrument and Technology, Mar./Apr. 1995, vol. 29 (2), pp. 125-133.
Yang X., et al., "Polyelectrolyte and Molecular Host Ion Self-Assembly to Multilayer Thin Films: An Approach to Thin Film Chemical Sensors," Sensors and Actuators B, vol. 45, 1997, pp. 87-92.
Ye L., et al., "High Current Density Wired' Quinoprotein Glucose Dehydrogenase Electrode," Analytical Chemistry, vol. 65, 1993, pp. 238-241.
Zamzow K.L., et al., "Development and Evaluation of a Wearable Blood Glucose Monitor," ASAIO Transactions, vol. 36 (3), 1990, pp. M588-M591.
Zavalkoff S.R., et al., "Evaluation of Conventional Blood Glucose Monitoring as an Indicator of Integrated Glucose Values Using a Continuous Subcutaneous Sensor," Diabetes Care, vol. 25(9), 2002, pp. 1603-1606.
Zethelius B., et al., "Use of Multiple Biomarkers to Improve the Prediction of Death From Cardiovascular Causes," N. Engl. J. Med., vol. 358, May 2008, pp. 2107-2116.
Zhang, et al., "Elimination of the Acetaminophen Interference in an Implantable Glucose Sensor," Analytical Chemistry, 1994, vol. 66 (7), pp. 1183-1188.
Zhang Y., et al., "Electrochemical Oxidation of H2O2 on Pt and Pt + Ir Electrodes in Physiological Buffer and its Applicability to H2O2-Based Biosensors," J. Electro Analytical Chemistry, vol. 345, 1993, pp. 253-271.
Zhang Y., et al., "In Vitro and In Vivo Evaluation of Oxygen Effects on a Glucose Oxidase Based Implantable Glucose Sensor," Analytica Chimica Acta, vol. 281, 1993, pp. 513-520.
Zhu, et al., "Fabrication and Characterization of Glucose Sensors Based on a Microarray H2O2 Electrode," Biosensors & Bioelectronics, 1994, vol. 9, pp. 295-300.
Zhu, et al., "Planar Amperometric Glucose Sensor Based on Glucose Oxidase Immobilized by Chitosan Film on Prussian blue Layer," Sensors, 2002, vol. 2, pp. 127-136.
Ziaie, et al., "A Single-Channel Implantable Microstimulator for Functional Neuromuscular Stimulation," IEEE Transactions on Biomedical Engineering, 1997, vol. 44(10), pp. 909-920.
Communication pursuant to Article 94(3) EPC for European Application No. 19165169.4 dated Oct. 23, 2020, 5 pages.
Communication pursuant to Rules 70(2) and 70a(2) EPC for European Application No. 20190044.6, dated Jan. 15, 2021, 2 pages.
Communication under rule 71(3) EPC for European Application No. 17198022.0 dated Feb. 8, 2021, 8 pages.
Communication Under Rule No. 71(3) for EP Application No. 19185160.9 dated Sep. 25, 2020, 183 pages.
Examination Report for European Application No. 11182622.8, dated Sep. 18, 2012;3 pages.
Extended European Search Report for Application No. 14184330.0 dated May 4, 2015, 11 pages.
Extended European Search Report for Application No. 20190044.6, dated Nov. 26, 2020, 12 pages.
International Search Report and Written Opinion for Application No. PCT/US2005/014969 dated Dec. 12, 2005, 8 pages.
Notice of Opposition for European Application No. 1986543, dated Jul. 25, 2012, 72 pages.
Office Action from European Patent Application No. 14184330.0, dated Dec. 14, 2020, 240 pages.
Office Action from European Patent Application No. 19165167.8, dated Nov. 10, 2020, 130 pages.
Submission in Opposition Proceedings for European Application No. 10195519.3, dated Nov. 9, 2020, 33 pages.
Summons to Oral Proceedings pursuant to Rule 115 (1) EPC for European Application No. 06736006.5, dated Jan. 29, 2021, 7 pages.
Summons to Oral Proceedings pursuant to Rule 115 (1) EPC for European Application No. 11182622.8, dated Jan. 29, 2021, 5 pages.
Supplementary European Search Report for Application No. 20204077.0, dated Jan. 12, 2021, 4 pages.
Office Action from European application No. 20156336.8, dated Feb. 17, 2021, 130 pages.
Parkes J.L., et al., "A New Consensus Error Grid to Evaluate the Clinical Significance of Inaccuracies in the Measurement of Blood Glucose," Diabetes Care, vol. 23, No. 8, Aug. 2000, pp. 1143-1148.

\* cited by examiner

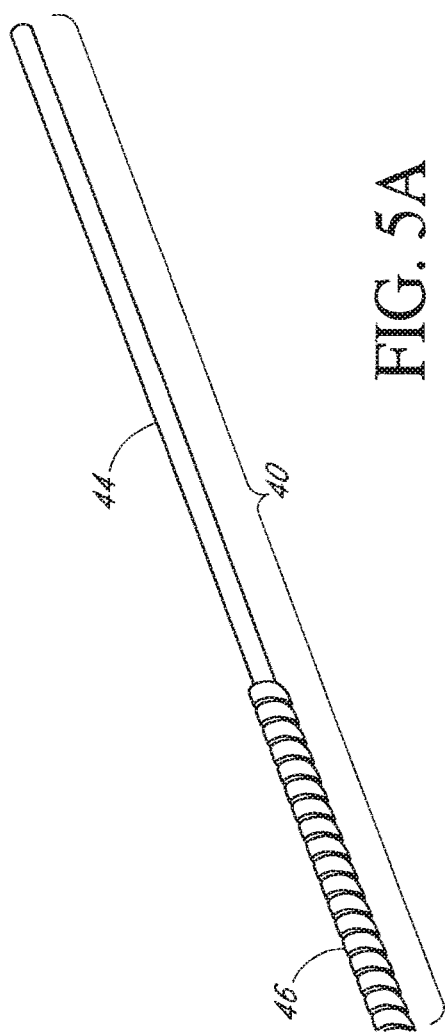

ANALYTE SENSOR

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/924,117, filed Jul. 8, 2020, which is a continuation of U.S. application Ser. No. 16/691,358, filed Nov. 21, 2019, now U.S. Pat. No. 10,709,362, which is a continuation of U.S. application Ser. No. 16/674,610, filed Nov. 5, 2019, now U.S. Pat. No. 10,722,152, which is a continuation of U.S. application Ser. No. 16/392,521, filed Apr. 23, 2019, which is a continuation of U.S. application Ser. No. 14/590,483, filed Jan. 6, 2015, now U.S. Pat. No. 10,314,525, which is a continuation of U.S. application Ser. No. 13/909,962, filed Jun. 4, 2013, now U.S. Pat. No. 9,247,900, which is a continuation of U.S. application Ser. No. 11/360,262, filed Feb. 22, 2006, now U.S. Pat. No. 8,615,282. Each of the aforementioned applications is incorporated by reference herein in its entirety, and each is hereby expressly made a part of this specification. The aforementioned application is incorporated by reference herein in its entirety, and is hereby expressly made a part of this specification.

FIELD OF THE INVENTION

The present invention relates generally to systems and methods for measuring an analyte in a host. More particularly, the present invention relates to systems and methods for transcutaneous measurement of glucose in a host.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional method. This inhibits the ability to make educated insulin therapy decisions.

A variety of sensors are known that use an electrochemical cell to provide output signals by which the presence or absence of an analyte, such as glucose, in a sample can be determined. For example, in an electrochemical cell, an analyte (or a species derived from it) that is electro-active generates a detectable signal at an electrode, and this signal can be used to detect or measure the presence and/or amount within a biological sample. In some conventional sensors, an enzyme is provided that reacts with the analyte to be measured, and the byproduct of the reaction is qualified or quantified at the electrode. An enzyme has the advantage that it can be very specific to an analyte and also, when the analyte itself is not sufficiently electro-active, can be used to interact with the analyte to generate another species which is electro-active and to which the sensor can produce a desired output. In one conventional amperometric glucose oxidase-based glucose sensor, immobilized glucose oxidase catalyses the oxidation of glucose to form hydrogen peroxide, which is then quantified by amperometric measurement (for example, change in electrical current) through a polarized electrode.

SUMMARY OF THE INVENTION

In a first aspect, a sensor for transcutaneous measurement of an analyte in a host is provided, the sensor comprising at least one electrode formed from a conductive material; and a membrane disposed on an electroactive portion of the electrode, wherein the membrane is configured to control an influx of the analyte therethrough, and wherein the membrane comprises a substantially non-smooth outer surface.

In an embodiment of the first aspect, the substantially non-smooth surface appears under magnification to resemble a super-positioning of disc shaped objects.

In an embodiment of the first aspect, the disc shaped objects comprise a rounded shape.

In an embodiment of the first aspect, the disc shaped objects have an average diameter of from about 5 microns to about 250 microns.

In an embodiment of the first aspect, the membrane further comprises an enzyme domain.

In an embodiment of the first aspect, the membrane further comprises an interference domain.

In an embodiment of the first aspect, the membrane further comprises an electrode domain.

In an embodiment of the first aspect, the membrane is at least partially formed by a vapor deposition coating process.

In an embodiment of the first aspect, the vapor deposition coating process comprises a physical vapor deposition coating process, e.g., ultrasonic vapor deposition.

In an embodiment of the first aspect, the membrane substantially resists ascorbate flux therethrough.

In an embodiment of the first aspect, the electrode comprises a wire comprising a conductive material, and wherein the sensor is configured for substantially continuous measurement of glucose in a host.

In a second aspect, a method for manufacturing a transcutaneous analyte sensor is provided, the method comprising the steps of providing at least one electrode comprising an electroactive portion; and applying a membrane to the electroactive port ion, wherein at least one layer of the membrane is applied by vapor deposition.

In an embodiment of the second aspect, the vapor deposition comprises physical vapor deposition.

In an embodiment of the second aspect, the physical vapor deposition comprises ultrasonic vapor deposition.

In an embodiment of the second aspect, the layer of the membrane is deposited in a vacuum chamber. The layer can be configured to resist flow of the analyte therethrough.

In an embodiment of the second aspect, at least one layer of the membrane is applied using an ultrasonic nozzle. The layer can be configured to resist flow of the analyte therethrough.

In an embodiment of the second aspect, the step of applying a membrane comprises applying an enzyme domain. The enzyme domain can be applied by dip coating.

In an embodiment of the second aspect, the step of applying a membrane comprises applying an electrode domain. The electrode domain can be applied by dip coating.

In an embodiment of the second aspect, the electrode comprises a wire comprising a conductive material, and wherein the sensor is configured for substantially continuous measurement of glucose in a host.

In a third aspect, a method for manufacturing a plurality of transcutaneous analyte sensors is provided, the method comprising providing a plurality of electrodes, each electrode comprising an electroactive portion; placing the plurality of electrodes into a vacuum chamber; and vapor depositing at least one membrane layer thereon.

In an embodiment of the third aspect, the membrane layer is configured to control influx of an analyte therethrough.

In an embodiment of the third aspect, wherein an in vitro sensitivity of the plurality of sensors deviates from a median in vitro sensitivity by less about 20%.

In an embodiment of the third aspect, an in vitro sensitivity of the plurality of sensors deviates from a median in vitro sensitivity by less about 16%.

In an embodiment of the third aspect, an in vitro sensitivity of the plurality of sensors deviates from a median in vitro sensitivity by less about 12%.

In an embodiment of the third aspect, the method further comprises curing the membrane layer. The curing step can include placing a plurality of electrodes, each comprising the membrane layer, into a vacuum oven, a convection oven, or a variable frequency microwave oven.

In an embodiment of the third aspect, each electrode comprises a wire comprising a conductive material, and wherein each sensor is configured for substantially continuous measurement of glucose in a host.

In a fourth aspect, a method for limiting use of an analyte sensor to a predetermined time period is provided, the method comprising providing a key associated with an analyte sensor, wherein the key is configured to control an amount of time over which information is obtained from the analyte sensor.

In an embodiment of the fourth aspect, the analyte sensor is a transcutaneous glucose sensor.

In an embodiment of the fourth aspect, the sensor is operatively connected to a receiver, wherein the receiver is configured to display sensor data.

In an embodiment of the fourth aspect, the receiver is configured to receive the key.

In an embodiment of the fourth aspect, the receiver is configured to control an amount of time over which information is displayed on the receiver from the sensor in response to the key.

In an embodiment of the fourth aspect, the key is a software key.

In an embodiment of the fourth aspect, the key is a unique code.

In an embodiment of the fourth aspect, the key is selected from the group consisting of a unique number, a receiver ID, a sensor duration, a number of sensor systems, and combinations thereof.

In an embodiment of the fourth aspect, the key is configured for use with a plurality of sensors.

In an embodiment of the fourth aspect, the key is provided by an information tag.

In a fifth aspect, a method for distributing and controlling use of implantable sensor systems comprising reusable and disposable parts, the method comprising providing a single-use device associated with the sensor system, wherein the single-use device is configured to be inserted into a host's tissue; providing a key associated with the single-use device; and providing a reusable device associated with a sensor system, wherein the reusable device is configured to provide sensor information responsive to receipt of the key.

In an embodiment of the fifth aspect, the reusable device comprises a receiver configured to receive sensor information.

In an embodiment of the fifth aspect, the reusable device further comprises an electronics unit configured to releasably mate with the single-use device.

In an embodiment of the fifth aspect, the method further comprises obtaining a package containing a plurality of single-use devices.

In an embodiment of the fifth aspect, the single-use device is a transcutaneous analyte sensor configured for insertion into a subcutaneous tissue of a host.

In an embodiment of the fifth aspect, the key comprises a written license code packaged with the single-use device.

In an embodiment of the fifth aspect, the step of providing the key comprises providing a license code via at least one communication selected from the group consisting of written communication, voice communication, and electronic communication.

In an embodiment of the fifth aspect, the reusable device is configured to receive the key via manual entry.

In an embodiment of the fifth aspect, the reusable device is configured to wirelessly receive the key.

In an embodiment of the fifth aspect, key comprises sensor duration information configured to enable the sensor system to control an amount of time over which information is obtained from the single-use device or is displayed by the reusable device.

In an embodiment of the fifth aspect, the single-use device comprises a transcutaneous analyte sensor configured for insertion in a subcutaneous tissue of a host, and wherein the key comprises sensor insertion information configured to enable the sensor system to control a number of sensor insertions.

In an embodiment of the fifth aspect, the single-use device comprises a transcutaneous analyte sensor configured for insertion in a subcutaneous tissue of a host, and wherein the step of inserting the single-use device into a host comprises using an applicator to insert the sensor into the host.

In an embodiment of the fifth aspect, the step of obtaining sensor information from the sensor system comprises at least one step selected from the group consisting of measurement of analyte information, digitalizing of sensor information, transmission of sensor information, receiving of sensor information, storing of sensor information, processing of sensor information, and displaying of sensor information.

In a sixth aspect, a method for limiting use of a glucose sensor system to a predetermined time period is provided, the method comprising inputting a key into a receiver, wherein the key is configured to control an amount of time over which information is obtained from a sensor system, after which time the sensor system is disabled such that glucose information cannot be obtained, wherein the sensor system is a transcutaneous glucose sensor system comprising a sensor configured for insertion into a tissue of a host and an electronics unit operatively connected to the sensor and configured to provide a signal representative of a glucose concentration in the host, and wherein the receiver is configured to receive the signal representative of a glucose concentration in the host and to display corresponding glucose information; and obtaining glucose information from the sensor.

In an embodiment of the sixth aspect, the step of inputting the key into the receiver is performed before the step of obtaining glucose information from the sensor.

In a seventh aspect, a device for measuring an analyte in a host is provided, the device comprising a sensor operably connected to sensor electronics, the sensor electronics configured for measuring an analyte in a host; at least one electrical contact configured to connect the sensor to the sensor electronics; and a sealing member, wherein the sealing member at least partially surrounds at least one of the sensor and the electrical contact, wherein the sealing member comprises a material having a durometer hardness of from about 5 Shore A to about 80 Shore A.

In an embodiment of the seventh aspect, the durometer hardness is from about 10 Shore A to about 50 Shore A.

In an embodiment of the seventh aspect, the durometer hardness is about 20 Shore A.

In an embodiment of the seventh aspect, the durometer hardness is about 50 Shore A In an embodiment of the seventh aspect, the sensor comprises a wire.

In an embodiment of the seventh aspect, the sensor comprises a planar substrate.

In an embodiment of the seventh aspect, the sealing material comprises a silicone.

In an embodiment of the seventh aspect, the device further comprises a sealant adjacent to the sealing member.

In an embodiment of the seventh aspect, the sensor electronics are housed within an electronics unit configured to mate with the electrical contact.

In an embodiment of the seventh aspect, the electronics unit and the sealing member are configured to mate to provide a compression force therebetween.

In an embodiment of the seventh aspect, the device further comprises at least one raised portion configured to provide a compression force to the sealing member when the electrical contact is connected to the sensor electronics.

In an eighth embodiment, a device for use in measuring an analyte in a host is provided, the device comprising a sensor operably connected to sensor electronics, the sensor electronics configured for measuring an analyte in a host; at least one electrical contact configured to operably connect the sensor to the sensor electronics; and a sealing member at least partially surrounding at least one of the sensor and the electrical contact, wherein the sealing member is configured to seal the electrical contact from moisture when the sensor is operably connected to the sensor electronics.

In an embodiment of the eighth aspect, the sealing member comprises a material having a durometer hardness of from about 5 Shore A to about 80 Shore A.

In an embodiment of the eighth aspect, the device further comprises a sealant adjacent to the sealing member.

In an embodiment of the eighth aspect, the device further comprises a housing on which the sealing member is disposed, wherein the housing is configured to mechanically or chemically hold the sealing member thereon.

In an embodiment of the eighth aspect, the device further comprises an adhesive configured to hold the sealing member on the housing.

In an embodiment of the eighth aspect, the device further comprises at least one protrusion configured to substantially mate with at least one depression, whereby the sealing member is held on the housing.

In an embodiment of the eighth aspect, the sealing member comprises at least one gap that is maintained when the electrical contact is operably connected to the sensor electronics.

In an embodiment of the eighth aspect, the sensor at least partially extends through the gap.

In an embodiment of the eighth aspect, the gap is filled with a sealant.

In an embodiment of the eighth aspect, the device further comprises at least one channel communicating between a first side of the sealing member and a second side of the sealing member.

In an embodiment of the eighth aspect, the channel is filled with a sealant.

In an embodiment of the eighth aspect, substantially no air gaps are adjacent to the electrical contact when the electrical contact is operably connected to the sensor electronics.

In an embodiment of the eighth aspect, the sealing member comprises a material selected from the group consisting of silicone, silicone/polyurethane hybrid, polyurethane, polysulfide, and mixtures thereof.

In an embodiment of the eighth aspect, the sealing member is self-lubricating.

In an embodiment of the eighth aspect, the sealing member comprises a sealant sandwiched between an upper portion of the sealing member and a lower portion of the sealing member.

In an embodiment of the eighth aspect, the device further comprises a guide tube configured to maintain an opening in the sealing member prior to sensor insertion into the host.

In an embodiment of the eighth aspect, the device further comprises a lubricant between the sealing member and the guide tube.

In a ninth aspect, a device for use in measuring an analyte in a host is provided, the device comprising a sensor operably connected to sensor electronics, the sensor electronics configured for measuring an analyte in a host; at least one electrical contact configured to connect the sensor to the sensor electronics, wherein the electrical contact comprises a material having a durometer hardness of from about 5 Shore A to about 80 Shore A; and a sealing member at least partially surrounding at least one of the sensor and the electrical contact, wherein the sealing member comprises a material having a durometer hardness of from about 5 Shore A to about 80 Shore A.

In an embodiment of the ninth aspect, the durometer hardness of the electrical contact is higher than the durometer hardness of the sealing member.

In an embodiment of the ninth aspect, the durometer hardness of the electrical contact is about 50 Shore A.

In an embodiment of the ninth aspect, the durometer hardness of the sealing member is higher than the durometer hardness of the contact.

In an embodiment of the ninth aspect, the durometer hardness of the sealing member is about 50 Shore A.

In an embodiment of the ninth aspect, the sealing member comprises a filler material.

In an embodiment of the ninth aspect, the filler material is configured to stiffen the sealing member.

In a tenth aspect, a sensor system for measuring an analyte concentration in a host is provided, the system comprising at least one electrode configured for implantation in a host and configured to measure an analyte concentration in a tissue of the host; sensor electronics operably connected to the electrode and configured to provide analyte data representative of an analyte concentration in the host; and an information tag comprising sensor information.

In an embodiment of the tenth aspect, the information tag comprises a memory.

In an embodiment of the tenth aspect, the information tag transmits information using at least one connection selected from the group consisting of a serial connection, a radio frequency connection, an acoustic frequency connection, an infrared frequency connection, and a magnetic induction connection.

In an embodiment of the tenth aspect, the system further comprises a mounting unit configured to maintain the sensor positioned transcutaneously within the tissue of the host.

In an embodiment of the tenth aspect, the information tag is embedded within the mounting unit.

In an embodiment of the tenth aspect, the system further comprises a receiver configured to receive the analyte data from the sensor electronics.

In an embodiment of the tenth aspect, the receiver is configured to read sensor information from the information tag.

In an embodiment of the tenth aspect, the system further comprises packaging configured to contain at least a portion of a sensor system during transport.

In an embodiment of the tenth aspect, the information tag is in or on the packaging.

In an embodiment of the tenth aspect, the sensor information comprises at least one item selected from the group consisting of manufacturing information, calibration information, identification information, expiration information, sensor duration information, and archived data.

In an embodiment of the tenth aspect, the sensor information comprises a license code.

In an eleventh aspect, a transcutaneous analyte sensor assembly is provided, the assembly comprising a mounting unit adapted for mounting on a skin of a host; an electronics unit configured to releasably mate with the mounting unit; a sensor configured to measure a concentration of an analyte in the host, wherein the sensor is operably connected to the electronics unit when the electronics unit is mated to the mounting unit; and an information tag comprising sensor information.

In an embodiment of the eleventh aspect, the sensor information is embedded in an information tag within the mounting unit.

In an embodiment of the eleventh aspect, the assembly further comprises a receiver, wherein the receiver is configured to read sensor information from the information tag.

In an embodiment of the eleventh aspect, the information tag comprises a memory.

In an embodiment of the eleventh aspect, the information tag transmits information using at least one connection selected from the group consisting of a serial connection, a radio frequency connection, an acoustic frequency connection, an infrared frequency connection, and a magnetic induction connection.

In an embodiment of the eleventh aspect, the sensor information is embedded within the electronics unit.

In an embodiment of the eleventh aspect, the assembly further comprises packaging configured to contain the sensor assembly during transport, wherein the information tag is provided in or on the packaging.

In an embodiment of the eleventh aspect, the assembly further comprises a receiver, wherein the receiver is configured to read the sensor information from the information tag.

In an embodiment of the eleventh aspect, the sensor information comprises information configured to trigger initialization of the sensor.

In a twelfth aspect, a transcutaneous glucose sensor system is provided, the sensor system comprising a mounting unit adapted for mounting on a skin of a host; a sensor configured to measure an analyte concentration in the host; sensor electronics operably connected to the sensor, wherein the sensor is configured to provide data representative of an analyte concentration in the host; a receiver remote from the mounting unit and configured to receive sensor data from the electronics unit representative of a measured analyte concentration; and an information tag configured to provide sensor information selected from the group consisting of manufacturing information, calibration information, identification information, expiration information, sensor duration information, archived data, license code information, and combinations thereof.

In an embodiment of the twelfth aspect, the receiver is configured to read sensor information from the information tag.

In an embodiment of the twelfth aspect, the electronics unit is configured to releasably mate with the mounting unit, and wherein the electronics unit is operably connected to the sensor when the electronics unit is mated to the mounting unit.

In a thirteenth aspect, a device configured for placement on a skin surface of a host is provided, the device comprising a sensor configured for transcutaneous insertion into a host and operatively connected to sensor electronics for processing data obtained from the sensor; and a housing adapted for placement on a skin surface of the host and coupled to the sensor electronics, wherein at least one of the housing and the sensor electronics comprises a user interface configured to communicate information responsive to processed sensor data.

In an embodiment of the thirteenth aspect, the user interface comprises a screen configured to display at least one numerical value.

In an embodiment of the thirteenth aspect, the user interface comprises a screen configured to display trend information.

In an embodiment of the thirteenth aspect, the user interface comprises a screen configured to display graphical information.

In an embodiment of the thirteenth aspect, the user interface is configured to communicate information audibly.

In an embodiment of the thirteenth aspect, the user interface is configured to communicate information tactilely.

In an embodiment of the thirteenth aspect, the user interface is configured to provide information to the host in response to activation of a button.

In an embodiment of the thirteenth aspect, the sensor electronics are configured to alert the host when the sensor data is outside a predetermined boundary.

In an embodiment of the thirteenth aspect, the sensor electronics are configured to filter the sensor data.

In an embodiment of the thirteenth aspect, the sensor electronics are configured to calibrate the sensor data.

In an embodiment of the thirteenth aspect, the device further comprises a receiver, wherein the receiver is configured to communicate with the sensor electronics.

In an embodiment of the thirteenth aspect, the receiver is configured to request information from the sensor electronics.

In an embodiment of the thirteenth aspect, the sensor electronics are configured to transmit sensor data responsive to a request by the receiver.

In an embodiment of the thirteenth aspect, the receiver and the sensor electronics are operatively connected by at least one connection selected from the group consisting of a cable, a radio frequency connection, an optical connection, an inductive coupling connection, an infrared connection, and a microwave connection.

In an embodiment of the thirteenth aspect, the sensor electronics are releasably attachable to the housing.

In a fourteenth aspect, a transcutaneous glucose sensing device is provided, the device comprising a glucose sensor configured for transcutaneous insertion through a skin of a host; and an on-skin housing coupled to the sensor, wherein the on-skin housing is adhered to the skin, and wherein the on-skin housing comprises sensor electronics configured to process sensor data and to provide sensor data to the host via a user interface.

In an embodiment of the fourteenth aspect, the user interface is configured to provide sensor data by at least method selected from the group consisting of visually, audibly, and tactilely.

In an embodiment of the fourteenth aspect, the user interface is housed on or in the on-skin housing.

In an embodiment of the fourteenth aspect, the user interface is operatively connected to the on-skin housing via at least one wire.

In an embodiment of the fourteenth aspect, the user interface is configured to be worn on the host at a location remote from the on-skin housing.

In an embodiment of the fourteenth aspect, the user interface is configured to be worn on clothing of the host, and wherein the on-skin housing in configured to be worn on the skin of the host.

In an embodiment of the fourteenth aspect, the user interface is directly wired to the on-skin housing.

In an embodiment of the fourteenth aspect, the sensor electronics are releasably attachable to the on-skin housing.

In a fifteenth aspect, a transcutaneous glucose sensor system is provided, the system comprising a glucose sensor configured for transcutaneous insertion through skin of a host; an on-skin device coupled to the sensor and comprising electronics configured to process data obtained from the sensor; and a receiver remote from the on-skin device configured to request information from the on-skin device.

In an embodiment of the fifteenth aspect, the on-skin device is configured to provide sensor information indicative of a glucose value of the host by at least one method selected from the group consisting of visual, audible, and tactile.

In an embodiment of the fifteenth aspect, the on-skin device is configured to provide filtered sensor data by at least one method selected from the group consisting of visual, audible, and tactile.

In an embodiment of the fifteenth aspect, the on-skin device is configured to provide calibrated sensor data by at least one method selected from the group consisting of visual, audible, and tactile.

BRIEF DESCRIPTION OF THE DRAWINGS

FIG. 5A is an expanded cutaway view of a proximal portion of a sensor.

DETAILED DESCRIPTION OF THE PREFERRED EMBODIMENT

Figure 1:
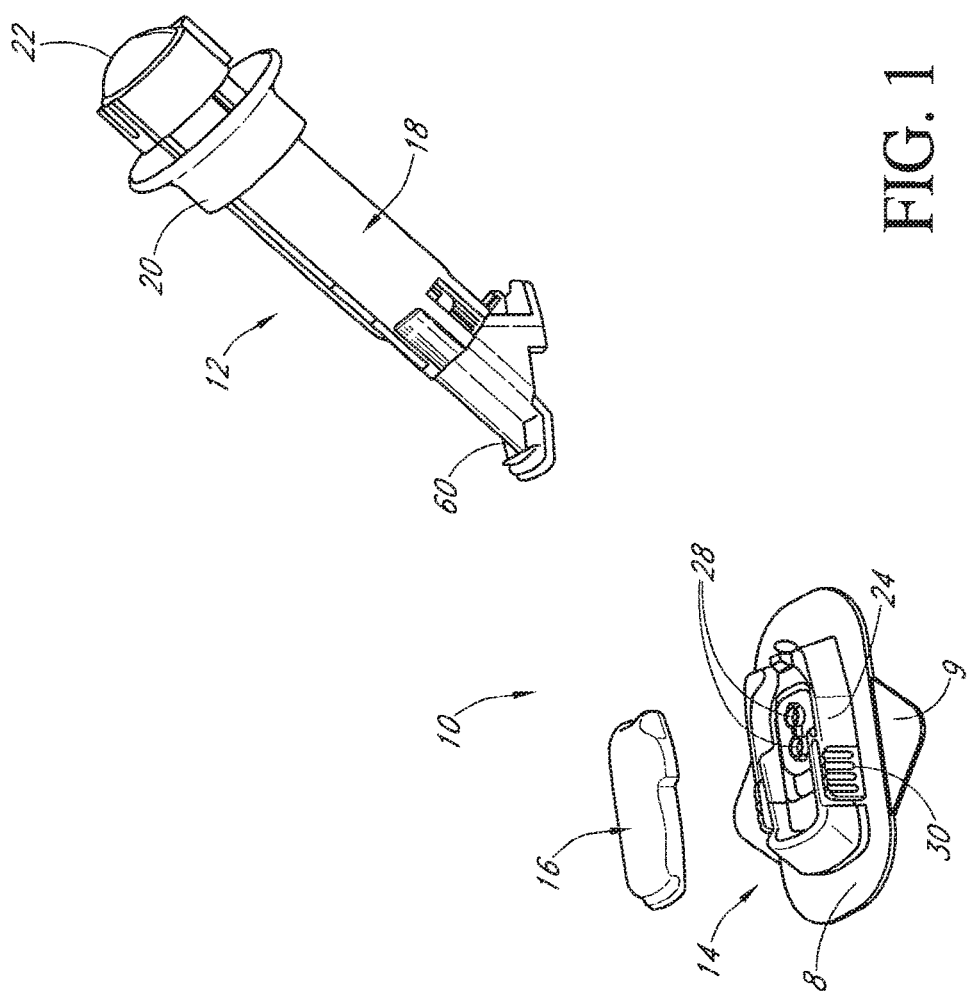
FIG. 1 is a perspective view of a transcutaneous analyte sensor system, including an applicator, a mounting unit, and an electronics unit.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV- 1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A–1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The term "host" as used herein is a broad term, and is to be given its ordinary and customary meaning to a person of ordinary skill in the art (and is not to be limited to a special or customized meaning), and refers without limitation to mammals, particularly humans.

The term "exit-site" as used herein is a broad term, and is to be given its ordinary and customary meaning to a person of ordinary skill in the art (and is not to be limited to a special or customized meaning), and refers without limitation to the area where a medical device (for example, a sensor and/or needle) exits from the host's body.

The term "continuous (or continual) analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and or intermittently (regularly or irregularly) performed, for example, about every 5 to 10 minutes.

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. For example, a working electrode measures hydrogen peroxide produced by the enzyme-catalyzed reaction of the analyte detected, which reacts to create an electric current. Glucose analyte can be detected utilizing glucose oxidase, which produces $H_2O_2$ as a byproduct. $H_2O_2$ reacts with the surface of the working electrode, producing two protons ($2H^+$), two electrons ($2e^-$) and one molecule of oxygen ($O_2$), which produces the electronic current being detected.

The term "electronic connection" as used herein is a broad term, and is to be given its ordinary and customary meaning to a person of ordinary skill in the art (and is not to be limited to a special or customized meaning), and refers without limitation to any electronic connection known to those in the art that can be utilized to interface the sensing region electrodes with the electronic circuitry of a device, such as mechanical (for example, pin and socket) or soldered electronic connections.

The term "sensing region" as used herein is a broad term, and is to be given its ordinary and customary meaning to a person of ordinary skill in the art (and is not to be limited to a special or customized meaning), and refers without limitation to the region of a monitoring device responsible for the detection of a particular analyte. The sensing region generally comprises a non-conductive body, a working electrode (anode), a reference electrode (optional), and/or a counter electrode (cathode) passing through and secured within the body forming electrochemically reactive surfaces on the body and an electronic connective means at another location on the body, and a multi-domain membrane affixed to the body and covering the electrochemically reactive surface.

The term "high oxygen solubility domain" as used herein is a broad term, and is to be given its ordinary and customary meaning to a person of ordinary skill in the art (and is not to be limited to a special or customized meaning), and refers without limitation to a domain composed of a material that has higher oxygen solubility than aqueous media such that it concentrates oxygen from the biological fluid surrounding the membrane system. The domain can act as an oxygen reservoir during times of minimal oxygen need and has the capacity to provide, on demand, a higher oxygen gradient to facilitate oxygen transport across the membrane. Thus, the ability of the high oxygen solubility domain to supply a higher flux of oxygen to critical domains when needed can improve overall sensor function.

The term "domain" as used herein is a broad term, and is to be given its ordinary and customary meaning to a person of ordinary skill in the art (and is not to be limited to a special or customized meaning), and refers without limitation to a region of the membrane system that can be a layer, a uniform or non-uniform gradient (for example, an anisotropic region of a membrane), or a portion of a membrane.

The term "distal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively far from the reference point than another element.

The term "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively near to the reference point than another element.

The term "in vivo portion" as used herein is a broad term, and is to be given its ordinary and customary meaning to a person of ordinary skill in the art (and is not to be limited to a special or customized meaning), and refers without limitation to the portion of the device (for example, a sensor) adapted for insertion into and/or existence within a living body of a host.

The term "ex vivo portion" as used herein is a broad term, and is to be given its ordinary and customary meaning to a person of ordinary skill in the art (and is not to be limited to a special or customized meaning), and refers without limitation to the portion of the device (for example, a sensor) adapted to remain and/or exist outside of a living body of a host.

The terms "raw data stream", "raw data signal", and "data stream" as used herein are broad terms, and are to be given their ordinary and customary meaning to a person of ordinary skill in the art (and are not to be limited to a special or customized meaning), and refer without limitation to an analog or digital signal from the analyte sensor directly related to the measured analyte. For example, the raw data stream is digital data in "counts" converted by an A/D converter from an analog signal (for example, voltage or amps) representative of an analyte concentration. The terms broadly encompass a plurality of time spaced data points from a substantially continuous analyte sensor, each of which comprises individual measurements taken at time intervals ranging from fractions of a second up to, for example, 1, 2, or 5 minutes or longer.

The term "count" as used herein is a broad term, and is to be given its ordinary and customary meaning to a person of ordinary skill in the art (and is not to be limited to a special or customized meaning), and refers without limitation to a unit of measurement of a digital signal. For example, a raw data stream or raw data signal measured in counts is directly related to a voltage (for example, converted by an A/D converter), which is directly related to current from the working electrode.

The term "physiologically feasible" as used herein is a broad term, and is to be given its ordinary and customary meaning to a person of ordinary skill in the art (and is not to be limited to a special or customized meaning), and refers without limitation to one or more physiological parameters obtained from continuous studies of glucose data in humans and/or animals. For example, a maximal sustained rate of change of glucose in humans of about 4 mg/dL/min to about 6 mg/dL/min and a maximum acceleration of the rate of change of about 0.1 mg/dL/min/min to about 0.2 mg/dL/min/min are deemed physiologically feasible limits. Values outside of these limits are considered non-physiological and are likely a result of, e.g., signal error.

The term "ischemia" as used herein is a broad term, and is to be given its ordinary and customary meaning to a person of ordinary skill in the art (and is not to be limited to a special or customized meaning), and refers without limitation to local and temporary deficiency of blood supply due to obstruction of circulation to a part (for example, a sensor). Ischemia can be caused, for example, by mechanical obstruction (for example, arterial narrowing or disruption) of the blood supply.

The term "matched data pairs" as used herein is a broad term, and is to be given its ordinary and customary meaning to a person of ordinary skill in the art (and is not to be limited to a special or customized meaning), and refers without limitation to reference data (for example, one or more reference analyte data points) matched with substantially time corresponding sensor data (for example, one or more sensor data points).

The term "Clarke Error Grid" as used herein is a broad term, and is to be given its ordinary and customary meaning to a person of ordinary skill in the art (and is not to be limited to a special or customized meaning), and refers without limitation to an error grid analysis, for example, an error grid analysis used to evaluate the clinical significance of the difference between a reference glucose value and a sensor generated glucose value, taking into account 1) the value of the reference glucose measurement, 2) the value of the sensor glucose measurement, 3) the relative difference between the two values, and 4) the clinical significance of this difference. See Clarke et al., "Evaluating Clinical Accuracy of Systems for Self-Monitoring of Blood Glucose" Diabetes Care, Volume 10, Number 5, September-October 1987.

The term "Consensus Error Grid" as used herein is a broad term, and is to be given its ordinary and customary meaning to a person of ordinary skill in the art (and is not to be limited to a special or customized meaning), and refers without limitation to an error grid analysis that assigns a specific level of clinical risk to any possible error between two time corresponding measurements, e.g., glucose measurements. The Consensus Error Grid is divided into zones signifying the degree of risk posed by the deviation. See Parkes et al., "A New Consensus Error Grid to Evaluate the Clinical Significance of Inaccuracies in the Measurement of Blood Glucose" Diabetes Care, Volume 23, Number 8, August 2000.

The term "clinical acceptability" as used herein is a broad term, and is to be given its ordinary and customary meaning to a person of ordinary skill in the art (and is not to be limited to a special or customized meaning), and refers without limitation to determination of the risk of an inaccuracy to a patient. Clinical acceptability considers a deviation between time corresponding analyte measurements (for example, data from a glucose sensor and data from a reference glucose monitor) and the risk (for example, to the decision making of a person with diabetes) associated with that deviation based on the analyte value indicated by the sensor and/or reference data. An example of clinical acceptability can be 85% of a given set of measured analyte values within the "A" and "B" region of a standard Clarke Error Grid when the sensor measurements are compared to a standard reference measurement.

The terms "sensor" and "sensor system" as used herein are broad terms, and are to be given their ordinary and customary meaning to a person of ordinary skill in the art (and are not to be limited to a special or customized meaning), and refer without limitation to the component or region of a device by which an analyte can be quantified.

The term "needle" as used herein is a broad term, and is to be given its ordinary and customary meaning to a person of ordinary skill in the art (and is not to be limited to a special or customized meaning), and refers without limitation to a slender hollow instrument for introducing material into or removing material from the body.

The terms "operatively connected," "operatively linked," "operably connected," and "operably linked" as used herein are broad terms, and are to be given their ordinary and customary meaning to a person of ordinary skill in the art (and are not to be limited to a special or customized meaning), and refer without limitation to one or more components linked to one or more other components. The terms can refer to a mechanical connection, an electrical connection, or a connection that allows transmission of signals between the components. For example, one or more electrodes can be used to detect the amount of analyte in a sample and to convert that information into a signal; the signal can then be transmitted to a circuit. In such an example, the electrode is "operably linked" to the electronic circuitry.

The term "baseline" as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation $y=mx+b$, the value of b represents the baseline of the signal.

The terms "sensitivity" and "slope" as used herein are broad terms, and are to be given their ordinary and customary meaning to a person of ordinary skill in the art (and are not to be limited to a special or customized meaning), and refer without limitation to an amount of electrical current produced by a predetermined amount (unit) of the measured analyte. For example, in one preferred embodiment, a sensor has a sensitivity (or slope) of about 3.5 to about 7.5 picoAmps of current for every 1 mg/dL of glucose analyte.

The term "membrane system" as used herein is a broad term, and is to be given its ordinary and customary meaning to a person of ordinary skill in the art (and is not to be limited to a special or customized meaning), and refers without limitation to a permeable or semi-permeable membrane that can be comprised of two or more domains and is typically constructed of materials of one or more microns in thickness, which is permeable to oxygen and is optionally permeable to, e.g., glucose or another analyte. In one example, the membrane system comprises an immobilized glucose oxidase enzyme, which enables a reaction to occur between glucose and oxygen whereby a concentration of glucose can be measured.

The terms "processor module" and "microprocessor" as used herein are broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer.

The terms "smoothing" and "filtering" as used herein are broad terms, and are to be given their ordinary and customary meaning to a person of ordinary skill in the art (and are not to be limited to a special or customized meaning), and refer without limitation to modification of a set of data to make it smoother and more continuous or to remove or diminish outlying points, for example, by performing a moving average of the raw data stream.

The term "algorithm" as used herein is a broad term, and is to be given its ordinary and customary meaning to a person of ordinary skill in the art (and is not to be limited to a special or customized meaning), and refers without limitation to a computational process (for example, programs) involved in transforming information from one state to another, for example, by using computer processing.

The term "regression" as used herein is a broad term, and is to be given its ordinary and customary meaning to a person of ordinary skill in the art (and is not to be limited to a special or customized meaning), and refers without limitation to finding a line for which a set of data has a minimal measurement (for example, deviation) from that line. Regression can be linear, non-linear, first order, second order, or the like. One example of regression is least squares regression.

The term "calibration" as used herein is a broad term, and is to be given its ordinary and customary meaning to a person of ordinary skill in the art (and is not to be limited to a special or customized meaning), and refers without limitation to the process of determining the relationship between the sensor data and the corresponding reference data, which can be used to convert sensor data into meaningful values substantially equivalent to the reference data. In some embodiments, namely, in continuous analyte sensors, calibration can be updated or recalibrated over time as changes in the relationship between the sensor data and reference data occur, for example, due to changes in sensitivity, baseline, transport, metabolism, or the like.

The terms "interferents" and "interfering species" as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte concentration. In one example of an electrochemical sensor, interfering species are compounds with an oxidation potential that overlap that of the analyte to be measured, thereby producing a false positive signal.

The terms "chloridization" and "chloridizing" as used herein are broad terms, and are to be given their ordinary and customary meaning to a person of ordinary skill in the art (and are not to be limited to a special or customized meaning), and refer without limitation to treatment or preparation with chloride. The term "chloride" as used herein, is a broad term and is used in its ordinary sense, including, without limitation, to refer to Cl⁻ ions, sources of Cl⁻ ions, and salts of hydrochloric acid. Chloridization and chloridizing methods include, but are not limited to, chemical and electrochemical methods.

The term "R-value" as used herein is a broad term, and is to be given its ordinary and customary meaning to a person of ordinary skill in the art (and is not to be limited to a special or customized meaning), and refers without limitation to one conventional way of summarizing the correlation of data; that is, a statement of what residuals (e.g., root mean square deviations) are to be expected if the data are fitted to a straight line by the a regression.

The terms "data association" and "data association function" as used herein are broad terms, and are to be given their ordinary and customary meaning to a person of ordinary skill in the art (and are not to be limited to a special or customized meaning), and refer without limitation to a statistical analysis of data and particularly its correlation to, or deviation from, from a particular curve. A data association function is used to show data association. For example, the data that forms that calibration set as described herein can be analyzed mathematically to determine its correlation to, or deviation from, a curve (e.g., line or set of lines) that defines the conversion function; this correlation or deviation is the data association. A data association function is used to determine data association. Examples of data association functions include, but are not limited to, linear regression, non-linear mapping/regression, rank (e.g., non-parametric) correlation, least mean square fit, mean absolute deviation (MAD), mean absolute relative difference. In one such example, the correlation coefficient of linear regression is indicative of the amount of data association of the calibration set that forms the conversion function, and thus the quality of the calibration.

The term "quality of calibration" as used herein is a broad term, and is to be given its ordinary and customary meaning to a person of ordinary skill in the art (and is not to be limited to a special or customized meaning), and refers without limitation to the statistical association of matched data pairs in the calibration set used to create the conversion function. For example, an R-value can be calculated for a calibration set to determine its statistical data association, wherein an R-value greater than 0.79 determines a statistically acceptable calibration quality, while an R-value less than 0.79 determines statistically unacceptable calibration quality.

The term "congruence" as used herein is a broad term, and is to be given its ordinary and customary meaning to a person of ordinary skill in the art (and is not to be limited to a special or customized meaning), and refers without limitation to the quality or state of agreeing, coinciding, or being concordant. In one example, congruence can be determined using rank correlation.

The term "concordant" as used herein is a broad term, and is to be given its ordinary and customary meaning to a person of ordinary skill in the art (and is not to be limited to a special or customized meaning), and refers without limitation to being in agreement or harmony, and/or free from discord.

The phrase "continuous glucose sensing" as used herein is a broad term, and is to be given its ordinary and customary meaning to a person of ordinary skill in the art (and is not to be limited to a special or customized meaning), and refers without limitation to the period in which monitoring of plasma glucose concentration is continuously or continually performed, for example, at time intervals ranging from fractions of a second up to, for example, 1, 2, or 5 minutes, or longer.

The term "single point glucose monitor" as used herein is a broad term, and is to be given its ordinary and customary meaning to a person of ordinary skill in the art (and is not to be limited to a special or customized meaning), and refers without limitation to a device that can be used to measure a glucose concentration within a host at a single point in time, for example, some embodiments utilize a small volume in vitro glucose monitor that includes an enzyme membrane such as described with reference to U.S. Pat. Nos. 4,994,167 and 4,757,022. It should be understood that single point glucose monitors can measure multiple samples (for example, blood or interstitial fluid); however only one sample is measured at a time and typically requires some user initiation and/or interaction.

The term "biological sample" as used herein is a broad term, and is to be given its ordinary and customary meaning to a person of ordinary skill in the art (and is not to be limited to a special or customized meaning), and refers without limitation to sample of a host body, for example blood, interstitial fluid, spinal fluid, saliva, urine, tears, sweat, or the like.

The terms "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. For example, the interference domain of the preferred embodiments is configured to resist a sufficient amount of interfering species such that tracking of glucose levels can be achieved, which may include an amount greater than 50 percent, an amount greater than 60 percent, an amount greater than 70 percent, an amount greater than 80 percent, and an amount greater than 90 percent of interfering species.

The terms "cellulosic derivatives" and "cellulosic polymers" as used herein are broad terms, and are to be given their ordinary and customary meaning to a person of ordinary skill in the art (and are not to be limited to a special or customized meaning), and refer without limitation to derivatives of cellulose formed by reaction with carboxylic acid anhydrides. Examples of cellulosic derivatives include cellulose acetate, 2-hydroxyethyl cellulose, cellulose acetate phthalate, cellulose acetate propionate, cellulose acetate butyrate, cellulose acetate trimellitate, and the like.

The term "cellulose acetate" as used herein is a broad term, and is to be given its ordinary and customary meaning to a person of ordinary skill in the art (and is not to be limited to a special or customized meaning), and refers without limitation to any of several compounds obtained by treating cellulose with acetic anhydride.

The term "cellulose acetate butyrate" as used herein is a broad term, and is to be given its ordinary and customary meaning to a person of ordinary skill in the art (and is not to be limited to a special or customized meaning), and refers without limitation to any of several compounds obtained by treating cellulose with acetic anhydride and butyric anhydride.

The term "Nafion®" as used herein is a broad term, and is to be given its ordinary and customary meaning to a person of ordinary skill in the art (and is not to be limited to a special or customized meaning), and refers without limitation to DuPont's trademark of a sulfonated tetrafluorethylene polymer modified from Teflon® developed in the late 1960s. In general, Nafion® is a perfluorinated polymer that contains small proportions of sulfonic or carboxylic ionic functional groups.

The terms "crosslink" and "crosslinking" as used herein are broad terms, and are to be given their ordinary and customary meaning to a person of ordinary skill in the art (and are not to be limited to a special or customized meaning), and refer without limitation to joining (adjacent chains of a polymer or protein) by creating covalent bonds. Crosslinking can be accomplished by techniques such as thermal reaction, chemical reaction or by providing ionizing radiation (for example, electron beam radiation, UV radiation, or gamma radiation). In preferred embodiments, crosslinking utilizes a technique that forms free radicals, for example, electron beam exposure.

The term "ionizing radiation" as used herein is a broad term, and is to be given its ordinary and customary meaning to a person of ordinary skill in the art (and is not to be limited to a special or customized meaning), and refers without limitation to radiation consisting of particles, X-ray beams, electron beams, UV beams, or gamma ray beams, which produce ions in the medium through which it passes.

The term "casting" as used herein is a broad term, and is to be given its ordinary and customary meaning to a person of ordinary skill in the art (and is not to be limited to a special or customized meaning), and refers without limitation to a process where a fluid material is applied to a surface or surfaces and allowed to cure or dry. The term is broad enough to encompass a variety of coating techniques, for example, using a draw-down machine (i.e., drawing-down), dip coating, spray coating, spin coating, or the like.

The term "dip coating" as used herein is a broad term, and is to be given its ordinary and customary meaning to a person of ordinary skill in the art (and is not to be limited to a special or customized meaning), and refers without limitation to coating which involves dipping an object or material into a liquid coating substance.

The term "spray coating" as used herein is a broad term, and is to be given its ordinary and customary meaning to a person of ordinary skill in the art (and is not to be limited to a special or customized meaning), and refers without limitation to coating which involves spraying a liquid coating substance onto an object or material.

The term "spin coating" as used herein is a broad term, and is to be given its ordinary and customary meaning to a person of ordinary skill in the art (and is not to be limited to a special or customized meaning), and refers without limitation to a coating process in which a thin film is created by dropping a raw material solution onto a substrate while it is rotating.

The terms "solvent" and "solvent systems" as used herein are broad terms, and are to be given their ordinary and customary meaning to a person of ordinary skill in the art (and are not to be limited to a special or customized meaning), and refer without limitation to substances (e.g., liquids) capable of dissolving or dispersing one or more other substances. Solvents and solvent systems can include compounds and/or solutions that include components in addition to the solvent itself.

The term "baseline" as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation $y=mx+b$, the value of b represents the baseline of the signal.

The terms "sensitivity" and "slope" as used herein are broad terms, and are to be given their ordinary and customary meaning to a person of ordinary skill in the art (and are not to be limited to a special or customized meaning), and refer without limitation to an amount of electrical current produced by a predetermined amount (unit) of the measured analyte. For example, in one preferred embodiment, a sensor has a sensitivity (or slope) of about 3.5 to about 7.5 picoAmps of current for every 1 mg/dL of glucose analyte.

The terms "baseline and/or sensitivity shift," "baseline and/or sensitivity drift," "shift," and "drift" as used herein are broad terms, and are to be given their ordinary and customary meaning to a person of ordinary skill in the art (and are not to be limited to a special or customized meaning), and refer without limitation to a change in the baseline and/or sensitivity of the sensor signal over time. While the term "shift" generally refers to a substantially distinct change over a relatively short time period, and the term "drift" generally refers to a substantially gradual change over a relatively longer time period, the terms can be used interchangeably and can also be generally referred to as "change" in baseline and/or sensitivity.

The terms "sealant" and "lubricant" as used herein are broad terms, and are to be given their ordinary and customary meaning to a person of ordinary skill in the art (and are not to be limited to a special or customized meaning), and refer without limitation to a material with a low surface tension that repels and/or blocks moisture, for example, oil, grease, or gel. Sealants or lubricants can be used to fill gaps and/or to repel or block water. One exemplary sealant is petroleum jelly.

Sensor System

The preferred embodiments relate to the use of an analyte sensor that measures a concentration of analyte of interest or a substance indicative of the concentration or presence of the analyte. In some embodiments, the sensor is a continuous device, for example a subcutaneous, transdermal (e.g., transcutaneous), or intravascular device. In some embodiments, the device can analyze a plurality of intermittent blood samples. The analyte sensor can use any method of analyte-sensing, including enzymatic, chemical, physical, electrochemical, spectrophotometric, polarimetric, calorimetric, radiometric, or the like.

The analyte sensor uses any method, including invasive, minimally invasive, and non-invasive sensing techniques, to provide an output signal indicative of the concentration of the analyte of interest. The output signal is typically a raw signal that is used to provide a useful value of the analyte of interest to a user, such as a patient or physician, who can be using the device. Accordingly, appropriate smoothing, calibration, and evaluation methods can be applied to the raw signal and/or system as a whole to provide relevant and acceptable estimated analyte data to the user.

The methods and devices of preferred embodiments can be employed in a continuous glucose sensor that measures a concentration of glucose or a substance indicative of a concentration or a presence of glucose. However, certain methods and devices of preferred embodiments are also suitable for use in connection with non-continuous (e.g., single point measurement or finger stick) monitors, such as the OneTouch® system manufactured by LifeScan, Inc., or monitors as disclosed in U.S. Pat. Nos. 5,418,142; 5,515,170; 5,526,120; 5,922,530; 5,968,836; and 6,335,203. In some embodiments, the glucose sensor is an invasive, minimally-invasive, or non-invasive device, for example a subcutaneous, transdermal, or intravascular device. In some embodiments, the device can analyze a plurality of intermittent biological samples, such as blood, interstitial fluid, or the like. The glucose sensor can use any method of glucose-measurement, including colorimetric, enzymatic, chemical, physical, electrochemical, spectrophotometric, polarimetric, calorimetric, radiometric, or the like. In alternative embodiments, the sensor can be any sensor capable of determining the level of an analyte in the body, for example oxygen, lactase, hormones, cholesterol, medicaments, viruses, or the like.

The glucose sensor uses any method to provide an output signal indicative of the concentration of the glucose. The output signal is typically a raw data stream that is used to provide a value indicative of the measured glucose concentration to a patient or doctor, for example.

One exemplary embodiment described in detail below utilizes an implantable glucose sensor. Another exemplary embodiment described in detail below utilizes a transcutaneous glucose sensor.

In one alternative embodiment, the continuous glucose sensor comprises a transcutaneous sensor such as described in U.S. Pat. No. 6,565,509 to Say et al. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al. In another alternative embodiment, the continuous glucose sensor comprises a refillable subcutaneous sensor such as described with reference to U.S. Pat. No. 6,512,939 to Colvin et al. In another alternative embodiment, the continuous glucose sensor comprises an intravascular sensor such as described with reference to U.S. Pat. No. 6,477,395 to Schulman et al. In another alternative embodiment, the continuous glucose sensor comprises an intravascular sensor such as described with reference to U.S. Pat. No. 6,424,847 to Mastrototaro et al. All of the above patents are incorporated in their entirety herein by reference.

Although a few exemplary embodiments of continuous glucose sensors are illustrated and described herein, it should be understood that the disclosed embodiments are applicable to any device capable of single analyte, substantially continual or substantially continuous measurement of a concentration of analyte of interest and providing an output signal that represents the concentration of that analyte.

In a first exemplary embodiment, a transcutaneous analyte sensor system is provided that includes an applicator for inserting the transdermal analyte sensor under a host's skin. The sensor system includes a sensor for sensing the analyte, wherein the sensor is associated with a mounting unit adapted for mounting on the skin of the host. The mounting unit houses the electronics unit associated with the sensor and is adapted for fastening to the host's skin. In certain embodiments, the system further includes a receiver for receiving and/or processing sensor data.

FIG. 1 is a perspective view of a transcutaneous analyte sensor system 10. In the preferred embodiment of a system as depicted in FIG. 1, the sensor includes an applicator 12, a mounting unit 14, and an electronics unit 16. The system can further include a receiver 158, such as is described in more detail with reference to FIG. 15.

The mounting unit (housing) 14 includes a base 24 adapted for mounting on the skin of a host, a sensor adapted for transdermal insertion through the skin of a host (see FIG. 4A), and one or more contacts 28 configured to provide secure electrical contact between the sensor and the electronics unit 16. The mounting unit 14 is designed to maintain the integrity of the sensor in the host so as to reduce or eliminate translation of motion between the mounting unit, the host, and/or the sensor.

In one embodiment, an applicator 12 is provided for inserting the sensor 32 through the host's skin at the appropriate insertion angle with the aid of a needle (see FIGS. 6 through 8), and for subsequent removal of the needle using a continuous push-pull action. Preferably, the applicator comprises an applicator body 18 that guides the applicator components (see FIGS. 6 through 8) and includes an applicator body base 60 configured to mate with the mounting unit 14 during insertion of the sensor into the host. The mate between the applicator body base 60 and the mounting unit 14 can use any known mating configuration, for example, a snap-fit, a press-fit, an interference-fit, or the like, to discourage separation during use. One or more release latches 30 enable release of the applicator body base 60, for example, when the applicator body base 60 is snap fit into the mounting unit 14.

The electronics unit 16 includes hardware, firmware, and/or software that enable measurement of levels of the analyte via the sensor. For example, the electronics unit 16 can comprise a potentiostat, a power source for providing power to the sensor, other components useful for signal processing, and preferably an RF module for transmitting data from the electronics unit 16 to a receiver (see FIGS. 14 to 16). Electronics can be affixed to a printed circuit board (PCB), or the like, and can take a variety of forms. For example, the electronics can take the form of an integrated circuit (IC), such as an Application-Specific Integrated Circuit (ASIC), a microcontroller, or a processor. Preferably, electronics unit 16 houses the sensor electronics, which comprise systems and methods for processing sensor analyte data. Examples of systems and methods for processing sensor analyte data are described in more detail in U.S. Publication No. US-2005-0027463-A1.

After insertion of the sensor using the applicator 12, and subsequent release of the applicator 12 from the mounting unit 14 (see FIGS. 8B to 8D), the electronics unit 16 is configured to releasably mate with the mounting unit 14 in a manner similar to that described above with reference to the applicator body base 60. The electronics unit 16 includes contacts on its backside (not shown) configured to electrically connect with the contacts 28, such as are described in more detail with reference to FIGS. 2 through 4. In one embodiment, the electronics unit 16 is configured with programming, for example initialization, calibration reset, failure testing, or the like, each time it is initially inserted into the mounting unit 14 and/or each time it initially communicates with the sensor 32.

Mounting Unit

Figure 2:
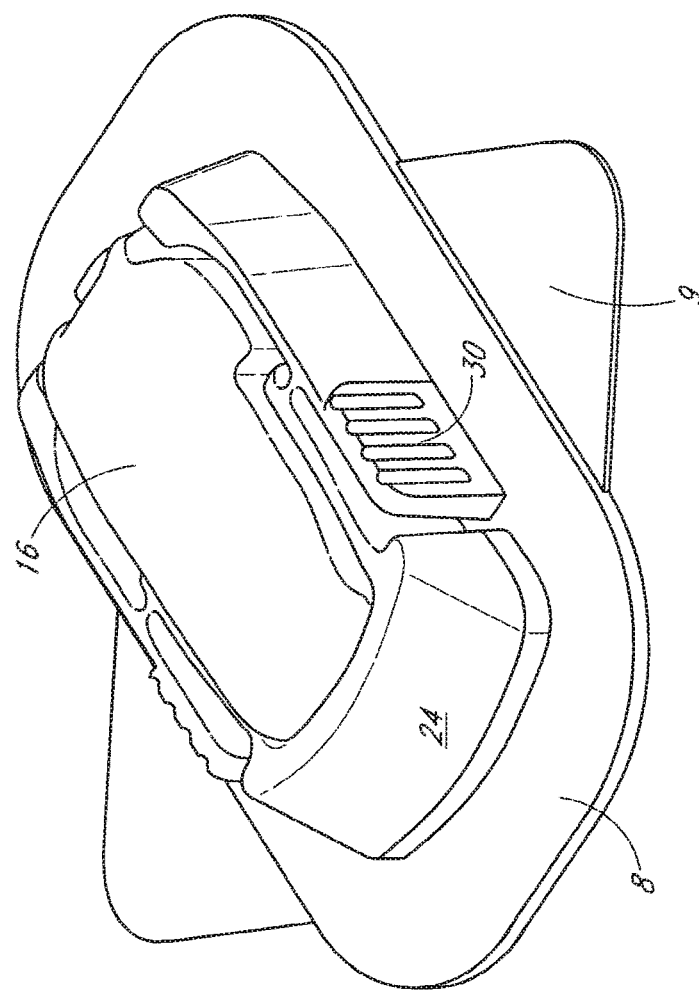
FIG. 2 is a perspective view of a mounting unit, including the electronics unit in its functional position.
Figure 12A:
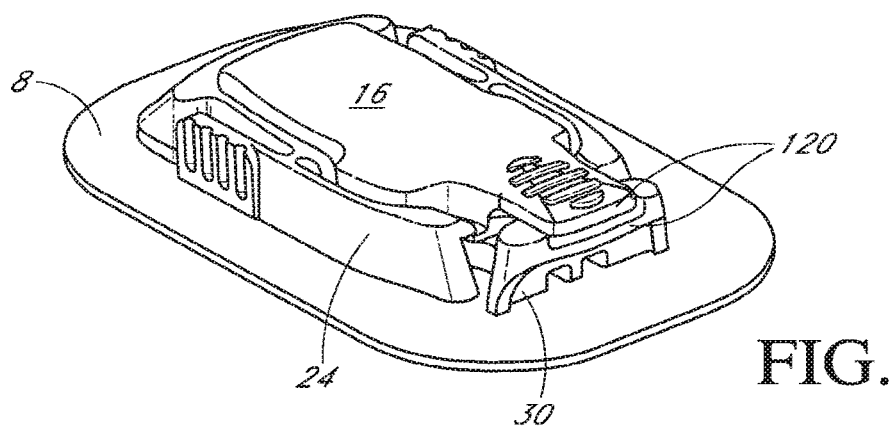
FIGS. 12A to 12C are perspective and side views, respectively, of the sensor system showing the sensor, mounting unit, and electronics unit in their functional positions.
Figure 12B:
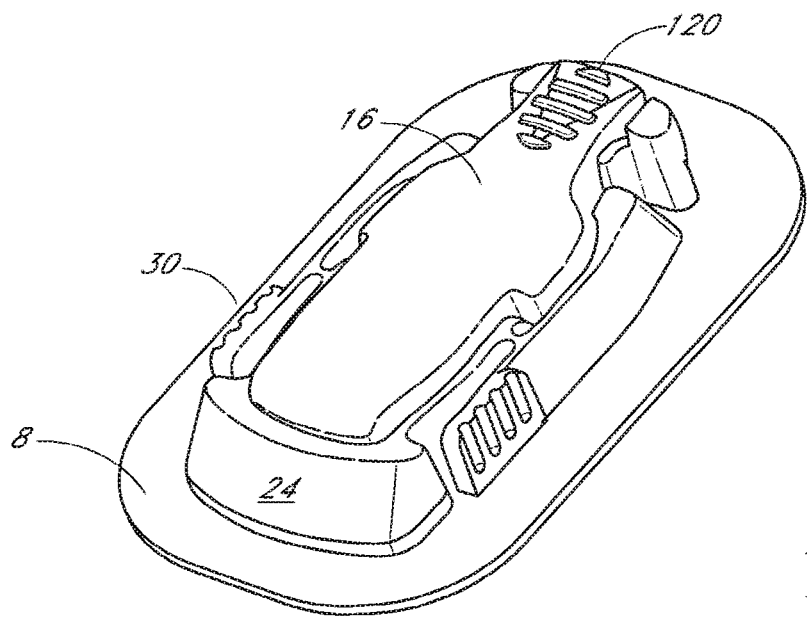
Figure 12C:
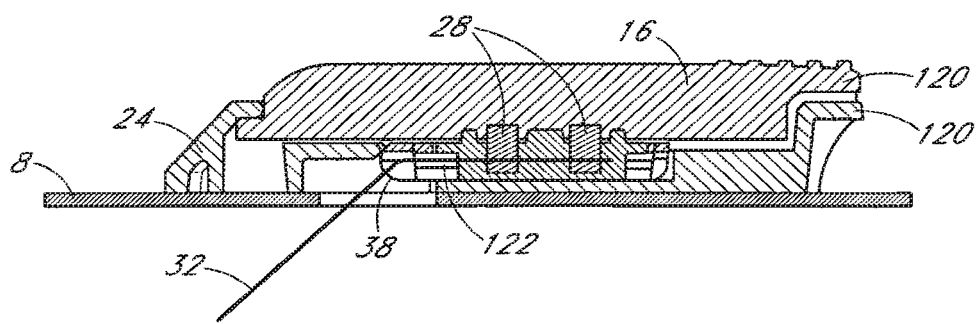

FIG. 2 is a perspective view of a sensor system of a preferred embodiment, shown in its functional position, including a mounting unit and an electronics unit matingly engaged therein. FIGS. 12A to 12C illustrate the sensor is its functional position for measurement of an analyte concentration in a host.

In preferred embodiments, the mounting unit 14, also referred to as a housing, comprises a base 24 adapted for fastening to a host's skin. The base can be formed from a variety of hard or soft materials, and preferably comprises a low profile for minimizing protrusion of the device from the host during use. In some embodiments, the base 24 is formed at least partially from a flexible material, which is believed to provide numerous advantages over conventional transcutaneous sensors, which, unfortunately, can suffer from motion-related artifacts associated with the host's movement when the host is using the device. For example, when a transcutaneous analyte sensor is inserted into the host, various movements of the sensor (for example, relative movement between the in vivo portion and the ex vivo portion, movement of the skin, and/or movement within the host (dermis or subcutaneous)) create stresses on the device and can produce noise in the sensor signal. It is believed that even small movements of the skin can translate to discomfort and/or motion-related artifact, which can be reduced or obviated by a flexible or articulated base. Thus, by providing flexibility and/or articulation of the device against the host's skin, better conformity of the sensor system 10 to the regular use and movements of the host can be achieved. Flexibility or articulation is believed to increase adhesion (with the use of an adhesive pad) of the mounting unit 14 onto the skin, thereby decreasing motion-related artifact that can otherwise translate from the host's movements and reduced sensor performance.

Figure 3:
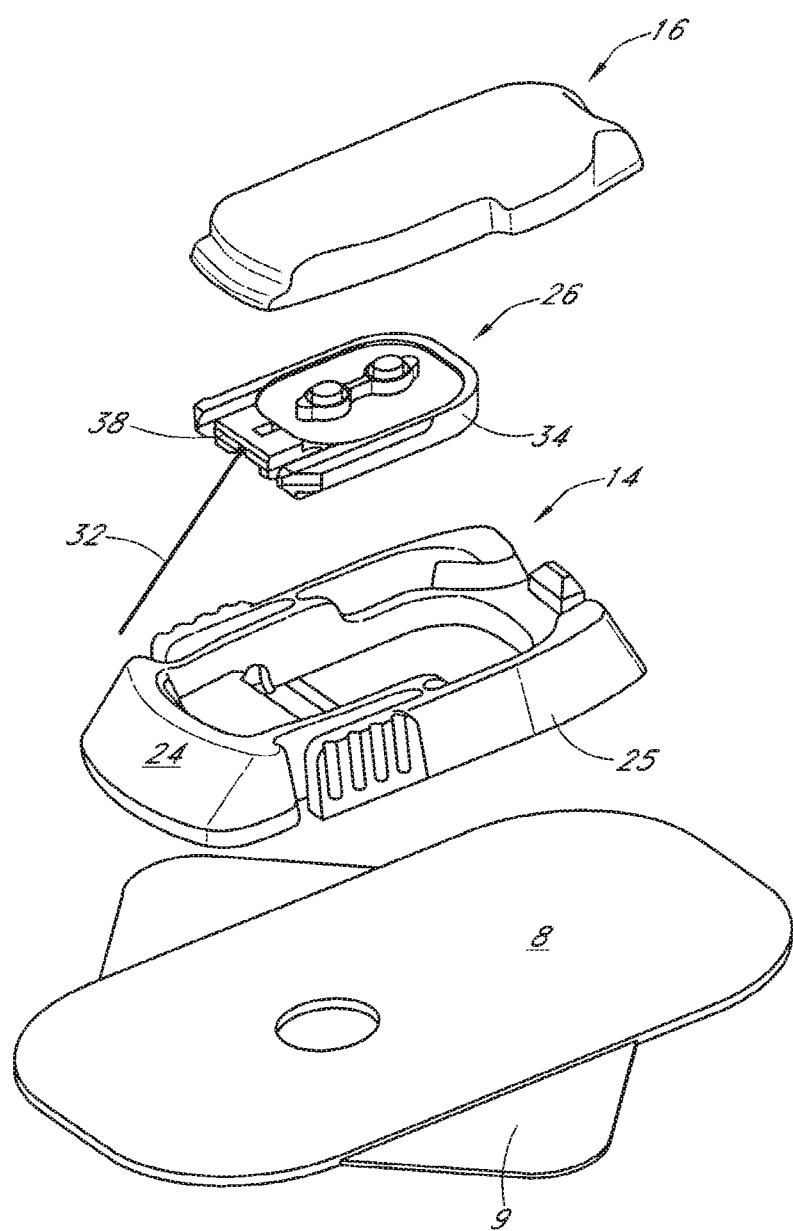
FIG. 3 is an exploded perspective view of a mounting unit, showing its individual components.

FIG. 3 is an exploded perspective view of a sensor system of a preferred embodiment, showing a mounting unit, an associated contact subassembly, and an electronics unit. In some embodiments, the contacts 28 are mounted on or in a subassembly hereinafter referred to as a contact subassembly 26 (see FIG. 4A), which includes a contact holder 34 configured to fit within the base 24 of the mounting unit 14 and a hinge 38 that allows the contact subassembly 26 to pivot between a first position (for insertion) and a second position (for use) relative to the mounting unit 14, which is described in more detail with reference to FIGS. 10 and 11. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs.

In certain embodiments, the mounting unit 14 is provided with an adhesive pad 8, preferably disposed on the mounting unit's back surface and preferably including a releasable backing layer 9. Thus, removing the backing layer 9 and pressing the base portion 24 of the mounting unit onto the host's skin adheres the mounting unit 14 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin).

In preferred embodiments, the adhesive pad 8 is formed from spun-laced, open- or closed-cell foam, and/or non-woven fibers, and includes an adhesive disposed thereon, however a variety of adhesive pads appropriate for adhesion to the host's skin can be used, as is appreciated by one skilled in the art of medical adhesive pads. In some embodiments, a double-sided adhesive pad is used to adhere the mounting unit to the host's skin. In other embodiments, the adhesive pad includes a foam layer, for example, a layer wherein the foam is disposed between the adhesive pad's side edges and acts as a shock absorber.

In some embodiments, the surface area of the adhesive pad 8 is greater than the surface area of the mounting unit's back surface. Alternatively, the adhesive pad can be sized with substantially the same surface area as the back surface of the base portion. Preferably, the adhesive pad has a surface area on the side to be mounted on the host's skin that is greater than about 1, 1.25, 1.5, 1.75, 2, 2.25, or 2.5, times the surface area of the back surface 25 of the mounting unit base 24. Such a greater surface area can increase adhesion between the mounting unit and the host's skin, minimize movement between the mounting unit and the host's skin, and/or protect the wound exit-site (sensor insertion site) from environmental and/or biological contamination. In some alternative embodiments, however, the adhesive pad can be smaller in surface area than the back surface assuming a sufficient adhesion can be accomplished.

In some embodiments, the adhesive pad 8 is substantially the same shape as the back surface 25 of the base 24, although other shapes can also be advantageously employed, for example, butterfly-shaped, round, square, or rectangular. The adhesive pad backing can be designed for two-step release, for example, a primary release wherein only a portion of the adhesive pad is initially exposed to allow adjustable positioning of the device, and a secondary release wherein the remaining adhesive pad is later exposed to firmly and securely adhere the device to the host's skin once appropriately positioned. The adhesive pad is preferably waterproof. Preferably, a stretch-release adhesive pad is provided on the back surface of the base portion to enable easy release from the host's skin at the end of the useable life of the sensor, as is described in more detail with reference to FIGS. 9A to 9C.

In some circumstances, it has been found that a conventional bond between the adhesive pad and the mounting unit may not be sufficient, for example, due to humidity that can cause release of the adhesive pad from the mounting unit. Accordingly, in some embodiments, the adhesive pad can be bonded using a bonding agent activated by or accelerated by an ultraviolet, acoustic, radio frequency, or humidity cure. In some embodiments, a eutectic bond of first and second composite materials can form a strong adhesion. In some embodiments, the surface of the mounting unit can be pretreated utilizing ozone, plasma, chemicals, or the like, in order to enhance the bondability of the surface.

A bioactive agent is preferably applied locally at the insertion site (exit-site) prior to or during sensor insertion. Suitable bioactive agents include those which are known to discourage or prevent bacterial growth and infection, for example, anti-inflammatory agents, antimicrobials, antibiotics, or the like. It is believed that the diffusion or presence of a bioactive agent can aid in prevention or elimination of bacteria adjacent to the exit-site. Additionally or alternatively, the bioactive agent can be integral with or coated on the adhesive pad, or no bioactive agent at all is employed.

Figure 4A:
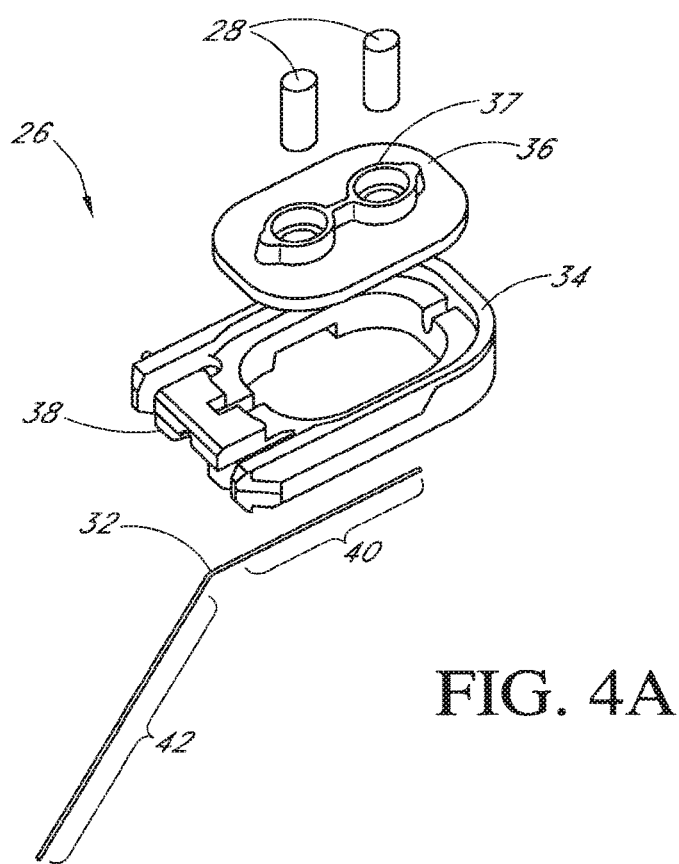
FIG. 4A is an exploded perspective view of a contact subassembly, showing its individual components.

FIG. 4A is an exploded perspective view of the contact subassembly 26 in one embodiment, showing its individual components. Preferably, a watertight (waterproof or water-resistant) sealing member 36, also referred to as a sealing material or seal, fits within a contact holder 34 and provides a watertight seal configured to surround the electrical connection at the electrode terminals within the mounting unit in order to protect the electrodes (and the respective operable connection with the contacts of the electronics unit 16) from damage due to moisture, humidity, dirt, and other external environmental factors. In one embodiment, the sealing member 36 is formed from an elastomeric material, such as silicone; however, a variety of other elastomeric or sealing materials can also be used, for example, silicone-polyurethane hybrids, polyurethanes, and polysulfides. Preferably, the sealing member is configured to compress within the contact subassembly when the electronics unit is mated to the mounting unit. In some embodiments, the sealing member 36 comprises a self-lubricating material, for example, self-lubricating silicone or other materials impregnated with or otherwise comprising a lubricant configured to be released during use. In some embodiments, the sealing member 36 includes a self-sealing material, for example, one that leaches out a sealant such as a silicone oil. In some embodiments, bumps, ridges, or other raised portions (not shown), can be added to a component of the sensor system, such as to the contact subassembly 26 (e.g., housing adjacent to the sealing member), electronics unit 16 and/or sealing member 36 to provide additional compression and improve the seal formed around the contacts 28 and/or sensor 32 when the contacts 28 are mated to the sensor electronics.

Preferably, the sealing member is selected using a durometer. A durometer is an instrument used for measuring the indentation hardness of rubber, plastics, and other materials. Durometers are built to various standards from ASTM, DIN, JIS, and ISO. The hardness of plastics is most commonly measured by the Shore (Durometer) test or Rockwell hardness test. Both methods measure the resistance of plastics toward indentation and provide an empirical hardness value. Shore Hardness, using either the Shore A or Shore D scale, is the preferred method for rubbers/elastomers and is also commonly used for softer plastics such as polyolefins, fluoropolymers, and vinyls. The Shore A scale is used for softer rubbers while the Shore D scale is used for harder ones. In preferred embodiments, the Shore A scale is employed in connection with selection of a sealing member.

The Shore hardness is measured with a Durometer and sometimes referred to as "Durometer hardness." The hardness value is determined by the penetration of the Durometer indenter foot into the sample. Because of the resilience of rubbers and plastics, the indentation reading may change over time, so the indentation time is sometimes reported along with the hardness number. The ASTM test method designation for the Shore Durometer hardness test is ASTM D2240. The results obtained from this test are a useful measure of relative resistance to indentation of various grades of polymers.

Using a durometer in the selection of a sealing member enables selection of a material with optimal durometer hardness that balances the advantages of a lower durometer hardness with the advantages of a higher durometer hardness. For example, when a guide tube (e.g., cannula) is utilized to maintain an opening in a silicone sealing member prior to sensor insertion, a compression set (e.g., some retention of a compressed shape caused by compression of the material over time) within the silicone can result due to compression over time of the sealing member by the guide tube. Compression set can also result from certain sterilization procedures (e.g., radiation sterilization such as electron beam or gamma radiation). Unfortunately, in some circumstances, the compression set of the sealing member may cause gaps or incompleteness of contact between the sealing member and the contacts and/or sensor. In general, a lower durometer hardness provides a better conformation (e.g., seal) surrounding the contacts and/or sensor as compared to a higher durometer hardness. Additionally, a lower durometer hardness enables a design wherein less force is required to create the seal (e.g., to snap the electronics unit into the mounting unit, for example, as in the embodiment illustrated in FIG. 4A) as compared to a higher durometer hardness, thereby increasing the ease of use of the device. However, the benefits of a lower durometer hardness silicone material must be balanced with potential disadvantages in manufacturing. For example, lower durometer hardness silicones are often produced by compounding with a silicone oil. In some circumstances, it is believed that some silicone oil may leach or migrate during manufacture and/or sterilization, which may corrupt aspects of the manufacturing process (e.g., adhesion of glues and/or effectiveness of coating processes). Additionally, a higher durometer hardness material generally provides greater stability of the material, which may reduce or avoid damage to the sealing member cause by pressure or other forces.

It is generally preferred that a sealing member 36 with a durometer hardness of from about 5 to about 80 Shore A is employed, more preferably a durometer hardness of from about 10 to about 50 Shore A, and even more preferably from about 20 to about 50 Shore A. In one embodiment, of a transcutaneous analyte sensor, the sealing member is fabricated using a silicone of about 20 Shore A to maximize the conformance of the seal around the contacts and/or sensor while minimizing the force required to compress the silicone for that conformance. In another embodiment, the sealing member is formed from a silicone of about 50 Shore A so as to provide increased strength of the sealing member (e.g., its resistance to compression). While a few representative examples have been provided above, one skilled in the art appreciates that higher or lower durometer hardness sealing material may also be suitable for use.

In one alternative embodiment, a sealing member 36 with a durometer hardness of about 10 Shore A is used. In this embodiment, the sealing material tends to "weep" out, further increasing conformance of the seal against the adjacent parts. In another alternative embodiment, a sealing material with a durometer hardness of about 0 (zero) Shore A is used as a sealant and/or in combination with a sealant, also referred to as a lubricant, which in some embodiments is a hydrophobic fluid filling material such as a grease, silicone, petroleum jelly, or the like. Preferably, the sensor and/or contacts are encased in a housing that contains the sealant, causing the material to "squeeze" around contacts and/or sensor. Any suitable hydrophobic fluid filling material can be employed. Especially preferred are synthetic or petroleum hydrocarbon-based materials, silicone-based materials, ester-based greases, and other pharmaceutical-grade materials.

In some embodiments, the sealing member can comprise a material that has been modified to enhance the desirable properties of the sealing member 36. For example, one or more filler materials or stiffening agents such as glass beads, polymer beads, composite beads, beads comprising various inert materials, carbon black, talc, titanium oxide, silicone dioxide, and the like. In some embodiments, the filler material is incorporated into the sealing member material to mechanically stiffen the sealing member. In general, however, use of a filler material or stiffening agent in the sealing member material can provide a variety of enhanced properties including increased modulus of elasticity, crosslink density, hardness, and stiffness, and decreased creep, for example. In some alternative embodiments, gases are chemically (or otherwise) injected into the sealing member material. For example, the sealing material can comprise a polymeric foam (e.g., a polyurethane foam, a latex foam, a styrene-butadiene foam, and the like), or a dispersion of gas bubbles in a grease or jelly.

In alternative embodiments, the seal 36 is designed to form an interference fit with the electronics unit and can be formed from a variety of materials, for example, flexible plastics, or noble metals. One of ordinary skill in the art appreciates that a variety of designs can be employed to provide a seal surrounding electrical contacts such as described herein. For example, the contact holder 34 can be integrally designed as a part of the mounting unit, rather than as a separate piece thereof. Additionally or alternatively, a sealant can be provided in or around the sensor (e.g., within or on the contact subassembly or sealing member), such as is described in more detail with reference to FIGS. 11A and 11B. In general, sealing materials with durometer hardnesses in the described ranges can provide improved sealing in a variety of sensor applications. For example, a sealing member as described in the preferred embodiments (e.g., selected using a durometer to ensure optimal durometer hardness, and the like) can be implemented adjacent to and/or to at least partially surrounding the sensor in a variety of sensor designs, including, for example, the sensor designs of the preferred embodiments, as well as a planar substrate such as described in U.S. Pat. No. 6,175,752.

In the illustrated embodiment of FIG. 4A, the sealing member 36 is formed with a raised portion 37 surrounding the contacts 28. The raised portion 37 enhances the interference fit surrounding the contacts 28 when the electronics unit 16 is mated to the mounting unit 14. Namely, the raised portion surrounds each contact and presses against the electronics unit 16 to form a tight seal around the electronics unit. However, a variety of alternative sealing member configurations are described with reference to FIGS. 4D to 4H, below.

Contacts 28 fit within the seal 36 and provide for electrical connection between the sensor 32 and the electronics unit 16. In general, the contacts are designed to ensure a stable mechanical and electrical connection of the electrodes that form the sensor 32 (see FIG. 5A to 5C) to mutually engaging contacts 28 thereon. A stable connection can be provided using a variety of known methods, for example, domed metallic contacts, cantilevered fingers, pogo pins, or the like, as is appreciated by one skilled in the art.

Figure 10A:
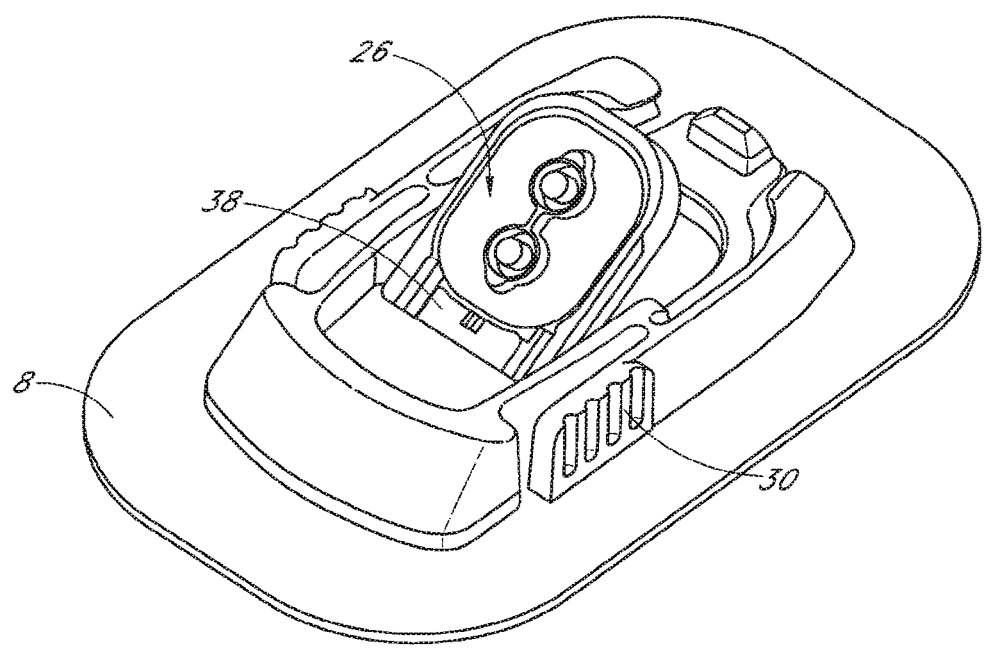
FIGS. 10A and 10B are perspective and side cross-sectional views, respectively, of a sensor system showing the mounting unit immediately following sensor insertion and release of the applicator from the mounting unit.
Figure 10B:
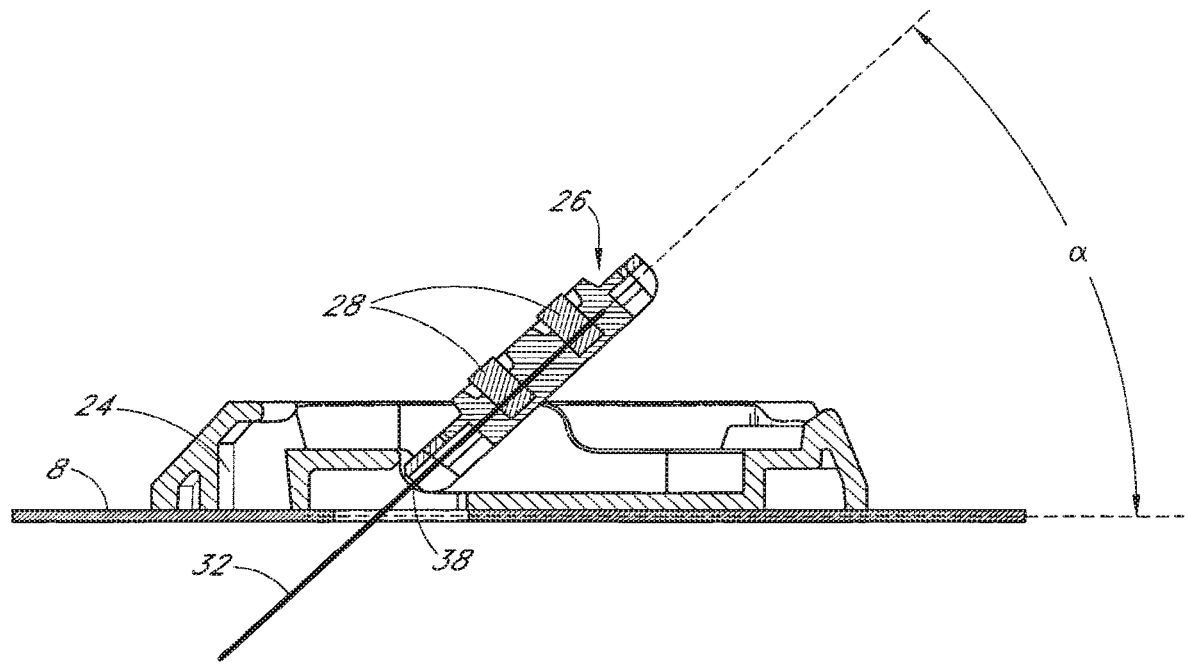
Figure 11A:
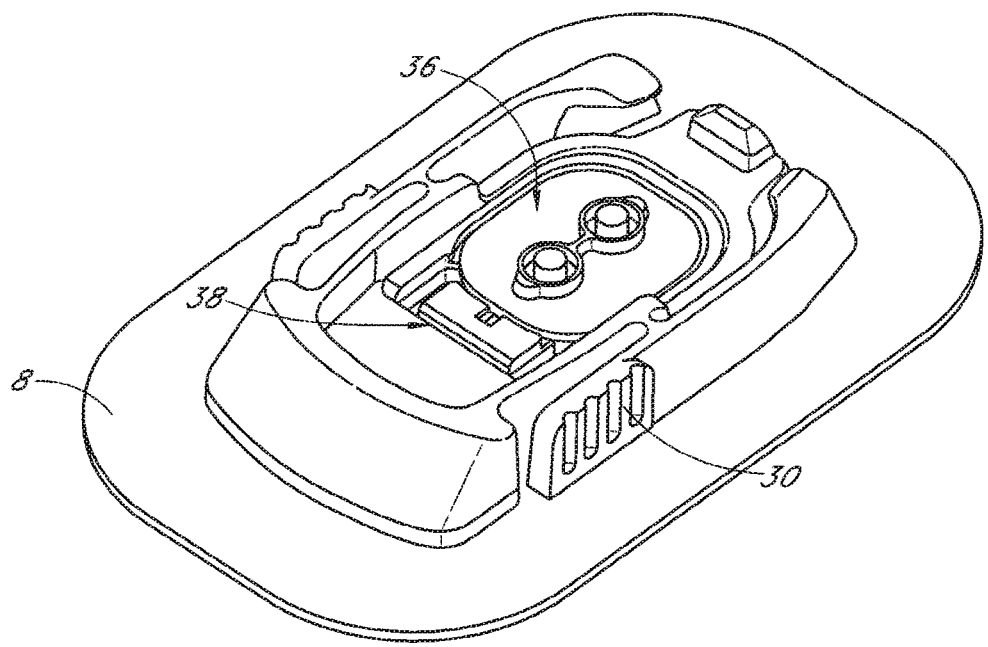
FIGS. 11A and 11B are perspective and side cross-sectional views, respectively, of a sensor system showing the mounting unit after pivoting the contact subassembly to its functional position.
Figure 11B:
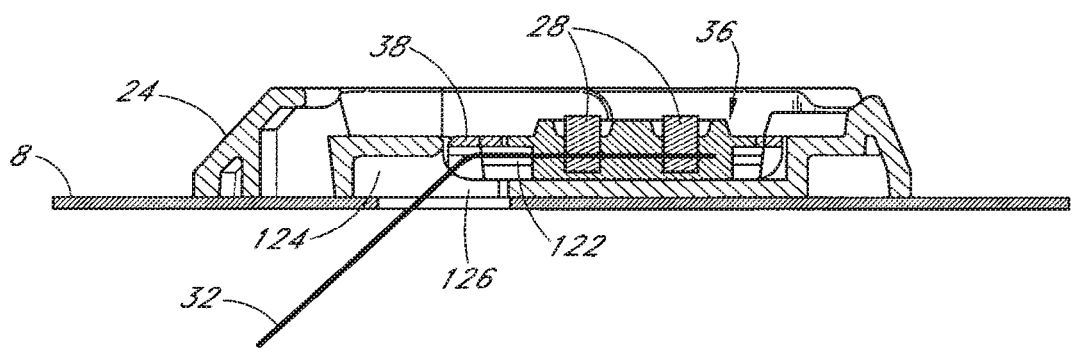

In preferred embodiments, the contacts 28 are formed from a conductive elastomeric material, such as a carbon black elastomer, through which the sensor 32 extends (see FIGS. 10B and 11B). Conductive elastomers are advantageously employed because their resilient properties create a natural compression against mutually engaging contacts, forming a secure press fit therewith. In some embodiments, conductive elastomers can be molded in such a way that pressing the elastomer against the adjacent contact performs a wiping action on the surface of the contact, thereby creating a cleaning action during initial connection. Additionally, in preferred embodiments, the sensor 32 extends through the contacts 28 wherein the sensor is electrically and mechanically secure by the relaxation of elastomer around the sensor (see FIGS. 7A to 7D).

In an alternative embodiment, a conductive, stiff plastic forms the contacts, which are shaped to comply upon application of pressure (for example, a leaf-spring shape). Contacts of such a configuration can be used instead of a metallic spring, for example, and advantageously avoid the need for crimping or soldering through compliant materials; additionally, a wiping action can be incorporated into the design to remove contaminants from the surfaces during connection. Non-metallic contacts can be advantageous because of their seamless manufacturability, robustness to thermal compression, non-corrosive surfaces, and native resistance to electrostatic discharge (ESD) damage due to their higher-than-metal resistance.

Figure 4B:
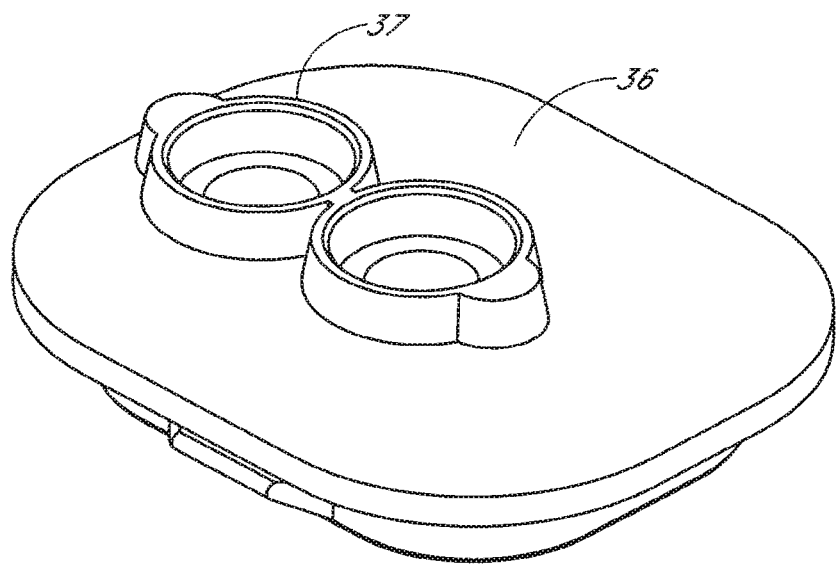
FIG. 4B is a perspective view of an alternative contact configuration.
Figure 4C:
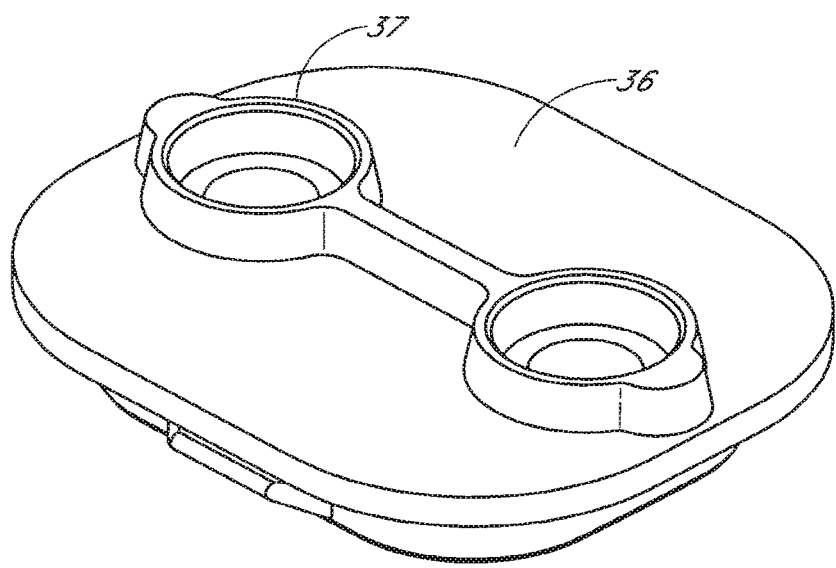
FIG. 4C is a perspective view of another alternative contact configuration.

FIGS. 4B and 4C are perspective views of alternative contact configurations. FIG. 4B is an illustration of a narrow contact configuration. FIG. 4C is an illustration of a wide contact configuration. One skilled in the art appreciates that a variety of configurations are suitable for the contacts of the preferred embodiments, whether elastomeric, stiff plastic or other materials are used. In some circumstances, it can be advantageous to provide multiple contact configurations (such as illustrated in FIGS. 4A to 4C) to differentiate sensors from each other. In other words, the architecture of the contacts can include one or more configurations each designed (keyed) to fit with a particular electronics unit. See section entitled "Differentiation of Sensor Systems" below, which describes systems and methods for differentiating (keying) sensor systems.

FIGS. 4D to 4H are schematic cross-sectional views of a portion of the contact subassembly; namely, a variety of alternative embodiments of the sealing member 36 are illustrated. In each of these embodiments (e.g., FIGS. 4D to 4H), a sensor 32 is shown, which is configured for operable connection to sensor electronics for measuring an analyte in a host such as described in more detail elsewhere herein. Additionally, two electrical contacts 28, as described in more detail elsewhere herein, are configured to operably connect the sensor to the sensor electronics. Thus, the sealing member 36 in each of these alternative configurations (e.g., FIGS. 4D to 4H) at least partially surrounds the sensor and/or the electrical contacts to seal the electrical contacts from moisture when the sensor is operably connected to the sensor electronics.

Figure 4D:
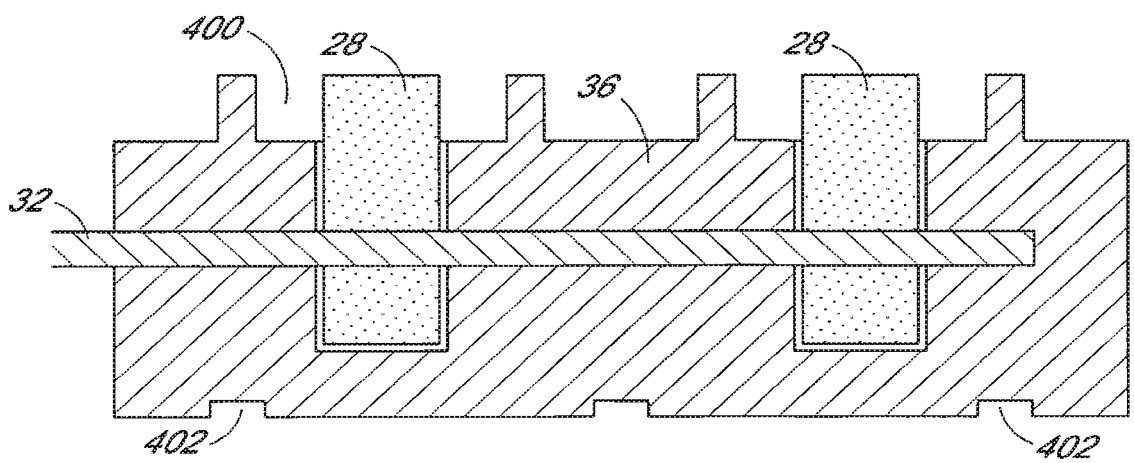
FIGS. 4D to 4H are schematic cross-sectional views of a portion of the contact subassembly; namely, a variety of embodiments illustrating alternative sealing member configurations.

FIG. 4D is a schematic cross-sectional view of the sealing member 36 in an embodiment similar to FIG. 4A, including gaps 400 that are maintained when the one or more electrical contacts are operably connected to the sensor electronics. Preferably, these air gaps provide for some flexibility of the sealing member 36 to deform or compress to seal the electrical contacts 28 from moisture or other environmental effects.

In certain circumstances, such as during sensor insertion or needle/guide tube retraction (see FIGS. 7A to 7D), a sealing member with a certain elasticity can be compressed or deformed by the insertion and/or retraction forces applied thereto. Accordingly in some embodiments, the sealing member is configured to be maintained (e.g., held substantially in place) on the housing (e.g., contact subassembly 26 or base 34) without substantial translation, deformation, and/or compression (e.g., during sensor insertion). FIG. 4D illustrates one such implementation, wherein one or more depressions 402 are configured to receive mating protrusions (e.g., on the base 34 of the contact subassembly 26, not shown). A variety of male-female or other such mechanical structures can be implemented to hold the sealing member in place, as is appreciated by one skilled in the art. In one alternative embodiment, an adhesive (not shown) is configured to adhere the sealing member 36 to the housing (e.g., base 34 of the contact subassembly 26) to provide substantially the same benefit of holding the sealing member during sensor insertion/retraction without substantial deformation, as described in more detail, above. In another embodiment, the base 34 of the contact subassembly 26 (or equivalent structure) comprises reinforcing mechanical supports configured to hold the sealing member as described above. One skilled in the art appreciates a variety of mechanical and/or chemical methods that can be implemented to maintain a sealing member substantially stationary (e.g., without substantial translation, deformation and/or compression) when compression and/or deformation forces are applied thereto. Although one exemplary embodiment is illustrated with reference to FIG. 4D, a wide variety of systems and methods for holding the sealing member can be implemented with a sealing member of any particular design.

Figure 4E:
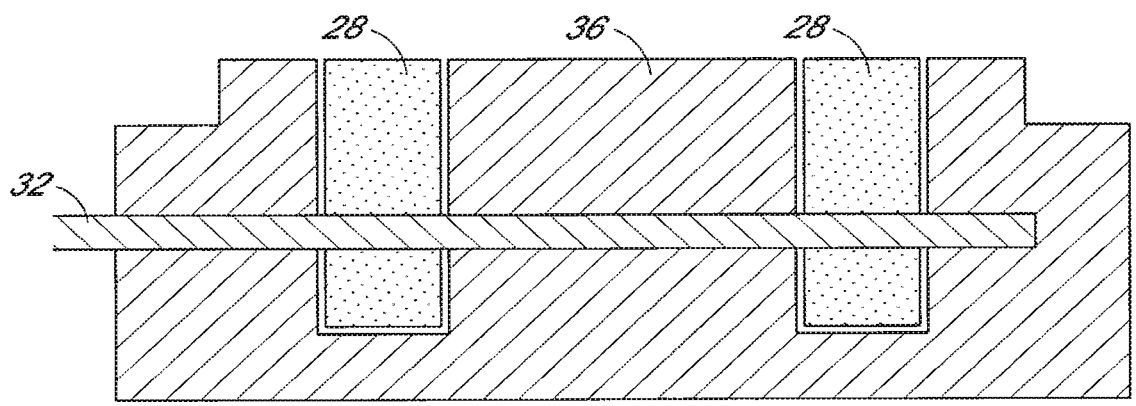

FIG. 4E is a schematic cross-sectional view of the sealing member 36 in an alternative embodiment without gaps. In certain circumstances, full contact between mating members may be preferred.

Figure 4F:
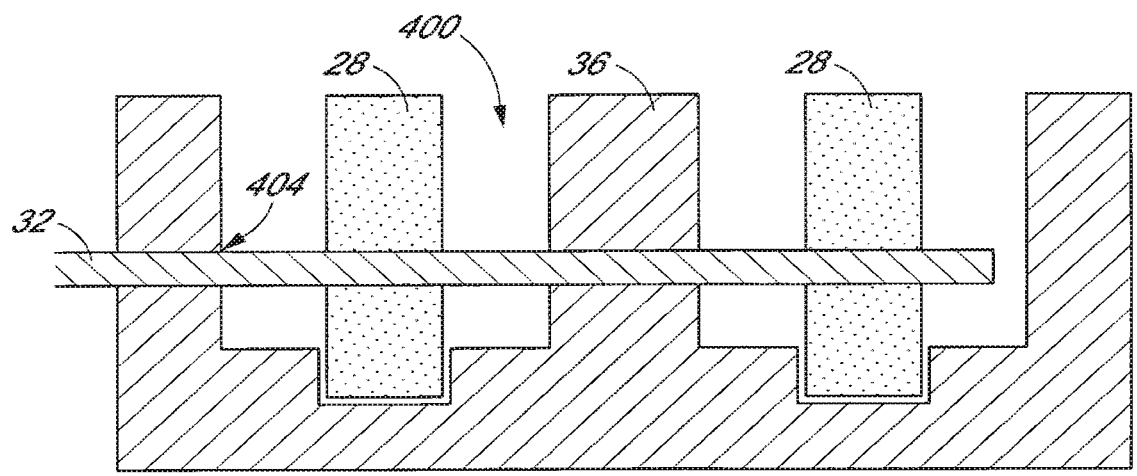

In certain circumstances moisture may "wick" along the length of the sensor (e.g., from an exposed end) through the sealing member 36 to the contacts 28. FIG. 4F is a schematic cross-sectional view of a sealing member 36 in an alternative embodiment wherein one or more gaps 400 are provided. In this embodiment, the gaps 400 extend into the sealing member and encompass at least a portion of the sensor 32. The gaps 400 or "deep wells" of FIG. 4F are designed to interrupt the path that moisture may take, avoiding contact of the moisture at the contacts 28. If moisture is able to travel along the path of the sensor, the abrupt change of surface tension at the opening 404 of the gap 400 in the sealing member 36 substantially deters the moisture from traveling to the contacts 28.

Figure 4G:
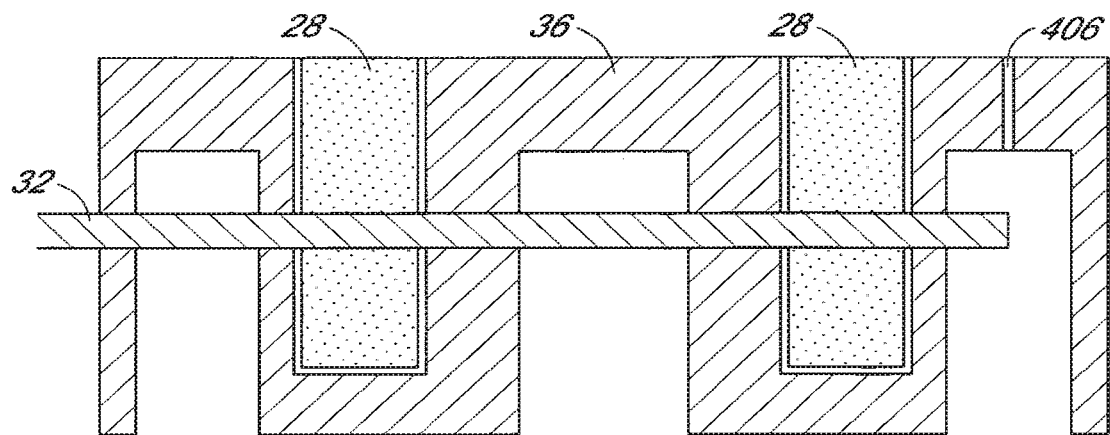

FIG. 4G is a schematic cross-sectional view of the sealing member 36 in another alternative embodiment wherein one or more gaps 400 are provided. In this embodiment, the gaps extend from the bottom side of the sealing member 36, which can be helpful in maintaining a stable position of the contacts 28 and/or reduces "pumping" of air gaps in some situations.

In some embodiments, gaps 400 can be filled by a sealant, which also may be referred to as a lubricant, for example, oil, grease, or gel. In one exemplary embodiment, the sealant includes petroleum jelly and is used to provide a moisture barrier surrounding the sensor. Referring to FIG. 4F, filling the gaps 400 with a sealant provides an additional moisture barrier to reduce or avoid moisture from traveling to the contacts 28. Sealant can be used to fill gaps or crevices in any sealing member configuration.

In some sealing member configurations, it can be advantageous to provide a channel 406 through the sealing member 36 in order to create an additional pathway for sealant (e.g. lubricant) in order to expel air and/or to provide a path for excess sealant to escape. In some embodiments, more than one channel is provided.

Figure 4H:
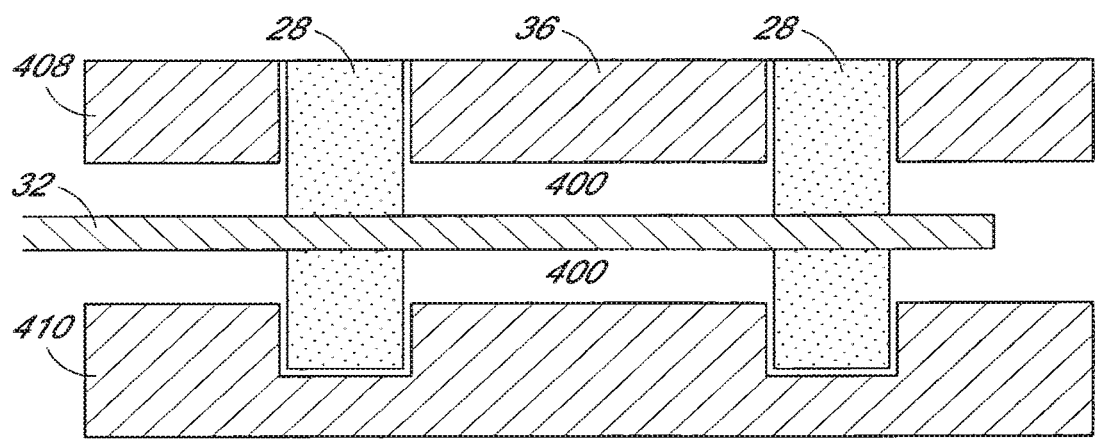

FIG. 4H is a schematic cross-sectional view of a sealing member 36 in an alternative embodiment wherein a large gap 400 is provided between the sealing member upper portion 408 and the sealing member lower portion 410. These portions 408, 410 may or may not be connected; however, they are configured to sandwich the sensor and sealant (e.g., grease) therebetween. The sealing member 36 illustrated with reference to FIG. 4H can provide ease of manufacture and/or product assembly with a comprehensive sealing ability. Additional gaps (with or without sealant) can be provided in a variety of locations throughout the sealing member 36; these additional gaps, for example, provide space for excess sealant.

Sensor

Preferably, the sensor 32 includes a distal portion 42, also referred to as the in vivo portion, adapted to extend out of the mounting unit for insertion under the host's skin, and a proximal portion 40, also referred to as an ex vivo portion, adapted to remain above the host's skin after sensor insertion and to operably connect to the electronics unit 16 via contacts 28. Preferably, the sensor 32 includes two or more electrodes: a working electrode 44 and at least one additional electrode, which can function as a counter electrode and/or reference electrode, hereinafter referred to as the reference electrode 46. A membrane system is preferably deposited over the electrodes, such as described in more detail with reference to FIGS. 5A to 5C, below.

FIG. 5A is an expanded cutaway view of a proximal portion 40 of the sensor in one embodiment, showing working and reference electrodes. In the illustrated embodiments, the working and reference electrodes 44, 46 extend through the contacts 28 to form electrical connection therewith (see FIGS. 10B and 11B). Namely, the working electrode 44 is in electrical contact with one of the contacts 28 and the reference electrode 46 is in electrical contact with the other contact 28, which in turn provides for electrical connection with the electronics unit 16 when it is mated with the mounting unit 14. Mutually engaging electrical contacts permit operable connection of the sensor 32 to the electronics unit 16 when connected to the mounting unit 14; however other methods of electrically connecting the electronics unit 16 to the sensor 32 are also possible. In some alternative embodiments, for example, the reference electrode can be configured to extend from the sensor and connect to a contact at another location on the mounting unit (e.g., non-coaxially). Detachable connection between the mounting unit 14 and electronics unit 16 provides improved manufacturability, namely, the relatively inexpensive mounting unit 14 can be disposed of when replacing the sensor system after its usable life, while the relatively more expensive electronics unit 16 can be reused with multiple sensor systems.

In alternative embodiments, the contacts 28 are formed into a variety of alternative shapes and/or sizes. For example, the contacts 28 can be discs, spheres, cuboids, and the like. Furthermore, the contacts 28 can be designed to extend from the mounting unit in a manner that causes an interference fit within a mating cavity or groove of the electronics unit, forming a stable mechanical and electrical connection therewith.

Figure 5B:
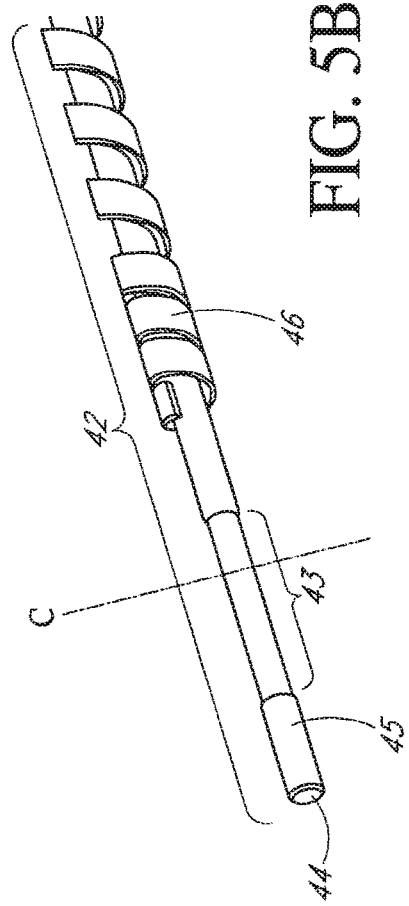
FIG. 5B is an expanded cutaway view of a distal portion of a sensor.

FIG. 5B is an expanded cutaway view of a distal portion of the sensor in one embodiment, showing working and reference electrodes. In preferred embodiments, the sensor is formed from a working electrode 44 and a reference electrode 46 helically wound around the working electrode 44. An insulator 45 is disposed between the working and reference electrodes to provide necessary electrical insulation therebetween. Certain portions of the electrodes are exposed to enable electrochemical reaction thereon, for example, a window 43 can be formed in the insulator to expose a portion of the working electrode 44 for electrochemical reaction.

In preferred embodiments, each electrode is formed from a fine wire with a diameter of from about 0.001 or less to about 0.010 inches or more, for example, and is formed from, e.g., a plated insulator, a plated wire, or bulk electrically conductive material. Although the illustrated electrode configuration and associated text describe one preferred method of forming a transcutaneous sensor, a variety of known transcutaneous sensor configurations can be employed with the transcutaneous analyte sensor system of the preferred embodiments, such as U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al, for example. All of the above patents are incorporated in their entirety herein by reference and are not inclusive of all applicable analyte sensors; in general, it should be understood that the disclosed embodiments are applicable to a variety of analyte sensor configurations. It is noted that much of the description of the preferred embodiments, for example the membrane system described below, can be implemented not only with in vivo sensors, but also with in vitro sensors, such as blood glucose meters (SMBG).

In preferred embodiments, the working electrode comprises a wire formed from a conductive material, such as platinum, platinum-iridium, palladium, graphite, gold, carbon, conductive polymer, alloys, or the like. Although the electrodes can by formed by a variety of manufacturing techniques (bulk metal processing, deposition of metal onto a substrate, or the like), it can be advantageous to form the electrodes from plated wire (e.g., platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

The working electrode 44 is configured to measure the concentration of an analyte. In an enzymatic electrochemical sensor for detecting glucose, for example, the working electrode measures the hydrogen peroxide produced by an enzyme catalyzed reaction of the analyte being detected and creates a measurable electronic current For example, in the detection of glucose wherein glucose oxidase produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected.

In preferred embodiments, the working electrode 44 is covered with an insulating material 45, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). While not wishing to be bound by theory, it is believed that the lubricious (e.g., smooth) coating (e.g., parylene) on the sensors of the preferred embodiments contributes to minimal trauma and extended sensor life. FIG. 23 shows transcutaneous glucose sensor data and corresponding blood glucose values over approximately seven days in a human, wherein the transcutaneous glucose sensor data was formed with a parylene coating on at least a portion of the device. While parylene coatings are generally preferred, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode may not require a coating of insulator.

The reference electrode 46, which can function as a reference electrode alone, or as a dual reference and counter electrode, is formed from silver, silver/silver chloride, or the like. Preferably, the reference electrode 46 is juxtapositioned and/or twisted with or around the working electrode 44; however other configurations are also possible (e.g., an intradermal or on-skin reference electrode). In the illustrated embodiments, the reference electrode 46 is helically wound around the working electrode 44. The assembly of wires is then optionally coated or adhered together with an insulating material, similar to that described above, so as to provide an insulating attachment.

In some embodiments, a silver wire is formed onto the sensor as described above, and subsequently chloridized to form silver/silver chloride reference electrode. Advantageously, chloridizing the silver wire as described herein enables the manufacture of a reference electrode with optimal in vivo performance. Namely, by controlling the quantity and amount of chloridization of the silver to form silver/silver chloride, improved break-in time, stability of the reference electrode, and extended life has been shown with the preferred embodiments (see FIGS. 22 and 23). Additionally, use of silver chloride as described above allows for relatively inexpensive and simple manufacture of the reference electrode.

In embodiments wherein an outer insulator is disposed, a portion of the coated assembly structure can be stripped or otherwise removed, for example, by hand, excimer lasing, chemical etching, laser ablation, grit-blasting (e.g., with sodium bicarbonate or other suitable grit), or the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, e.g., a parylene coating without damaging, e.g., an underlying platinum conductor. One additional advantage of sodium bicarbonate blasting includes its polishing action on the metal as it strips the polymer layer, thereby eliminating a cleaning step that might otherwise be necessary.

In the embodiment illustrated in FIG. 5B, a radial window 43 is formed through the insulating material 45 to expose a circumferential electroactive surface of the working electrode. Additionally, sections 41 of electroactive surface of the reference electrode are exposed. For example, the 41 sections of electroactive surface can be masked during deposition of an outer insulating layer or etched after deposition of an outer insulating layer.

In some applications, cellular attack or migration of cells to the sensor can cause reduced sensitivity and/or function of the device, particularly after the first day of implantation. However, when the exposed electroactive surface is distributed circumferentially about the sensor (e.g., as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

In some embodiments, the working electrode has a diameter of from about 0.001 inches or less to about 0.010 inches or more, preferably from about 0.002 inches to about 0.008 inches, and more preferably from about 0.004 inches to about 0.005 inches. The length of the window can be from about 0.1 mm (about 0.004 inches) or less to about 2 mm (about 0.078 inches) or more, and preferably from about 0.5 mm (about 0.02 inches) to about 0.75 mm (0.03 inches). In such embodiments, the exposed surface area of the working electrode is preferably from about 0.000013 in$^2$ (0.0000839 cm$^2$) or less to about 0.0025 in$^2$ (0.016129 cm$^2$) or more (assuming a diameter of from about 0.001 inches to about 0.010 inches and a length of from about 0.004 inches to about 0.078 inches). The preferred exposed surface area of the working electrode is selected to produce an analyte signal with a current in the picoAmp range, such as is described in more detail elsewhere herein. However, a current in the picoAmp range can be dependent upon a variety of factors, for example the electronic circuitry design (e.g., sample rate, current draw, A/D converter bit resolution, etc.), the membrane system (e.g., permeability of the analyte through the membrane system), and the exposed surface area of the working electrode. Accordingly, the exposed electroactive working electrode surface area can be selected to have a value greater than or less than the above-described ranges taking into consideration alterations in the membrane system and/or electronic circuitry. In preferred embodiments of a glucose sensor, it can be advantageous to minimize the surface area of the working electrode while maximizing the diffusivity of glucose in order to optimize the signal-to-noise ratio while maintaining sensor performance in both high and low glucose concentration ranges.

In some alternative embodiments, the exposed surface area of the working (and/or other) electrode can be increased by altering the cross-section of the electrode itself. For example, in some embodiments the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example.

In some alternative embodiments, additional electrodes can be included within the assembly, for example, a three-electrode system (working, reference, and counter electrodes) and/or an additional working electrode (e.g., an electrode which can be used to generate oxygen, which is configured as a baseline subtracting electrode, or which is configured for measuring additional analytes). U.S. Publication No. US-2005-0161346-A1 and U.S. Publication No. US-2005-0143635-A1 describe some systems and methods for implementing and using additional working, counter, and/or reference electrodes. In one implementation wherein the sensor comprises two working electrodes, the two working electrodes are juxtapositioned (e.g., extend parallel to each other), around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline and the additional working electrode is configured to measure a baseline signal consisting of baseline only (e.g., configured to be substantially similar to the first working electrode without an enzyme disposed thereon). In this way, the baseline signal can be subtracted from the first signal to produce a glucose-only signal that is substantially not subject to fluctuations in the baseline and/or interfering species on the signal.

Although the preferred embodiments illustrate one electrode configuration including one bulk metal wire helically wound around another bulk metal wire, other electrode configurations are also contemplated. In an alternative embodiment, the working electrode comprises a tube with a reference electrode disposed or coiled inside, including an insulator therebetween. Alternatively, the reference electrode comprises a tube with a working electrode disposed or coiled inside, including an insulator therebetween. In another alternative embodiment, a polymer (e.g., insulating) rod is provided, wherein the electrodes are deposited (e.g., electro-plated) thereon. In yet another alternative embodiment, a metallic (e.g., steel) rod is provided, coated with an insulating material, onto which the working and reference electrodes are deposited. In yet another alternative embodiment, one or more working electrodes are helically wound around a reference electrode.

Preferably, the electrodes and membrane systems of the preferred embodiments are coaxially formed, namely, the electrodes and/or membrane system all share the same central axis. While not wishing to be bound by theory, it is believed that a coaxial design of the sensor enables a symmetrical design without a preferred bend radius. Namely, in contrast to prior art sensors comprising a substantially planar configuration that can suffer from regular bending about the plane of the sensor, the coaxial design of the preferred embodiments do not have a preferred bend radius and therefore are not subject to regular bending about a particular plane (which can cause fatigue failures and the like). However, non-coaxial sensors can be implemented with the sensor system of the preferred embodiments.

In addition to the above-described advantages, the coaxial sensor design of the preferred embodiments enables the diameter of the connecting end of the sensor (proximal portion) to be substantially the same as that of the sensing end (distal portion) such that the needle is able to insert the sensor into the host and subsequently slide back over the sensor and release the sensor from the needle, without slots or other complex multi-component designs.

In one such alternative embodiment, the two wires of the sensor are held apart and configured for insertion into the host in proximal but separate locations. The separation of the working and reference electrodes in such an embodiment can provide additional electrochemical stability with simplified manufacture and electrical connectivity. It is appreciated by one skilled in the art that a variety of electrode configurations can be implemented with the preferred embodiments.

In some embodiments, the sensor includes an antimicrobial portion configured to extend through the exit-site when the sensor is implanted in the host. Namely, the sensor is designed with in vivo and ex vivo portions as described in more detail elsewhere herein; additionally, the sensor comprises a transition portion, also referred to as an antimicrobial portion, located between the in vivo and ex vivo portions 42, 40. The antimicrobial portion is designed to provide antimicrobial effects to the exit-site and adjacent tissue when implanted in the host.

In some embodiments, the antimicrobial portion comprises silver, e.g., the portion of a silver reference electrode that is configured to extend through the exit-site when implanted. Although exit-site infections are a common adverse occurrence associated with some conventional transcutaneous medical devices, the devices of preferred embodiments are designed at least in part to minimize infection, to minimize irritation, and/or to extend the duration of implantation of the sensor by utilizing a silver reference electrode to extend through the exit-site when implanted in a patient. While not wishing to be bound by theory, it is believed that the silver may reduce local tissue infections (within the tissue and at the exit-site); namely, steady release of molecular quantities of silver is believed to have an antimicrobial effect in biological tissue (e.g., reducing or preventing irritation and infection), also referred to as passive antimicrobial effects. Although one example of passive antimicrobial effects is described herein, one skilled in the art can appreciate a variety of passive anti-microbial systems and methods that can be implemented with the preferred embodiments. Additionally, it is believed that antimicrobial effects can contribute to extended life of a transcutaneous analyte sensor, enabling a functional lifetime past a few days, e.g., seven days or longer. FIG. 23 shows transcutaneous glucose sensor data and corresponding blood glucose values over approximately seven days in a human, wherein the transcutaneous glucose sensor data was formed with a silver transition portion that extended through the exit-site after sensor implantation.

In some embodiments, active antimicrobial systems and methods are provided in the sensor system in order to further enhance the antimicrobial effects at the exit-site. In one such embodiment, an auxiliary silver wire is disposed on or around the sensor, wherein the auxiliary silver wire is connected to electronics and configured to pass a current sufficient to enhance its antimicrobial properties (active antimicrobial effects), as is appreciated by one skilled in the art. The current can be passed continuously or intermittently, such that sufficient antimicrobial properties are provided. Although one example of active antimicrobial effects is described herein, one skilled in the art can appreciate a variety of active anti-microbial systems and methods that can be implemented with the preferred embodiments.

Anchoring Mechanism

It is preferred that the sensor remains substantially stationary within the tissue of the host, such that migration or motion of the sensor with respect to the surrounding tissue is minimized. Migration or motion is believed to cause inflammation at the sensor implant site due to irritation, and can also cause noise on the sensor signal due to motion-related artifact, for example. Therefore, it can be advantageous to provide an anchoring mechanism that provides support for the sensor's in vivo portion to avoid the above-mentioned problems. Combining advantageous sensor geometry with an advantageous anchoring minimizes additional parts and allows for an optimally small or low profile design of the sensor. In one embodiment the sensor includes a surface topography, such as the helical surface topography provided by the reference electrode surrounding the working electrode. In alternative embodiments, a surface topography could be provided by a roughened surface, porous surface (e.g. porous parylene), ridged surface, or the like. Additionally (or alternatively), the anchoring can be provided by prongs, spines, barbs, wings, hooks, a bulbous portion (for example, at the distal end), an S-bend along the sensor, a rough surface topography, a gradually changing diameter, combinations thereof, or the like, which can be used alone or in combination with the helical surface topography to stabilize the sensor within the subcutaneous tissue.

Variable Stiffness

As described above, conventional transcutaneous devices are believed to suffer from motion artifact associated with host movement when the host is using the device. For example, when a transcutaneous analyte sensor is inserted into the host, various movements on the sensor (for example, relative movement within and between the subcutaneous space, dermis, skin, and external portions of the sensor) create stresses on the device, which is known to produce artifacts on the sensor signal. Accordingly, there are different design considerations (for example, stress considerations) on various sections of the sensor. For example, the distal portion 42 of the sensor can benefit in general from greater flexibility as it encounters greater mechanical stresses caused by movement of the tissue within the patient and relative movement between the in vivo and ex vivo portions of the sensor. On the other hand, the proximal portion 40 of the sensor can benefit in general from a stiffer, more robust design to ensure structural integrity and/or reliable electrical connections. Additionally, in some embodiments wherein a needle is retracted over the proximal portion 40 of the device (see FIGS. 6 to 8), a stiffer design can minimize crimping of the sensor and/or ease in retraction of the needle from the sensor. Thus, by designing greater flexibility into the in vivo (distal) portion 42, the flexibility is believed to compensate for patient movement, and noise associated therewith. By designing greater stiffness into the ex vivo (proximal) portion 40, column strength (for retraction of the needle over the sensor), electrical connections, and integrity can be enhanced. In some alternative embodiments, a stiffer distal end and/or a more flexible proximal end can be advantageous as described in U.S. Publication No. US-2006-0015024-A1.

The preferred embodiments provide a distal portion 42 of the sensor 32 designed to be more flexible than a proximal portion 40 of the sensor. The variable stiffness of the preferred embodiments can be provided by variable pitch of any one or more helically wound wires of the device, variable cross-section of any one or more wires of the device, and/or variable hardening and/or softening of any one or more wires of the device, such as is described in more detail with reference to U.S. Publication No. US-2006-0015024-A1.

Membrane System

Figure 5C:
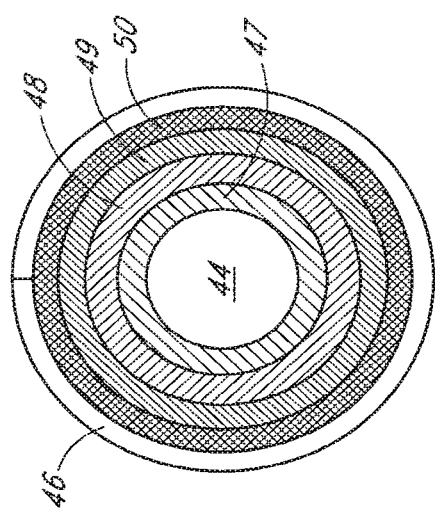
FIG. 5C is a cross-sectional view through the sensor of FIG. 5B on line C-C, showing an exposed electroactive surface of a working electrode surrounded by a membrane system.

FIG. 5C is a cross-sectional view through the sensor on line C-C of FIG. 5B showing the exposed electroactive surface of the working electrode surrounded by the membrane system in one embodiment. Preferably, a membrane system is deposited over at least a portion of the electroactive surfaces of the sensor 32 (working electrode and optionally reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface. Some examples of suitable membrane systems are described in U.S. Publication No. US-2005-0245799-A1.

In general, the membrane system includes a plurality of domains, for example, an electrode domain 47, an interference domain 48, an enzyme domain 49 (for example, including glucose oxidase), and a resistance domain 50, as shown in FIG. 5C, and can include a high oxygen solubility domain, and/or a bioprotective domain (not shown), such as is described in more detail in U.S. Publication No. US-2005-

0245799-A1, and such as is described in more detail below. The membrane system can be deposited on the exposed electroactive surfaces using known thin film techniques (for example, vapor deposition, spraying, electro-depositing, dipping, or the like). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art.

In some embodiments, one or more domains of the membrane systems are formed from materials such as described above in connection with the porous layer, such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. U.S. Publication No. US-2005-0245799-A1 describes biointerface and membrane system configurations and materials that may be applied to the preferred embodiments.

Electrode Domain

In selected embodiments, the membrane system comprises an electrode domain. The electrode domain 47 is provided to ensure that an electrochemical reaction occurs between the electroactive surfaces of the working electrode and the reference electrode, and thus the electrode domain 47 is preferably situated more proximal to the electroactive surfaces than the interference and/or enzyme domain. Preferably, the electrode domain includes a coating that maintains a layer of water at the electrochemically reactive surfaces of the sensor. In other words, the electrode domain is present to provide an environment between the surfaces of the working electrode and the reference electrode which facilitates an electrochemical reaction between the electrodes. For example, a humectant in a binder material can be employed as an electrode domain; this allows for the full transport of ions in the aqueous environment. The electrode domain can also assist in stabilizing the operation of the sensor by accelerating electrode start-up and drifting problems caused by inadequate electrolyte. The material that forms the electrode domain can also provide an environment that protects against pH-mediated damage that can result from the formation of a large pH gradient due to the electrochemical activity of the electrodes.

In one embodiment, the electrode domain 47 includes a flexible, water-swellable, hydrogel film having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain 47 is formed of a curable mixture of a urethane polymer and a hydrophilic polymer. Particularly preferred coatings are formed of a polyurethane polymer having carboxylate or hydroxyl functional groups and non-ionic hydrophilic polyether segments, wherein the polyurethane polymer is crosslinked with a water soluble carbodiimide (e.g., 1-ethyl-3-(3-dimethylaminopropyl)carbodiimide (EDC)) in the presence of polyvinylpyrrolidone and cured at a moderate temperature of about 50° C.

In some preferred embodiments, the electrode domain 47 is formed from a hydrophilic polymer such as polyvinylpyrrolidone (PVP). An electrode domain formed from PVP has been shown to reduce break-in time of analyte sensors; for example, a glucose sensor utilizing a cellulosic-based interference domain such as described in more detail below.

Preferably, the electrode domain is deposited by vapor deposition, spray coating, dip coating, or other thin film techniques on the electroactive surfaces of the sensor. In one preferred embodiment, the electrode domain is formed by dip-coating the electroactive surfaces in an electrode layer solution and curing the domain for a time of from about 15 minutes to about 30 minutes at a temperature of from about 40° C. to about 55° C. (and can be accomplished under vacuum (e.g., 20 to 30 mmHg)). In embodiments wherein dip-coating is used to deposit the electrode domain, a preferred insertion rate of from about 1 to about 3 inches per minute into the electrode layer solution, with a preferred dwell time of from about 0.5 to about 2 minutes in the electrode layer solution, and a preferred withdrawal rate of from about 0.25 to about 2 inches per minute from the electrode layer solution provide a functional coating. However, values outside of those set forth above can be acceptable or even desirable in certain embodiments, for example, depending upon solution viscosity and solution surface tension, as is appreciated by one skilled in the art. In one embodiment, the electroactive surfaces of the electrode system are dip-coated one time (one layer) and cured at 50° C. under vacuum for 20 minutes.

Although an independent electrode domain 47 is described herein, in some embodiments sufficient hydrophilicity can be provided in the interference domain and/or enzyme domain (the domain adjacent to the electroactive surfaces) so as to provide for the full transport of ions in the aqueous environment (e.g. without a distinct electrode domain). In these embodiments, an electrode domain is not necessary.

Interference Domain

Interferents are molecules or other species that are reduced or oxidized at the electrochemically reactive surfaces of the sensor, either directly or via an electron transfer agent, to produce a false positive analyte signal. In preferred embodiments, an interference domain 48 is provided that substantially restricts, resists, or blocks the flow of one or more interfering species. Some known interfering species for a glucose sensor, as described in more detail above, include acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. In general, the interference domain of the preferred embodiments is less permeable to one or more of the interfering species than to the analyte, e.g., glucose.

In one embodiment, the interference domain 48 is formed from one or more cellulosic derivatives. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like.

In one preferred embodiment, the interference domain 48 is formed from cellulose acetate butyrate. Cellulose acetate butyrate with a molecular weight of about 10,000 daltons to about 75,000 daltons, preferably from about 15,000, 20,000, or 25,000 daltons to about 50,000, 55,000, 60,000, 65,000, or 70,000 daltons, and more preferably about 20,000 daltons is employed. In certain embodiments, however, higher or lower molecular weights can be preferred. Additionally, a casting solution or dispersion of cellulose acetate butyrate at a weight percent of about 15% to about 25%, preferably from about 15%, 16%, 17%, 18%, 19% to about 20%, 21%, 22%, 23%, 24% or 25%, and more preferably about 18% is preferred. Preferably, the casting solution includes a solvent or solvent system, for example an acetone:ethanol solvent system. Higher or lower concentrations can be preferred in certain embodiments. A plurality of layers of cellulose acetate butyrate can be advantageously combined to form the interference domain in some embodiments, for example, three layers can be employed. It can be desirable to employ a mixture of cellulose acetate butyrate components with different molecular weights in a single solution, or to deposit multiple layers of cellulose acetate butyrate from different solutions comprising cellulose acetate butyrate of different molecular weights, different concentrations, and/or different chemistries (e.g., functional groups). It can also be desirable to include additional substances in the casting solutions or dispersions, e.g., functionalizing agents, crosslinking agents, other polymeric substances, substances capable of modifying the hydrophilicity/hydrophobicity of the resulting layer, and the like.

In one alternative embodiment, the interference domain 48 is formed from cellulose acetate. Cellulose acetate with a molecular weight of about 30,000 daltons or less to about 100,000 daltons or more, preferably from about 35,000, 40,000, or 45,000 daltons to about 55,000, 60,000, 65,000, 70,000, 75,000, 80,000, 85,000, 90,000, or 95,000 daltons, and more preferably about 50,000 daltons is preferred. Additionally, a casting solution or dispersion of cellulose acetate at a weight percent of about 3% to about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 8% is preferred. In certain embodiments, however, higher or lower molecular weights and/or cellulose acetate weight percentages can be preferred. It can be desirable to employ a mixture of cellulose acetates with molecular weights in a single solution, or to deposit multiple layers of cellulose acetate from different solutions comprising cellulose acetates of different molecular weights, different concentrations, or different chemistries (e.g., functional groups). It can also be desirable to include additional substances in the casting solutions or dispersions such as described in more detail above.

Layer(s) prepared from combinations of cellulose acetate and cellulose acetate butyrate, or combinations of layer(s) of cellulose acetate and layer(s) of cellulose acetate butyrate can also be employed to form the interference domain 48.

In some alternative embodiments, additional polymers, such as Nafion®, can be used in combination with cellulosic derivatives to provide equivalent and/or enhanced function of the interference domain 48. As one example, a 5 wt % Nafion® casting solution or dispersion can be used in combination with a 8 wt % cellulose acetate casting solution or dispersion, e.g., by dip coating at least one layer of cellulose acetate and subsequently dip coating at least one layer Nafion® onto a needle-type sensor such as described with reference to the preferred embodiments. Any number of coatings or layers formed in any order may be suitable for forming the interference domain of the preferred embodiments.

In some alternative embodiments, more than one cellulosic derivative can be used to form the interference domain 48 of the preferred embodiments. In general, the formation of the interference domain on a surface utilizes a solvent or solvent system in order to solvate the cellulosic derivative (or other polymer) prior to film formation thereon. In preferred embodiments, acetone and ethanol are used as solvents for cellulose acetate; however one skilled in the art appreciates the numerous solvents that are suitable for use with cellulosic derivatives (and other polymers). Additionally, one skilled in the art appreciates that the preferred relative amounts of solvent can be dependent upon the cellulosic derivative (or other polymer) used, its molecular weight, its method of deposition, its desired thickness, and the like. However, a percent solute of from about 1% to about 25% is preferably used to form the interference domain solution so as to yield an interference domain having the desired properties. The cellulosic derivative (or other polymer) used, its molecular weight, method of deposition, and desired thickness can be adjusted, depending upon one or more other of the parameters, and can be varied accordingly as is appreciated by one skilled in the art.

In some alternative embodiments, other polymer types that can be utilized as a base material for the interference domain 48 including polyurethanes, polymers having pendant ionic groups, and polymers having controlled pore size, for example. In one such alternative embodiment, the interference domain includes a thin, hydrophobic membrane that is non-swellable and restricts diffusion of low molecular weight species. The interference domain 48 is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Publication No. US-2005-0115832-A1, U.S. Publication No. US-2005-0176136-A1, U.S. Publication No. US-2005-0161346-A1, and U.S. Publication No. US-2005-0143635-A1. In some alternative embodiments, a distinct interference domain is not included.

In preferred embodiments, the interference domain 48 is deposited directly onto the electroactive surfaces of the sensor for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes can also be desirable in certain embodiments, but thinner membranes are generally preferred because they have a lower impact on the rate of diffusion of hydrogen peroxide from the enzyme membrane to the electrodes.

In general, the membrane systems of the preferred embodiments can be formed and/or deposited on the exposed electroactive surfaces (e.g., one or more of the working and reference electrodes) using known thin film techniques (for example, casting, spray coating, drawing down, electro-depositing, dip coating, and the like), however casting or other known application techniques can also be utilized. Preferably, the interference domain is deposited by vapor deposition, spray coating, or dip coating. In one exemplary embodiment of a needle-type (transcutaneous) sensor such as described herein, the interference domain is formed by dip coating the sensor into an interference domain solution using an insertion rate of from about 20 inches/min to about 60 inches/min, preferably 40 inches/min, a dwell time of from about 0 minute to about 5 seconds, preferably 0 seconds, and a withdrawal rate of from about 20 inches/minute to about 60 inches/minute, preferably about 40 inches/minute, and curing (drying) the domain from about 1 minute to about 30 minutes, preferably from about 3 minutes to about 15 minutes (and can be accomplished at room temperature or under vacuum (e.g., 20 to 30 mmHg)). In one exemplary embodiment including cellulose acetate butyrate interference domain, a 3-minute cure (i.e., dry) time is preferred between each layer applied. In another exemplary embodiment employing a cellulose acetate interference domain, a 15 minute cure (i.e., dry) time is preferred between each layer applied.

The dip process can be repeated at least one time and up to 10 times or more. The preferred number of repeated dip processes depends upon the cellulosic derivative(s) used, their concentration, conditions during deposition (e.g., dipping) and the desired thickness (e.g., sufficient thickness to provide functional blocking of (or resistance to) certain interferents), and the like. In some embodiments, 1 to 3 microns may be preferred for the interference domain thickness; however, values outside of these can be acceptable or even desirable in certain embodiments, for example, depending upon viscosity and surface tension, as is appreciated by one skilled in the art. In one exemplary embodiment, an interference domain is formed from three layers of cellulose acetate butyrate. In another exemplary embodiment, an interference domain is formed from 10 layers of cellulose acetate. In alternative embodiments, the interference domain can be formed using any known method and combination of cellulose acetate and cellulose acetate butyrate, as will be appreciated by one skilled in the art.

In some embodiments, the electroactive surface can be cleaned prior to application of the interference domain 48. In some embodiments, the interference domain 48 of the preferred embodiments can be useful as a bioprotective or biocompatible domain, namely, a domain that interfaces with host tissue when implanted in an animal (e.g., a human) due to its stability and biocompatibility.

Enzyme Domain

In preferred embodiments, the membrane system further includes an enzyme domain 49 disposed more distally from the electroactive surfaces than the interference domain 48; however other configurations can be desirable. In the preferred embodiments, the enzyme domain provides an enzyme to catalyze the reaction of the analyte and its co-reactant, as described in more detail below. In the preferred embodiments of a glucose sensor, the enzyme domain includes glucose oxidase; however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase, are subject to deactivation as a function of time even in ambient conditions, this behavior is compensated for in forming the enzyme domain. Preferably, the enzyme domain is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. Preferably, the enzyme is immobilized within the domain. See, e.g., U.S. patent application Ser. No. 10/896,639 filed on Jul. 21, 2004 and entitled "Oxygen Enhancing Membrane Systems for Implantable Device."

In preferred embodiments, the enzyme domain is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. However in some embodiments, the enzyme domain can be deposited directly onto the electroactive surfaces. Preferably, the enzyme domain is deposited by spray or dip coating. In one embodiment of needle-type (transcutaneous) sensor such as described herein, the enzyme domain is formed by dip coating the interference domain coated sensor into an enzyme domain solution and curing the domain for from about 15 to about 30 minutes at a temperature of from about 40° C. to about 55° C. (and can be accomplished under vacuum (e.g., 20 to 30 mmHg)). In embodiments wherein dip coating is used to deposit the enzyme domain at room temperature, a preferred insertion rate of from about 0.25 inch per minute to about 3 inches per minute, with a preferred dwell time of from about 0.5 minutes to about 2 minutes, and a preferred withdrawal rate of from about 0.25 inch per minute to about 2 inches per minute provides a functional coating. However, values outside of those set forth above can be acceptable or even desirable in certain embodiments, for example, depending upon viscosity and surface tension, as is appreciated by one skilled in the art. In one embodiment, the enzyme domain is formed by dip coating two times (namely, forming two layers) in an enzyme domain solution and curing at 50° C. under vacuum for 20 minutes. However, in some embodiments, the enzyme domain can be formed by dip coating and/or spray coating one or more layers at a predetermined concentration of the coating solution, insertion rate, dwell time, withdrawal rate, and/or desired thickness.

Resistance Domain

In preferred embodiments, the membrane system includes a resistance domain 50 disposed more distal from the electroactive surfaces than the enzyme domain. Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21(1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain includes a semipermeable membrane that controls the flux of oxygen and glucose to the underlying enzyme domain, preferably rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Publication No. US-2005-0090607-A1.

In a preferred embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In preferred embodiments, the resistance domain is deposited onto the enzyme domain to yield a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. Preferably, the resistance domain is deposited onto the enzyme domain by vapor deposition, spray coating, or dip coating. In one preferred embodiment, spray coating is the preferred deposition technique. The spraying process atomizes and mists the solution, and therefore most or all of the solvent is evaporated prior to the coating material settling on the underlying domain, thereby minimizing contact of the solvent with the enzyme.

In another preferred embodiment, physical vapor deposition (e.g., ultrasonic vapor deposition) is used for coating one or more of the membrane domain(s) onto the electrodes, wherein the vapor deposition apparatus and process include an ultrasonic nozzle that produces a mist of micro-droplets in a vacuum chamber. In these embodiments, the micro-droplets move turbulently within the vacuum chamber, isotropically impacting and adhering to the surface of the substrate. Advantageously, vapor deposition as described above can be implemented to provide high production throughput of membrane deposition processes (e.g., at least about 20 to about 200 or more electrodes per chamber), greater consistency of the membrane on each sensor, and increased uniformity of sensor performance, for example, as described below.

In some embodiments, depositing the resistance domain (for example, as described in the preferred embodiments above) includes formation of a membrane system that substantially blocks or resists ascorbate (a known electrochemical interferant in hydrogen peroxide-measuring glucose sensors). While not wishing to be bound by theory, it is believed that during the process of depositing the resistance domain as described in the preferred embodiments, a structural morphology is formed that is characterized in that ascorbate does not substantially permeate therethrough.

In a preferred embodiment, the resistance domain is deposited on the enzyme domain by spray coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Although a variety of spraying or deposition techniques can be used, spraying the resistance domain material and rotating the sensor at least one time by 180° can typically provide adequate coverage by the resistance domain. Spraying the resistance domain material and rotating the sensor at least two times by 120° provides even greater coverage (one layer of 360° coverage), thereby ensuring resistivity to glucose, such as is described in more detail above.

In preferred embodiments, the resistance domain is spray coated and subsequently cured for a time of from about 15 minutes to about 90 minutes at a temperature of from about 40° C. to about 60° C. (and can be accomplished under vacuum (e.g., from 20 to 30 mmHg)). A cure time of up to about 90 minutes or more can be advantageous to ensure complete drying of the resistance domain.

In one embodiment, the resistance domain is formed by spray coating at least six layers (namely, rotating the sensor seventeen times by 120° for at least six layers of 360° coverage) and curing at 50° C. under vacuum for 60 minutes. However, the resistance domain can be formed by dip coating or spray coating any layer or plurality of layers, depending upon the concentration of the solution, insertion rate, dwell time, withdrawal rate, and/or the desired thickness of the resulting film. Additionally, curing in a convention oven can also be employed.

In certain embodiments, a variable frequency microwave oven can be used to cure the membrane domains/layers. In general, microwave ovens directly excite the rotational mode of solvents. Consequently, microwave ovens cure coatings from the inside out rather than from the outside in as with conventional convection ovens. This direct rotational mode excitation is responsible for the typically observed "fast" curing within a microwave oven. In contrast to conventional microwave ovens, which rely upon a fixed frequency of emission that can cause arcing of dielectric (metallic) substrates if placed within a conventional microwave oven, Variable Frequency Microwave (VFM) ovens emit thousands of frequencies within 100 milliseconds, which substantially eliminates arcing of dielectric substrates. Consequently, the membrane domains/layers can be cured even after deposition on metallic electrodes as described herein. While not wishing to be bound by theory, it is believe that VFM curing can increase the rate and completeness of solvent evaporation from a liquid membrane solution applied to a sensor, as compared to the rate and completeness of solvent evaporation observed for curing in conventional convection ovens.

In certain embodiments, VFM is can be used together with convection oven curing to further accelerate cure time. In some sensor applications wherein the membrane is cured prior to application on the electrode (see, for example, U.S. Publication No. US-2005-0245799-A1, which is incorporated herein by reference in its entirety), conventional microwave ovens (e.g., fixed frequency microwave ovens) can be used to cure the membrane layer.

Treatment of Interference Domain/Membrane System

Although the above-described methods generally include a curing step in formation of the membrane system, including the interference domain, the preferred embodiments further include an additional treatment step, which can be performed directly after the formation of the interference domain and/or some time after the formation of the entire membrane system (or anytime in between). In some embodiments, the additional treatment step is performed during (or in combination with) sterilization of the sensor.

In some embodiments, the membrane system (or interference domain) is treated by exposure to ionizing radiation, for example, electron beam radiation, UV radiation, X-ray radiation, gamma radiation, and the like. Alternatively, the membrane can be exposed to visible light when suitable photoinitiators are incorporated into the interference domain. While not wishing to be bound by theory, it is believed that exposing the interference domain to ionizing radiation substantially crosslinks the interference domain and thereby creates a tighter, less permeable network than an interference domain that has not been exposed to ionizing radiation.

In some embodiments, the membrane system (or interference domain) is crosslinked by forming free radicals, which may include the use of ionizing radiation, thermal initiators, chemical initiators, photoinitiators (e.g., UV and visible light), and the like. Any suitable initiator or any suitable initiator system can be employed, for example, α-hydroxyketone, α-aminoketone, ammonium persulfate (APS), redox systems such as APS/bisulfite, or potassium permanganate. Suitable thermal initiators include but are not limited to potassium persulfate, ammonium persulfate, sodium persulfate, and mixtures thereof.

In embodiments wherein electron beam radiation is used to treat the membrane system (or interference domain), a preferred exposure time is from about 6k or 12 kGy to about 25 or 50 kGy, more preferably about 25 kGy. However, one skilled in the art appreciates that choice of molecular weight, composition of cellulosic derivative (or other polymer), and/or the thickness of the layer can affect the preferred exposure time of membrane to radiation. Preferably, the exposure is sufficient for substantially crosslinking the interference domain to form free radicals, but does not destroy or significantly break down the membrane or does not significantly damage the underlying electroactive surfaces.

In embodiments wherein UV radiation is employed to treat the membrane, UV rays from about 200 nm to about 400 nm are preferred; however values outside of this range can be employed in certain embodiments, dependent upon the cellulosic derivative and/or other polymer used.

In some embodiments, for example, wherein photoinitiators are employed to crosslink the interference domain, one or more additional domains can be provided adjacent to the interference domain for preventing delamination that may be caused by the crosslinking treatment. These additional domains can be "tie layers" (i.e., film layers that enhance adhesion of the interference domain to other domains of the membrane system). In one exemplary embodiment, a membrane system is formed that includes the following domains: resistance domain, enzyme domain, electrode domain, and cellulosic-based interference domain, wherein the electrode domain is configured to ensure adhesion between the enzyme domain and the interference domain. In embodiments wherein photoinitiators are employed to crosslink the interference domain, UV radiation of greater than about 290 nm is preferred. Additionally, from about 0.01 to about 1 wt % photoinitiator is preferred weight-to-weight with a preselected cellulosic polymer (e.g., cellulose acetate); however values outside of this range can be desirable dependent upon the cellulosic polymer selected.

In general, sterilization of the transcutaneous sensor can be completed after final assembly, utilizing methods such as electron beam radiation, gamma radiation, glutaraldehyde treatment, or the like. The sensor can be sterilized prior to or after packaging. In an alternative embodiment, one or more sensors can be sterilized using variable frequency microwave chamber(s), which can increase the speed and reduce the cost of the sterilization process. In another alternative embodiment, one or more sensors can be sterilized using ethylene oxide (EtO) gas sterilization, for example, by treating with 100% ethylene oxide, which can be used when the sensor electronics are not detachably connected to the sensor and/or when the sensor electronics must undergo a sterilization process. In one embodiment, one or more packaged sets of transcutaneous sensors (e.g., 1, 2, 3, 4, or 5 sensors or more) are sterilized simultaneously.

Signal Response

Advantageously, sensors with the membrane system of the preferred embodiments, including an electrode domain 47 and/or interference domain 48, an enzyme domain 49, and a resistance domain 50, provide stable signal response to increasing glucose levels of from about 40 to about 400 mg/dL, and sustained function (at least 90% signal strength) even at low oxygen levels (for example, at about 0.6 mg/L $O_2$). While not wishing to be bound by theory, it is believed that the resistance domain provides sufficient resistivity, or the enzyme domain provides sufficient enzyme, such that oxygen limitations are seen at a much lower concentration of oxygen as compared to prior art sensors.

In preferred embodiments, a sensor signal with a current in the picoAmp range is preferred, which is described in more detail elsewhere herein. However, the ability to produce a signal with a current in the picoAmp range can be dependent upon a combination of factors, including the electronic circuitry design (e.g., A/D converter, bit resolution, and the like), the membrane system (e.g., permeability of the analyte through the resistance domain, enzyme concentration, and/or electrolyte availability to the electrochemical reaction at the electrodes), and the exposed surface area of the working electrode. For example, the resistance domain can be designed to be more or less restrictive to the analyte depending upon to the design of the electronic circuitry, membrane system, and/or exposed electroactive surface area of the working electrode.

Accordingly, in preferred embodiments, the membrane system is designed with a sensitivity of from about 1 pA/mg/dL to about 100 pA/mg/dL, preferably from about 5 pA/mg/dL to 25 pA/mg/dL, and more preferably from about 3.5 to about 7.5 pA/mg/dL. While not wishing to be bound by any particular theory, it is believed that membrane systems designed with a sensitivity in the preferred ranges permit measurement of the analyte signal in low analyte and/or low oxygen situations. Namely, conventional analyte sensors have shown reduced measurement accuracy in low analyte ranges due to lower availability of the analyte to the sensor and/or have shown increased signal noise in high analyte ranges due to insufficient oxygen necessary to react with the amount of analyte being measured. While not wishing to be bound by theory, it is believed that the membrane systems of the preferred embodiments, in combination with the electronic circuitry design and exposed electrochemical reactive surface area design, support measurement of the analyte in the picoAmp range, which enables an improved level of resolution and accuracy in both low and high analyte ranges not seen in the prior art.

Mutarotase Enzyme

In some embodiments, mutarotase, an enzyme that converts α D-glucose to β D-glucose, is incorporated into the membrane system. Mutarotase can be incorporated into the enzyme domain and/or can be incorporated into another domain of the membrane system. In general, glucose exists in two distinct isomers, α and β, which are in equilibrium with one another in solution and in the blood or interstitial fluid. At equilibrium, α is present at a relative concentration of about 35.5% and β is present in the relative concentration of about 64.5% (see Okuda et. al., *Anal Biochem.* 1971 September; 43(1):312-5). Glucose oxidase, which is a conventional enzyme used to react with glucose in glucose sensors, reacts with β D-glucose and not with α D-glucose. Since only the β D-glucose isomer reacts with the glucose oxidase, errant readings may occur in a glucose sensor responsive to a shift of the equilibrium between the α D-glucose and the β D-glucose. Many compounds, such as calcium, can affect equilibrium shifts of a D-glucose and β D-glucose. For example, as disclosed in U.S. Pat. No. 3,964,974 to Banaugh et al., compounds that exert a mutarotation accelerating effect on α D-glucose include histidine, aspartic acid, imidazole, glutamic acid, a hydroxyl pyridine, and phosphate.

Accordingly, a shift in α D-glucose and β D-glucose equilibrium can cause a glucose sensor based on glucose oxidase to err high or low. To overcome the risks associated with errantly high or low sensor readings due to equilibrium shifts, the sensor of the preferred embodiments can be configured to measure total glucose in the host, including α D-glucose and β D-glucose by the incorporation of the mutarotase enzyme, which converts α D-glucose to β D-glucose.

Although sensors of some embodiments described herein include an interference domain in order to block or reduce one or more interferents, sensors with the membrane systems of the preferred embodiments, including an electrode domain 47, an enzyme domain 48, and a resistance domain 49, have been shown to inhibit ascorbate without an additional interference domain. Namely, the membrane system of the preferred embodiments, including an electrode domain 47, an enzyme domain 48, and a resistance domain 49, has been shown to be substantially non-responsive to ascorbate in physiologically acceptable ranges. While not wishing to be bound by theory, it is believed that the processing process of spraying the depositing the resistance domain by spray coating, as described herein, forms results in a structural morphology that is substantially resistance resistant to ascorbate.

Oxygen Conduit

As described above, certain sensors depend upon an enzyme within the membrane system through which the host's bodily fluid passes and in which the analyte (for example, glucose) within the bodily fluid reacts in the presence of a co-reactant (for example, oxygen) to generate a product. The product is then measured using electrochemical methods, and thus the output of an electrode system functions as a measure of the analyte. For example, when the sensor is a glucose oxidase based glucose sensor, the species measured at the working electrode is $H_2O_2$. An enzyme, glucose oxidase, catalyzes the conversion of oxygen and glucose to hydrogen peroxide and gluconate according to the following reaction:

$$\text{Glucose} + O_2 \rightarrow \text{Gluconate} + H_2O_2$$

Because for each glucose molecule reacted there is a proportional change in the product, $H_2O_2$, one can monitor the change in $H_2O_2$ to determine glucose concentration. Oxidation of $H_2O_2$ by the working electrode is balanced by reduction of ambient oxygen, enzyme generated $H_2O_2$ and other reducible species at a counter electrode, for example. See Fraser, D. M., "An Introduction to In Vivo Biosensing: Progress and Problems." In "Biosensors and the Body," D. M. Fraser, ed., 1997, pp. 1-56 John Wiley and Sons, New York))

In vivo, glucose concentration is generally about one hundred times or more that of the oxygen concentration. Consequently, oxygen is a limiting reactant in the electrochemical reaction, and when insufficient oxygen is provided to the sensor, the sensor is unable to accurately measure glucose concentration. Thus, depressed sensor function or inaccuracy is believed to be a result of problems in availability of oxygen to the enzyme and/or electroactive surface(s).

Accordingly, in an alternative embodiment, an oxygen conduit (for example, a high oxygen solubility domain formed from silicone or fluorochemicals) is provided that extends from the ex vivo portion of the sensor to the in vivo portion of the sensor to increase oxygen availability to the enzyme. The oxygen conduit can be formed as a part of the coating (insulating) material or can be a separate conduit associated with the assembly of wires that forms the sensor.

Porous Biointerface Materials

In alternative embodiments, the distal portion 42 includes a porous material disposed over some portion thereof, which modifies the host's tissue response to the sensor. In some embodiments, the porous material surrounding the sensor advantageously enhances and extends sensor performance and lifetime in the short term by slowing or reducing cellular migration to the sensor and associated degradation that would otherwise be caused by cellular invasion if the sensor were directly exposed to the in vivo environment. Alternatively, the porous material can provide stabilization of the sensor via tissue ingrowth into the porous material in the long term. Suitable porous materials include silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(l-lysine), poly (L-lactic acid), hydroxyethylmethacrylate, hydroxyapeptite, alumina, zirconia, carbon fiber, aluminum, calcium phosphate, titanium, titanium alloy, nintinol, stainless steel, and CoCr alloy, or the like, such as are described in U.S. Publication No. US-2005-0031689-A1 and U.S. Publication No. US-2005-0112169-A1.

In some embodiments, the porous material surrounding the sensor provides unique advantages in the short term (e.g., one to 30 days) that can be used to enhance and extend sensor performance and lifetime. However, such materials can also provide advantages in the long term too (e.g., greater than 30 days). Particularly, the in vivo portion of the sensor (the portion of the sensor that is implanted into the host's tissue) is encased (partially or fully) in a porous material. The porous material can be wrapped around the sensor (for example, by wrapping the porous material around the sensor or by inserting the sensor into a section of porous material sized to receive the sensor). Alternately, the porous material can be deposited on the sensor (for example, by electrospinning of a polymer directly thereon). In yet other alternative embodiments, the sensor is inserted into a selected section of porous biomaterial. Other methods for surrounding the in vivo portion of the sensor with a porous material can also be used as is appreciated by one skilled in the art.

The porous material surrounding the sensor advantageously slows or reduces cellular migration to the sensor and associated degradation that would otherwise be caused by cellular invasion if the sensor were directly exposed to the in vivo environment. Namely, the porous material provides a barrier that makes the migration of cells towards the sensor more tortuous and therefore slower (providing short term advantages). It is believed that this reduces or slows the sensitivity loss normally observed in a short-term sensor over time.

In an embodiment wherein the porous material is a high oxygen solubility material, such as porous silicone, the high oxygen solubility porous material surrounds some of or the entire in vivo portion 42 of the sensor. High oxygen solubility materials are materials that dynamically retain a high availability of oxygen that can be used to compensate for the local oxygen deficit during times of transient ischemia (e.g., silicone and fluorocarbons). It is believed that some signal noise normally seen by a conventional sensor can be attributed to an oxygen deficit. In one exemplary embodiment, porous silicone surrounds the sensor and thereby effectively increases the concentration of oxygen local (proximal) to the sensor. Thus, an increase in oxygen availability proximal to the sensor as achieved by this embodiment ensures that an excess of oxygen over glucose is provided to the sensor; thereby reducing the likelihood of oxygen limited reactions therein. Accordingly, by providing a high oxygen solubility material (e.g., porous silicone) surrounding the in vivo portion of the sensor, it is believed that increased oxygen availability, reduced signal noise, longevity, and ultimately enhanced sensor performance can be achieved.

Bioactive Agents

In some alternative embodiments, a bioactive agent is incorporated into the above described porous material and/or membrane system, which diffuses out into the environment adjacent to the sensing region, such as is described in U.S. Publication No. US-2005-0031689-A1. Additionally or alternately, a bioactive agent can be administered locally at the exit-site or implantation-site. Suitable bioactive agents are those that modify the host's tissue response to the sensor, for example anti-inflammatory agents, anti-infective agents, anesthetics, inflammatory agents, growth factors, immunosuppressive agents, antiplatelet agents, anti-coagulants, anti-proliferates, ACE inhibitors, cytotoxic agents, anti-barrier cell compounds, vascularization-inducing compounds, antisense molecules, or mixtures thereof, such as are described in more detail in co-pending U.S. Patent Publication No. US-2005-0031689-A1.

In embodiments wherein the porous material is designed to enhance short-term (e.g., from about 1 to about 30 days) lifetime or performance of the sensor, a suitable bioactive agent can be chosen to ensure that tissue ingrowth does not substantially occur within the pores of the porous material. Namely, by providing a tissue modifying bioactive agent, such as an anti-inflammatory agent (for example, Dexamethasone), substantially tissue ingrowth can be inhibited, at least in the short term, in order to maintain sufficient glucose transport through the pores of the porous material to maintain a stable sensitivity.

In embodiments wherein the porous material is designed to enhance long-term (e.g., from about a day to about a year or more) lifetime or performance of the sensor, a suitable bioactive agent, such as a vascularization-inducing compound or anti-barrier cell compound, can be chosen to encourage tissue ingrowth without barrier cell formation.

In some alternative embodiments, the in vivo portion of the sensor is designed with porosity therethrough, for example, a design wherein the sensor wires are configured in a mesh, loose helix configuration (namely, with spaces between the wires), or with micro-fabricated holes therethrough. Porosity within the sensor modifies the host's tissue response to the sensor, because tissue ingrowth into and/or through the in vivo portion of the sensor increases stability of the sensor and/or improves host acceptance of the sensor, thereby extending the lifetime of the sensor in vivo.

Sensor Manufacture

In some embodiments, the sensor is manufactured partially or wholly using a continuous reel-to-reel process, wherein one or more manufacturing steps are automated. In such embodiments, a manufacturing process can be provided substantially without the need for manual mounting and fixing steps and substantially without the need human interaction. A process can be utilized wherein a plurality of sensors of the preferred embodiments, including the electrodes, insulator, and membrane system, are continuously manufactured in a semi-automated or automated process.

In one embodiment, a plurality of twisted pairs is continuously formed into a coil, wherein a working electrode is coated with an insulator material around which a plurality of reference electrodes is wound. The plurality of twisted pairs are preferably indexed and subsequently moved from one station to the next whereby the membrane system is serially deposited according to the preferred embodiments. Preferably, the coil is continuous and remains as such during the entire sensor fabrication process, including winding of the electrodes, insulator application, and membrane coating processes. After drying of the membrane system, each individual sensor is cut from the continuous coil.

A continuous reel-to-reel process for manufacturing the sensor eliminates possible sensor damage due to handling by eliminating handling steps, and provides faster manufacturing due to faster trouble shooting by isolation when a product fails. Additionally, a process run can be facilitated because of elimination of steps that would otherwise be required (e.g., steps in a manual manufacturing process). Finally, increased or improved product consistency due to consistent processes within a controlled environment can be achieved in a machine or robot driven operation.

In certain embodiments, vapor deposition (e.g., physical vapor deposition) is utilized to deposit one or more of the membrane domains onto the sensor. Vapor deposition can be used to coat one or more insulating layers onto the electrodes and one or more of the domains of the membrane system onto the electrochemically reactive surfaces. The vapor deposition process can be a part of a continuous manufacturing process, for example, a semi-automated or fully-automated manufacturing process. Physical vapor deposition processes are generally preferred. In such physical vapor deposition processes in the gas phase for forming a thin film, source material is physically transferred in a vacuum to the substrate without any chemical reaction(s) involved. Physical vapor deposition processes include evaporation (e.g., by thermal or e-beam) and sputtering processes. In alternative embodiments, chemical vapor deposition can be used. In chemical vapor deposition processes for depositing a thin film, the substrate is exposed to one or more volatile precursors, which react and/or decompose on the substrate surface to produce the desired deposit. Advantageously, vapor deposition processes can be implemented to provide high production throughput of membrane deposition processes (e.g., deposition on at least about 20 to about 200 or more electrodes per chamber), greater consistency of the membrane on each sensor, and increased uniformity of sensor performance, as described below.

Applicator

Figure 6:
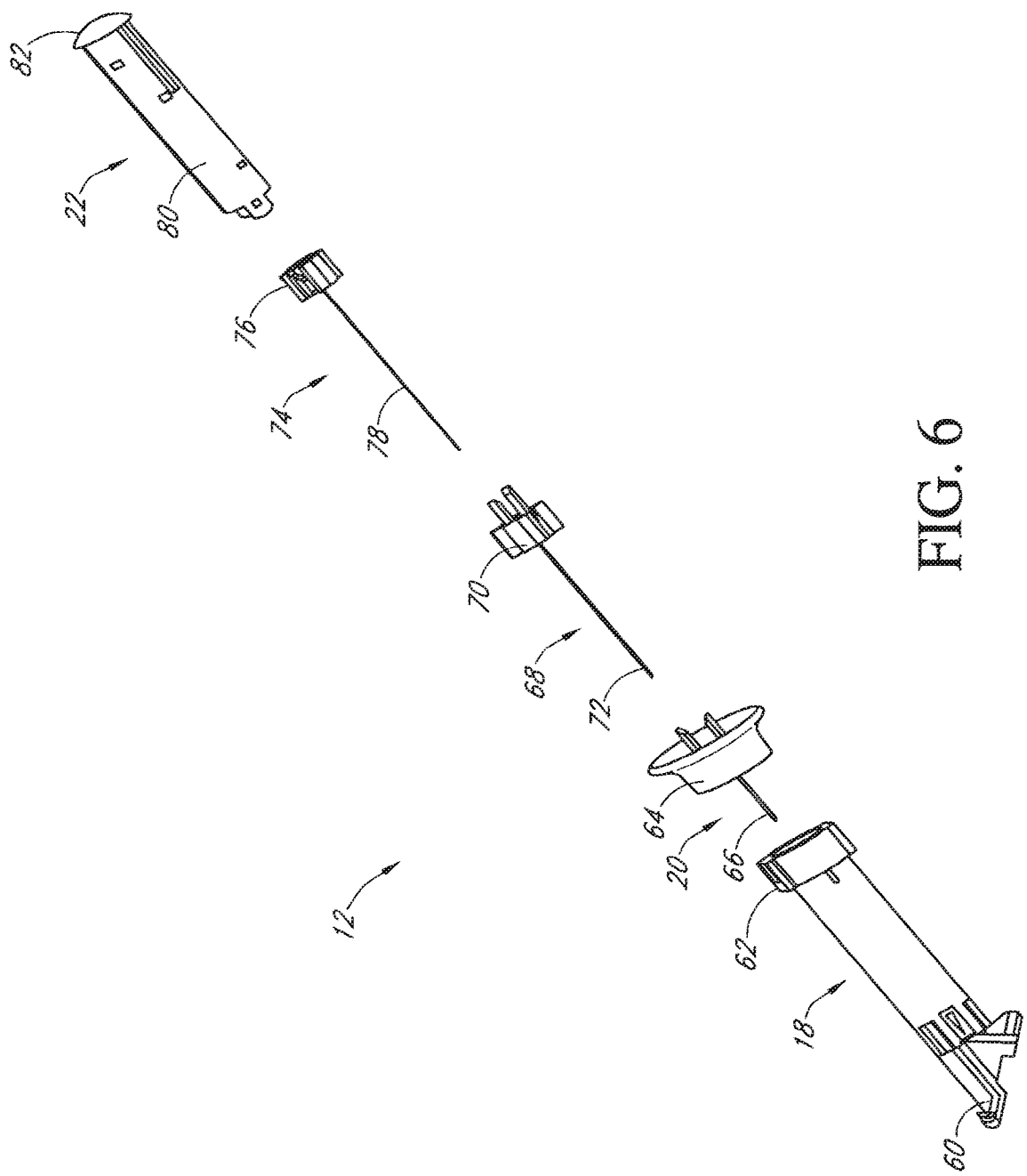
FIG. 6 is an exploded side view of an applicator, showing the components that facilitate sensor insertion and subsequent needle retraction.

FIG. 6 is an exploded side view of an applicator, showing the components that enable sensor and needle insertion. In this embodiment, the applicator 12 includes an applicator body 18 that aides in aligning and guiding the applicator components. Preferably, the applicator body 18 includes an applicator body base 60 that matingly engages the mounting unit 14 and an applicator body cap 62 that enables appropriate relationships (for example, stops) between the applicator components.

The guide tube subassembly 20 includes a guide tube carrier 64 and a guide tube 66. In some embodiments, the guide tube is a cannula. The guide tube carrier 64 slides along the applicator body 18 and maintains the appropriate relative position of the guide tube 66 during insertion and subsequent retraction. For example, prior to and during insertion of the sensor, the guide tube 66 extends through the contact subassembly 26 to maintain an opening that enables easy insertion of the needle therethrough (see FIGS. 7A to 7D). During retraction of the sensor, the guide tube subassembly 20 is pulled back, engaging with and causing the needle and associated moving components to retract back into the applicator 12 (See FIGS. 7C and 7D). In some embodiments, a lubricant (e.g., petroleum jelly) is placed within the sealing member 36 of the contact subassembly such that it surrounds the guide tube (e.g., cannula), thereby allowing the guide tube to easily retract back into the applicator, for example, without causing compression or deformation of the sealing member 36.

A needle subassembly 68 is provided that includes a needle carrier 70 and needle 72. The needle carrier 70 cooperates with the other applicator components and carries the needle 72 between its extended and retracted positions. The needle can be of any appropriate size that can encompass the sensor 32 and aid in its insertion into the host. Preferred sizes include from about 32 gauge or less to about 18 gauge or more, more preferably from about 28 gauge to about 25 gauge, to provide a comfortable insertion for the host. Referring to the inner diameter of the needle, approximately 0.006 inches to approximately 0.023 inches is preferable, and 0.013 inches is most preferable. The needle carrier 70 is configured to engage with the guide tube carrier 64, while the needle 72 is configured to slidably nest within the guide tube 66, which allows for easy guided insertion (and retraction) of the needle through the contact subassembly 26.

A push rod subassembly 74 is provided that includes a push rod carrier 76 and a push rod 78. The push rod carrier 76 cooperates with other applicator components to ensure that the sensor is properly inserted into the host's skin, namely the push rod carrier 76 carries the push rod 78 between its extended and retracted positions. In this embodiment, the push rod 78 is configured to slidably nest within the needle 72, which allows for the sensor 32 to be pushed (released) from the needle 72 upon retraction of the needle, which is described in more detail with reference to FIGS. 7A through 7D. In some embodiments, a slight bend or serpentine shape is designed into or allowed in the sensor in order to maintain the sensor within the needle by interference. While not wishing to be bound by theory, it is believed that a slight friction fit of the sensor within the needle minimizes motion of the sensor during withdrawal of the needle and maintains the sensor within the needle prior to withdrawal of the needle.

A plunger subassembly 22 is provided that includes a plunger 80 and plunger cap 82. The plunger subassembly 22 cooperates with other applicators components to ensure proper insertion and subsequent retraction of the applicator components. In this embodiment, the plunger 80 is configured to engage with the push rod to ensure the sensor remains extended (namely, in the host) during retraction, such as is described in more detail with reference to FIG. 7C.

Sensor Insertion

Figure 7A:
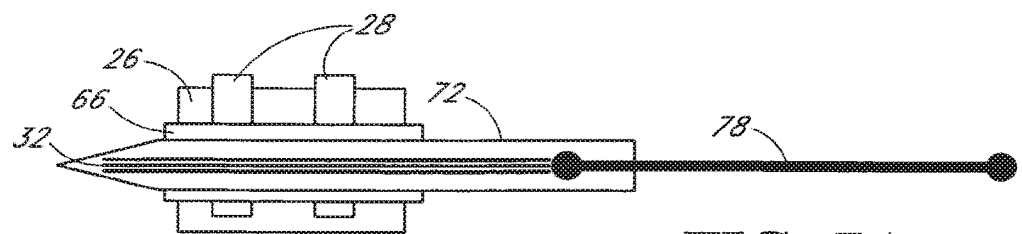
FIGS. 7A to 7D are schematic side cross-sectional views that illustrate applicator components and their cooperating relationships.
Figure 7B:
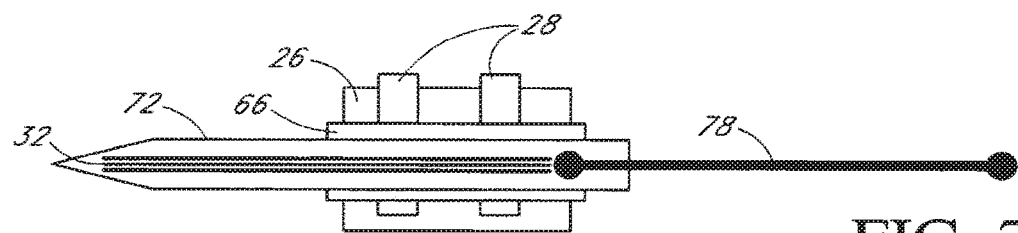
Figure 7C:
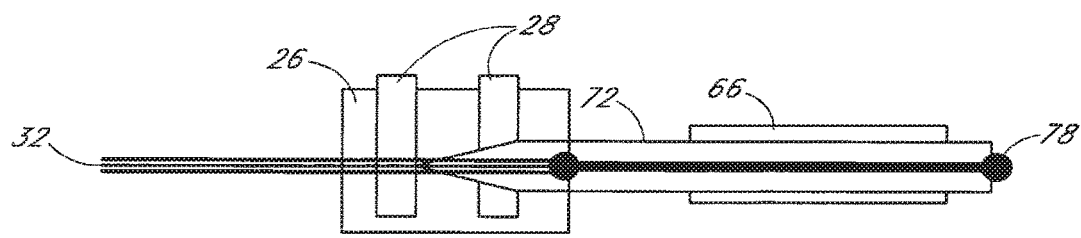
Figure 7D:
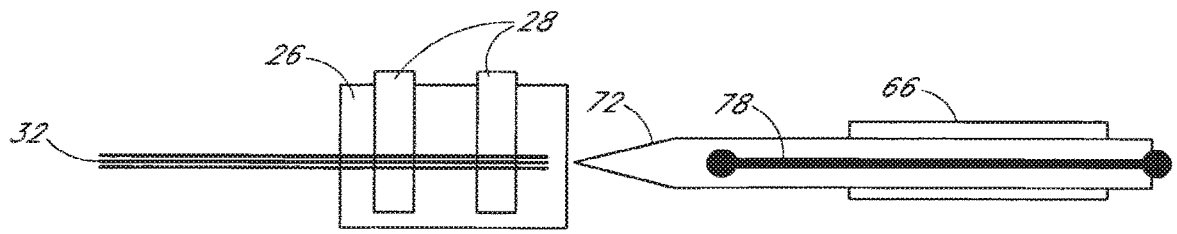

FIGS. 7A through 7D are schematic side cross-sectional views that illustrate the applicator components and their cooperating relationships at various stages of sensor insertion. FIG. 7A illustrates the needle and sensor loaded prior to sensor insertion. FIG. 7B illustrates the needle and sensor after sensor insertion. FIG. 7C illustrates the sensor and needle during needle retraction. FIG. 7D illustrates the sensor remaining within the contact subassembly after needle retraction. Although the embodiments described herein suggest manual insertion and/or retraction of the various components, automation of one or more of the stages can also be employed. For example, spring-loaded mechanisms that can be triggered to automatically insert and/or retract the sensor, needle, or other cooperative applicator components can be implemented.

Referring to FIG. 7A, the sensor 32 is shown disposed within the needle 72, which is disposed within the guide tube 66. In this embodiment, the guide tube 66 is provided to maintain an opening within the contact subassembly 26 and/or contacts 28 to provide minimal friction between the needle 72 and the contact subassembly 26 and/or contacts 28 during insertion and retraction of the needle 72. However, the guide tube is an optional component, which can be advantageous in some embodiments wherein the contact subassembly 26 and/or the contacts 28 are formed from an elastomer or other material with a relatively high friction coefficient, and which can be omitted in other embodiments wherein the contact subassembly 26 and or the contacts 28 are formed from a material with a relatively low friction coefficient (for example, hard plastic or metal). A guide tube, or the like, can be preferred in embodiments wherein the contact subassembly 26 and/or the contacts 28 are formed from a material designed to frictionally hold the sensor 32 (see FIG. 7D), for example, by the relaxing characteristics of an elastomer, or the like. In these embodiments, the guide tube is provided to ease insertion of the needle through the contacts, while allowing for a frictional hold of the contacts on the sensor 32 upon subsequent needle retraction. Stabilization of the sensor in or on the contacts 28 is described in more detail with reference to FIG. 7D and following. Although FIG. 7A illustrates the needle and sensor inserted into the contacts subassembly as the initial loaded configuration, alternative embodiments contemplate a step of loading the needle through the guide tube 66 and/or contacts 28 prior to sensor insertion.

Referring to FIG. 7B, the sensor 32 and needle 72 are shown in an extended position. In this stage, the pushrod 78 has been forced to a forward position, for example by pushing on the plunger shown in FIG. 6, or the like. The plunger 22 (FIG. 6) is designed to cooperate with other of the applicator components to ensure that sensor 32 and the needle 72 extend together to a forward position (as shown); namely, the push rod 78 is designed to cooperate with other of the applicator components to ensure that the sensor 32 maintains the forward position simultaneously within the needle 72.

Referring to FIG. 7C, the needle 72 is shown during the retraction process. In this stage, the push rod 78 is held in its extended (forward) position in order to maintain the sensor 32 in its extended (forward) position until the needle 72 has substantially fully retracted from the contacts 28. Simultaneously, the cooperating applicator components retract the needle 72 and guide tube 66 backward by a pulling motion (manual or automated) thereon. In preferred embodiments, the guide tube carrier 64 (FIG. 6) engages with cooperating applicator components such that a backward (retraction) motion applied to the guide tube carrier retracts the needle 72 and guide tube 66, without (initially) retracting the push rod 78. In an alternative embodiment, the push rod 78 can be omitted and the sensor 32 held it its forward position by a cam, elastomer, or the like, which is in contact with a portion of the sensor while the needle moves over another portion of the sensor. One or more slots can be cut in the needle to maintain contact with the sensor during needle retraction.

Referring to FIG. 7D, the needle 72, guide tube 66, and push rod 78 are all retracted from contact subassembly 26, leaving the sensor 32 disposed therein. The cooperating applicator components are designed such that when the needle 72 has substantially cleared from the contacts 28 and/or contact subassembly 26, the push rod 78 is retracted along with the needle 72 and guide tube 66. The applicator 12 can then be released (manually or automatically) from the contacts 28, such as is described in more detail elsewhere herein, for example with reference to FIGS. 8D and 9A.

The preferred embodiments are generally designed with elastomeric contacts to ensure a retention force that retains the sensor 32 within the mounting unit 14 and to ensure stable electrical connection of the sensor 32 and its associated contacts 28. Although the illustrated embodiments and associated text describe the sensor 32 extending through the contacts 28 to form a friction fit therein, a variety of alternatives are contemplated. In one alternative embodiment, the sensor is configured to be disposed adjacent to the contacts (rather than between the contacts). The contacts can be constructed in a variety of known configurations, for example, metallic contacts, cantilevered fingers, pogo pins, or the like, which are configured to press against the sensor after needle retraction.

It is generally preferred that a contact 28 is formed from a material with a durometer hardness of from about 5 to about 80 Shore A, more preferably from about 10 to about 50 Shore A, and even more preferably from about 20 to about 50 Shore A. In one implementation of a transcutaneous analyte sensor as described with reference to the preferred embodiments, the contact 28 is formed from a material with a durometer hardness of about 20 Shore A to maximize conformance (e.g., compression) of the contact around the sensor and/or within the sealing member. In another implementation of a transcutaneous analyte sensor as described with reference to the preferred embodiments, the contact 28 is formed from a material with a durometer hardness of about 50 Shore A to increase the strength of the contact 28 (e.g., increase resistance to compression). While a few examples have been provided above, one skilled in the art will appreciate that higher or lower durometer hardness sealing materials can also be advantageously employed.

In some embodiments, the durometer hardness of the elastomeric contacts 28 is higher than the durometer hardness of the sealing member 36. In one example, the durometer hardness of the contacts is about 50 Shore A and the durometer hardness of the sealing member is about 20 Shore A; however, a variety of durometer hardness materials within the preferred range (typically, from about 5 Shore A to about 80 Shore A) can be chosen. In these embodiments, the higher durometer hardness contacts generally provide greater stability while the lower durometer hardness sealing member generally provides superior compression and/or seal around the contacts.

In some embodiments, the durometer hardness of the sealing member 36 is higher than the durometer hardness of the elastomeric contacts 28. In one example, the durometer hardness of the sealing member is about 50 Shore A and the durometer hardness of the contacts is about 20 Shore A, however a variety of durometer hardness materials within the preferred range (typically, from about 5 Shore A to about 80 Shore A) can be chosen. In these embodiments, the higher durometer hardness sealing member provides greater stability while the lower durometer hardness contacts provide superior compression and/or seal.

The illustrated embodiments are designed with coaxial contacts 28; namely, the contacts 28 are configured to contact the working and reference electrodes 44, 46 axially along the proximal portion 40 of the sensor 32 (see FIG. 5A). As shown in FIG. 5A, the working electrode 44 extends farther than the reference electrode 46, which allows coaxial connection of the electrodes 44, 46 with the contacts 28 at locations spaced along the proximal of the sensor (see also FIGS. 9B and 10B). Although the illustrated embodiments employ a coaxial design, other designs are contemplated within the scope of the preferred embodiments. For example, the reference electrode can be positioned substantially adjacent to (but spaced apart from) the working electrode at the proximal portion of the sensor. In this way, the contacts 28 can be designed side-by-side rather than co-axially along the axis of the sensor.

Figure 8A:
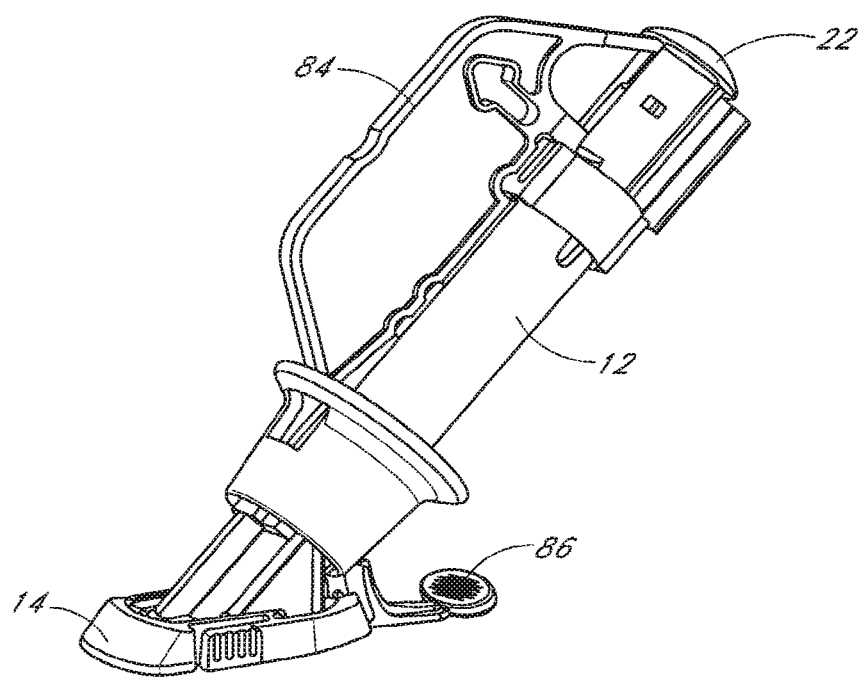
FIG. 8A is a perspective view of an applicator and mounting unit in one embodiment including a safety latch mechanism.

FIG. 8A is a perspective view of an applicator and mounting unit in one embodiment including a safety latch mechanism 84. The safety latch mechanism 84 is configured to lock the plunger subassembly 22 in a stationary position such that it cannot be accidentally pushed prior to release of the safety latch mechanism. In this embodiment, the sensor system 10 is preferably packaged (e.g., shipped) in this locked configuration, wherein the safety latch mechanism 84 holds the plunger subassembly 22 in its extended position, such that the sensor 32 cannot be prematurely inserted (e.g., accidentally released). The safety latch mechanism 84 is configured such that a pulling force shown in the direction of the arrow (see FIG. 8A) releases the lock of the safety latch mechanism on the plunger subassembly, thereby allowing sensor insertion. Although one safety latch mechanism that locks the plunger subassembly is illustrated and described herein, a variety of safety latch mechanism configurations that lock the sensor to prevent it from prematurely releasing (i.e., that lock the sensor prior to release of the safety latch mechanism) are contemplated, as can be appreciated by one skilled in the art, and fall within the scope of the preferred embodiments.

FIG. 8A additionally illustrates a force-locking mechanism 86 included in certain alternative embodiments of the sensor system, wherein the force-locking mechanism 86 is configured to ensure a proper mate between the electronics unit 16 and the mounting unit 14 (see FIG. 12A, for example). In embodiments wherein a seal is formed between the mounting unit and the electronics unit, as described in more detail elsewhere herein, an appropriate force may be required to ensure a seal has sufficiently formed therebetween; in some circumstances, it can be advantageous to ensure the electronics unit has been properly mated (e.g., snap-fit or sealingly mated) to the mounting unit. Accordingly, upon release of the applicator 12 from the mounting unit 14 (after sensor insertion), and after insertion of the electronics unit 16 into the mounting unit 14, the force-locking mechanism 86 allows the user to ensure a proper mate and/or seal therebetween. In practice, a user pivots (e.g., lifts or twists) the force-locking mechanism such that it provides force on the electronics unit 16 by pulling up on the circular tab illustrated in FIG. 8A; the force-locking mechanism is preferably released thereafter. Although one system and one method for providing a secure and/or sealing fit between the electronics unit and the mounting unit are illustrated, various other force-locking mechanisms can be employed that utilize a variety of systems and methods for providing a secure and/or sealing fit between the electronics unit and the mounting unit (housing).

Figure 8B:
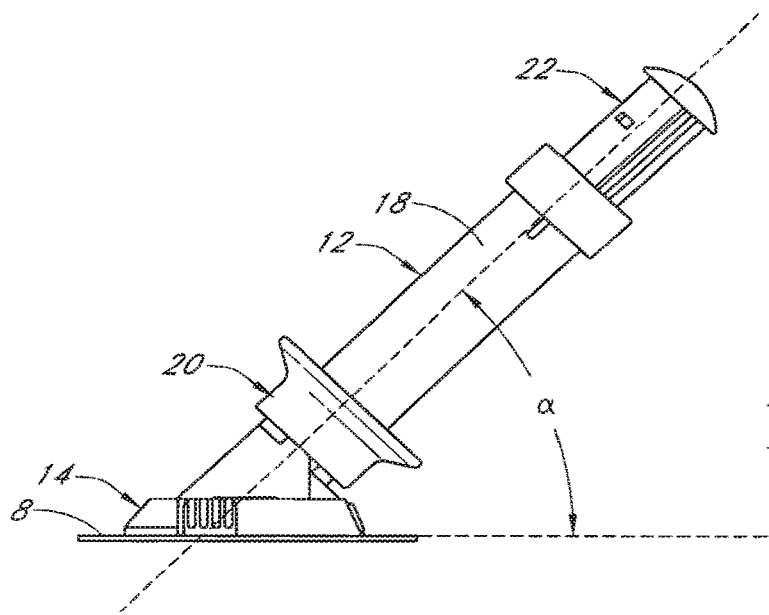
FIG. 8B is a side view of an applicator matingly engaged to a mounting unit in one embodiment, prior to sensor insertion.
Figure 8C:
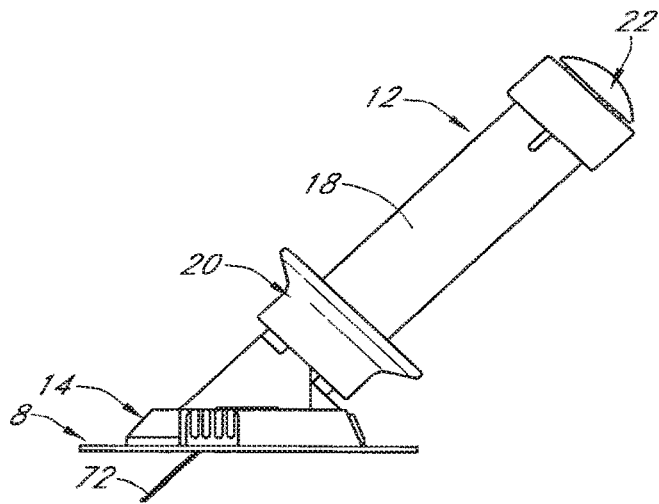
FIG. 8C is a side view of a mounting unit and applicator depicted in the embodiment of FIG. 8B, after the plunger subassembly has been pushed, extending the needle and sensor from the mounting unit.
Figure 8D:
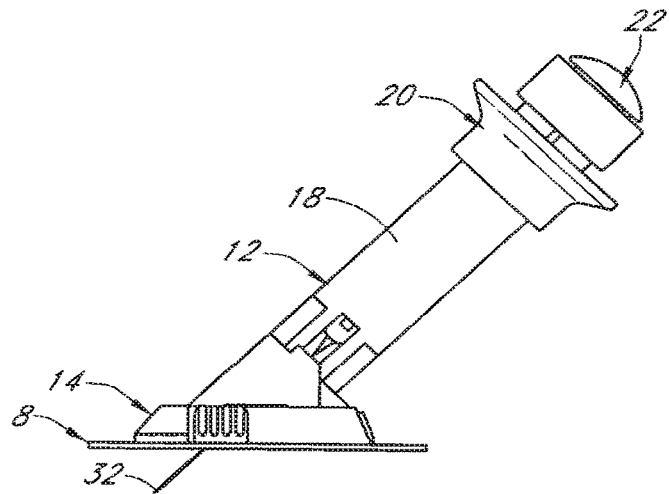
FIG. 8D is a side view of a mounting unit and applicator depicted in the embodiment of FIG. 8B, after the guide tube subassembly has been retracted, retracting the needle back into the applicator.

FIGS. 8B to 8D are side views of an applicator and mounting unit in one embodiment, showing various stages of sensor insertion. FIG. 8B is a side view of the applicator matingly engaged to the mounting unit prior to sensor insertion. FIG. 8C is a side view of the mounting unit and applicator after the plunger subassembly has been pushed, extending the needle and sensor from the mounting unit (namely, through the host's skin). FIG. 8D is a side view of the mounting unit and applicator after the guide tube subassembly has been retracted, retracting the needle back into the applicator. Although the drawings and associated text illustrate and describe embodiments wherein the applicator is designed for manual insertion and/or retraction, automated insertion and/or retraction of the sensor/needle, for example, using spring-loaded components, can alternatively be employed.

The preferred embodiments advantageously provide a system and method for easy insertion of the sensor and subsequent retraction of the needle in a single push-pull motion. Because of the mechanical latching system of the applicator, the user provides a continuous force on the plunger cap 82 and guide tube carrier 64 that inserts and retracts the needle in a continuous motion. When a user grips the applicator, his or her fingers grasp the guide tube carrier 64 while his or her thumb (or another finger) is positioned on the plunger cap 82. The user squeezes his or her fingers and thumb together continuously, which causes the needle to insert (as the plunger slides forward) and subsequently retract (as the guide tube carrier slides backward) due to the system of latches located within the applicator (FIGS. 6 to 8) without any necessary change of grip or force, leaving the sensor implanted in the host. In some embodiments, a continuous torque, when the applicator components are configured to rotatingly engage one another, can replace the continuous force. Some prior art sensors, in contrast to the sensors of the preferred embodiments, suffer from complex, multi-step, or multi-component insertion and retraction steps to insert and remove the needle from the sensor system.

FIG. 8B shows the mounting unit and applicator in the ready position. The sensor system can be shipped in this configuration, or the user can be instructed to mate the applicator 12 with the mounting unit 14 prior to sensor insertion. The insertion angle α is preferably fixed by the mating engagement of the applicator 12. In the illustrated embodiment, the insertion angle α is fixed in the applicator 12 by the angle of the applicator body base 60 with the shaft of the applicator body 18. However, a variety of systems and methods of ensuring proper placement can be implemented. Proper placement ensures that at least a portion of the sensor 32 extends below the dermis of the host upon insertion. In alternative embodiments, the sensor system 10 is designed with a variety of adjustable insertion angles. A variety of insertion angles can be advantageous to accommodate a variety of insertion locations and/or individual dermis configurations (for example, thickness of the dermis). In preferred embodiments, the insertion angle α is from about 0 to about 90 degrees, more preferably from about 30 to about 60 degrees, and even more preferably about 45 degrees.

In practice, the mounting unit is placed at an appropriate location on the host's skin, for example, the skin of the arm, thigh, or abdomen. Thus, removing the backing layer 9 from the adhesive pad 8 and pressing the base portion of the mounting unit on the skin adheres the mounting unit to the host's skin.

FIG. 8C shows the mounting unit and applicator after the needle 72 has been extended from the mounting unit 14 (namely, inserted into the host) by pushing the push rod subassembly 22 into the applicator 12. In this position, the sensor 32 is disposed within the needle 72 (namely, in position within the host), and held by the cooperating applicator components. In alternative embodiments, the mounting unit and/or applicator can be configured with the needle/sensor initially extended. In this way, the mechanical design can be simplified and the plunger-assisted insertion step can be eliminated or modified. The needle can be simply inserted by a manual force to puncture the host's skin, and only one (pulling) step is required on the applicator, which removes the needle from the host's skin.

FIG. 8D shows the mounting unit and applicator after the needle 72 has been retracted into the applicator 12, exposing the sensor 32 to the host's tissue. During needle retraction, the push rod subassembly maintains the sensor in its extended position (namely, within the host). In preferred embodiments, retraction of the needle irreversibly locks the needle within the applicator so that it cannot be accidentally and/or intentionally released, reinserted, or reused. The applicator is preferably configured as a disposable device to reduce or eliminate a possibility of exposure of the needle after insertion into the host. However a reusable or reloadable applicator is also contemplated in some alternative embodiments. After needle retraction, the applicator 12 can be released from the mounting unit, for example, by pressing the release latch(es) 30, and the applicator disposed of appropriately. In alternative embodiments, other mating and release configurations can be implemented between the mounting unit and the applicator, or the applicator can automatically release from the mounting unit after sensor insertion and subsequent needle retraction. In one alternative embodiment, a retention hold (e.g., ball and detent configuration) holds and releases the electronics unit (or applicator).

In one alternative embodiment, the mounting unit is configured to releasably mate with the applicator and electronics unit in a manner such that when the applicator is releasably mated to the mounting unit (e.g., after sensor insertion), the electronics unit is configured to slide into the mounting unit, thereby triggering release of the applicator and simultaneous mating of the electronics unit to the mounting unit. Cooperating mechanical components, for example, sliding ball and detent type configurations, can be used to accomplish the simultaneous mating of electronics unit and release of the applicator.

Figure 8E:
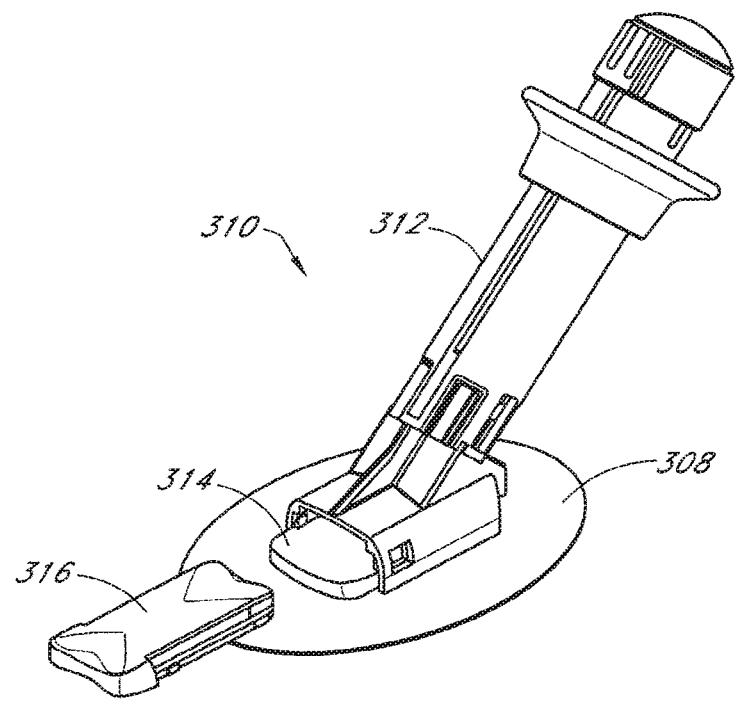
FIG. 8E is a perspective view of an applicator, in an alternative embodiment, matingly engaged to the mounting unit after to sensor insertion.
Figure 8F:
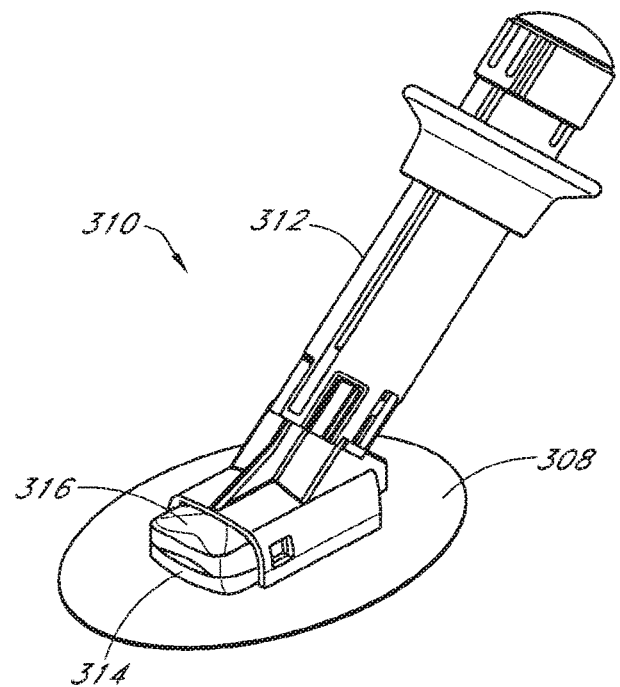
FIG. 8F is a perspective view of the mounting unit and applicator, as depicted in the alternative embodiment of FIG. 8E, matingly engaged while the electronics unit is slidingly inserted into the mounting unit.
Figure 8G:
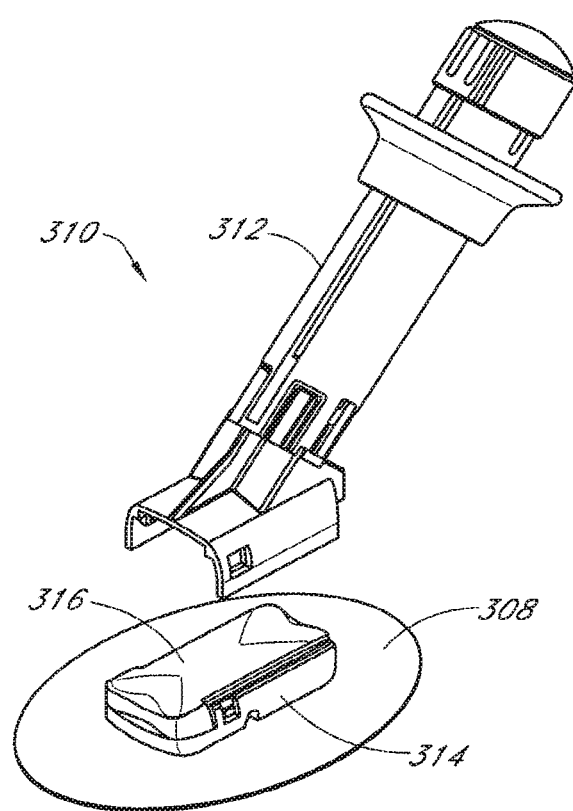
FIG. 8G is a perspective view of the electronics unit, as depicted in the alternative embodiment of FIG. 8E, matingly engaged to the mounting unit after the applicator has been released.

FIGS. 8E to 8G are perspective views of a sensor system 310 of an alternative embodiment, including an applicator 312, electronics unit 316, and mounting unit 314, showing various stages of applicator release and/or electronic unit mating. FIG. 8E is a perspective view of the applicator matingly engaged to the mounting unit after sensor insertion. FIG. 8F is a perspective view of the mounting unit and applicator matingly engaged while the electronics unit is slidingly inserted into the mounting unit. FIG. 8G is a perspective view of the electronics unit matingly engaged with the mounting unit after the applicator has been released.

In general, the sensor system 310 comprises a sensor adapted for transcutaneous insertion into a host's skin; a housing 314 adapted for placement adjacent to the host's skin; an electronics unit 316 releasably attachable to the housing; and an applicator 312 configured to insert the sensor through the housing 314 and into the skin of the host, wherein the applicator 312 is adapted to releasably mate with the housing 314, and wherein the system 310 is configured to release the applicator 312 from the housing when the electronics unit 316 is attached to the housing 314.

FIG. 8E shows the sensor system 310 after the sensor has been inserted and prior to release of the applicator 312. In this embodiment, the electronics unit 316 is designed to slide into the mounting unit 314. Preferably, the electronics unit 316 is configured and arranged to slide into the mounting unit 314 in only one orientation. In the illustrated embodiment, the insertion end is slightly tapered and dovetailed in order to guide insertion of the electronics unit 316 into the housing 314; however other self-alignment configurations are possible. In this way, the electronics unit 316 self-aligns and orients the electronics unit 316 in the housing, ensuring a proper fit and a secure electronic connection with the sensor.

FIG. 8F shows the sensor system 310 after the electronics unit 316 has been inserted therein. Preferably, the electronic unit 316 slide-fits into the mounting unit. In some embodiments, the sensor system 310 can be designed to allow the electronics unit 316 to be attached to the mounting unit 314 (i.e., operably connected to the sensor) before the sensor system 310 is affixed to the host. Advantageously, this design provides mechanical stability for the sensor during transmitter insertion.

FIG. 8G shows the sensor system 310 upon release of the applicator 312 from the mounting unit 314 and electronics unit 316. In this embodiment, the sensor system 310 is configured such that mating the electronics unit to the mounting unit triggers the release of the applicator 312 from the mounting unit 314.

Thus, the above described sensor system 310, also referred to as the slide-in system, allows for self-alignment of the electronics unit, creates an improved seal around the contacts due to greater holding force, provides mechanical stability for the sensor during insertion of the electronics unit, and causes automatic release of the applicator and simultaneous lock of the electronics unit into the mounting unit.

Although the overall design of the sensor system 10 results in a miniaturized volume as compared to numerous conventional devices, as described in more detail below; the sensor system 310 further enables a reduction in volume, as compared to, for example, the sensor system 10 described above.

Figure 8I:
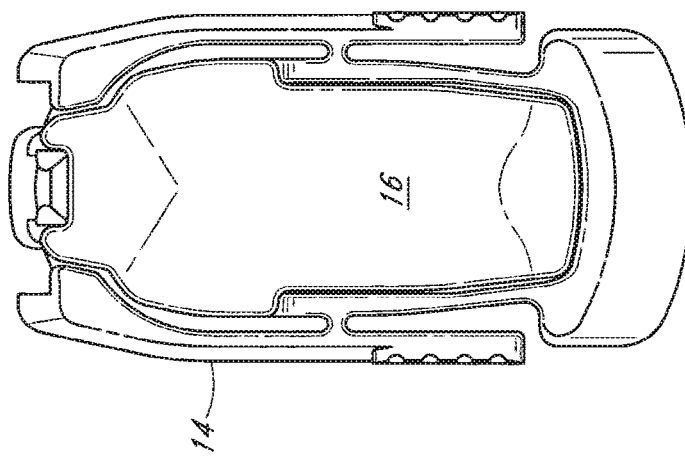
FIGS. 8H and 8I are comparative top views of the sensor system shown in the alternative embodiment illustrated in FIGS. 8E to 8G as compared to the embodiments illustrated in FIGS. 8B to 8D.
Figure 8H:
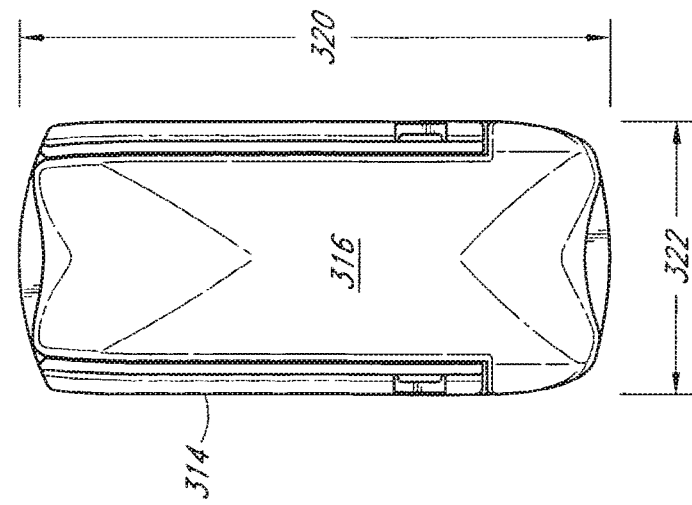

FIGS. 8H and 8I are comparative top views of the sensor system shown in the alternative embodiment illustrated in FIGS. 8E to 8G and compared to the embodiments illustrated elsewhere (see FIGS. 1 to 3 and 10 to 12, for example). Namely, the alternative embodiment described with reference to FIGS. 8E to 8G further enables reduced size (e.g., mass, volume, and the like) of the device as compared to certain other devices. It has been discovered that the size (including volume and/or surface area) of the device can affect the function of the device. For example, motion of the mounting unit/electronics unit caused by external influences (e.g., bumping or other movement on the skin) is translated to the sensor in vivo, causing motion artifact (e.g., an effect on the signal, or the like). Accordingly, by enabling a reduction of size, a more stable signal with overall improved patient comfort can be achieved.

Accordingly, slide-in system 310 described herein, including the systems and methods for inserting the sensor and connecting the electronics unit to the mounting unit, enables the mounting unit 316/electronics unit 314 subassembly to have a volume of less than about 10 $cm^3$, more preferably less than about 8 cm³, and even more preferably less than about 6 cm³, 5 cm³, or 4 cm³ or less. In general, the mounting unit 316/electronics unit 314 subassembly comprises a first major surface and a second major surface opposite the first major surface. The first and second major surfaces together preferably account for at least about 50% of the surface area of the device; the first and second major surfaces each define a surface area, wherein the surface area of each major surface is less than or equal to about 10 cm², preferably less than or equal to about 8 cm², and more preferably less than or equal to about 6.5 cm², 6 cm², 5.5 cm², 5 cm², 4.5 cm², or 4 cm² or less. Typically, the mounting unit 316/electronics unit 314 subassembly has a length 320 of less than about 40 mm by a width 322 of less than about 20 mm and a thickness of less than about 10 mm, and more preferably a length 320 less than or equal to about 35 mm by a width 322 less than or equal to about 18 mm by a thickness of less than or equal to about 9 mm.

In some embodiments, the mounting unit 14/electronics unit 16 assembly has the following dimensional properties: preferably a length of about 6 cm or less, more preferably about 5 cm or less, more preferably still about 4.6 cm or less, even more preferably 4 cm or less, and most preferably about 3 cm or less; preferably a width of about 5 cm or less, more preferably about 4 cm or less, even more preferably 3 cm or less, even more preferably still about 2 cm or less, and most preferably about 1.5 cm or less; and/or preferably a thickness of about 2 cm or less, more preferably about 1.3 cm or less, more preferably still about 1 cm or less, even more preferably still about 0.7 cm or less, and most preferably about 0.5 cm or less. The mounting unit 14/electronics unit 16 assembly preferably has a volume of about 20 cm³ or less, more preferably about 10 cm³ or less, more preferably still about 5 cm³ or less, and most preferably about 3 cm³ or less; and preferably weighs 12 g or less, more preferably about 9 g or less, and most preferably about 6 g or less, although in some embodiments the electronics unit may weigh more than about 12 g, e.g., up to about 25 g, 45 g, or 90 g.

In some embodiments, the sensor 32 exits the base of the mounting unit 14 at a location distant from an edge of the base. In some embodiments, the sensor 32 exits the base of the mounting unit 14 at a location substantially closer to the center than the edges thereof. While not wishing to be bound by theory, it is believed that by providing an exit port for the sensor 32 located away from the edges, the sensor 32 can be protected from motion between the body and the mounting unit, snagging of the sensor by an external source, and/or environmental contaminants (e.g., microorganisms) that can migrate under the edges of the mounting unit. In some embodiments, the sensor exits the mounting unit away from an outer edge of the device. FIG. 23 shows transcutaneous glucose sensor data and corresponding blood glucose values obtained over approximately seven days in a human, wherein the transcutaneous glucose sensor data was configured with an exit port situated at a location substantially closer to the center than the edges of the base.

In some alternative embodiments, however, the sensor exits the mounting unit 14 at an edge or near an edge of the device. In some embodiments, the mounting unit is configured such that the exit port (location) of the sensor is adjustable; thus, in embodiments wherein the depth of the sensor insertion is adjustable, six-degrees of freedom can thereby be provided.

Extensible Adhesive Pad

In certain embodiments, an adhesive pad is used with the sensor system. A variety of design parameters are desirable when choosing an adhesive pad for the mounting unit. For example: 1) the adhesive pad can be strong enough to maintain full contact at all times and during all movements (devices that release even slightly from the skin have a greater risk of contamination and infection), 2) the adhesive pad can be waterproof or water permeable such that the host can wear the device even while heavily perspiring, showering, or even swimming in some cases, 3) the adhesive pad can be flexible enough to withstand linear and rotational forces due to host movements, 4) the adhesive pad can be comfortable for the host, 5) the adhesive pad can be easily releasable to minimize host pain, 6) and/or the adhesive pad can be easily releasable so as to protect the sensor during release. Unfortunately, these design parameters are difficult to simultaneously satisfy using known adhesive pads, for example, strong medical adhesive pads are available but are usually non-precise (for example, requiring significant "ripping" force during release) and can be painful during release due to the strength of their adhesion.

Figure 9A:
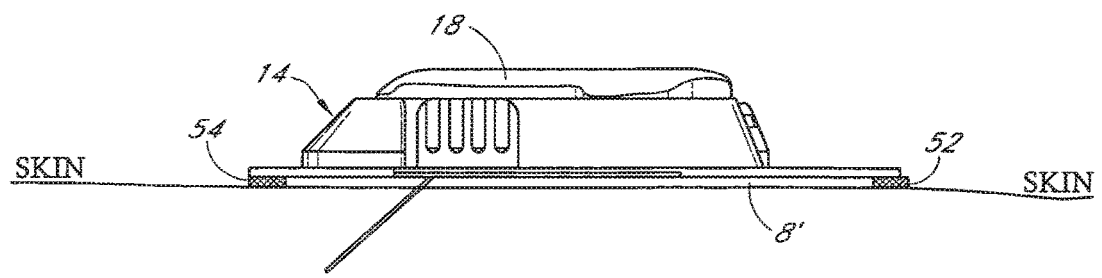
FIGS. 9A to 9C are side views of an applicator and mounting unit, showing stages of sensor insertion.

Therefore, the preferred embodiments provide an adhesive pad 8' for mounting the mounting unit onto the host, including a sufficiently strong medical adhesive pad that satisfies one or more strength and flexibility requirements described above, and further provides a for easy, precise and pain-free release from the host's skin. FIG. 9A is a side view of the sensor assembly, illustrating the sensor implanted into the host with mounting unit adhered to the host's skin via an adhesive pad in one embodiment. Namely, the adhesive pad 8' is formed from an extensible material that can be removed easily from the host's skin by stretching it lengthwise in a direction substantially parallel to (or up to about 35 degrees from) the plane of the skin. It is believed that this easy, precise, and painless removal is a function of both the high extensibility and easy stretchability of the adhesive pad.

In one embodiment, the extensible adhesive pad includes a polymeric foam layer or is formed from adhesive pad foam. It is believed that the conformability and resiliency of foam aids in conformation to the skin and flexibility during movement of the skin. In another embodiment, a stretchable solid adhesive pad, such as a rubber-based or an acrylate-based solid adhesive pad can be used. In another embodiment, the adhesive pad comprises a film, which can aid in increasing load bearing strength and rupture strength of the adhesive pad.

Figure 9B:
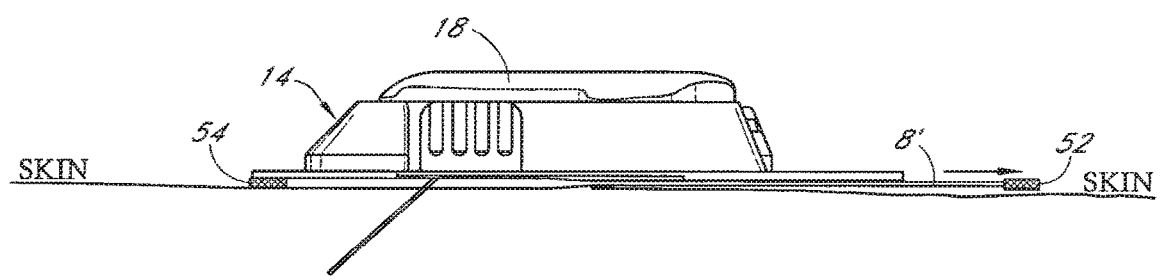
Figure 9C:
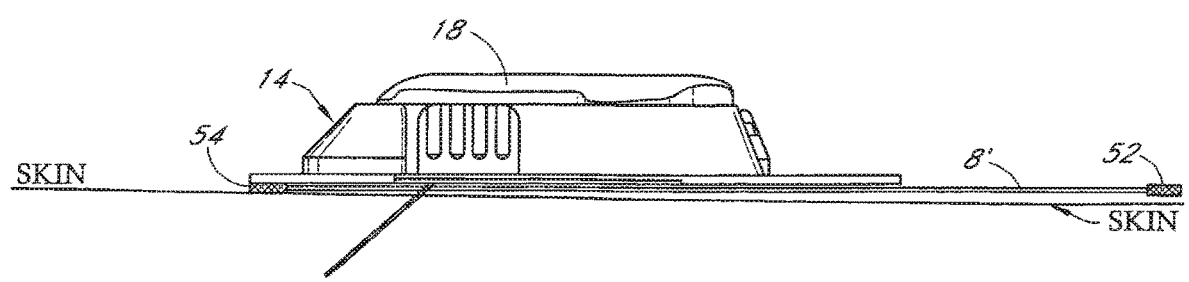

FIGS. 9B to 9C illustrate initial and continued release of the mounting unit from the host's skin by stretching the extensible adhesive pad in one embodiment. To release the device, the backing adhesive pad is pulled in a direction substantially parallel to (or up to about 35 degrees from) the plane of the device. Simultaneously, the extensible adhesive pad stretches and releases from the skin in a relatively easy and painless manner.

In one implementation, the mounting unit is bonded to the host's skin via a single layer of extensible adhesive pad 8', which is illustrated in FIGS. 9A to 9C. The extensible adhesive pad includes a substantially non-extensible pull-tab 52, which can include a light adhesive pad layer that allows it to be held on the mounting unit 14 prior to release. Additionally, the adhesive pad can further include a substantially non-extensible holding tab 54, which remains attached to the mounting unit during release stretching to discourage complete and/or uncontrolled release of the mounting unit from the skin.

In one alternative implementation, the adhesive pad 8' includes two-sides, including the extensible adhesive pad and a backing adhesive pad (not shown). In this embodiment, the backing adhesive pad is bonded to the mounting unit's back surface 25 while the extensible adhesive pad 8' is bonded to the host's skin. Both adhesive pads provide sufficient strength, flexibility, and waterproof or water permeable characteristics appropriate for their respective surface adhesion. In some embodiments, the backing and extensible adhesive pads are particularly designed with an optimized bond for their respective bonding surfaces (namely, the mounting unit and the skin).

In another alternative implementation, the adhesive pad 8' includes a double-sided extensible adhesive pad surrounding a middle layer or backing layer (not shown). The backing layer can comprise a conventional backing film or can be formed from foam to enhance comfort, conformability, and flexibility. Preferably, each side of the double-sided adhesive pad is respectively designed for appropriate bonding surface (namely, the mounting unit and skin). A variety of alternative stretch-release configurations are possible. Controlled release of one or both sides of the adhesive pad can be facilitated by the relative lengths of each adhesive pad side, by incorporation of a non-adhesive pad zone, or the like.

FIGS. 10A and 10B are perspective and side cross-sectional views, respectively, of the mounting unit immediately following sensor insertion and release of the applicator from the mounting unit. In one embodiment, such as illustrated in FIGS. 10A and 10B, the contact subassembly 26 is held in its insertion position, substantially at the insertion angle α of the sensor. Maintaining the contact subassembly 26 at the insertion angle α during insertion enables the sensor 32 to be easily inserted straight through the contact subassembly 26. The contact subassembly 26 further includes a hinge 38 that allows movement of the contact subassembly 26 from an angled to a flat position. The term "hinge," as used herein, is a broad term and is used in its ordinary sense, including, without limitation, a mechanism that allows articulation of two or more parts or portions of a device. The term is broad enough to include a sliding hinge, for example, a ball and detent type hinging mechanism.

Although the illustrated embodiments describe a fixed insertion angle designed into the applicator, alternative embodiments can design the insertion angle into other components of the system. For example, the insertion angle can be designed into the attachment of the applicator with the mounting unit, or the like. In some alternative embodiments, a variety of adjustable insertion angles can be designed into the system to provide for a variety of host dermis configurations.

FIG. 10B illustrates the sensor 32 extending from the mounting unit 14 by a preselected distance, which defines the depth of insertion of the sensor into the host. The dermal and subcutaneous make-up of animals and humans is variable and a fixed depth of insertion may not be appropriate for all implantations. Accordingly, in an alternative embodiment, the distance that the sensor extends from the mounting unit is adjustable to accommodate a variety of host body-types. For example, the applicator 12 can be designed with a variety of adjustable settings, which control the distance that the needle 72 (and therefore the sensor 32) extends upon sensor insertion. One skilled in the art appreciates a variety of means and mechanisms can be employed to accommodate adjustable sensor insertion depths, which are considered within the scope of the preferred embodiments. The preferred insertion depth is from about 0.1 mm or less to about 2 cm or more, preferably from about 0.15, 0.2, 0.25, 0.3, 0.35, 0.4, or 0.45 mm to about 0.5, 0.6, 0.7, 0.8, 0.9, 1, 1.1, 1.2, 1.3, 1.4, 1.5, 1.6, 1.7, 1.8, or 1.9 cm.

FIGS. 11A and 11B are perspective and side cross-sectional views, respectively, of the mounting unit after articulating the contact subassembly to its functional position (which is also referred to as an inserted, implanted, or sensing position). The hinge 38 enables the contact subassembly 26 to tilt from its insertion position (FIG. 10) to its functional position (FIG. 11) by pressing downward on the contact subassembly, for example. Certain embodiments provide this pivotal movement via two separate pieces (the contact subassembly 26 and the mounting unit 14 connected by a hinge, for example, a mechanical or adhesive pad joint or hinge. A variety of pivoting, articulating, and/or hinging mechanisms can be employed with the sensors of preferred embodiments. For example, the hinge can be formed as a part of the contact subassembly 26. The contact subassembly can be formed from a flexible piece of material (such as silicone, urethane rubber, or other flexible or elastomeric material), wherein the material is sufficiently flexible to enable bending or hinging of the contact subassembly from an angle appropriate for insertion (FIGS. 10A and 10B) to a lower functional configuration (FIGS. 11A and 11B).

The relative pivotal movement of the contact subassembly is advantageous, for example, for enabling the design of a low profile device while providing support for an appropriate needle insertion angle. In its insertion position, the sensor system is designed for easy sensor insertion while forming a stable electrical connection with the associated contacts 28. In its functional position, the sensor system maintains a low profile for convenience, comfort, and discreetness during use. Thus, the sensor systems of preferred embodiments are advantageously designed with a hinging configuration to provide an optimum guided insertion angle while maintaining a low profile device during sensor use.

In some embodiments, a shock-absorbing member or feature is incorporated into the design of the sensor and configured to absorb movement of the in vivo and/or ex vivo portion of the sensor. Conventional analyte sensors can suffer from motion-related artifact associated with host movement when the host is using the device. For example, when a transcutaneous analyte sensor is inserted into the host, various movements on the sensor (for example, relative movement between the in vivo portion and the ex vivo portion and/or movement within the host) create stresses on the device and can produce noise in the sensor signal. Accordingly in some embodiments, a shock-absorbing member is located on the sensor/mounting unit in a location that absorbs stresses associated with the above-described movement.

In the preferred embodiments, the sensor 32 bends from a substantially straight to substantially bent configuration upon pivoting of the contact subassembly from the insertion to functional position. The substantially straight sensor configuration during insertion advantageously provides ease of sensor insertion, while the substantial bend in the sensor in its functional position advantageously provides stability on the proximal end of the sensor with flexibility/mobility on the distal end of the sensor. Additionally, motion within the mounting unit (e.g., caused by external forces to the mounting unit, movement of the skin, and the like) does not substantially translate to the in vivo portion of the sensor. Namely, the bend formed within the sensor 32 functions to break column strength, causing flexion that effectively absorbs movements on the sensor during use. Additionally, the sensor can be designed with a length such that when the contact subassembly 26 is pivoted to its functional position (FIG. 10B), the sensor pushes forward and flexes, allowing it to absorb motion between the in vivo and ex vivo portions of the sensor. It is believed that both of the above advantages minimize motion artifact on the sensor signal and/or minimize damage to the sensor caused by movement, both of which (motion artifact and damage) have been observed in conventional transcutaneous sensors.

In some alternative embodiments, the shock-absorbing member can be an expanding and contracting member, such as a spring, accordion, telescoping, or bellows-type device. In general, the shock absorbing member can be located such that relative movement between the sensor, the mounting unit, and the host is absorbed without (or minimally) affecting the connection of the sensor to the mounting unit and/or the sensor stability within the implantation site; for example, the shock-absorbing member can be formed as a part of or connected to the sensor 32.

FIGS. 12A to 12C are perspective and side views of a sensor system including the mounting unit 14 and electronics unit 16 attached thereto. After sensor insertion, the transcutaneous analyte sensor system 10 measures a concentration of an analyte or a substance indicative of the concentration or presence of the analyte as described above. Although the examples are directed to a glucose sensor, the analyte sensor can be a sensor capable of determining the level of any suitable analyte in the body, for example, oxygen, lactase, insulin, hormones, cholesterol, medicaments, viruses, or the like. Once the electronics unit 16 is connected to the mounting unit 14, the sensor 32 is able to measure levels of the analyte in the host.

Detachable connection between the mounting unit 14 and electronics unit 16 provides improved manufacturability, namely, the relatively inexpensive mounting unit 14 can be disposed of when replacing the sensor system after its usable life, while the relatively more expensive electronics unit 16 can be reusable with multiple sensor systems. In certain embodiments, the electronics unit 16 is configured with programming, for example, initialization, calibration reset, failure testing, or the like, each time it is initially inserted into the cavity and/or each time it initially communicates with the sensor 32. However, an integral (non-detachable) electronics unit can be configured as is appreciated by one skilled in the art.

Referring to the mechanical fit between the mounting unit 14 and the electronics unit 16 (and/or applicator 12), a variety of mechanical joints are contemplated, for example, snap fit, interference fit, or slide fit. In the illustrated embodiment of FIGS. 12A to 12C, tabs 120 are provided on the mounting unit 14 and/or electronics unit 16 that enable a secure connection therebetween. The tabs 120 of the illustrated embodiment can improve ease of mechanical connection by providing alignment of the mounting unit and electronics unit and additional rigid support for force and counter force by the user (e.g., fingers) during connection. However, other configurations with or without guiding tabs are contemplated, such as illustrated in FIGS. 10 and 11, for example.

In some circumstances, a drift of the sensor signal can cause inaccuracies in sensor performance and/or require re-calibration of the sensor. Accordingly, it can be advantageous to provide a sealant, whereby moisture (e.g., water and water vapor) cannot substantially penetrate to the sensor and its connection to the electrical contacts. The sealant described herein can be used alone or in combination with the sealing member 36 described in more detail above, to seal the sensor from moisture in the external environment.

Preferably, the sealant fills in holes, crevices, or other void spaces between the mounting unit 14 and electronics unit 16 and/or around the sensor 32 within the mounting unit 32. For example, the sealant can surround the sensor in the portion of the sensor 32 that extends through the contacts 28. Additionally, the sealant can be disposed within the additional void spaces, for example a hole 122 that extends through the sealing member 36.

Preferably, the sealant comprises a water impermeable material or compound, for example, oil, grease, or gel. In one exemplary embodiment, the sealant, which also can be referred to as a lubricant in certain embodiments, comprises petroleum jelly and is used to provide a moisture barrier surrounding the sensor 32. In one experiment, petroleum jelly was liquefied by heating, after which a sensor 32 was immersed into the liquefied petroleum jelly to coat the outer surfaces thereof. The sensor was then assembled into a housing and inserted into a host, during which deployment the sensor was inserted through the electrical contacts 28 and the petroleum jelly conforming therebetween. Sensors incorporating petroleum jelly, such as described above, when compared to sensors without the petroleum jelly moisture barrier exhibited less or no signal drift over time when studied in a humid or submersed environment. While not wishing to be bound by theory, it is believed that incorporation of a moisture barrier surrounding the sensor, especially between the sensor and its associated electrical contacts, reduces or eliminates the effects of humidity on the sensor signal. The viscosity of grease or oil-based moisture barriers allows penetration into and through even small cracks or crevices within the sensor and mounting unit, displacing moisture and thereby increasing the sealing properties thereof. U.S. Pat. Nos. 4,259,540 and 5,285,513 disclose materials suitable for use as a water impermeable material (sealant).

Referring to the electrical fit between the sensor 32 and the electronics unit 16, contacts 28 (through which the sensor extends) are configured to electrically connect with mutually engaging contacts on the electronics unit 16. A variety of configurations are contemplated; however, the mutually engaging contacts operatively connect upon detachable connection of the electronics unit 16 with the mounting unit 14, and are substantially sealed from external moisture by sealing member 36. Even with the sealing member, some circumstances can exist wherein moisture can penetrate into the area surrounding the sensor 32 and or contacts, for example, exposure to a humid or wet environment (e.g., caused by sweat, showering, or other environmental causes). It has been observed that exposure of the sensor to moisture can be a cause of baseline signal drift of the sensor over time. For example in a glucose sensor, the baseline is the component of a glucose sensor signal that is not related to glucose (the amount of signal if no glucose is present), which is ideally constant over time. However, some circumstances my exist wherein the baseline can fluctuate over time, also referred to as drift, which can be caused, for example, by changes in a host's metabolism, cellular migration surrounding the sensor, interfering species, humidity in the environment, and the like.

In some embodiments, the mounting unit is designed to provide ventilation (e.g., a vent hole 124) between the exit-site and the sensor. In certain embodiments, a filter (not shown) is provided in the vent hole 124 that allows the passage of air, while preventing contaminants from entering the vent hole 124 from the external environment. While not wishing to be bound by theory, it is believed that ventilation to the exit-site (or to the sensor 32) can reduce or eliminate trapped moisture or bacteria, which can otherwise increase the growth and/or lifetime of bacteria adjacent to the sensor.

In some alternative embodiments, a sealing material is provided, which seals the needle and/or sensor from contamination of the external environment during and after sensor insertion. For example, one problem encountered in conventional transcutaneous devices is infection of the exit-site of the wound. For example, bacteria or contaminants can migrate from ex vivo, for example, any ex vivo portion of the device or the ex vivo environment, through the exit-site of the needle/sensor, and into the subcutaneous tissue, causing contamination and infection. Bacteria and/or contaminants can originate from handling of the device, exposed skin areas, and/or leakage from the mounting unit (external to) on the host. In many conventional transcutaneous devices, there exists some path of migration for bacteria and contaminants to the exit-site, which can become contaminated during sensor insertion or subsequent handling or use of the device. Furthermore, in some embodiments of a transcutaneous analyte sensor, the insertion-aiding device (for example, needle) is an integral part of the mounting unit; namely, the device stores the insertion device after insertion of the sensor, which is isolated from the exit-site (namely, point-of-entry of the sensor) after insertion.

Accordingly, these alternative embodiments provide a sealing material on the mounting unit, interposed between the housing and the skin, wherein the needle and/or sensor are adapted to extend through, and be sealed by, the sealing material. The sealing material is preferably formed from a flexible material that substantially seals around the needle/sensor. Appropriate flexible materials include malleable materials, elastomers, gels, greases, or the like (e.g., see U.S. Pat. Nos. 4,259,540 and 5,285,513). However, not all embodiments include a sealing material, and in some embodiments a clearance hole or other space surrounding the needle and/or sensor is preferred.

In one embodiment, the base 24 of the mounting unit 14 is formed from a flexible material, for example silicone, which by its elastomeric properties seals the needle and/or sensor at the exit port 126, such as is illustrated in FIGS. 11A and 11B. Thus, sealing material can be formed as a unitary or integral piece with the back surface 25 of the mounting unit 14, or with an adhesive pad 8 on the back surface of the mounting unit, however alternatively can be a separate part secured to the device. In some embodiments, the sealing material can extend through the exit port 126 above or below the plane of the adhesive pad surface, or the exit port 126 can comprise a septum seal such as those used in the medical storage and disposal industries (for example, silica gel sandwiched between upper and lower seal layers, such as layers comprising chemically inert materials such as PTFE). A variety of known septum seals can be implemented into the exit port of the preferred embodiments described herein. Whether the sealing material is integral with or a separate part attached to the mounting unit 14, the exit port 126 is advantageously sealed so as to reduce or eliminate the migration of bacteria or other contaminants to or from the exit-site of the wound and/or within the mounting unit.

During use, a host or caretaker positions the mounting unit at the appropriate location on or near the host's skin and prepares for sensor insertion. During insertion, the needle aids in sensor insertion, after which the needle is retracted into the mounting unit leaving the sensor in the subcutaneous tissue. In this embodiment, the exit-port 126 includes a layer of sealing material, such as a silicone membrane, that encloses the exit-port in a configuration that protects the exit-site from contamination that can migrate from the mounting unit or spacing external to the exit-site. Thus, when the sensor 32 and/or needle 72 extend through, for example, an aperture or a puncture in the sealing material, to provide communication between the mounting unit and subcutaneous space, a seal is formed therebetween. Elastomeric sealing materials can be advantageous in some embodiments because the elasticity provides a conforming seal between the needle/sensor and the mounting unit and/or because the elasticity provides shock-absorbing qualities allowing relative movement between the device and the various layers of the host's tissue, for example.

In some alternative embodiments, the sealing material includes a bioactive agent incorporated therein. Suitable bioactive agents include those which are known to discourage or prevent bacteria and infection, for example, anti-inflammatory, antimicrobials, antibiotics, or the like. It is believed that diffusion or presence of a bioactive agent can aid in prevention or elimination of bacteria adjacent to the exit-site.

In practice, after the sensor 32 has been inserted into the host's tissue, and an electrical connection formed by mating the electronics unit 16 to the mounting unit 14, the sensor measures an analyte concentration continuously or continually, for example, at an interval of from about fractions of a second to about 10 minutes or more.

Figure 13:
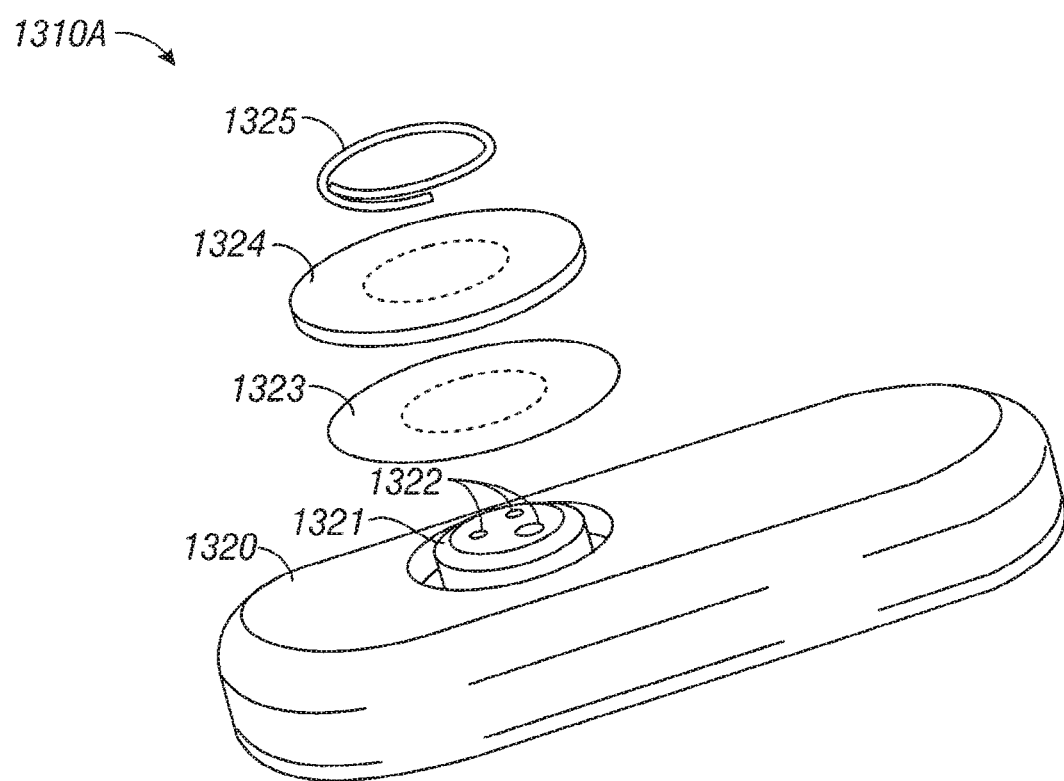
FIG. 13 is an exploded perspective view of one exemplary embodiment of a continuous glucose sensor

FIG. 13 is an exploded perspective view of one exemplary embodiment of a continuous glucose sensor 1310A. In this embodiment, the sensor is preferably wholly implanted into the subcutaneous tissue of a host, such as described in co-pending patent application Ser. No. 10/885,476 filed Jul. 6, 2004 and entitled "SYSTEMS AND METHODS FOR MANUFACTURE OF AN ANALYTE-MEASURING DEVICE INCLUDING A MEMBRANE SYSTEM"; U.S. Publication No. US-2005-0245799-A1; U.S. Publication No. US-2005-0192557-A1; U.S. Publication No. US-2004-0199059-A1; U.S. Publication No. US-2005-0027463-A1; and U.S. Pat. No. 6,001,067. In this exemplary embodiment, a body 1320 and a sensing region 1321 house the electrodes 1322 and sensor electronics (see FIG. 14). The three electrodes 1322 are operably connected to the sensor electronics (see FIG. 14) and are covered by a sensing membrane 1323 and a biointerface membrane 1324, which are attached by a clip 1325.

In one embodiment, the three electrodes 1322 include a platinum working electrode, a platinum counter electrode, and a silver/silver chloride reference electrode. The top ends of the electrodes are in contact with an electrolyte phase (not shown), which is a free-flowing fluid phase disposed between the sensing membrane 1323 and the electrodes 1322. The sensing membrane 1323 includes an enzyme, for example, glucose oxidase, and covers the electrolyte phase. The biointerface membrane 1324 covers the sensing membrane 1323 and serves, at least in part, to protect the sensor 1310A from external forces that can result in environmental stress cracking of the sensing membrane 1323. U.S. Publication No. US-2005-0112169-A1 describes a biointerface membrane that can be used in conjunction with the preferred embodiments.

In one embodiment, the biointerface membrane 1324 generally includes a cell disruptive domain most distal from the electrochemically reactive surfaces and a cell impermeable domain less distal from the electrochemically reactive surfaces than the cell disruptive domain. The cell disruptive domain is preferably designed to support tissue ingrowth, disrupt contractile forces typically found in a foreign body response, encourage vascularity within the membrane, and disrupt the formation of a barrier cell layer. The cell impermeable domain is preferably resistant to cellular attachment, impermeable to cells, and composed of a biostable material.

In one embodiment, the sensing membrane 1323 generally provides one or more of the following functions: 1) protection of the exposed electrode surface from the biological environment, 2) diffusion resistance (limitation) of the analyte, 3) a catalyst for enabling an enzymatic reaction, 4) limitation or blocking of interfering species, and 5) hydrophilicity at the electrochemically reactive surfaces of the sensor interface, such as described in U.S. Publication No. US-2005-0245799-A1. Accordingly, the sensing membrane 1323 preferably includes a plurality of domains or layers, for example, an electrolyte domain, an interference domain, an enzyme domain (for example, glucose oxidase), a resistance domain, and can additionally include an oxygen domain (not shown), and/or a bioprotective domain (not shown), such as described in more detail herein and in U.S. Publication No. US-2005-0245799-A1. However, it is understood that a sensing membrane modified for other devices, for example, by including fewer or additional domains is within the scope of the preferred embodiments.

In some embodiments, the domains of the biointerface and sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. U.S. Publication No. US-2005-0245799-A1 describes biointerface and sensing membrane configurations and materials that can be applied to the preferred embodiments.

In the illustrated embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

In one embodiment, a potentiostat is employed to monitor the electrochemical reaction at the electrochemical cell. The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose value, such as is described herein.

Sensor Electronics

The following description of sensor electronics associated with the electronics unit is applicable to a variety of continuous analyte sensors, such as non-invasive, minimally invasive, and/or invasive (e.g., transcutaneous and wholly implantable) sensors. For example, the sensor electronics and data processing as well as the receiver electronics and data processing described below can be incorporated into the wholly implantable glucose sensor disclosed in U.S. Publication No. US-2005-0245799-A1 and U.S. patent application Ser. No. 10/885,476 filed Jul. 6, 2004 and entitled, "SYSTEMS AND METHODS FOR MANUFACTURE OF AN ANALYTE-MEASURING DEVICE INCLUDING A MEMBRANE SYSTEM."

Figure 14A:
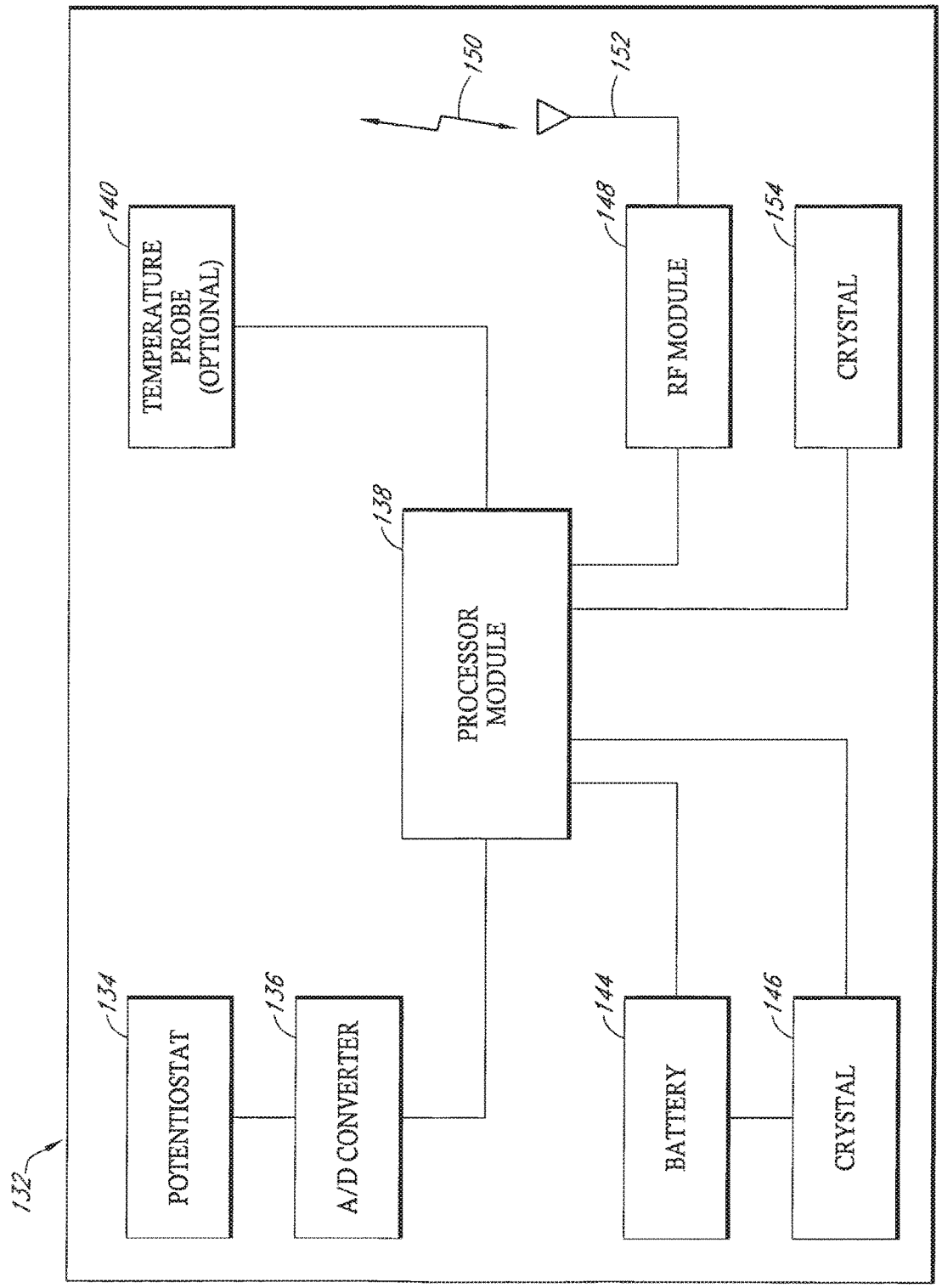
FIG. 14A is a block diagram that illustrates electronics associated with a sensor system.

FIG. 14 is a block diagram that illustrates the electronics 132 associated with the sensor system 10 in one embodiment. In this embodiment, a potentiostat 134 is shown, which is operably connected to an electrode system (such as described above) and provides a voltage to the electrodes, which biases the sensor to enable measurement of an current signal indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device.

An A/D converter 136 digitizes the analog signal into a digital signal, also referred to as "counts" for processing. Accordingly, the resulting raw data stream in counts, also referred to as raw sensor data, is directly related to the current measured by the potentiostat 134.

A processor module 138 includes the central control unit that controls the processing of the sensor electronics 132. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Publication No. US-2005-0043598-A1). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, or the like.

In some embodiments, the processor module comprises a digital filter, for example, an infinite impulse response (IIR) or finite impulse response (FIR) filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a preamble, a unique identifier identifying the electronics unit, the receiver, or both, (e.g., sensor ID code), data (e.g., raw data, filtered data, and/or an integrated value) and/or error detection or correction. Preferably, the data (transmission) packet has a length of from about 8 bits to about 128 bits, preferably about 48 bits; however, larger or smaller packets can be desirable in certain embodiments. The processor module can be configured to transmit any combination of raw and/or filtered data. In one exemplary embodiment, the transmission packet contains a fixed preamble, a unique ID of the electronics unit, a single five-minute average (e.g., integrated) sensor data value, and a cyclic redundancy code (CRC).

In some embodiments, the processor module further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable from about 2 seconds to about 850 minutes, more preferably from about 30 second to about 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.)

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter 136 is configured to continuously measure the current flowing at the working electrode and to convert the current measurement to digital values representative of the current. In one embodiment, the current flow is measured by a charge counting device (e.g., a capacitor). Preferably, a charge counting device provides a value (e.g., digital value) representative of the current flow integrated over time (e.g., integrated value). In some embodiments, the value is integrated over a few seconds, a few minutes, or longer. In one exemplary embodiment, the value is integrated over 5 minutes; however, other integration periods can be chosen. Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

In some embodiments, the electronics unit is programmed with a specific ID, which is programmed (automatically or by the user) into a receiver to establish a secure wireless communication link between the electronics unit and the receiver. Preferably, the transmission packet is Manchester encoded; however, a variety of known encoding techniques can also be employed.

A battery 144 is operably connected to the sensor electronics 132 and provides the power for the sensor. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal 96 is operably connected to the processor 138 and maintains system time for the computer system as a whole, for example for the programmable acquisition time within the processor module.

Optional temperature probe 140 is shown, wherein the temperature probe is located on the electronics assembly or the glucose sensor itself. The temperature probe can be used to measure ambient temperature in the vicinity of the glucose sensor. This temperature measurement can be used to add temperature compensation to the calculated glucose value.

An RF module 148 is operably connected to the processor 138 and transmits the sensor data from the sensor to a receiver within a wireless transmission 150 via antenna 152. In some embodiments, a second quartz crystal 154 provides the time base for the RF carrier frequency used for data transmissions from the RF transceiver. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. In some embodiments, the RF module employs a one-way RF communication link to provide a simplified ultra low power data transmission and receiving scheme. The RF transmission can be OOK or FSK modulated, preferably with a radiated transmission power (EIRP) fixed at a single power level of typically less than about 100 microwatts, preferably less than about 75 microwatts, more preferably less than about 50 microwatts, and most preferably less than about 25 microwatts.

Additionally, in wholly implantable devices, the carrier frequency is adapted for physiological attenuation levels, which is accomplished by tuning the RF module in a simulated in vivo environment to ensure RF functionality after implantation; accordingly, the preferred glucose sensor can sustain sensor function for 3 months, 6 months, 12 months, or 24 months or more.

When a sensor is first implanted into host tissue, the sensor and receiver are initialized. This is referred to as start-up mode, and involves optionally resetting the sensor data and calibrating the sensor 32. In selected embodiments, mating the electronics unit 16 to the mounting unit triggers a start-up mode. In other embodiments, the start-up mode is triggered by the receiver, which is described in more detail with reference to FIG. 21, below.

Preferably, the electronics unit 16 indicates to the receiver (FIGS. 15 and 17) that calibration is to be initialized (or re-initialized). The electronics unit 16 transmits a series of bits within a transmitted data packet wherein a sensor code can be included in the periodic transmission of the device. The status code is used to communicate sensor status to the receiving device. The status code can be inserted into any location in the transmitted data packet, with or without other sensor information. In one embodiment, the status code is designed to be unique or near unique to an individual sensor, which can be accomplished using a value that increments, decrements, or changes in some way after the transmitter detects that a sensor has been removed and/or attached to the transmitter. In an alternative embodiment, the status code can be configured to follow a specific progression, such as a BCD interpretation of a Gray code.

In some embodiments, the sensor electronics 132 are configured to detect a current drop to zero in the working electrode 44 associated with removal of a sensor 32 from the host (or the electronics unit 16 from the mounting unit 14), which can be configured to trigger an increment of the status code. If the incremented value reaches a maximum, it can be designed to roll over to 0. In some embodiments, the sensor electronics are configured to detect a voltage change cycle associated with removal and/or re-insertion of the sensor, which can be sensed in the counter electrode (e.g., of a three-electrode sensor), which can be configured to trigger an increment of the status code.

In some embodiments, the sensor electronics 132 can be configured to send a special value (for example, 0) that indicates that the electronics unit is not attached when removal of the sensor (or electronics unit) is detected. This special value can be used to trigger a variety of events, for example, to halt display of analyte values. Incrementing or decrementing routines can be used to skip this special value.

Information Tag

In certain embodiments, it can be useful to provide readable information in or on the sensor system (e.g., the mounting unit and/or sensor packaging) to identify characteristics about the sensor. Although the following description is mostly drawn to providing sensor information on the mounting unit or the packaging, other parts of the sensor system can house the information tag, for example, the tag can be embedded within the electronics unit. Additionally, when implemented in a wholly implantable sensor (see, e.g., U.S. Publication No. US-2005-0245799-A1), the information tag can be embedded in any portion of the implantable device (e.g., electronics or on a chip within the body of the implantable device).

In general, the information tag includes information about the sensor manufacture, calibration, identification, expiration, intended sensor duration (e.g., insertion time period), archived data (e.g., most recent 1 hour of analyte data), license code/key information, and the like. In one embodiment, the information tag is provided on a single-use portion of the device (e.g., the mounting unit) and the sensor information is related to the single-use device, for example, information such as license code, sensor duration, and expiration information that can be useful to an associated reusable device (e.g., receiver). Preferably, the information tag is readable by a device or person in a manner that permits easy data transfer (e.g., of the license code or intended sensor duration) with minimal user interaction. Preferably, the information tag has an electronic component including a memory for storing the sensor information; however, visual information tags (e.g., barcodes) can also be employed. In some embodiments, the information tag comprises a readable chip, wherein the chip transmits information using one or more of the following technologies: radio frequency, infrared, optical, acoustic, magnetic induction, and the like.

In one embodiment, the information tag includes a serial identification chip (e.g., a serial memory product such as manufactured by Maxim Integrated Products, Inc. of Sunnyvale, Calif.), also referred to as a one-wire interface. In this embodiment, a port is provided on the sensor system (e.g., the receiver) that receives the serial identification chip and reads the information thereon. In practice, a user inserts the serial identification chip into the sensor system (e.g., a port on the receiver), which allows transmission of the sensor information therein. In some embodiments, the information tag is provided in or on the sensor system packaging.

In one alternative embodiment, the information tag includes a Radio Frequency Identification (RFID) chip. RFID is a wireless data collection technology that uses electronic tags for storing data. RFID tags (or chips) are read when they are within the proximity of a transmitted radio signal. Because RFID tags can hold substantial amounts of data, the RFID tag can be used for tracking individual items. There are two types of RFID tags: passive and active. "Passive" tags have no power source but use the electromagnetic waves from a reader (e.g., the receiver) up to approximately 15 feet away to transmit back their contents. "Active" tags use a battery to transmit up to about 1,500 feet.

In some embodiments, an information tag is embedded in or on the on-skin housing (e.g., mounting unit and/or transmitter). Preferably, the receiver is configured to interrogate the information tag to obtain particular information; however, an information tag with two-way communication can also be employed. In one embodiment, the information tag includes a serial number or other identification information for the sensor. In another embodiment, the information tag is configured to initialize the sensor/receiver. In another embodiment, the information tag includes a calibration code that is used by the receiver during calibration of the sensor. In another embodiment, the information tag includes expiration information. In yet another embodiment, the information tag includes a key or license code. In alternative embodiments, the information tag uniquely identifies the sensor 32 and allows the transmitter to adjust the sensor ID code accordingly and/or to transmit the unique identifier to the receiver 158. The information tag can be configured to include various combinations of the above-referenced information, or additional information useful to operation of the sensor.

In some embodiments, the electronics unit 16 is configured to include additional contacts, which are designed to sense a specific resistance, or passive value, in the sensor system while the electronics unit is attached to the mounting unit. Preferably, these additional contacts are configured to detect information about a sensor, for example, whether the sensor is operatively connected to the mounting unit, the sensor's ID, a calibration code, or the like. For example, subsequent to sensing the passive value, the sensor electronics can be configured to change the sensor ID code by either mapping the value to a specific code, or internally detecting that the code is different and adjusting the sensor ID code in a predictable manner. As another example, the passive value can include information on parameters specific to a sensor (such as in vitro sensitivity information as described elsewhere herein).

In some embodiments, the electronics unit 16 includes additional contacts configured to communicate with a chip disposed in the mounting unit 14. In this embodiment, the chip is designed with a unique or near-unique signature that can be detected by the electronics unit 16 and noted as different, and/or transmitted to the receiver 158 as the sensor ID code.

In some situations, it can be desirable to wait an amount of time after insertion of the sensor to allow the sensor to equilibrate in vivo, also referred to as "break-in." Accordingly, the sensor electronics can be configured to aid in decreasing the break-in time of the sensor by applying different voltage settings (for example, starting with a higher voltage setting and then reducing the voltage setting) to speed the equilibration process.

In some situations, the sensor may not properly deploy, connect to, or otherwise operate as intended. Accordingly, the sensor electronics can be configured such that if the current obtained from the working electrode, or the subsequent conversion of the current into digital counts, for example, is outside of an acceptable threshold, then the sensor is marked with an error flag, or the like. The error flag can be transmitted to the receiver to instruct the user to reinsert a new sensor, or to implement some other error correction.

The above-described detection and transmission methods can be advantageously employed to minimize or eliminate human interaction with the sensor, thereby minimizing human error and/or inconvenience. Additionally, the sensors of preferred embodiments do not require that the receiver be in proximity to the transmitter during sensor insertion. Any one or more of the above described methods of detecting and transmitting insertion of a sensor and/or electronics unit can be combined or modified, as is appreciated by one skilled in the art.

On-Skin Device

Figure 14B:
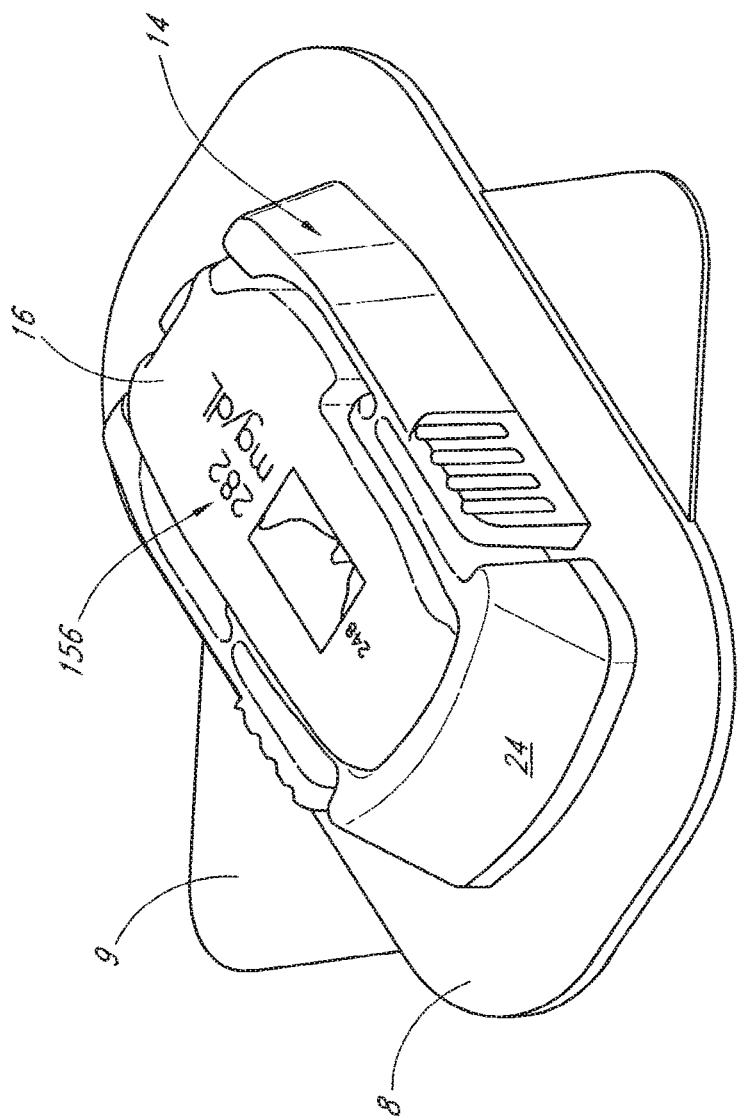
FIG. 14B is a perspective view of an alternative embodiment, wherein the electronics unit and/or mounting unit, hereinafter referred to as the "on-skin device," is configured to communicate sensor information directly to the user (e.g., host).

FIG. 14B is a perspective view of an alternative embodiment, wherein the electronics unit and/or mounting unit, hereinafter referred to as the "on-skin device," is configured to communicate sensor information directly to the user (host). The electronics unit can be detachable from the mounting unit in certain embodiments. In other embodiments, the electronics unit is not detachable from the mounting unit. FIG. 14B shows an embodiment wherein the electronics unit 16 and mounting unit 14 collectively form the on-skin device. The on-skin device further includes a user interface 156, which in the illustrated embodiment includes a readable screen that displays sensor information; however, other user interface configurations can also be employed.

In some embodiments, the user interface 156 of the on-skin device is configured to vibrate or audibly sound in order to attract the attention of the host, e.g., when a glucose level has risen beyond a set threshold. Although in the illustrated embodiment, the user interface of the on-skin device is configured with an LCD screen, other methods of data communication are possible, e.g., computer-generated audible information, tactile signals, or other user interface types. The term "user interface" as used herein is a broad term, and is to be given its ordinary and customary meaning to a person of ordinary skill in the art (and is not to be limited to a special or customized meaning), and refers without limitation to any method of communication to the user. In embodiments wherein the user interface is a visible display, the display can include one or more of: a number representing the analyte value, trend information (e.g., arrows that represent a speed and/or direction of the rising or falling of the analyte levels), a color-metric reading (e.g., green, red, or one or more other colors), a graph that represents historical and/or present analyte information, and the like. A variety of displays and/or interface types can be user selectable in some embodiments.

In one alternative embodiment, the on-skin device is configured to provide a signal, for example, one- two- or three beeps, long- or short-beeps, or vibrations representative of a certain condition, for example, one-beep to indicate a glucose level within the target range, two-beeps to indicate a glucose level in the target range that is rising or falling quickly, and three-beeps to indicate a glucose level that is outside target range. In some embodiments, the signal is responsive to a user's request for information, for example, by pressing a button. In such an embodiment, an "info" button is provided (not shown), which is configured to provide these signals (or other communication) responsive to a user activating (pressing) the button.

In these embodiments, the on-skin device preferably houses the sensor electronics, which provide systems and methods for measuring, processing, and/or displaying of the sensor data. The sensor electronics generally include hardware, firmware, and/or software that enable measurement of levels of the analyte via the sensor and that enable audible, tactile, or visible communication or display of the sensor data. Accordingly, the sensor electronics preferably enable processing of and displaying of sensor data, for example, the sensor electronics include programming for retrospectively and/or prospectively initiating a calibration, converting sensor data, updating the calibration, and/or evaluating the calibration for the analyte sensor, for example, such as is described in more detail herein with reference to the sensor electronics and/or receiver electronics.

The electronics can be affixed to a printed circuit board (PCB), or the like, and can take a variety of forms. For example, the electronics can take the form of an integrated circuit (IC), such as an Application-Specific Integrated Circuit (ASIC), a microcontroller, or a processor, such as described in more detail herein with reference to sensor electronics and/or receiver electronics. In some embodiments, the sensor electronics comprise a digital filter, for example, an IIR or FIR filter, configured to smooth the raw data stream from the A/D converter.

In an embodiment wherein the sensor electronics are at least partially removably attached to the on-skin device, a system can be provided to enable docking of the electronics, and thereby downloading and viewing of the sensor data on a remote device, e.g., a sensor receiver, PDA, computer system, docking station, insulin pump, or the like. In one such embodiment, the on-skin device provides numerical sensor information; however, a user can dock the removable sensor electronics of the on-skin device onto the remote device to view additional information (e.g., graphical sensor information). Alternatively, the on-skin device can be used instead of the receiver to store and process all of the necessary data until a receiver is available for the transfer of data (or enabling a system that does not require a separate receiver). In some alternative embodiments, the on-skin device communicates with the receiver via a cable, radio frequency, optical, inductive coupling, infrared, microwave or other known methods of data transmission. In one such exemplary embodiment, the on-skin device is configured to communicate with the receiver when "requested" by the receiver. For example, when the receiver is held in close proximity (e.g., within 3 meters) of the device, transmission of sensor data can be requested (e.g., using data transmission methods such as inductive coupling, optical, infrared, or the like.)

In some alternative embodiments, a user interface is provided with the on-skin device; however, such a user interface is located in a remote site from the on-skin device (e.g., via wiring). In one such embodiment, the on-skin device is configured to be worn (e.g., adhered) on the skin (e.g., under clothing) of the host and the user interface is configured to be visible to the user (e.g., worn on clothing or a belt loop, or clipped to the host's clothing). In some embodiments, the user interface is a miniature LCD and/or is configured to provide numerical or audible values.

An on-skin device with data communication directly therefrom can provide improved convenience to the patient (e.g., there is no need for the patient to keep track of the receiver and maintain it within a predetermined range of the sensor at all times) and increased ease of use (e.g., fewer parts for the patient to understand, program, and/or carry). Additionally, circumstances exist (e.g., on airplanes, while swimming, etc.) where a patient may not be able to carry a receiver or during which time certain wireless transmissions may not be permitted; however, with an on-skin user-communicating device, the patient will not be without critical sensor data.

Additionally, the on-skin device as described in the preferred embodiments is sufficiently miniature so as to enable adhesion of the device to a discreet insertion location (e.g., under the user's clothing in certain embodiments). Preferably, the on-skin device has a length of less than about 40 mm and a width of less than about 20 mm and a thickness of less than about 10 mm, and more preferably a length less than or equal to about 35 mm and a width less than or equal to about 18 mm and a thickness of less than or equal to about 9 mm. The dimensions associated with the electronics unit/mounting unit subassembly are described in greater detail elsewhere herein.

Receiver

Figure 15:
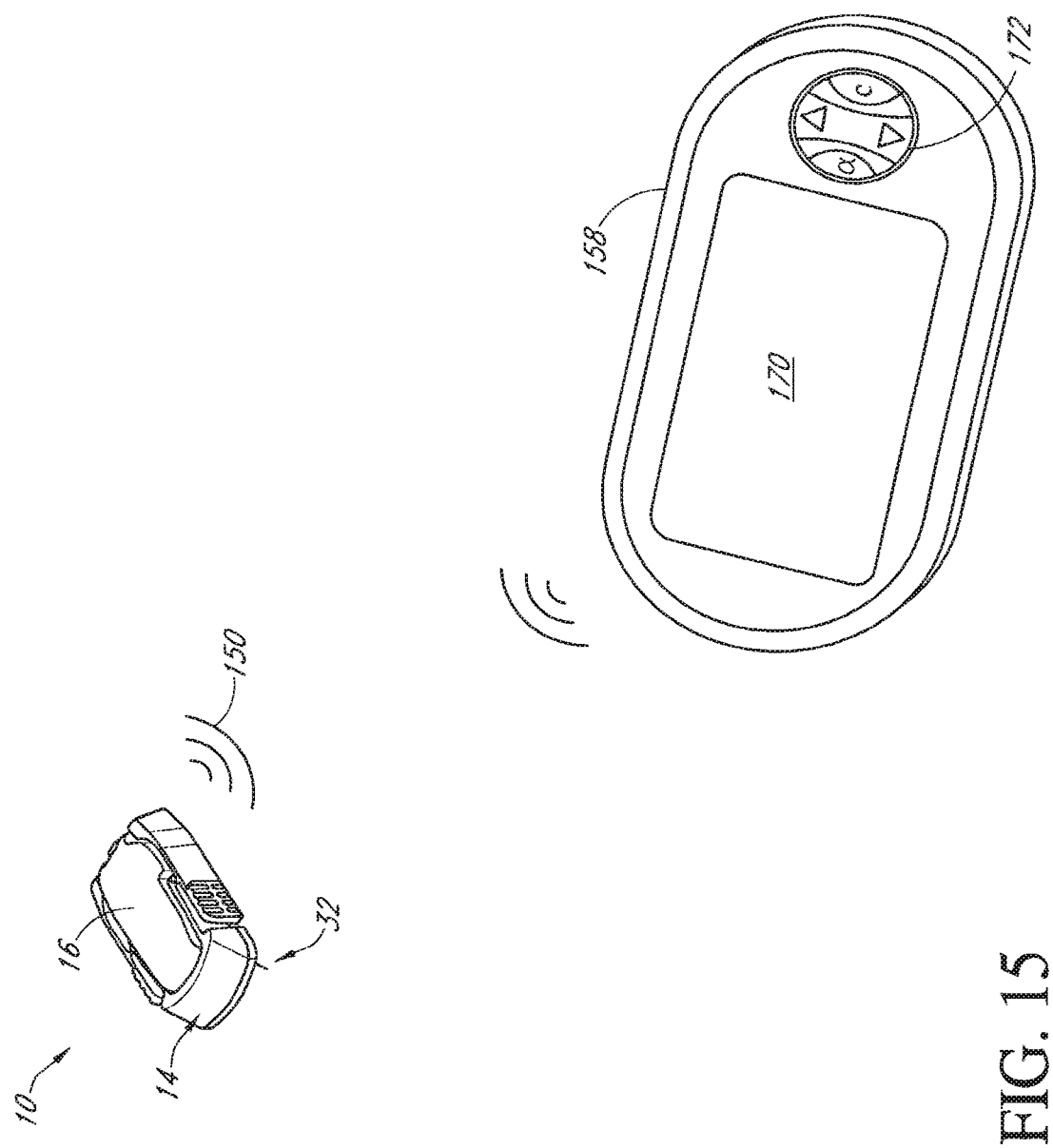
FIG. 15 is a perspective view of a sensor system wirelessly communicating with a receiver.
Figure 16A:
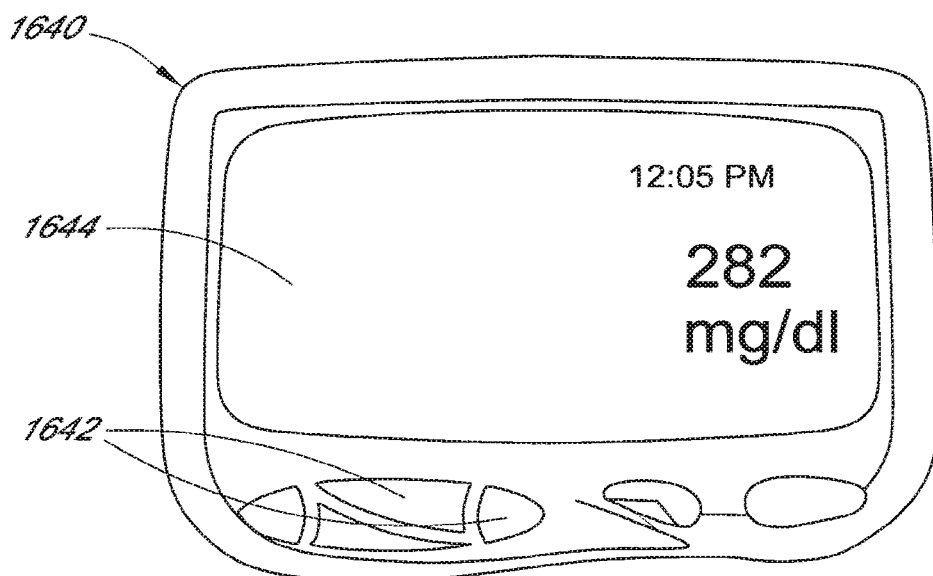
FIG. 16A illustrates a first embodiment wherein the receiver shows a numeric representation of the estimated analyte value on its user interface, which is described in more detail elsewhere herein.
Figure 16B:
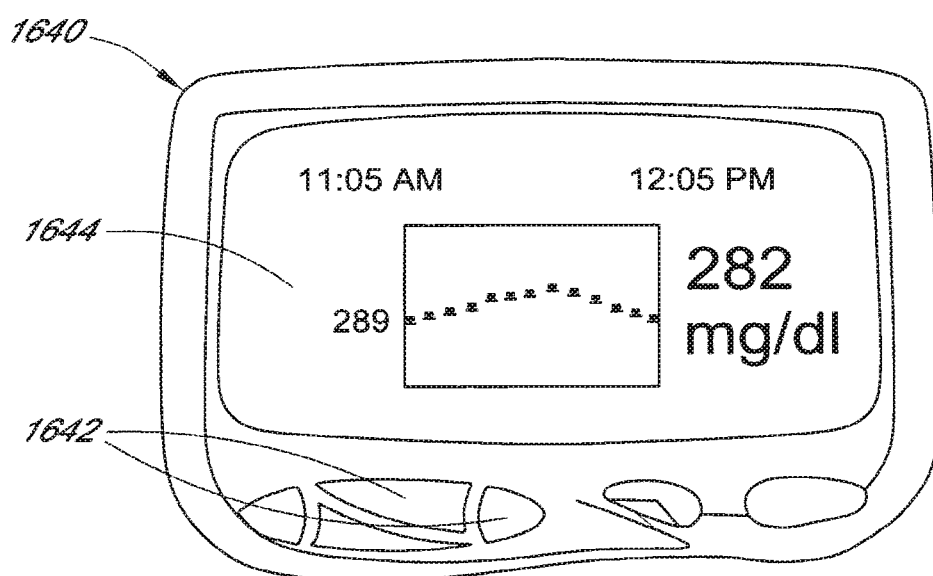
FIG. 16B illustrates a second embodiment wherein the receiver shows an estimated glucose value and one hour of historical trend data on its user interface, which is described in more detail elsewhere herein.
Figure 16C:
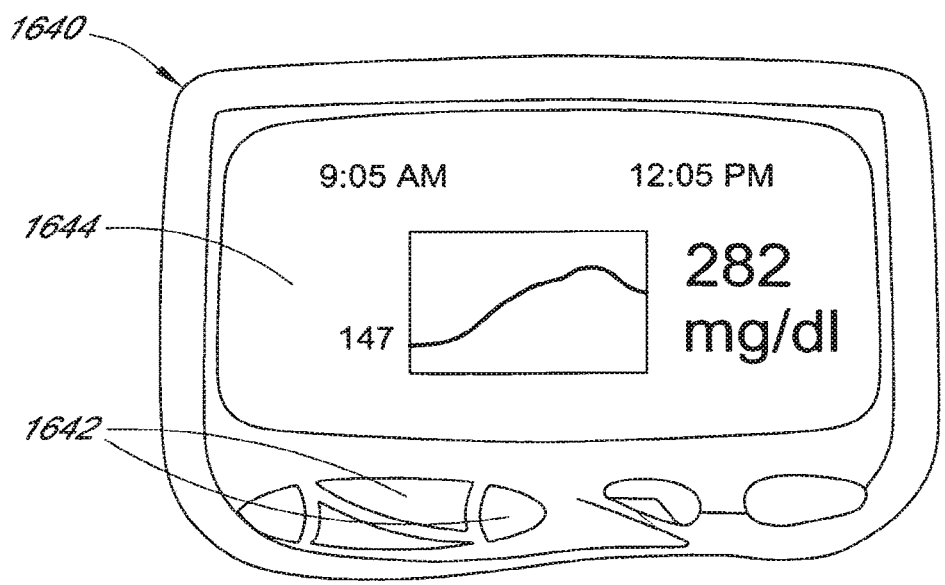
FIG. 16C illustrates a third embodiment wherein the receiver shows an estimated glucose value and three hours of historical trend data on its user interface, which is described in more detail elsewhere herein.
Figure 16D:
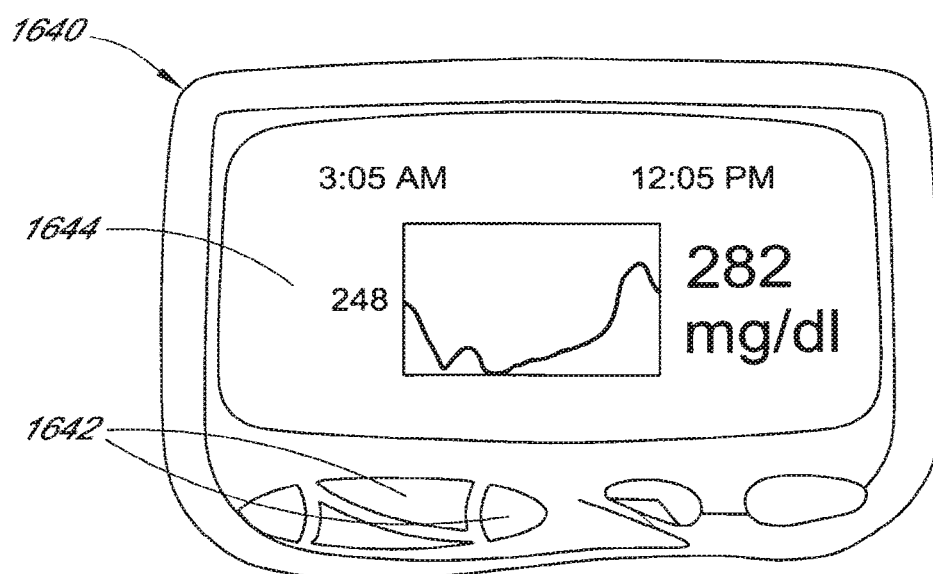
FIG. 16D illustrates a fourth embodiment wherein the receiver shows an estimated glucose value and nine hours of historical trend data on its user interface, which is described in more detail elsewhere herein.

FIG. 15 is a perspective view of a sensor system, including wireless communication between a sensor and a receiver. Preferably the electronics unit 16 is wirelessly connected to a receiver 158 via one- or two-way RF transmissions or the like. However, a wired connection is also contemplated. The receiver 158 provides much of the processing and display of the sensor data, and can be selectively worn and/or removed at the host's convenience. Thus, the sensor system 10 can be discreetly worn, and the receiver 158, which provides much of the processing and display of the sensor data, can be selectively worn and/or removed at the host's convenience. Particularly, the receiver 158 includes programming for retrospectively and/or prospectively initiating a calibration, converting sensor data, updating the calibration, evaluating received reference and sensor data, and evaluating the calibration for the analyte sensor, such as described in more detail with reference to U.S. Publication No. US-2005-0027463-A1.

FIGS. 16A to 16D are schematic views of a receiver in first, second, third, and fourth embodiments, respectively. A receiver 1640 comprises systems necessary to receive, process, and display sensor data from an analyte sensor, such as described elsewhere herein. Particularly, the receiver 1640 can be a pager-sized device, for example, and comprise a user interface that has a plurality of buttons 1642 and a liquid crystal display (LCD) screen 1644, and which can include a backlight. In some embodiments the user interface can also include a keyboard, a speaker, and a vibrator such as described with reference to FIG. 17A.

In some embodiments a user is able to toggle through some or all of the screens shown in FIGS. 16A to 16D using a toggle button on the receiver. In some embodiments, the user is able to interactively select the type of output displayed on their user interface. In some embodiments, the sensor output can have alternative configurations.

Receiver Electronics

Figure 17A:
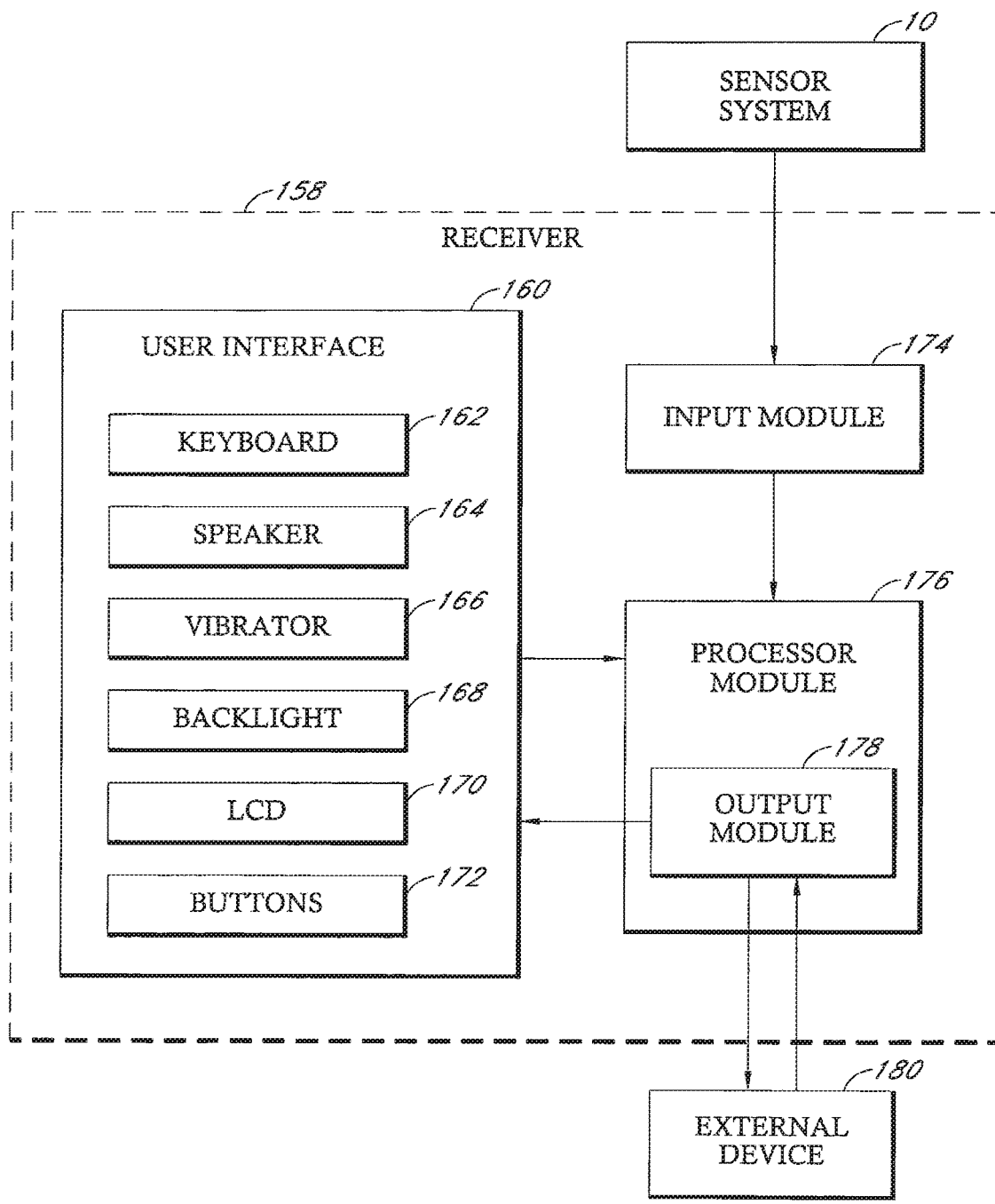
FIG. 17A is a block diagram that illustrates a configuration of a medical device including a continuous analyte sensor, a receiver, and an external device.

FIG. 17A is a block diagram that illustrates the configuration of the medical device in one embodiment, including a continuous analyte sensor, a receiver, and an external device. In general, the analyte sensor system is any sensor configuration that provides an output signal indicative of a concentration of an analyte (e.g., invasive, minimally-invasive, and/or non-invasive sensors as described above). The output signal is sent to a receiver 158 and received by an input module 174, which is described in more detail below. The output signal is typically a raw data stream that is used to provide a useful value of the measured analyte concentration to a patient or a doctor, for example. In some embodiments, the raw data stream can be continuously or periodically algorithmically smoothed or otherwise modified to diminish outlying points that do not accurately represent the analyte concentration, for example due to signal noise or other signal artifacts, such as described in U.S. Pat. No. 6,931,327.

Referring again to FIG. 17A, the receiver 158, which is operatively linked to the sensor system 10, receives a data stream from the sensor system 10 via the input module 174. In one embodiment, the input module includes a quartz crystal operably connected to an RF transceiver (not shown) that together function to receive and synchronize data streams from the sensor system 10. However, the input module 174 can be configured in any manner that is capable of receiving data from the sensor. Once received, the input module 174 sends the data stream to a processor 176 that processes the data stream, such as is described in more detail below.

The processor 176 is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, or the like. The processor includes hardware and software that performs the processing described herein, for example flash memory provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing.

Preferably, the input module 174 or processor module 176 performs a Cyclic Redundancy Check (CRC) to verify data integrity, with or without a method of recovering the data if there is an error. In some embodiments, error correction techniques such as those that use Hamming codes or Reed-Solomon encoding/decoding methods are employed to correct for errors in the data stream. In one alternative embodiment, an iterative decoding technique is employed, wherein the decoding is processed iteratively (e.g., in a closed loop) to determine the most likely decoded signal. This type of decoding can allow for recovery of a signal that is as low as 0.5 dB above the noise floor, which is in contrast to conventional non-iterative decoding techniques (such as Reed-Solomon), which requires approximately 3 dB or about twice the signal power to recover the same signal (e.g., a turbo code).

An output module 178, which is integral with and/or operatively connected with the processor 176, includes programming for generating output based on the data stream received from the sensor system 10 and its processing incurred in the processor 176. In some embodiments, output is generated via a user interface 160.

Figure 17B:
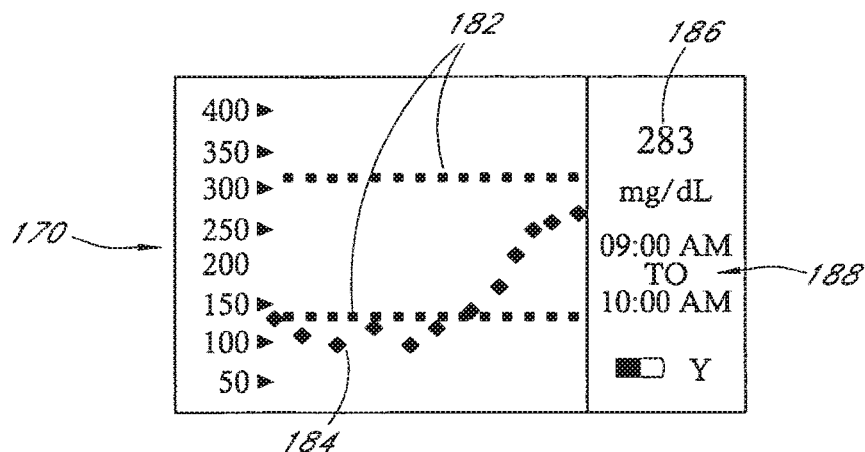
FIGS. 17B to 17D are illustrations of receiver liquid crystal displays showing embodiments of screen displays.
Figure 17C:
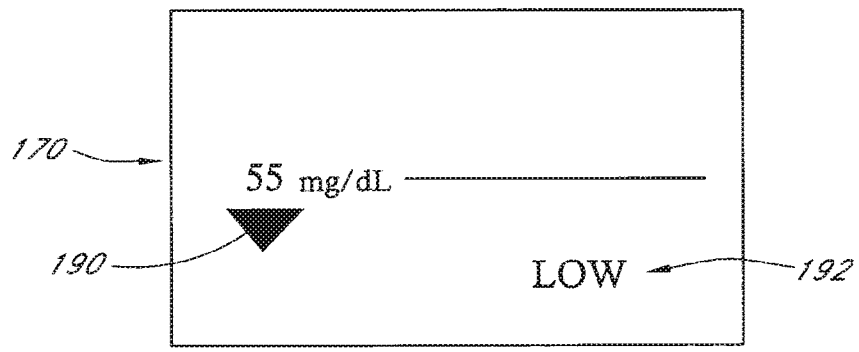
Figure 17D:
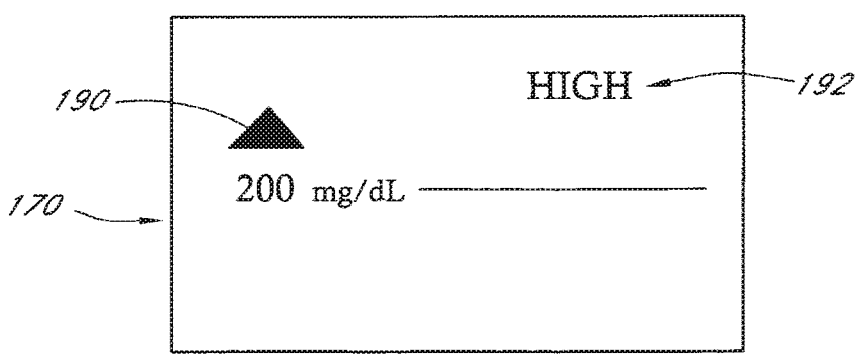

The user interface 160 comprises a keyboard 162, speaker 164, vibrator 166, backlight 168, liquid crystal display (LCD) screen 170, and one or more buttons 172. The components that comprise the user interface 160 include controls to allow interaction of the user with the receiver. The keyboard 162 can allow, for example, input of user information about himself/herself, such as mealtime, exercise, insulin administration, customized therapy recommendations, and reference analyte values. The speaker 164 can produce, for example, audible signals or alerts for conditions such as present and/or estimated hyperglycemic or hypoglycemic conditions in a person with diabetes. The vibrator 166 can provide, for example, tactile signals or alerts for reasons such as described with reference to the speaker, above. The backlight 168 can be provided, for example, to aid the user in reading the LCD 170 in low light conditions. The LCD 170 can be provided, for example, to provide the user with visual data output, such as is described in U.S. Publication No. US-2005-0203360-A1. FIGS. 17B to 17D illustrate some additional visual displays that can be provided on the screen 170. In some embodiments, the LCD is a touch-activated screen, enabling each selection by a user, for example, from a menu on the screen. The buttons 172 can provide for toggle, menu selection, option selection, mode selection, and reset, for example. In some alternative embodiments, a microphone can be provided to allow for voice-activated control.

In some embodiments, prompts or messages can be displayed on the user interface to convey information to the user, such as reference outlier values, requests for reference analyte values, therapy recommendations, deviation of the measured analyte values from the estimated analyte values, or the like. Additionally, prompts can be displayed to guide the user through calibration or trouble-shooting of the calibration.

In some embodiments, the receiver and/or a device connected to the receiver is configured to audibly output the user's analyte value(s), trend information (increasing or decreasing analyte values), and the like, hereinafter referred to as the audible output module. In some embodiments, the audible output module additionally includes: high and low blood glucose limits at which the module will audibly output the user's analyte value and/or trend information; English and non-English language versions; and choice of male or female voice. In some embodiments, the audible output is transmitted to an earbud worn by the patient for use where privacy is required or by a patient who is somewhat audibly impaired. The audible output module can be particularly advantageous in applications wherein the user is visually and/or hearing impaired, or is unable to visually check their receiver due to other circumstances (e.g., operating a motor vehicle or machinery, engaged in a business meeting or social event, or the like).

Additionally, data output from the output module 178 can provide wired or wireless, one- or two-way communication between the receiver 158 and an external device 180. The external device 180 can be any device that wherein interfaces or communicates with the receiver 158. In some embodiments, the external device 180 is a computer, and the receiver 158 is able to download historical data for retrospective analysis by the patient or physician, for example. In some embodiments, the external device 180 is a modem or other telecommunications station, and the receiver 158 is able to send alerts, warnings, emergency messages, or the like, via telecommunication lines to another party, such as a doctor or family member. In some embodiments, the external device 180 is an insulin pen, and the receiver 158 is able to communicate therapy recommendations, such as insulin amount and time to the insulin pen. In some embodiments, the external device 180 is an insulin pump, and the receiver 158 is able to communicate therapy recommendations, such as insulin amount and time to the insulin pump. The external device 180 can include other technology or medical devices, for example pacemakers, implanted analyte sensor patches, other infusion devices, telemetry devices, or the like.

The user interface 160, including keyboard 162, buttons 172, a microphone (not shown), and the external device 180, can be configured to allow input of data. Data input can be helpful in obtaining information about the patient (for example, meal time, exercise, or the like), receiving instructions from a physician (for example, customized therapy recommendations, targets, or the like), and downloading software updates, for example. Keyboard, buttons, touch-screen, and microphone are all examples of mechanisms by which a user can input data directly into the receiver. A server, personal computer, personal digital assistant, insulin pump, and insulin pen are examples of external devices that can provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual. While a few examples of data input have been provided here, a variety of information can be input, which can be helpful in data processing.

FIG. 17B is an illustration of an LCD screen 170 showing continuous and single point glucose information in the form of a trend graph 184 and a single numerical value 186. The trend graph shows upper and lower boundaries 182 representing a target range between which the host should maintain his/her glucose values. Preferably, the receiver is configured such that these boundaries 182 can be configured or customized by a user, such as the host or a care provider. By providing visual boundaries 182, in combination with continuous analyte values over time (e.g., a trend graph 184), a user can better learn how to control his/her analyte concentration (e.g., a person with diabetes can better learn how to control his/her glucose concentration) as compared to single point (single numerical value 186) alone. Although FIG. 17B illustrates a 1 hour trend graph (e.g., depicted with a time range 188 of 1 hour), a variety of time ranges can be represented on the screen 170, for example, 3 hour, 9 hour, 1 day, and the like.

FIG. 17C is an illustration of an LCD screen 170 showing a low alert screen that can be displayed responsive to a host's analyte concentration falling below a lower boundary (see boundaries 182). In this exemplary screen, a host's glucose concentration has fallen to 55 mg/dL, which is below the lower boundary set in FIG. 17B, for example. The arrow 190 represents the direction of the analyte trend, for example, indicating that the glucose concentration is continuing to drop. The annotation 192 ("LOW") is helpful in immediately and clearly alerting the host that his/her glucose concentration has dropped below a preset limit, and what may be considered to be a clinically safe value, for example. FIG. 17D is an illustration of an LCD screen 170 showing a high alert screen that can be displayed responsive to a host's analyte concentration rising above an upper boundary (see boundaries 182). In this exemplary screen, a host's glucose concentration has risen to 200 mg/dL, which is above a boundary set by the host, thereby triggering the high alert screen. The arrow 190 represents the direction of the analyte trend, for example, indicating that the glucose concentration is continuing to rise. The annotation 192 ("HIGH") is helpful in immediately and clearly alerting the host that his/her glucose concentration has above a preset limit, and what may be considered to be a clinically safe value, for example.

Although a few exemplary screens are depicted herein, a variety of screens can be provided for illustrating any of the information described in the preferred embodiments, as well as additional information. A user can toggle between these screens (e.g., using buttons 172) and/or the screens can be automatically displayed responsive to programming within the receiver 158, and can be simultaneously accompanied by another type of alert (audible or tactile, for example).

In some embodiments the receiver 158 can have a length of from about 8 cm to about 15 cm, a width of from about 3.5 cm to about 10 cm, and/or a thickness of from about 1 cm to about 3.5 cm. In some embodiments the receiver 158 can have a volume of from about 120 cm$^3$ to about 180 cm$^3$, and can have a weight of from about 70 g to 130 g. The dimensions and volume can be higher or lower, depending, e.g., on the type of devices integrated (e.g., finger stick devices, pumps, PDAs, and the like.), the type of user interface employed, and the like.

In some embodiments, the receiver 158 is an application-specific device. In some embodiments the receiver 158 can be a device used for other functions, such as are described in U.S. Pat. No. 6,558,320. For example, the receiver 158 can be integrated into a personal computer (PC), a personal digital assistant (PDA), a cell phone, or another fixed or portable computing device. The integration of the receiver 158 function into a more general purpose device can comprise the addition of software and/or hardware to the device. Communication between the sensor electronics 16 and the receiver 158 function of the more general purpose device can be implemented with wired or wireless technologies. For example, a PDA can be configured with a data communications port and/or a wireless receiver. After the user establishes a communication link between the electronics unit 16 and the PDA, the electronics unit 16 transmits data to the PDA which then processes the data according to software which has been loaded thereon so as to display.

Algorithms

Figure 18A:
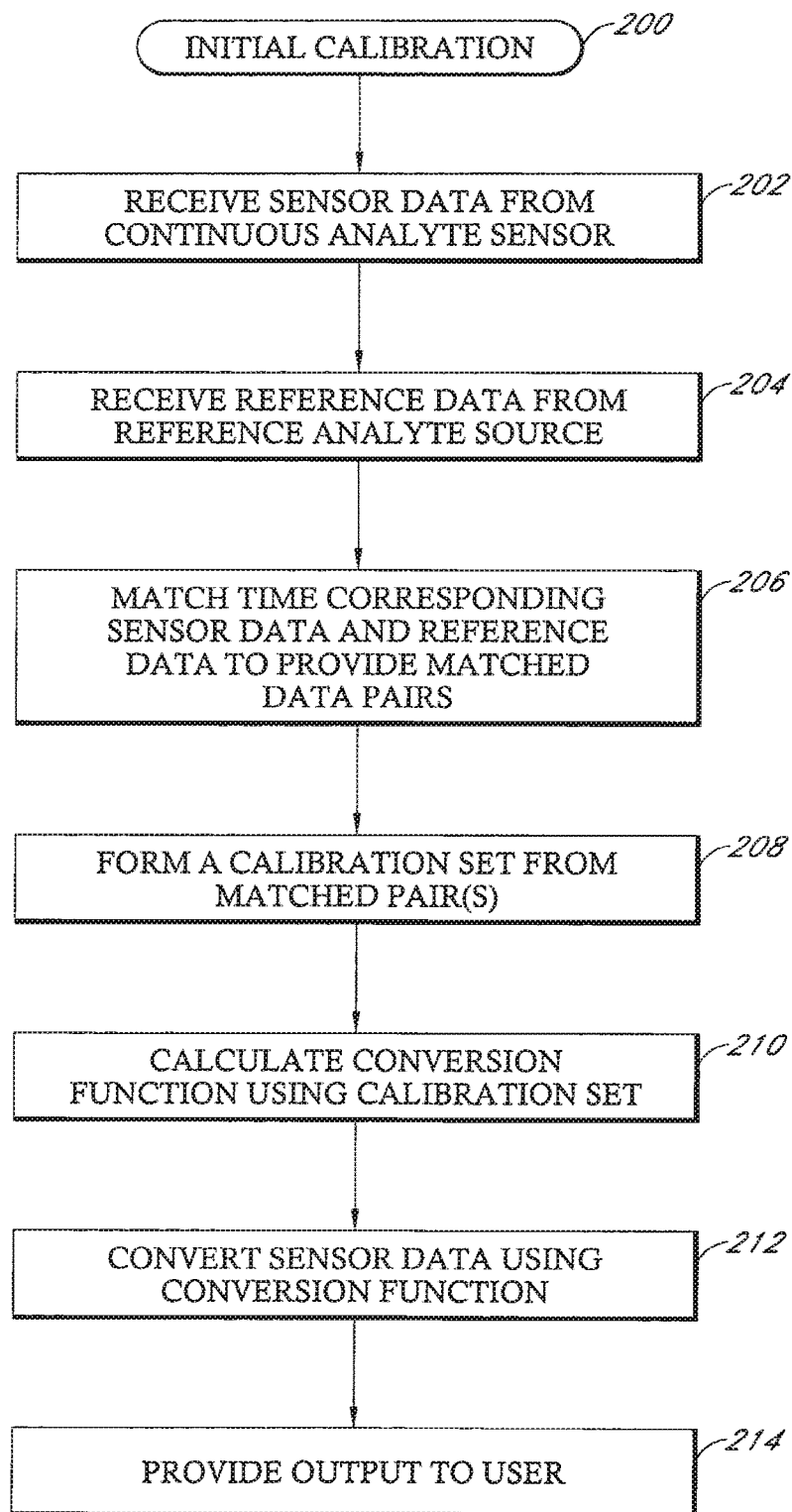
FIG. 18A is a flow chart that illustrates the initial calibration and data output of sensor data.

FIG. 18A provides a flow chart 200 that illustrates the initial calibration and data output of the sensor data in one embodiment, wherein calibration is responsive to reference analyte data. Initial calibration, also referred to as start-up mode, occurs at the initialization of a sensor, for example, the first time an electronics unit is used with a particular sensor. In certain embodiments, start-up calibration is triggered when the system determines that it can no longer remain in normal or suspended mode, which is described in more detail with reference to FIG. 21.

Calibration of an analyte sensor comprises data processing that converts sensor data signal into an estimated analyte measurement that is meaningful to a user. Accordingly, a reference analyte value is used to calibrate the data signal from the analyte sensor.

At block 202, a sensor data receiving module, also referred to as the sensor data module, receives sensor data (e.g., a data stream), including one or more time-spaced sensor data points, from the sensor 32 via the receiver 158, which can be in wired or wireless communication with the sensor 32. The sensor data point(s) can be smoothed (filtered) in certain embodiments using a filter, for example, a finite impulse response (FIR) or infinite impulse response (IIR) filter. During the initialization of the sensor, prior to initial calibration, the receiver receives and stores the sensor data, however it can be configured to not display any data to the user until initial calibration and, optionally, stabilization of the sensor has been established. In some embodiments, the data stream can be evaluated to determine sensor break-in (equilibration of the sensor in vitro or in vivo).

At block 204, a reference data receiving module, also referred to as the reference input module, receives reference data from a reference analyte monitor, including one or more reference data points. In one embodiment, the reference analyte points can comprise results from a self-monitored blood analyte test (e.g., finger stick test). For example, the user can administer a self-monitored blood analyte test to obtain an analyte value (e.g., point) using any known analyte sensor, and then enter the numeric analyte value into the computer system. Alternatively, a self-monitored blood analyte test is transferred into the computer system through a wired or wireless connection to the receiver (e.g. computer system) so that the user simply initiates a connection between the two devices, and the reference analyte data is passed or downloaded between the self-monitored blood analyte test and the receiver.

In yet another embodiment, the self-monitored analyte monitor (e.g., SMBG) is integral with the receiver so that the user simply provides a blood sample to the receiver, and the receiver runs the analyte test to determine a reference analyte value, such as is described in more detail herein and with reference to U.S. Publication No. US-2005-0154271-A1 which describes some systems and methods for integrating a reference analyte monitor into a receiver for a continuous analyte sensor.

In some embodiments, the integrated receiver comprises a microprocessor which can be programmed to process sensor data to perform the calibration. Such programming, which is stored in a computer readable memory, can also comprise data acceptability testing using criteria such as that discussed above with reference to FIG. 18A. For example the microprocessor can be programmed so as to determine the rate of change of glucose concentration based on the continuous sensor data, and perform calibration only if the rate of change is below a predetermined threshold, such as 2 mg/dL/min. In some embodiments the receiver can also comprise modules to perform a calibration procedure such as is described herein. Such modules include, but are not limited to an input module, a data matching module, a calibration module, a conversion function module, a sensor data transformation module, a calibration evaluation module, a clinical module, a stability module, and a user interface, each of which have been described herein.

The monitor can be of any suitable configuration. For example, in one embodiment, the reference analyte points can comprise results from a self-monitored blood analyte test (e.g., from a finger stick test), such as those described in U.S. Pat. Nos. 6,045,567; 6,156,051; 6,197,040; 6,284,125; 6,413,410; and 6,733,655. In one such embodiment, the user can administer a self-monitored blood analyte test to obtain an analyte value (e.g., point) using any suitable analyte sensor, and then enter the numeric analyte value into the computer system (e.g., the receiver). In another such embodiment, a self-monitored blood analyte test comprises a wired or wireless connection to the receiver (e.g. computer system) so that the user simply initiates a connection between the two devices, and the reference analyte data is passed or downloaded between the self-monitored blood analyte test and the receiver. In yet another such embodiment, the self-monitored analyte test is integral with the receiver so that the user simply provides a blood sample to the receiver, and the receiver runs the analyte test to determine a reference analyte value.

The monitor can be of another configuration, for example, such as described in U.S. Pat. Nos. 4,994,167, 4,757,022, 6,551,494. In alternative embodiments, the single point glucose monitor of this modular embodiment can be configured as described with reference to U.S. Publication No. US-2005-0154271-A1. In yet alternative embodiments, the monitor (e.g., integrated receiver) can be configured using other glucose meter configurations, for example, such as described in U.S. Pat. No. 6,641,533 to Causey III, et al. Numerous advantages associated with the integrated receiver, such as ensuring accurate time stamping of the single point glucose test at the receiver and other advantages described herein, can be provided by an integrated continuous glucose receiver and single point glucose monitor, such as described herein.

In some alternative embodiments, the reference data is based on sensor data from another substantially continuous analyte sensor, e.g., a transcutaneous analyte sensor described herein, or another type of suitable continuous analyte sensor. In an embodiment employing a series of two or more transcutaneous (or other continuous) sensors, the sensors can be employed so that they provide sensor data in discrete or overlapping periods. In such embodiments, the sensor data from one continuous sensor can be used to calibrate another continuous sensor, or be used to confirm the validity of a subsequently employed continuous sensor.

In some embodiments, reference data can be subjected to "outlier detection" wherein the accuracy of a received reference analyte data is evaluated as compared to time-corresponding sensor data. In one embodiment, the reference data is compared to the sensor data on a modified Clarke Error Grid (e.g., a test similar to the Clarke Error Grid except the boundaries between the different regions are modified slightly) to determine if the data falls within a predetermined threshold. If the data is not within the predetermined threshold, then the receiver can be configured to request additional reference analyte data. If the additional reference analyte data confirms (e.g., closely correlates to) the first reference analyte data, then the first and second reference values are assumed to be accurate and calibration of the sensor is adjusted or re-initialized. Alternatively, if the second reference analyte value falls within the predetermined threshold, then the first reference analyte value is assumed to be an outlier and the second reference analyte value is used by the algorithm(s) instead. In one alternative embodiments of outlier detection, projection is used to estimate an expected analyte value, which is compared with the actual value and a delta evaluated for substantial correspondence. However, other methods of outlier detection are possible.

Certain acceptability parameters can be set for reference values received from the user. In some embodiments, the calibration process monitors the continuous analyte sensor data stream to determine a preferred time for capturing reference analyte concentration values for calibration of the continuous sensor data stream. In an example wherein the analyte sensor is a continuous glucose sensor, when data (for example, observed from the data stream) changes too rapidly, the reference glucose value may not be sufficiently reliable for calibration due to unstable glucose changes in the host. In contrast, when sensor glucose data are relatively stable (for example, relatively low rate of change), a reference glucose value can be taken for a reliable calibration. For example, in one embodiment, the receiver can be configured to only accept reference analyte values of from about 40 mg/dL to about 400 mg/dL. As another example, the receiver can be configured to only accept reference analyte values when the rate of change is less than a predetermined maximum, such as 1, 1.5, 2, 2.5, 3, or 3.5, mg/dL/min. As yet another example, the receiver can be configured to only accept reference analyte values when the rate of acceleration (or deceleration) is less than a predetermined maximum, such as 0.01 mg/dL/min$^2$, 0.02 mg/dL/min$^2$, 0.03 mg/dL/min$^2$, 0.04 mg/dL/min$^2$, or 0.05 mg/dL/min$^2$ or more.

In some embodiments, the reference data is pre-screened according to environmental and/or physiological issues, such as time of day, oxygen concentration, postural effects, and patient-entered environmental data. In one example embodiment, wherein the sensor comprises an implantable glucose sensor, an oxygen sensor within the glucose sensor is used to determine if sufficient oxygen is being provided to successfully complete the necessary enzyme and electrochemical reactions for glucose sensing. In another example wherein the sensor comprises an implantable glucose sensor, the counter electrode could be monitored for a "rail-effect," that is, when insufficient oxygen is provided at the counter electrode causing the counter electrode to reach operational (e.g., circuitry) limits. In some embodiments the receiver is configured such that when conditions for accepting reference analyte values are not met, the user is notified. Such notice can include an indication as to the cause of the unacceptability, such as low oxygen or high rate of analyte value change. In some embodiments the indication can also include an indication of suggested corrective action, such as moderately increasing muscular activity so as to increase oxygen levels or to wait until the rate of analyte value change reduces to an acceptable value.

In one embodiment, the calibration process can prompt the user via the user interface to "calibrate now" when the reference analyte values are considered acceptable. In some embodiments, the calibration process can prompt the user via the user interface to obtain a reference analyte value for calibration at intervals, for example when analyte concentrations are at high and/or low values. In some additional embodiments, the user interface can prompt the user to obtain a reference analyte value for calibration based at least in part upon certain events, such as meals, exercise, large excursions in analyte levels, faulty or interrupted data readings, or the like. In some embodiments, the algorithms can provide information useful in determining when to request a reference analyte value. For example, when analyte values indicate approaching clinical risk, the user interface can prompt the user to obtain a reference analyte value.

In yet another example embodiment, the patient is prompted to enter data into the user interface, such as meal times and/or amount of exercise, which can be used to determine likelihood of acceptable reference data. Evaluation data, such as described in the paragraphs above, can be used to evaluate an optimum time for reference analyte measurement. Correspondingly, the user interface can then prompt the user to provide a reference data point for calibration within a given time period. Consequently, because the receiver proactively prompts the user during optimum calibration times, the likelihood of error due to environmental and physiological limitations can decrease and consistency and acceptability of the calibration can increase.

At block 206, a data matching module, also referred to as the processor module, matches reference data (e.g., one or more reference analyte data points) with substantially time corresponding sensor data (e.g., one or more sensor data points) to provide one or more matched data pairs. One reference data point can be matched to one time corresponding sensor data point to form a matched data pair. Alternatively, a plurality of reference data points can be averaged (e.g., equally or non-equally weighted average, mean-value, median, or the like) and matched to one time corresponding sensor data point to form a matched data pair, one reference data point can be matched to a plurality of time corresponding sensor data points averaged to form a matched data pair, or a plurality of reference data points can be averaged and matched to a plurality of time corresponding sensor data points averaged to form a matched data pair.

In one embodiment, time corresponding sensor data comprises one or more sensor data points that occur from about 0 minutes to about 20 minutes after the reference analyte data time stamp (e.g., the time that the reference analyte data is obtained). In one embodiment, a 5-minute time delay is chosen to compensate for a system time-lag (e.g., the time necessary for the analyte to diffusion through a membrane(s) of an analyte sensor). In alternative embodiments, the time corresponding sensor value can be greater than or less than that of the above-described embodiment, for example ±60 minutes. Variability in time correspondence of sensor and reference data can be attributed to, for example, a longer or shorter time delay introduced by the data smoothing filter, or if the configuration of the analyte sensor incurs a greater or lesser physiological time lag.

In some implementations of the sensor, the reference analyte data is obtained at a time that is different from the time that the data is input into the receiver. Accordingly, the "time stamp" of the reference analyte (e.g., the time at which the reference analyte value was obtained) is not the same as the time at which the receiver obtained the reference analyte data. Therefore, some embodiments include a time stamp requirement that ensures that the receiver stores the accurate time stamp for each reference analyte value, that is, the time at which the reference value was actually obtained from the user.

In certain embodiments, tests are used to evaluate the best-matched pair using a reference data point against individual sensor values over a predetermined time period (e.g., about 30 minutes). In one such embodiment, the reference data point is matched with sensor data points at 5-minute intervals and each matched pair is evaluated. The matched pair with the best correlation can be selected as the matched pair for data processing. In some alternative embodiments, matching a reference data point with an average of a plurality of sensor data points over a predetermined time period can be used to form a matched pair.

In certain embodiments, the data matching module only forms matched pairs when a certain analyte value condition is satisfied. Such a condition can include any of the conditions discussed above with reference to embodiments pre-screening or conditionally accepting reference analyte value data at block 204.

At block 208, a calibration set module, also referred to as the calibration module or processor module, forms an initial calibration set from a set of one or more matched data pairs, which are used to determine the relationship between the reference analyte data and the sensor analyte data. The matched data pairs, which make up the initial calibration set, can be selected according to predetermined criteria. The criteria for the initial calibration set can be the same as, or different from, the criteria for the updated calibration sets. In certain embodiments, the number (n) of data pair(s) selected for the initial calibration set is one. In other embodiments, n data pairs are selected for the initial calibration set wherein n is a function of the frequency of the received reference data points. In various embodiments, two data pairs make up the initial calibration set or six data pairs make up the initial calibration set. In an embodiment wherein a substantially continuous analyte sensor provides reference data, numerous data points are used to provide reference data from more than 6 data pairs (e.g., dozens or even hundreds of data pairs). In one exemplary embodiment, a substantially continuous analyte sensor provides 288 reference data points per day (every five minutes for twenty-four hours), thereby providing an opportunity for a matched data pair 288 times per day, for example. While specific numbers of matched data pairs are referred to in the preferred embodiments, any suitable number of matched data pairs per a given time period can be employed.

In certain embodiments, the data pairs are selected only when a certain analyte value condition is satisfied. Such a condition can include any of the conditions discussed above with reference to embodiments pre-screening or conditionally accepting reference analyte value data at block 204. In certain embodiments, the data pairs that form the initial calibration set are selected according to their time stamp, for example, by waiting a predetermined "break-in" time period after implantation, the stability of the sensor data can be increased. In certain embodiments, the data pairs that form the initial calibration set are spread out over a predetermined time period, for example, a period of two hours or more. In certain embodiments, the data pairs that form the initial calibration set are spread out over a predetermined glucose range, for example, spread out over a range of at least 90 mg/dL or more.

At block 210, a conversion function module, also referred to as the conversion module or processor module, uses the calibration set to create a conversion function. The conversion function substantially defines the relationship between the reference analyte data and the analyte sensor data.

A variety of known methods can be used with the preferred embodiments to create the conversion function from the calibration set. In one embodiment, wherein a plurality of matched data points form the calibration set, a linear least squares regression is used to calculate the conversion function; for example, this regression calculates a slope and an offset using the equation $y=mx+b$. A variety of regression or other conversion schemes can be implemented herein.

In certain embodiments, the conversion function module only creates a conversion function when a certain analyte value condition is satisfied. Such a condition can include any of the conditions discussed above with reference to embodiments pre-screening or conditionally accepting reference analyte value data at block 204 or with reference to selecting data pairs at block 208.

In some alternative embodiments, the sensor is calibrated with a single-point through the use of a dual-electrode system to simplify sensor calibration. In one such dual-electrode system, a first electrode functions as a hydrogen peroxide sensor including a membrane system containing glucose-oxidase disposed thereon, which operates as described herein. A second electrode is a hydrogen peroxide sensor that is configured similar to the first electrode, but with a modified membrane system (with the enzyme domain removed, for example). This second electrode provides a signal composed mostly of the baseline signal, b.

In some dual-electrode systems, the baseline signal is (electronically or digitally) subtracted from the glucose signal to obtain a glucose signal substantially without baseline. Accordingly, calibration of the resultant difference signal can be performed by solving the equation y=mx with a single paired measurement. Calibration of the implanted sensor in this alternative embodiment can be made less dependent on the values/range of the paired measurements, less sensitive to error in manual blood glucose measurements, and can facilitate the sensor's use as a primary source of glucose information for the user. U.S. Publication No. US-2005-0143635-A1 describes systems and methods for subtracting the baseline from a sensor signal.

In some alternative dual-electrode system embodiments, the analyte sensor is configured to transmit signals obtained from each electrode separately (e.g., without subtraction of the baseline signal). In this way, the receiver can process these signals to determine additional information about the sensor and/or analyte concentration. For example, by comparing the signals from the first and second electrodes, changes in baseline and/or sensitivity can be detected and/or measured and used to update calibration (e.g., without the use of a reference analyte value). In one such example, by monitoring the corresponding first and second signals over time, an amount of signal contributed by baseline can be measured. In another such example, by comparing fluctuations in the correlating signals over time, changes in sensitivity can be detected and/or measured.

In some alternative embodiments, a regression equation y=mx+b is used to calculate the conversion function; however, prior information can be provided for m and/or b, thereby enabling calibration to occur with fewer paired measurements. In one calibration technique, prior information (e.g., obtained from in vivo or in vitro tests) determines a sensitivity of the sensor and/or the baseline signal of the sensor by analyzing sensor data from measurements taken by the sensor (e.g., prior to inserting the sensor). For example, if there exists a predictive relationship between in vitro sensor parameters and in vivo parameters, then this information can be used by the calibration procedure. For example, if a predictive relationship exists between in vitro sensitivity and in vivo sensitivity, $m \approx f(m_{in\ vitro})$, then the predicted m can be used, along with a single matched pair, to solve for b (b=y−mx). If, in addition, b can be assumed=0, for example with a dual-electrode configuration that enables subtraction of the baseline from the signal such as described above, then both m and b are known a priori, matched pairs are not needed for calibration, and the sensor can be completely calibrated e.g. without the need for reference analyte values (e.g. values obtained after implantation in vivo.)

In another alternative embodiment, prior information can be provided to guide or validate the baseline (b) and/or sensitivity (m) determined from the regression analysis. In this embodiment, boundaries can be set for the regression line that defines the conversion function such that working sensors are calibrated accurately and easily (with two points), and non-working sensors are prevented from being calibrated. If the boundaries are drawn too tightly, a working sensor may not enter into calibration. Likewise, if the boundaries are drawn too loosely, the scheme can result in inaccurate calibration or can permit non-working sensors to enter into calibration. For example, subsequent to performing regression, the resulting slope and/or baseline are tested to determine whether they fall within a predetermined acceptable threshold (boundaries). These predetermined acceptable boundaries can be obtained from in vivo or in vitro tests (e.g., by a retrospective analysis of sensor sensitivities and/or baselines collected from a set of sensors/patients, assuming that the set is representative of future data).

If the slope and/or baseline fall within the predetermined acceptable boundaries, then the regression is considered acceptable and processing continues to the next step (e.g., block 212). Alternatively, if the slope and/or baseline fall outside the predetermined acceptable boundaries, steps can be taken to either correct the regression or fail-safe such that a system will not process or display errant data. This can be useful in situations wherein regression results in errant slope or baseline values. For example, when points (matched pairs) used for regression are too close in value, the resulting regression statistically is less accurate than when the values are spread farther apart. As another example, a sensor that is not properly deployed or is damaged during deployment can yield a skewed or errant baseline signal.

In some alternative embodiments, the sensor system does not require initial and/or update calibration by the host; in these alternative embodiments, also referred to as "zero-point calibration" embodiments, use of the sensor system without requiring a reference analyte measurement for initial and/or update calibration is enabled. In general, the systems and methods of the preferred embodiments provide for stable and repeatable sensor manufacture, particularly when tightly controlled manufacturing processes are utilized. Namely, a batch of sensors of the preferred embodiments can be designed with substantially the same baseline (b) and/or sensitivity (m) (+/−10%) when tested in vitro. Additionally, the sensor of the preferred embodiments can be designed for repeatable m and b in vivo. Thus, an initial calibration factor (conversion function) can be programmed into the sensor (sensor electronics and/or receiver electronics) that enables conversion of raw sensor data into calibrated sensor data solely using information obtained prior to implantation (namely, initial calibration does not require a reference analyte value). Additionally, to obviate the need for recalibration (update calibration) during the life of the sensor, the sensor is designed to minimize drift of the sensitivity and/or baseline over time in vivo. Accordingly, the preferred embodiments can be manufactured for zero point calibration.

Figure 18B:
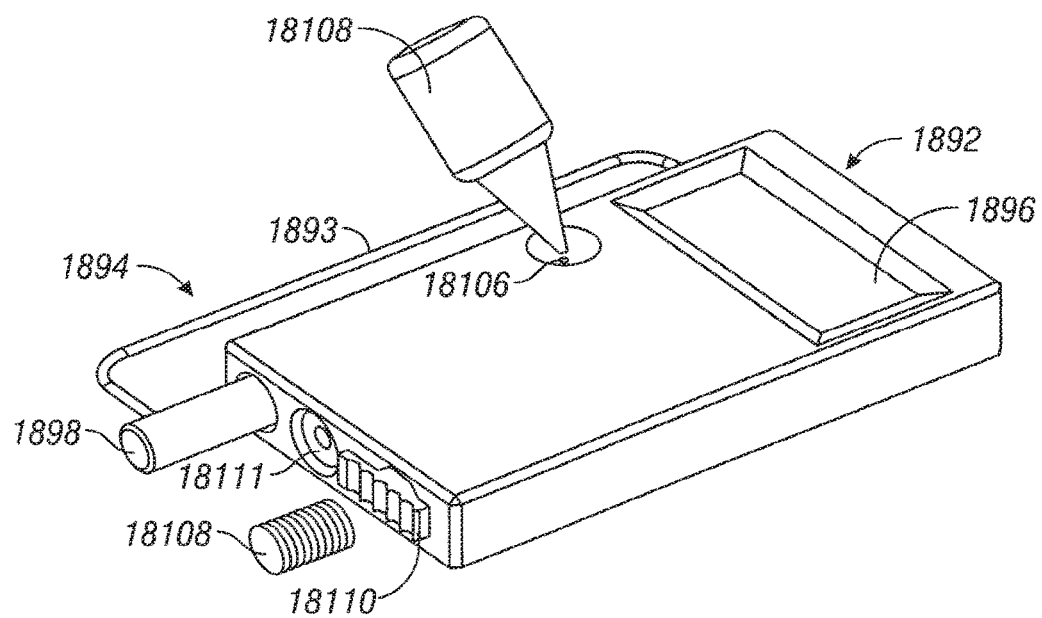
FIG. 18B is a graph that illustrates one example of using prior information for slope and baseline.
Figure 18C:
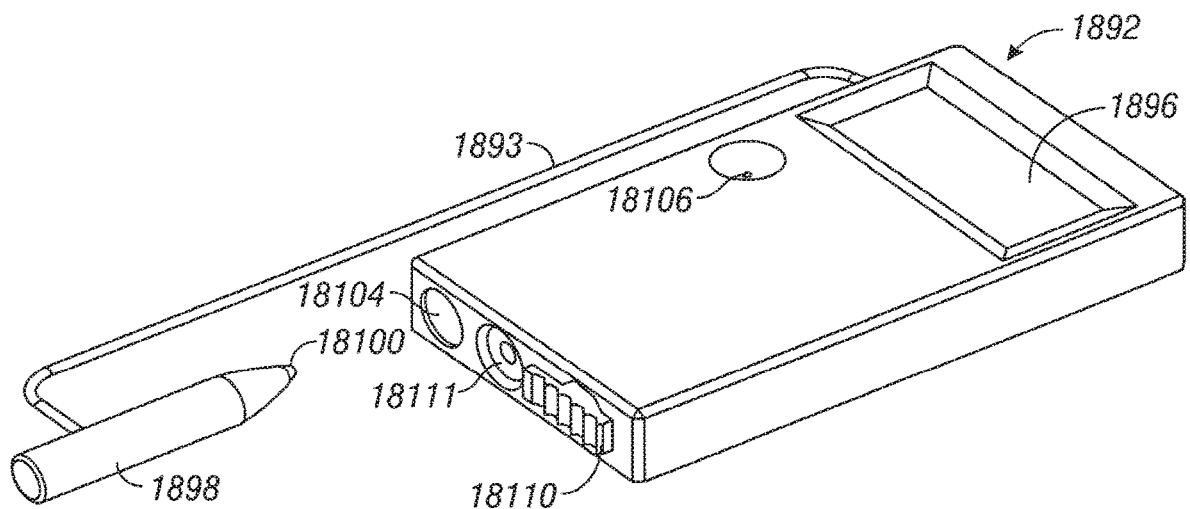
FIGS. 18C-G disclose integrated receiver housing 1892 and stylus 1998.
Figure 18D:
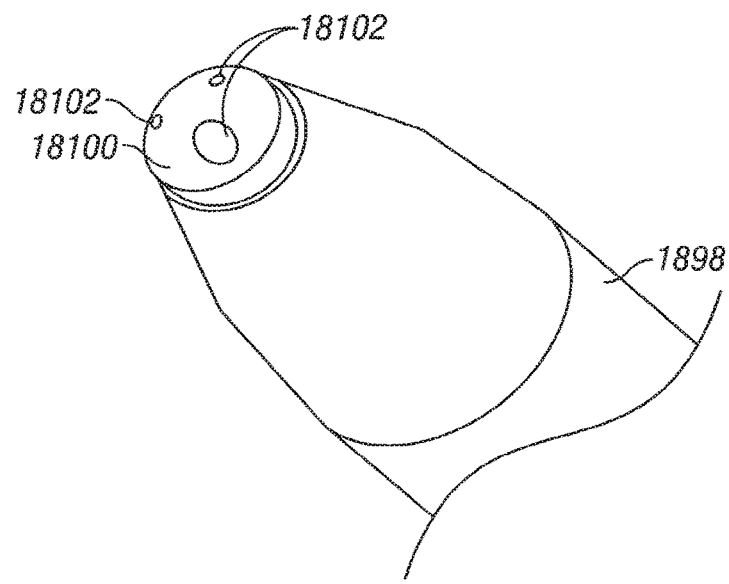
Figure 18E:
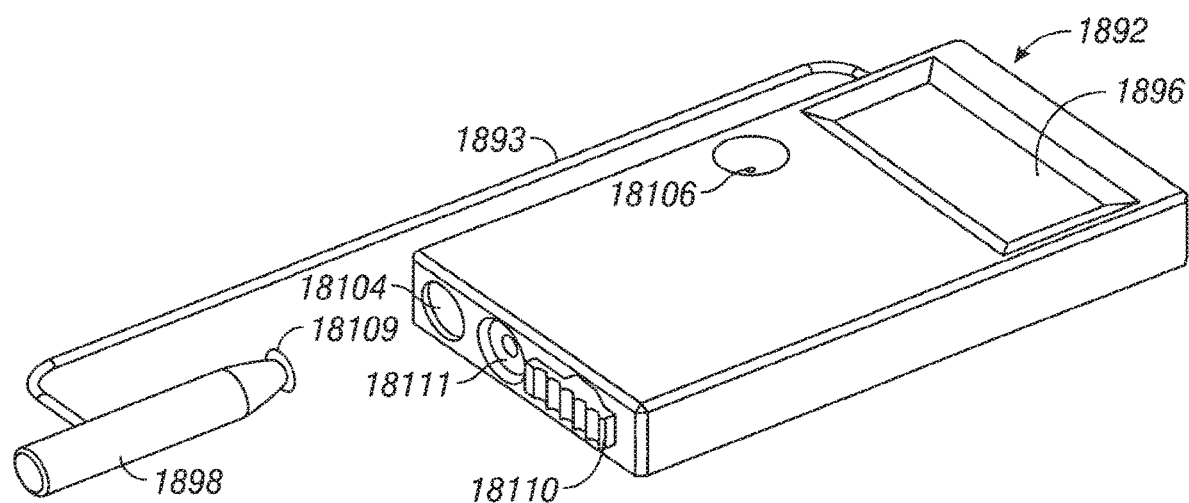
Figure 18F:
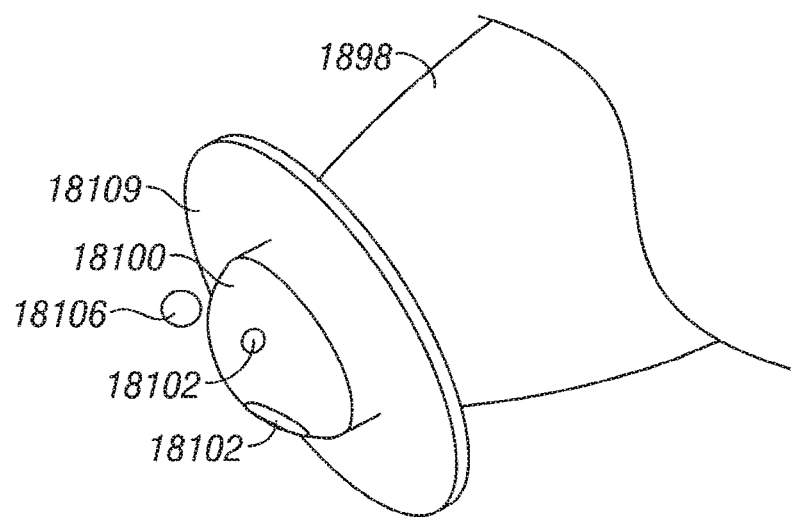
Figure 18G:
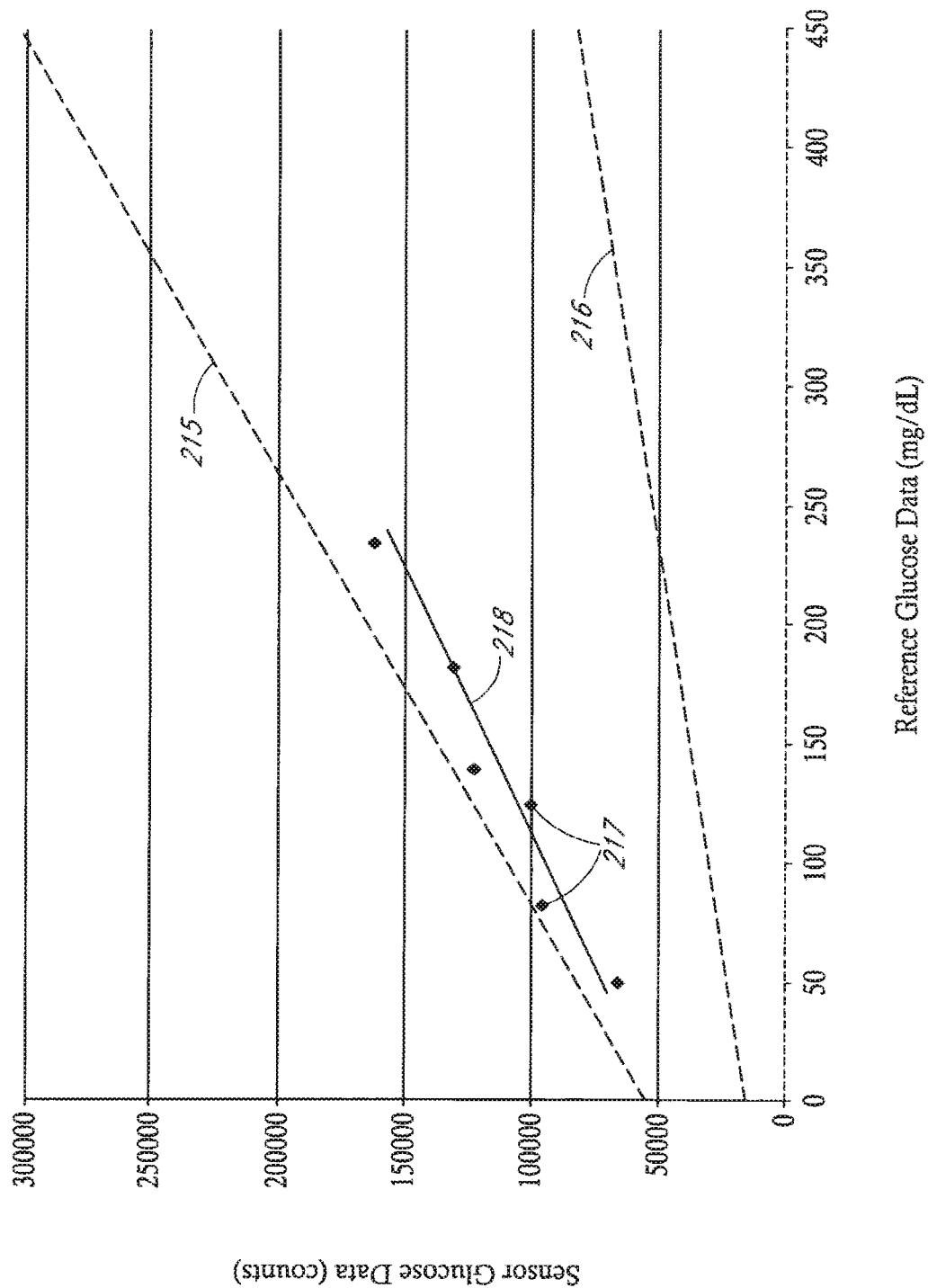

FIG. 18B is a graph that illustrates one example of using prior information for slope and baseline. The x-axis represents reference glucose data (blood glucose) from a reference glucose source in mg/dL; the y-axis represents sensor data from a transcutaneous glucose sensor of the preferred embodiments in counts. An upper boundary line 215 is a regression line that represents an upper boundary of "acceptability" in this example; the lower boundary line 216 is a regression line that represents a lower boundary of "acceptability" in this example. The boundary lines 215, 216 were obtained from retrospective analysis of in vivo sensitivities and baselines of glucose sensors as described in the preferred embodiments.

A plurality of matched data pairs 217 represents data pairs in a calibration set obtained from a glucose sensor as described in the preferred embodiments. The matched data pairs are plotted according to their sensor data and time-corresponding reference glucose data. A regression line 218 represents the result of regressing the matched data pairs 217 using least squares regression. In this example, the regression line falls within the upper and lower boundaries 215, 216 indicating that the sensor calibration is acceptable.

However, if the slope and/or baseline had fallen outside the predetermined acceptable boundaries, which would be illustrated in this graph by a line that crosses the upper and/or lower boundaries 215, 216, then the system is configured to assume a baseline value and re-run the regression (or a modified version of the regression) with the assumed baseline, wherein the assumed baseline value is derived from in vivo or in vitro testing. Subsequently, the newly derived slope and baseline are again tested to determine whether they fall within the predetermined acceptable boundaries. Similarly, the processing continues in response to the results of the boundary test. In general, for a set of matched pairs (e.g., calibration set), regression lines with higher slope (sensitivity) have a lower baseline and regression lines with lower slope (sensitivity) have a higher baseline. Accordingly, the step of assuming a baseline and testing against boundaries can be repeated using a variety of different assumed baselines based on the baseline, sensitivity, in vitro testing, and/or in vivo testing. For example, if a boundary test fails due to high sensitivity, then a higher baseline is assumed and the regression re-run and boundary-tested. It is preferred that after about two iterations of assuming a baseline and/or sensitivity and running a modified regression, the system assumes an error has occurred (if the resulting regression lines fall outside the boundaries) and fail-safe. The term "fail-safe" includes modifying the system processing and/or display of data responsive to a detected error avoid reporting of inaccurate or clinically irrelevant analyte values.

In these various embodiments utilizing an additional electrode, prior information (e.g., in vitro or in vivo testing), signal processing, or other information for assisting in the calibration process can be used alone or in combination to reduce or eliminate the dependency of the calibration on reference analyte values obtained by the host.

At block 212, a sensor data transformation module, also referred to as the calibration module, conversion module, or processor module, uses the conversion function to transform sensor data into substantially real-time analyte value estimates, also referred to as calibrated data, or converted sensor data, as sensor data is continuously (or intermittently) received from the sensor. For example, the sensor data, which can be provided to the receiver in "counts," is translated in to estimate analyte value(s) in mg/dL. In other words, the offset value at any given point in time can be subtracted from the raw value (e.g., in counts) and divided by the slope to obtain the estimate analyte value:

$$mg/dL = \frac{(rawvalue - \text{offset})}{\text{slope}}$$

In some alternative embodiments, the sensor and/or reference analyte values are stored in a database for retrospective analysis.

In certain embodiments, the sensor data transformation module only converts sensor data points into calibrated data points when a certain analyte value condition is satisfied. Such a condition can include any of the conditions discussed above with reference to embodiments pre-screening or conditionally accepting reference analyte value data at block 204, with reference to selecting data pairs at block 208, or with reference to creating a conversion function at block 210.

At block 214, an output module provides output to the user via the user interface. The output is representative of the estimated analyte value, which is determined by converting the sensor data into a meaningful analyte value. User output can be in the form of a numeric estimated analyte value, an indication of directional trend of analyte concentration, and/or a graphical representation of the estimated analyte data over a period of time, for example. Other representations of the estimated analyte values are also possible, for example audio and tactile.

In some embodiments, annotations are provided on the graph; for example, bitmap images are displayed thereon, which represent events experienced by the host. For example, information about meals, insulin, exercise, sensor insertion, sleep, and the like, can be obtained by the receiver (by user input or receipt of a transmission from another device) and displayed on the graphical representation of the host's glucose over time. It is believed that illustrating a host's life events matched with a host's glucose concentration over time can be helpful in educating the host to his or her metabolic response to the various events.

In yet another alternative embodiment, the sensor utilizes one or more additional electrodes to measure an additional analyte. Such measurements can provide a baseline or sensitivity measurement for use in calibrating the sensor. Furthermore, baseline and/or sensitivity measurements can be used to trigger events such as digital filtering of data or suspending display of data, all of which are described in more detail in U.S. Publication No. US-2005-0143635-A1.

Figure 19A:
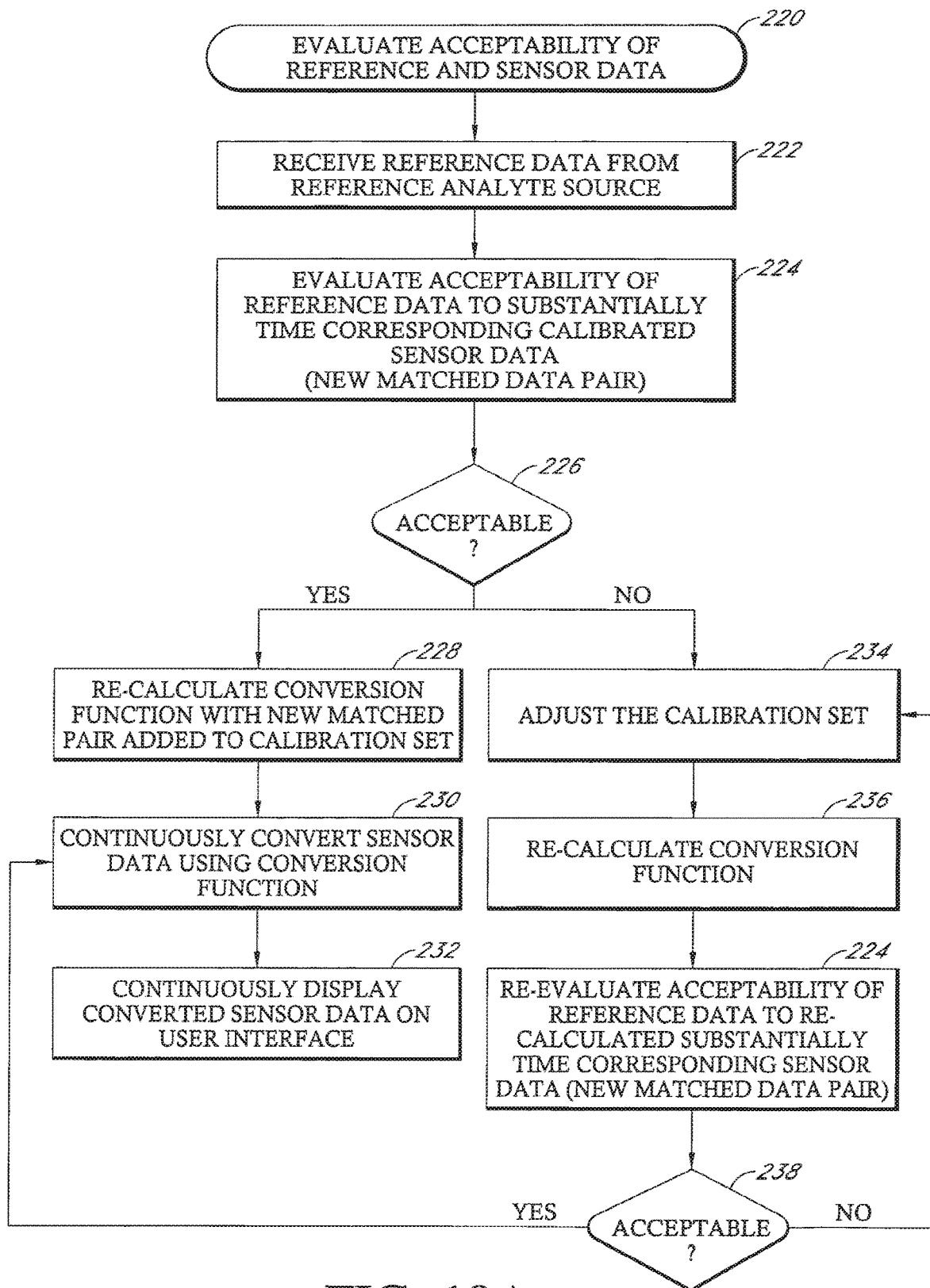
FIG. 19A is a flow chart that illustrates evaluation of reference and/or sensor data for statistical, clinical, and/or physiological acceptability.

FIG. 19A provides a flow chart 220 that illustrates a process which, for example, a stability module can use in the evaluation of reference and/or sensor data for stability, and/or for statistical, clinical, and/or physiological acceptability. Although some acceptability tests are disclosed herein, any known statistical, clinical, physiological standards and methodologies can be applied to evaluate the acceptability of reference and sensor analyte data.

In some embodiments, a stability determination module is provided, also referred to as the start-up module or processor module, which determines the stability of the analyte sensor over a period of time. Some analyte sensors can have an initial instability time period during which the analyte sensor is unstable for environmental, physiological, or other reasons. Initial sensor instability can occur, for example, when the analyte sensor is implanted subcutaneously; stabilization of the analyte sensor can be dependent upon the maturity of the tissue ingrowth around and within the sensor. Initial sensor instability can also occur when the analyte sensor is implemented transdermally; stabilization of the analyte sensor can be dependent upon electrode stabilization and/or the presence of sweat, for example.

Accordingly, in some embodiments, achieving sensor stability can include waiting a predetermined time period (e.g., an implantable subcutaneous sensor can require a time period for tissue growth, and a transcutaneous sensor can require time to equilibrate the sensor with the user's skin). In some embodiments, this predetermined waiting period is from about one minute to about six days, from about 1 day to about five days, or from about two days to about four days for a transcutaneous sensor and from about 1 day to about six weeks, from about 1 week to about five weeks, or about from two weeks to about four weeks for a subcutaneous sensor. In other embodiments for a transcutaneous sensor the waiting period is preferably from about 30 minutes to about 24 hours, or more preferably from about one hour to about 12 hours, or from about 2 hours to about 10 hours. In some embodiments, the sensitivity (e.g., sensor signal strength with respect to analyte concentration) can be used to determine the stability of the sensor; for example, amplitude and/or variability of sensor sensitivity can be evaluated to determine the stability of the sensor. In alternative embodiments, detection of pH levels, oxygen, hypochlorite, interfering species (e.g., ascorbate, urea, and/or acetaminophen), correlation between sensor and reference values (e.g., R-value), baseline drift, and/or offset, and the like can be used to determine the stability of the sensor. In one exemplary embodiment, wherein the sensor is a glucose sensor, a signal can be provided that is associated with interfering species (e.g., ascorbate, urea, acetaminophen and/or the like), which can be used to evaluate sensor stability. In another exemplary embodiment, wherein the sensor is a glucose sensor, the counter electrode can be monitored for oxygen deprivation, which can be used to evaluate sensor stability or functionality.

In some embodiments, the system (e.g., microprocessor) determines whether the analyte sensor is sufficiently stable according to certain criteria, such as are described above with reference to FIG. 18A. In one embodiment wherein the sensor is an implantable glucose sensor, the system waits a predetermined time period for sufficient tissue ingrowth and evaluates the sensor sensitivity (e.g., from about one minute to six weeks). In another embodiment, the receiver determines sufficient stability based on oxygen concentration near the sensor head. In yet another embodiment, the sensor determines sufficient stability based on a reassessment of baseline drift and/or offset. In yet another alternative embodiment, the system evaluates stability by monitoring the frequency content of the sensor data stream over a predetermined amount of time (e.g., 24 hours); in this alternative embodiment, a template (or templates) are provided that reflect acceptable levels of glucose physiology and are compared with the actual sensor data, wherein a predetermined degree of agreement between the template and the actual sensor data is indicative of sensor stability. A few examples of determinations of sufficient stability are described herein; however, a variety of known tests and parameters can be used to determine sensor stability without departing from the spirit and scope of the preferred embodiments. If the stability is determined to be insufficient, additional sensor data can be repeatedly taken at predetermined intervals until a sufficient degree of stability is achieved.

In some embodiments, a clinical acceptability evaluation module, also referred to as clinical module, evaluates the clinical acceptability of newly received reference data and/or time corresponding sensor data. In some embodiments clinical acceptability criteria can include any of the conditions discussed above with reference to FIG. 18A as to pre-screening or conditionally accepting reference analyte value data. In some embodiments of evaluating clinical acceptability, the rate of change of the reference data as compared to previously obtained data is assessed for clinical acceptability. That is, the rate of change and acceleration (or deceleration) of the concentration of many analytes in vivo have certain physiological limits within the body. Accordingly, a limit can be set to determine if the new matched pair is within a physiologically feasible range, indicated by a rate of change from the previous data that is within known physiological and/or statistical limits. Similarly, in some embodiments an algorithm that predicts a future value of an analyte can be used to predict and then compare an actual value to a time corresponding predicted value to determine if the actual value falls within a clinically acceptable range based on the predictive algorithm, for example.

Figure 19B:
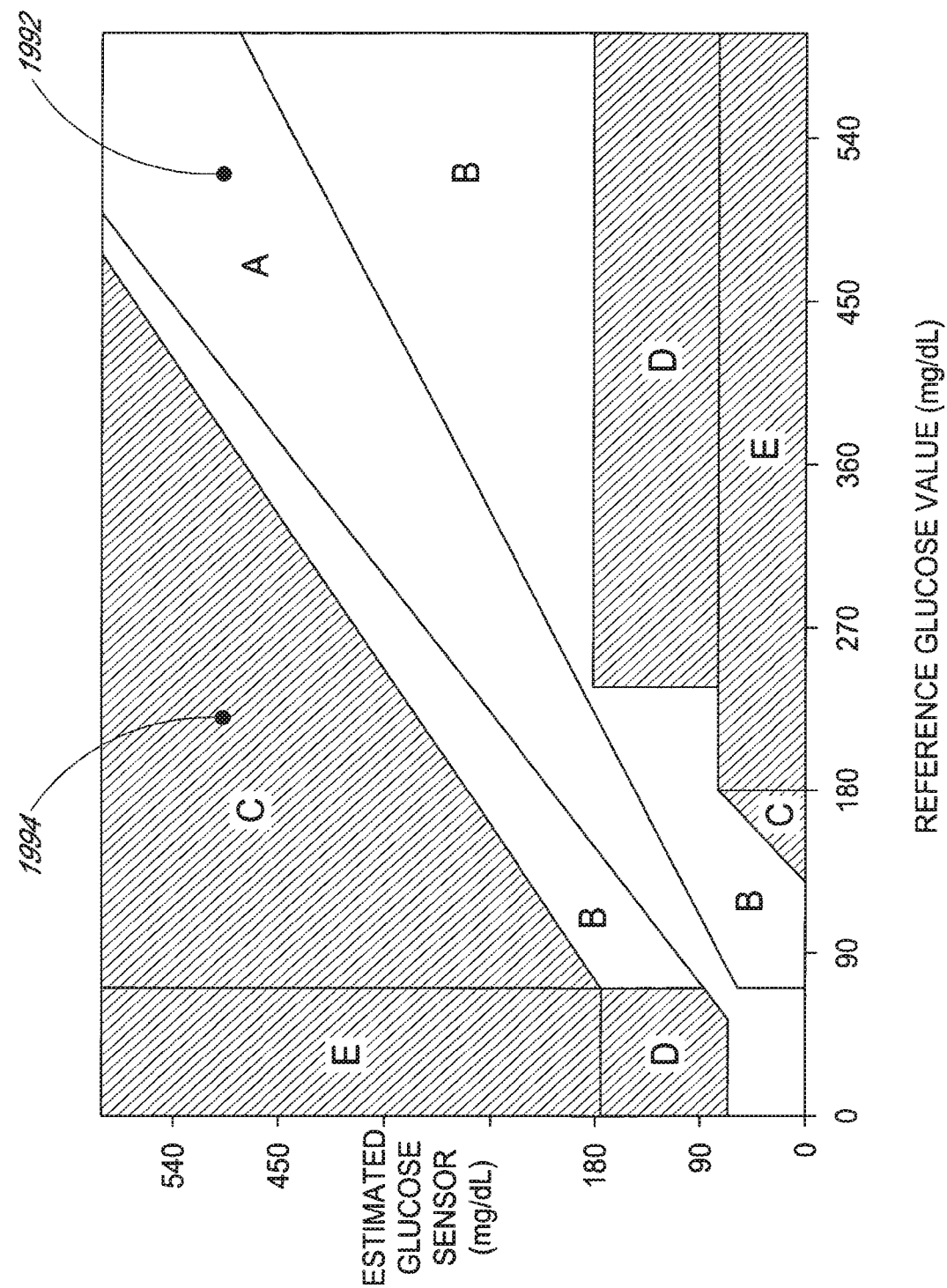
FIG. 19B is a graph of two data pairs on a Clarke Error Grid to illustrate the evaluation of clinical acceptability in one exemplary embodiment.

In one exemplary embodiment, the clinical acceptability evaluation module matches the reference data with a substantially time corresponding converted sensor value, and plots the matched data on a Clarke Error Grid. Such a Clarke Error Grid is described in more detail with reference to FIG. 19B, which is a graph of two data pairs on a Clarke Error Grid that illustrates the evaluation of clinical acceptability in one exemplary embodiment. The Clarke Error Grid can be used by the clinical acceptability evaluation module to evaluate the clinical acceptability of the disparity between a reference glucose value and a sensor glucose (e.g., estimated glucose) value, if any, in an embodiment wherein the sensor is a glucose sensor. The x-axis represents glucose reference glucose data and the y-axis represents estimated glucose sensor data. Matched data pairs are plotted accordingly to their reference and sensor values, respectively. In this embodiment, matched pairs that fall within the A and B regions of the Clarke Error Grid are considered clinically acceptable, while matched pairs that fall within the C, D, and E regions of the Clarke Error Grid are not considered clinically acceptable. Particularly, FIG. 19B shows a first matched pair 1992 is shown which falls within the A region of the Clarke Error Grid, and therefore is considered clinically acceptable. A second matched pair 1994 is shown which falls within the C region of the Clarke Error Grid, and therefore is not considered clinically acceptable.

A variety of other known methods of evaluating clinical acceptability can be utilized. In one alternative embodiment, the Consensus Grid is used to evaluate the clinical acceptability of reference and sensor data. In another alternative embodiment, a mean absolute difference calculation can be used to evaluate the clinical acceptability of the reference data. In another alternative embodiment, the clinical acceptability can be evaluated using any relevant clinical acceptability test, such as a known grid (e.g., Clarke Error or Consensus), and can include additional parameters such as time of day and/or an increasing or decreasing trend of the analyte concentration. In another alternative embodiment, a rate of change calculation can be used to evaluate clinical acceptability. In yet another alternative embodiment, wherein the reference data is received in substantially real time, the conversion function can be used to predict an estimated glucose value at a time corresponding to the time stamp of the reference analyte value (e.g. when there is a time lag of the sensor data such as described elsewhere herein). Accordingly, a threshold can be set for the predicted estimated glucose value and the reference analyte value disparity, if any.

The conventional analyte meters (e.g., self-monitored blood analyte tests) are known to have a ±20% error in analyte values. Gross errors in analyte readings are known to occur due to patient error in self-administration of the blood analyte test. For example, if the user has traces of sugar on his/her finger while obtaining a blood sample for a glucose concentration test, then the measured glucose value is likely to be much higher than the actual glucose value in the blood. Additionally, it is known that self-monitored analyte tests (e.g., test strips) are occasionally subject to manufacturing defects.

Another cause for error includes infrequency and time delay that may occur if a user does not self-test regularly, or if a user self-tests regularly but does not enter the reference value at the appropriate time or with the appropriate time stamp. Therefore, it can be advantageous to validate the acceptability of reference analyte values prior to accepting them as valid entries. Accordingly, the receiver evaluates the clinical acceptability of received reference analyte data prior to their acceptance as a valid reference value.

In one embodiment, the reference analyte data (and/or sensor analyte data) is evaluated with respect to substantially time corresponding sensor data (and/or substantially time corresponding reference analyte data) to determine the clinical acceptability of the reference analyte and/or sensor analyte data. A determination of clinical acceptability considers a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. Evaluating the clinical acceptability of reference and sensor analyte data, and controlling the user interface dependent thereon, can minimize clinical risk.

In one embodiment, the receiver evaluates clinical acceptability each time reference data is obtained. In another embodiment, the receiver evaluates clinical acceptability after the initial calibration and stabilization of the sensor. In some embodiments, the receiver evaluates clinical acceptability as an initial pre-screen of reference analyte data, for example after determining if the reference glucose measurement is from about 40 to about 400 mg/dL. In other embodiments, other methods of pre-screening data can be used, for example by determining if a reference analyte data value is physiologically feasible based on previous reference analyte data values (e.g., below a maximum rate of change).

In some embodiments, a calibration evaluation module evaluates the new matched pair(s) for selective inclusion into the calibration set. In some embodiments, the receiver simply adds the updated matched data pair into the calibration set, displaces the oldest and/or least concordant matched pair from the calibration set, and proceeds to recalculate the conversion function accordingly.

In some embodiments, the calibration evaluation includes evaluating only the new matched data pair. In some embodiments, the calibration evaluation includes evaluating all of the matched data pairs in the existing calibration set and including the new matched data pair; in such embodiments not only is the new matched data pair evaluated for inclusion (or exclusion), but additionally each of the data pairs in the calibration set are individually evaluated for inclusion (or exclusion). In some alternative embodiments, the calibration evaluation includes evaluating all possible combinations of matched data pairs from the existing calibration set and including the new matched data pair to determine which combination best meets the inclusion criteria. In some additional alternative embodiments, the calibration evaluation includes a combination of at least two of the above-described evaluation method.

Inclusion criteria include at least one criterion that defines a set of matched data pairs that form a substantially optimal calibration set. Such criteria can include any of the conditions discussed above with reference to FIG. 18A concerning methods of pre-screening or conditionally accepting reference analyte value data. One inclusion criterion involves the time stamp of the matched data pairs (that make up the calibration set) spanning at least a predetermined time period (e.g., three hours). Another inclusion criterion involves the time stamps of the matched data pairs not being more than a predetermined age (e.g., one week old). Another inclusion criterion involves the matched pairs of the calibration set having a substantially evenly distributed amount of high and low raw sensor data, estimated sensor analyte values, and/or reference analyte values. Another criterion involves all raw sensor data, estimated sensor analyte values, and/or reference analyte values being within a predetermined range (e.g., 40 to 400 mg/dL for glucose values). Another criterion involves a rate of change of the analyte concentration (e.g., from sensor data) during the time stamp of the matched pair(s). For example, sensor and reference data obtained during the time when the analyte concentration is undergoing a slow rate of change is typically less susceptible to inaccuracies caused by time lag and other physiological and non-physiological effects. Another criterion involves the congruence of respective sensor and reference data in each matched data pair; the matched pairs with the most congruence are chosen. Another criterion involves physiological changes (e.g., low oxygen due to a user's posture that may effect the function of a subcutaneously implantable analyte sensor) to ascertain a likelihood of error in the sensor value. Evaluation of calibration set criteria can involve evaluating one, some, or all of the above described inclusion criteria. It is contemplated that additional embodiments can comprise additional inclusion criteria not explicitly described herein.

In some embodiments, a quality evaluation module evaluates the quality of the calibration. In one embodiment, the quality of the calibration is based on the association of the calibration set data using statistical analysis. Statistical analysis can include any known cost function, such as linear regression, non-linear mapping/regression, rank (e.g., non-parametric) correlation, least mean square fit, mean absolute deviation (MAD), mean absolute relative difference, and the like. The result of the statistical analysis provides a measure of the association of data used in calibrating the system. A threshold of data association can be set to determine if sufficient quality is exhibited in a calibration set.

In another embodiment, the quality of the calibration is determined by evaluating the calibration set for clinical acceptability, such as, for example using a Clarke Error Grid, Consensus Grid, or clinical acceptability test. As an example, the matched data pairs that form the calibration set can be plotted on a Clarke Error Grid, such that when all matched data pairs fall within the A and B regions of the Clarke Error Grid, then the calibration is determined to be clinically acceptable.

In yet another alternative embodiment, the quality of the calibration is determined based initially on the association of the calibration set data using statistical analysis, and then by evaluating the calibration set for clinical acceptability. If the calibration set fails the statistical and/or the clinical test, the calibration processing recalculates the conversion function with a new (e.g., optimized) set of matched data pairs. In this embodiment, the processing loop iterates until the quality evaluation module: 1) determines clinical acceptability; 2) determines sufficient statistical data association; 3) determines both clinical acceptability and sufficient statistical data association; or 4) surpasses a threshold of iterations.

Calibration of analyte sensors can be variable over time; that is, the conversion function suitable for one point in time may not be suitable for another point in time (e.g., hours, days, weeks, or months later). For example, in an embodiment wherein the analyte sensor is subcutaneously implantable, the maturation of tissue ingrowth over time can cause variability in the calibration of the analyte sensor. As another example, physiological changes in the user (e.g., metabolism, interfering blood constituents, and lifestyle changes) can cause variability in the calibration of the sensor. Accordingly, a continuously updating calibration algorithm that includes reforming the calibration set, and thus recalculating the conversion function, over time according to a set of inclusion criteria is advantageous.

One cause for discrepancies in reference and sensor data is a sensitivity drift that can occur over time, when a sensor is inserted into a host and cellular invasion of the sensor begins to block transport of the analyte to the sensor, for example. Therefore, it can be advantageous to validate the acceptability of converted sensor data against reference analyte data, to determine if a drift of sensitivity has occurred and whether the calibration should be updated.

In one embodiment, the reference analyte data is evaluated with respect to substantially time corresponding converted sensor data to determine the acceptability of the matched pair. For example, clinical acceptability considers a deviation between time corresponding analyte measurements (for example, data from a glucose sensor and data from a reference glucose monitor) and the risk (for example, to the decision making of a person with diabetes) associated with that deviation based on the glucose value indicated by the sensor and/or reference data. Evaluating the clinical acceptability of reference and sensor analyte data, and controlling the user interface dependent thereon, can minimize clinical risk. Preferably, the receiver evaluates clinical acceptability each time reference data is obtained.

After initial calibration, such as is described in more detail with reference to FIG. 18, the sensor data receiving module 222 receives substantially continuous sensor data (e.g., a data stream) via a receiver and converts that data into estimated analyte values. As used herein, the term "substantially continuous" is a broad term and is used in its ordinary sense, without limitation, to refer to a data stream of individual measurements taken at time intervals (e.g., time-spaced) ranging from fractions of a second up to, e.g., 1, 2, or 5 minutes or more. As sensor data is continuously converted, it can be occasionally recalibrated in response to changes in sensor sensitivity (drift), for example. Initial calibration and re-calibration of the sensor require a reference analyte value. Accordingly, the receiver can receive reference analyte data at any time for appropriate processing.

At block 222, the reference data receiving module, also referred to as the reference input module, receives reference analyte data from a reference analyte monitor. In one embodiment, the reference data comprises one analyte value obtained from a reference monitor. In some alternative embodiments however, the reference data includes a set of analyte values entered by a user into the interface and averaged by known methods, such as are described elsewhere herein. In some alternative embodiments, the reference data comprises a plurality of analyte values obtained from another continuous analyte sensor.

The reference data can be pre-screened according to environmental and physiological issues, such as time of day, oxygen concentration, postural effects, and patient-entered environmental data. In one exemplary embodiment, wherein the sensor comprises an implantable glucose sensor, an oxygen sensor within the glucose sensor is used to determine if sufficient oxygen is being provided to successfully complete the necessary enzyme and electrochemical reactions for accurate glucose sensing. In another exemplary embodiment, the patient is prompted to enter data into the user interface, such as meal times and/or amount of exercise, which can be used to determine likelihood of acceptable reference data. In yet another exemplary embodiment, the reference data is matched with time-corresponding sensor data, which is then evaluated on a modified clinical error grid to determine its clinical acceptability.

Some evaluation data, such as described in the paragraph above, can be used to evaluate an optimum time for reference analyte measurement. Correspondingly, the user interface can then prompt the user to provide a reference data point for calibration within a given time period. Consequently, because the receiver proactively prompts the user during optimum calibration times, the likelihood of error due to environmental and physiological limitations can decrease and consistency and acceptability of the calibration can increase.

At block 224, the evaluation module, also referred to as acceptability module, evaluates newly received reference data. In one embodiment, the evaluation module evaluates the clinical acceptability of newly received reference data and time corresponding converted sensor data (new matched data pair). In one embodiment, a clinical acceptability evaluation module 224 matches the reference data with a substantially time corresponding converted sensor value, and determines the Clarke Error Grid coordinates. In this embodiment, matched pairs that fall within the A and B regions of the Clarke Error Grid are considered clinically acceptable, while matched pairs that fall within the C, D, and E regions of the Clarke Error Grid are not considered clinically acceptable.

A variety of other known methods of evaluating clinical acceptability can be utilized. In one alternative embodiment, the Consensus Grid is used to evaluate the clinical acceptability of reference and sensor data. In another alternative embodiment, a mean absolute difference calculation can be used to evaluate the clinical acceptability of the reference data. In another alternative embodiment, the clinical acceptability can be evaluated using any relevant clinical acceptability test, such as a known grid (e.g., Clarke Error or Consensus), and additional parameters, such as time of day and/or the increase or decreasing trend of the analyte concentration. In another alternative embodiment, a rate of change calculation can be used to evaluate clinical acceptability. In yet another alternative embodiment, wherein the received reference data is in substantially real time, the conversion function could be used to predict an estimated glucose value at a time corresponding to the time stamp of the reference analyte value (this can be required due to a time lag of the sensor data such as described elsewhere herein). Accordingly, a threshold can be set for the predicted estimated glucose value and the reference analyte value disparity, if any. In some alternative embodiments, the reference data is evaluated for physiological and/or statistical acceptability as described in more detail elsewhere herein.

At decision block 226, results of the evaluation are assessed. If acceptability is determined, then processing continues to block 228 to re-calculate the conversion function using the new matched data pair in the calibration set.

At block 228, the conversion function module re-creates the conversion function using the new matched data pair associated with the newly received reference data. In one embodiment, the conversion function module adds the newly received reference data (e.g., including the matched sensor data) into the calibration set, and recalculates the conversion function accordingly. In alternative embodiments, the conversion function module displaces the oldest, and/or least concordant matched data pair from the calibration set, and recalculates the conversion function accordingly.

At block 230, the sensor data transformation module uses the new conversion function (from block 228) to continually (or intermittently) convert sensor data into estimated analyte values, also referred to as calibrated data, or converted sensor data, such as is described in more detail above.

At block 232, an output module provides output to the user via the user interface. The output is representative of the estimated analyte value, which is determined by converting the sensor data into a meaningful analyte value. User output can be in the form of a numeric estimated analyte value, an indication of directional trend of analyte concentration, and/or a graphical representation of the estimated analyte data over a period of time, for example. Other representations of the estimated analyte values are also possible, for example audio and tactile.

If, however, acceptability is determined at decision block 226 as negative (unacceptable), then the processing progresses to block 234 to adjust the calibration set. In one embodiment of a calibration set adjustment, the conversion function module removes one or more oldest matched data pair(s) and recalculates the conversion function accordingly. In an alternative embodiment, the conversion function module removes the least concordant matched data pair from the calibration set, and recalculates the conversion function accordingly.

At block 236, the conversion function module re-creates the conversion function using the adjusted calibration set. While not wishing to be bound by theory, it is believed that removing the least concordant and/or oldest matched data pair(s) from the calibration set can reduce or eliminate the effects of sensor sensitivity drift over time, adjusting the conversion function to better represent the current sensitivity of the sensor.

At block 224, the evaluation module re-evaluates the acceptability of newly received reference data with time corresponding converted sensor data that has been converted using the new conversion function (block 236). The flow continues to decision block 238 to assess the results of the evaluation, such as described with reference to decision block 226, above. If acceptability is determined, then processing continues to block 230 to convert sensor data using the new conversion function and continuously display calibrated sensor data on the user interface.

If, however, acceptability is determined at decision block 226 as negative, then the processing loops back to block 234 to adjust the calibration set once again. This process can continue until the calibration set is no longer sufficient for calibration, for example, when the calibration set includes only one or no matched data pairs with which to create a conversion function. In this situation, the system can return to the initial calibration or start-up mode, which is described in more detail with reference to FIGS. 18 and 21, for example. Alternatively, the process can continue until inappropriate matched data pairs have been sufficiently purged and acceptability is positively determined.

In alternative embodiments, the acceptability is determined by a quality evaluation, for example, calibration quality can be evaluated by determining the statistical association of data that forms the calibration set, which determines the confidence associated with the conversion function used in calibration and conversion of raw sensor data into estimated analyte values. See, e.g., U.S. Publication No. US-2005-0027463-A1.

Alternatively, each matched data pair can be evaluated based on clinical or statistical acceptability such as described above; however, when a matched data pair does not pass the evaluation criteria, the system can be configured to ask for another matched data pair from the user. In this way, a secondary check can be used to determine whether the error is more likely due to the reference glucose value or to the sensor value. If the second reference glucose value substantially correlates to the first reference glucose value, it can be presumed that the reference glucose value is more accurate and the sensor values are errant. Some reasons for errancy of the sensor values include a shift in the baseline of the signal or noise on the signal due to low oxygen, for example. In such cases, the system can be configured to re-initiate calibration using the secondary reference glucose value. If, however, the reference glucose values do not substantially correlate, it can be presumed that the sensor glucose values are more accurate and the reference glucose values eliminated from the algorithm.

Figure 20:
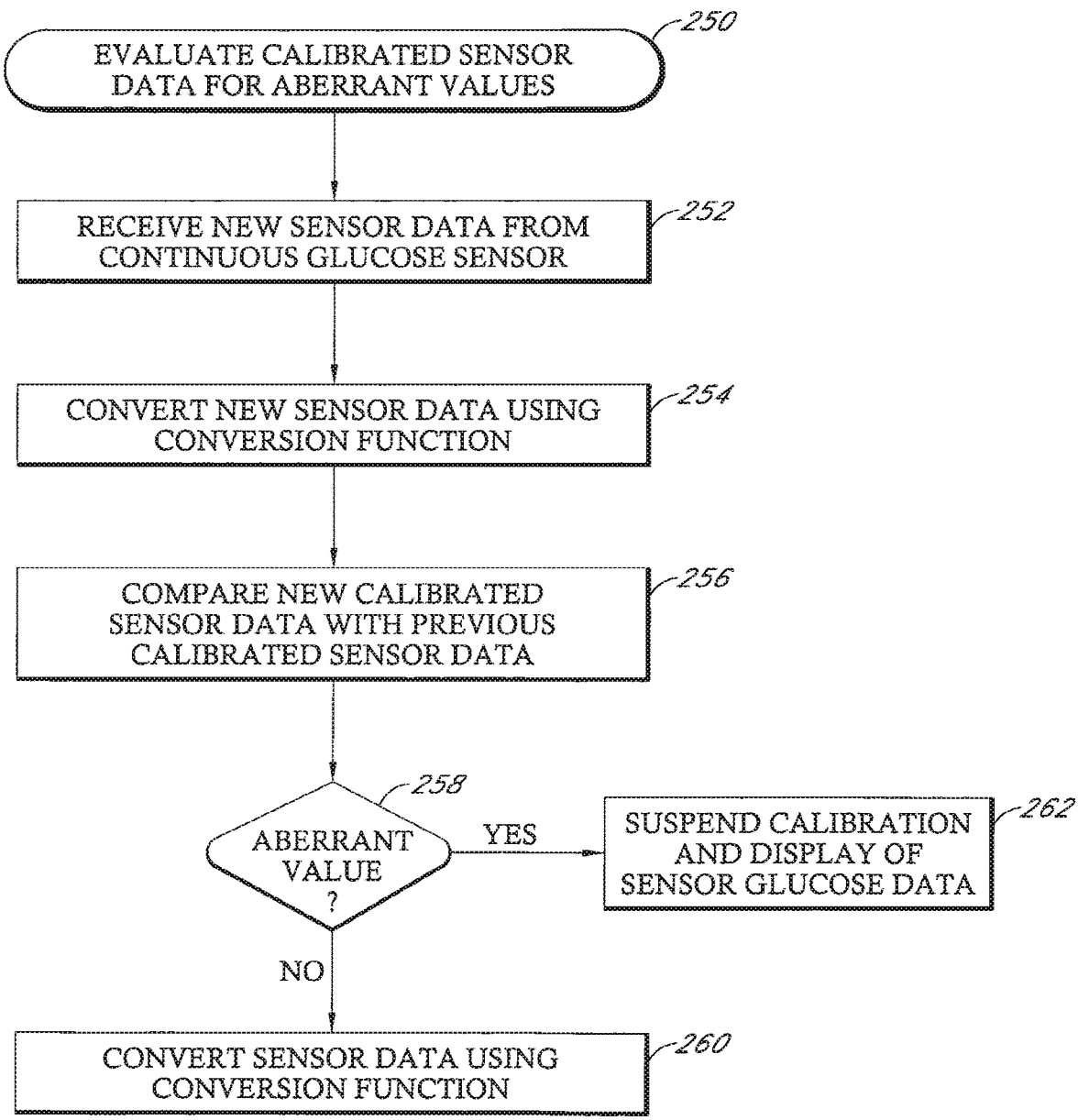
FIG. 20 is a flow chart that illustrates evaluation of calibrated sensor data for aberrant values.

FIG. 20 provides is a flow chart 250 that illustrates the evaluation of calibrated sensor data for aberrant values in one embodiment. Although sensor data are typically accurate and reliable, it can be advantageous to perform a self-diagnostic check of the calibrated sensor data prior to displaying the analyte data on the user interface.

One reason for anomalies in calibrated sensor data includes transient events, such as local ischemia at the implant site, which can temporarily cause erroneous readings caused by insufficient oxygen to react with the analyte. Accordingly, the flow chart 190 illustrates one self-diagnostic check that can be used to catch erroneous data before displaying it to the user.

At block 252, a sensor data receiving module, also referred to as the sensor data module, receives new sensor data from the sensor.

At block 254, the sensor data transformation module continuously (or intermittently) converts new sensor data into estimated analyte values, also referred to as calibrated data.

At block 256, a self-diagnostic module compares the new calibrated sensor data with previous calibrated sensor data, for example, the most recent calibrated sensor data value. In comparing the new and previous sensor data, a variety of parameters can be evaluated. In one embodiment, the rate of change and/or acceleration (or deceleration) of change of various analytes, which have known physiological limits within the body, and sensor data can be evaluated accordingly. For example, a limit can be set to determine if the new sensor data is within a physiologically feasible range, indicated by a rate of change from the previous data that is within known physiological (and/or statistical) limits. Similarly, any algorithm that predicts a future value of an analyte can be used to predict and then compare an actual value to a time corresponding predicted value to determine if the actual value falls within a statistically and/or clinically acceptable range based on the predictive algorithm, for example. In certain embodiments, identifying a disparity between predicted and measured analyte data can be used to identify a shift in signal baseline responsive to an evaluated difference between the predicted data and time-corresponding measured data. In some alternative embodiments, a shift in signal baseline and/or sensitivity can be determined by monitoring a change in the conversion function; namely, when a conversion function is re-calculated using the equation y=mx+b, a change in the values of m (sensitivity) or b (baseline) above a pre-selected "normal" threshold, can be used to trigger a fail-safe or further diagnostic evaluation.

Although the above-described self-diagnostics are generally employed with calibrated sensor data, some alternative embodiments are contemplated that check for aberrancy of consecutive sensor values prior to sensor calibration, for example, on the raw data stream and/or after filtering of the raw data stream. In certain embodiments, an intermittent or continuous signal-to-noise measurement can be evaluated to determine aberrancy of sensor data responsive to a signal-to-noise ratio above a set threshold. In certain embodiments, signal residuals (e.g., by comparing raw and filtered data) can be intermittently or continuously analyzed for noise above a set threshold. In certain embodiments, pattern recognition can be used to identify noise associated with physiological conditions, such as low oxygen (see, e.g., U.S. Publication No. US-2005-0043598-A1), or other known signal aberrancies. Accordingly, in these embodiments, the system can be configured, in response to aberrancies in the data stream, to trigger signal estimation, adaptively filter the data stream according to the aberrancy, or the like, as described in more detail in the above cited U.S. Publication No. US-2005-0043598-A1.

In another embodiment, reference analyte values are processed to determine a level of confidence, wherein reference analyte values are compared to their time-corresponding calibrated sensor values and evaluated for clinical or statistical accuracy. In yet another alternative embodiment, new and previous reference analyte data are compared in place of or in addition to sensor data. In general, there exist known patterns and limitations of analyte values that can be used to diagnose certain anomalies in raw or calibrated sensor and/or reference analyte data.

Block 193 describes additional systems and methods that can by utilized by the self-diagnostics module of the preferred embodiments.

At decision block 258, the system determines whether the comparison returned aberrant values. In one embodiment, the slope (rate of change) between the new and previous sensor data is evaluated, wherein values greater than +/−10, 15, 20, 25, or 30% or more change and/or +/−2, 3, 4, 5, 6 or more mg/dL/min, more preferably +/−4 mg/dL/min, rate of change are considered aberrant. In certain embodiments, other known physiological parameters can be used to determine aberrant values. However, a variety of comparisons and limitations can be set.

At block 260, if the values are not found to be aberrant, the sensor data transformation module continuously (or intermittently) converts received new sensor data into estimated analyte values, also referred to as calibrated data.

At block 262, if the values are found to be aberrant, the system goes into a suspended mode, also referred to as fail-safe mode in some embodiments, which is described in more detail below with reference to FIG. 21. In general, suspended mode suspends display of calibrated sensor data and/or insertion of matched data pairs into the calibration set. Preferably, the system remains in suspended mode until received sensor data is not found to be aberrant. In certain embodiments, a time limit or threshold for suspension is set, after which system and/or user interaction can be required, for example, requesting additional reference analyte data, replacement of the electronics unit, and/or reset.

In some alternative embodiments, in response to a positive determination of aberrant value(s), the system can be configured to estimate one or more glucose values for the time period during which aberrant values exist. Signal estimation generally refers to filtering, data smoothing, augmenting, projecting, and/or other methods for estimating glucose values based on historical data, for example. In one implementation of signal estimation, physiologically feasible values are calculated based on the most recent glucose data, and the aberrant values are replaced with the closest physiologically feasible glucose values. See also U.S. Publication No. US-2005-0027463-A1, U.S. Publication No. US-2005-0043598-A1, and U.S. Publication No. US-2005-0203360-A1.

Figure 21:
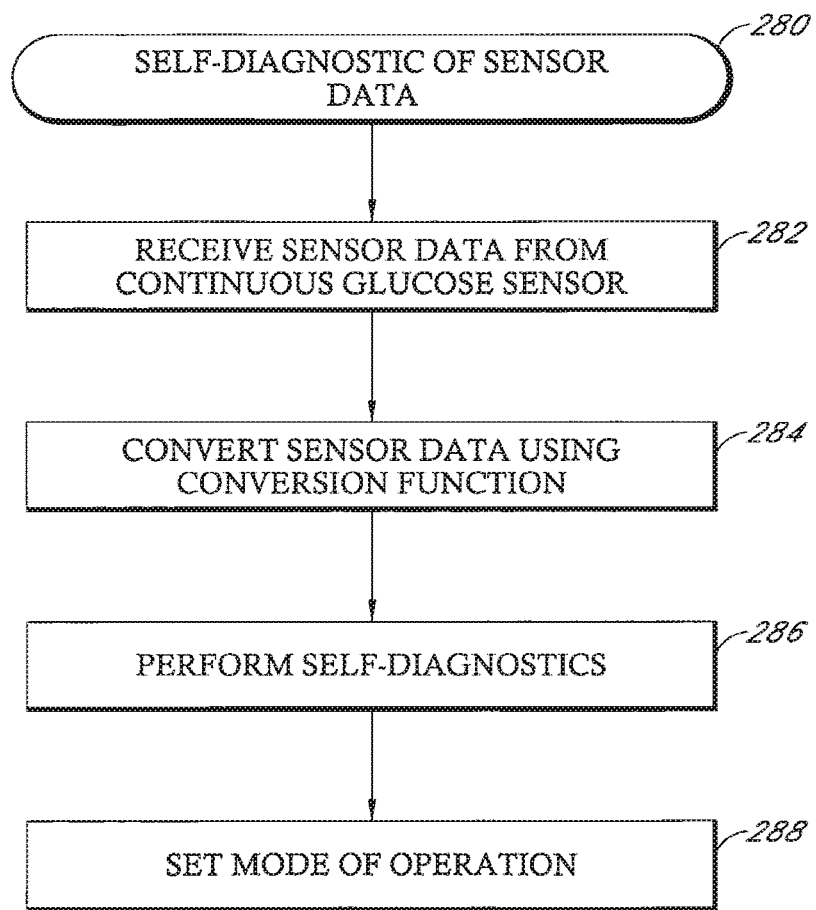
FIG. 21 is a flow chart that illustrates self-diagnostics of sensor data.

FIG. 21 provides a flow chart 280 that illustrates a self-diagnostic of sensor data in one embodiment. Although reference analyte values can useful for checking and calibrating sensor data, self-diagnostic capabilities of the sensor provide for a fail-safe for displaying sensor data with confidence and enable minimal user interaction (for example, requiring reference analyte values only as needed).

At block 282, a sensor data receiving module, also referred to as the sensor data module, receives new sensor data from the sensor.

At block 284, the sensor data transformation module continuously (or intermittently) converts received new sensor data into estimated analyte values, also referred to as calibrated data.

At block 286, a self-diagnostics module, also referred to as a fail-safe module, performs one or more calculations to determine the accuracy, reliability, and/or clinical acceptability of the sensor data. Some examples of the self-diagnostics module are described above, with reference block 256. The self-diagnostics module can be further configured to run periodically (e.g., intermittently or in response to a trigger), for example, on raw data, filtered data, calibrated data, predicted data, and the like.

In certain embodiments, the self-diagnostics module evaluates an amount of time since sensor insertion into the host, wherein a threshold is set for the sensor's usable life, after which time period the sensor is considered to be unreliable. In certain embodiments, the self-diagnostics module counts the number of times a failure or reset is required (for example, how many times the system is forced into suspended or start-up mode), wherein a count threshold is set for a predetermined time period, above which the system is considered to be unreliable. In certain embodiments, the self-diagnostics module compares newly received calibrated sensor data with previously calibrated sensor data for aberrant values, such as is described in more detail with reference to FIG. 5, above. In certain embodiments, the self-diagnostics module evaluates clinical acceptability, such as is described in more detail with reference to FIG. 20, above. In certain embodiments, diagnostics, such as are described in U.S. Publication No. US-2005-0161346-A1 and U.S. Publication No. US-2005-0143635-A1, can be incorporated into the systems of preferred embodiments for system diagnosis, for example, for identifying interfering species on the sensor signal and for identifying drifts in baseline and sensitivity of the sensor signal.

In some embodiments, an interface control module, also referred to as the fail-safe module, controls the user interface based upon the clinical acceptability of the reference data received. If the reference data is not considered clinically acceptable, then a fail-safe module begins the initial stages of fail-safe mode. In some embodiments, the initial stages of fail-safe mode include altering the user interface so that estimated sensor data is not displayed to the user. In some embodiments, the initial stages of fail-safe mode include prompting the user to repeat the reference analyte test and provide another reference analyte value. The repeated analyte value is then evaluated for clinical acceptability.

If the results of the repeated analyte test are determined to be clinically unacceptable, then the fail-safe module can alter the user interface to reflect full fail-safe mode. In one embodiment, full fail-safe mode includes discontinuing sensor analyte display output on the user interface. In other embodiments, color-coded information, trend information, directional information (e.g., arrows or angled lines), gauges, and/or other fail-safe information can be displayed, for example.

The initial stages of fail-safe mode and full fail safe mode can include user interface control, for example. Additionally, it is contemplated herein that a variety of different modes between initial and full fail-safe mode can be provided, depending on the relative quality of the calibration. In other words, the confidence level of the calibration quality can control a plurality of different user interface screens providing error bars, ±values, and the like. Similar screens can be implemented in various clinical acceptability embodiments.

At block 288 of FIG. 21, a mode determination module, which can be a part of the sensor evaluation module 224, determines in which mode the sensor is set (or remains in). In some embodiments, the system is programmed with three modes: 1) start-up mode; 2) normal mode; and 3) suspended mode. Although three modes are described herein, the preferred embodiments are not limited to the number or types of modes with which the system can be programmed. In some embodiments, the system is defined as "in-cal" (in calibration) in normal mode; otherwise, the system is defined as "out-of-cal' (out of calibration) in start-up and suspended mode. The terms as used herein are meant to describe the functionality and are not limiting in their definitions.

Preferably, a start-up mode is provided wherein the start-up mode is set when the system determines that it can no longer remain in suspended or normal mode (for example, due to problems detected by the self-diagnostics module, such as described in more detail above) and/or when the system is notified that a new sensor has been inserted. Upon initialization of start-up mode, the system ensures that any old matched data pairs and/or calibration information is purged. In start-up mode, the system initializes the calibration set, such as is described in more detail with reference to FIG. 14, above. Once the calibration set has been initialized, sensor data is ready for conversion and the system is set to normal mode.

Preferably, a normal mode is provided wherein the normal mode is set when the system is accurately and reliably converting sensor data, for example, wherein clinical acceptability is positively determined, aberrant values are negatively determined, and/or the self-diagnostics modules confirms reliability of data. In normal mode, the system continuously (or intermittently) converts (or calibrates) sensor data. Additionally, reference analyte values received by the system are matched with sensor data points and added to the calibration set.

In certain embodiments, the calibration set is limited to a predetermined number of matched data pairs, after which the systems purges old or less desirable matched data pairs when a new matched data pair is added to the calibration set. Less desirable matched data pairs can be determined by inclusion criteria, which include one or more criteria that define a set of matched data pairs that form a substantially optimal calibration set.

Unfortunately, some circumstances can exist wherein a system in normal mode is changed to start-up or suspended mode. In general, the system is programmed to change to suspended mode when a failure of clinical acceptability, aberrant value check, and/or other self-diagnostic evaluation is determined, such as described in more detail above, and wherein the system requires further processing to determine whether a system re-start is required (e.g., start-up mode). In general, the system changes to start-up mode when the system is unable to resolve itself in suspended mode and/or when the system detects that a new sensor has been inserted (e.g., via system trigger or user input).

Preferably, a suspended mode is provided wherein the suspended mode is set when a failure of clinical acceptability, aberrant value check, and/or other self-diagnostic evaluation determines unreliability of sensor data. In certain embodiments, the system enters suspended mode when a predetermined time period passes without receiving a reference analyte value. In suspended mode, the calibration set is not updated with new matched data pairs, and sensor data can optionally be converted, but not displayed on the user interface. The system can be changed to normal mode upon resolution of a problem (positive evaluation of sensor reliability from the self-diagnostics module, for example). The system can be changed to start-up mode when the system is unable to resolve itself in suspended mode and/or when the system detects a new sensor has been inserted (via system trigger or user input).

The systems of preferred embodiments, including a transcutaneous analyte sensor, mounting unit, electronics unit, applicator, and receiver for inserting the sensor, and measuring, processing, and displaying sensor data, provide improved convenience and accuracy because of their designed stability within the host's tissue with minimum invasive trauma, while providing a discreet and reliable data processing and display, thereby increasing overall host comfort, confidence, safety, and convenience. Namely, the geometric configuration, sizing, and material of the sensor of the preferred embodiments enable the manufacture and use of an atraumatic device for continuous measurement of analytes, in contrast to conventional continuous glucose sensors available to persons with diabetes, for example. Additionally, the sensor systems of preferred embodiments provide a comfortable and reliable system for inserting a sensor and measuring an analyte level for up to 30 days or more without surgery. The sensor systems of the preferred embodiments are designed for host comfort, with chemical and mechanical stability that provides measurement accuracy. Furthermore, the mounting unit is designed with a miniaturized and reusable electronics unit that maintains a low profile during use. The usable life of the sensor can be extended by incorporation of a bioactive agent into the sensor that provides local release of an anti-inflammatory, for example, in order to slow the subcutaneous foreign body response to the sensor.

After the usable life of the sensor (for example, due to a predetermined expiration, potential infection, or level of inflammation), the host can remove the transcutaneous sensor and mounting from the skin, and dispose of the sensor and mounting unit (preferably saving the electronics unit for reuse). Another transcutaneous sensor system can be inserted with the reusable electronics unit and thus provide continuous sensor output for long periods of time.

EXAMPLES

Figure 22A:
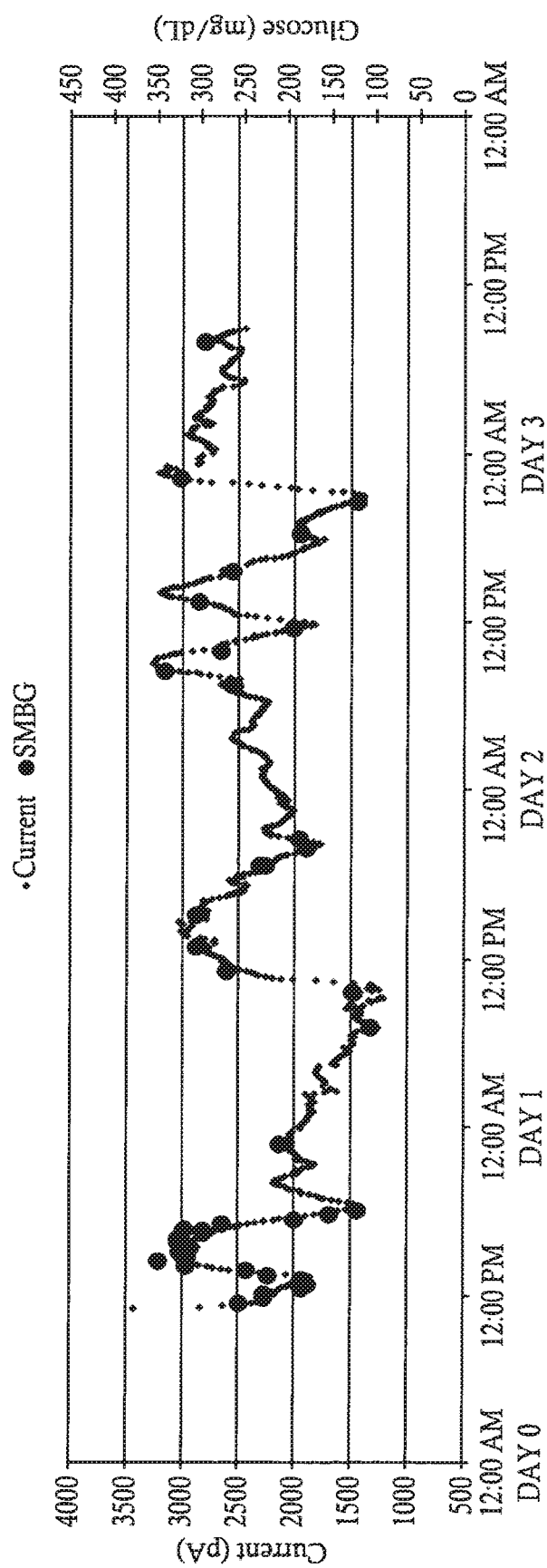
FIGS. 22A and 22B are graphical representations of glucose sensor data in a human obtained over approximately three days.

FIG. 22A is a graphical representation showing transcutaneous glucose sensor data and corresponding blood glucose values over time in a human. The x-axis represents time, the first y-axis represents current in picoAmps, and the second y-axis represents blood glucose in mg/dL. As depicted on the legend, the small diamond points represent the current measured from the working electrode of a transcutaneous glucose sensor of a preferred embodiment; while the larger points represent blood glucose values of blood withdrawn from a finger stick and analyzed using an in vitro self-monitoring blood glucose meter (SMBG).

A transcutaneous glucose sensor was built according to the preferred embodiments and implanted in a human host where it remained over a period of time. Namely, the sensor was built by providing a platinum wire, vapor-depositing the platinum with Parylene to form an insulating coating, helically winding a silver wire around the insulated platinum wire (to form a "twisted pair"), masking sections of the electroactive surface of the silver wire, vapor-depositing Parylene on the twisted pair, chloridizing the silver electrode to form silver chloride reference electrode, and removing a radial window on the insulated platinum wire to expose a circumferential electroactive working electrode surface area thereon, this assembly also referred to as a "parylene-coated twisted pair assembly."

An interference domain was formed on the parylene-coated twisted pair assembly by dip coating in an interference domain solution (7 weight percent of a 50,000 molecular weight cellulose acetate (Sigma-Aldrich, St. Louis, Mo.) in a 2:1 acetone/ethanol solvent solution), followed by drying at room temperature for 3 minutes. This interference domain solution dip coating step was repeated two more times to form an interference domain comprised of 3 layers of cellulose acetate on the assembly. The dip length (insertion depth) was adjusted to ensure that the cellulose acetate covered from the tip of the working electrode, over the exposed electroactive working electrode window, to cover a distal portion of the exposed electroactive reference electrode.

An enzyme domain was formed over the interference domain by subsequently dip coating the assembly in an enzyme domain solution and drying in a vacuum oven for 20 minutes at 50° C. This dip coating process was repeated once more to form an enzyme domain having two layers. A resistance domain was formed over the interference domain by subsequently spray coating the assembly with a resistance domain solution and drying the assembly in a vacuum oven for 60 minutes at 50° C. Additionally, the sensors were exposed to electron beam radiation at a dose of 25 kGy, while others (control sensors) were not exposed to electron beam radiation.

The graph of FIG. 22A illustrates approximately 3 days of data obtained by the electronics unit operably connected to the sensor implanted in the human host. Finger-prick blood samples were taken periodically and glucose concentration measured by a blood glucose meter (SMBG). The graphs show the subcutaneous sensor data obtained by the transcutaneous glucose sensor tracking glucose concentration as it rose and fell over time. The time-corresponding blood glucose values show the correlation of the sensor data to the blood glucose data, indicating appropriate tracking of glucose concentration over time.

The raw data signal obtained from the sensor electronics has a current measurement in the picoAmp range. Namely, for every unit (mg/dL) of glucose, approximately 3.5 pA or less to 7.5 pA or more current is measured. Generally, the approximately 3.5 to 7.5 pA/mg/dL sensitivity exhibited by the device can be attributed to a variety of design factors, including resistance of the membrane system to glucose, amount of enzyme in the membrane system, surface area of the working electrode, and electronic circuitry design. Accordingly, a current in the picoAmp range enables operation of an analyte sensor that: 1) requires (or utilizes) less enzyme (e.g., because the membrane system is highly resistive and allows less glucose through for reaction in the enzyme domain); 2) requires less oxygen (e.g., because less reaction of glucose in the enzyme domain requires less oxygen as a co-reactant) and therefore performs better during transient ischemia of the subcutaneous tissue; and 3) accurately measures glucose even in hypoglycemic ranges (e.g., because the electronic circuitry is able to measure very small amounts of glucose (hydrogen peroxide at the working electrode)). Advantageously, the analyte sensors of the preferred embodiments exhibit improved performance over convention analyte sensors at least in part because a current in the picoAmp range enables operation in conditions of less enzyme, and less oxygen, better resolution, lower power usage, and therefore better performance in the hypoglycemic range wherein lower mg/dL values conventionally have yielded lower accuracy.

Figure 22B:
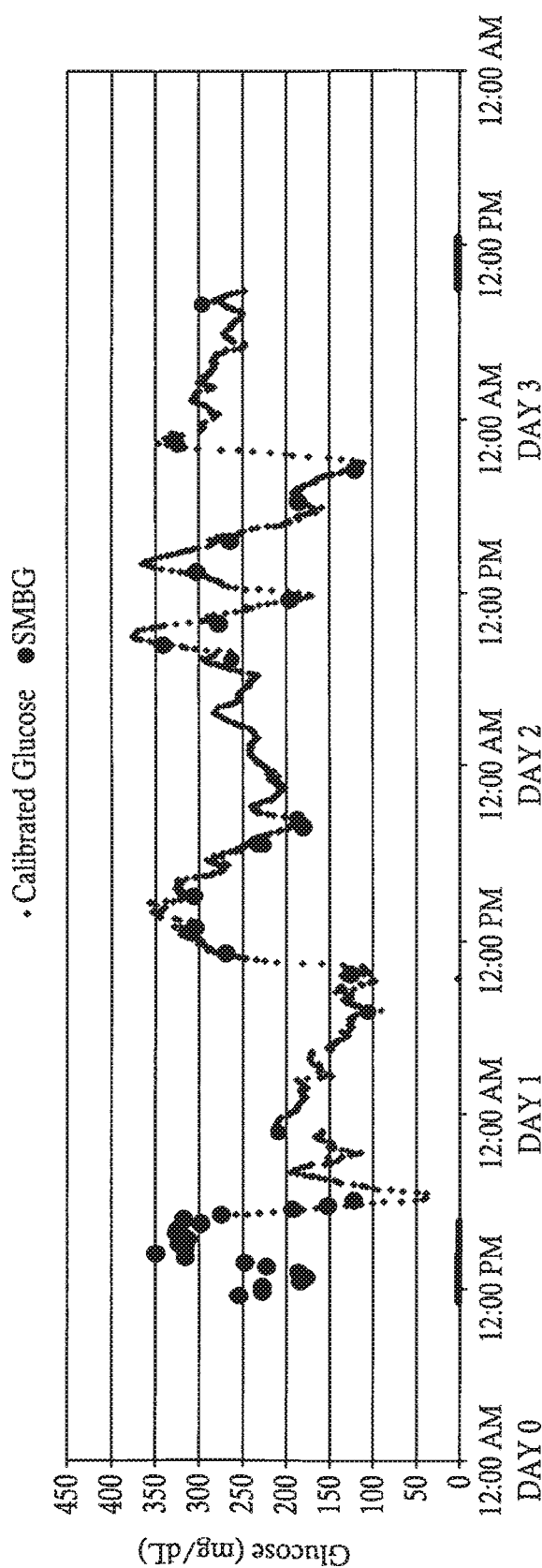

FIG. 22B is a graphical representation showing transcutaneous glucose sensor data and corresponding blood glucose values over time in a human. The x-axis represents time; the y-axis represents glucose concentration in mg/dL. As depicted on the legend, the small diamond points represent the calibrated glucose data measured from a transcutaneous glucose sensor of a preferred embodiment; while the larger points represent blood glucose values of blood withdrawn from a finger stick and analyzed using an in vitro self-monitoring blood glucose meter (SMBG). The calibrated glucose data corresponds to the data of FIG. 22A shown in current, except it has been calibrated using algorithms of the preferred embodiments. Accordingly, accurate subcutaneous measurement of glucose concentration has been measured and processed using the systems and methods of the preferred embodiments.

Figure 23A:
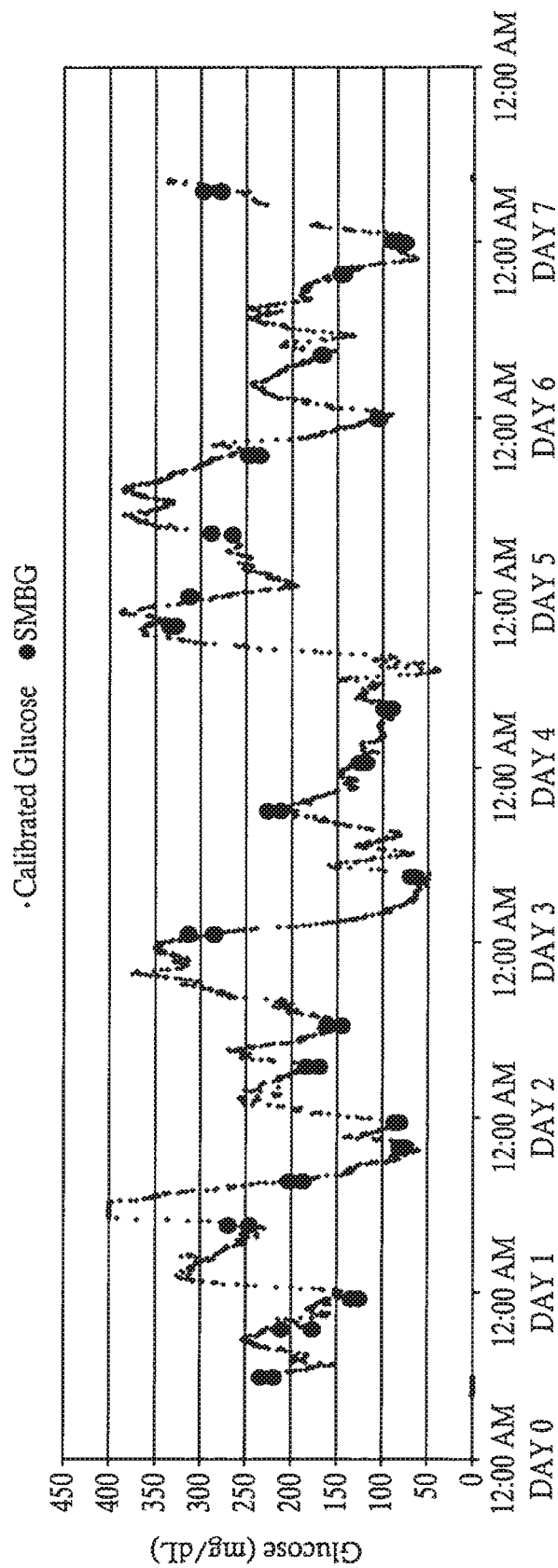
FIG. 23A is a graphical representation of glucose sensor data in a human obtained over approximately seven days.

FIG. 23A is a graphical representation showing transcutaneous glucose sensor data and corresponding blood glucose values obtained over approximately seven days in a human. The x-axis represents time; the y-axis represents glucose concentration in mg/dL. As depicted on the legend, the small diamond points represent the calibrated glucose data measured from a transcutaneous glucose sensor of a preferred embodiment; while the larger points represent blood glucose values of blood withdrawn from a finger stick and analyzed using an in vitro self-monitoring blood glucose meter (SMBG). The calibrated glucose data corresponds to a sensor that was implanted in a human for approximately seven days, showing an extended functional life, as compare to three days, for example.

Differentiation of Sensor Systems

Some embodiments provide sensor systems suitable for implantation for 1, 3, 5, 7, 10, 15, 20, 25, or 30 days or more. Alternatively, sensors designed for shorter or longer durations can have one or more specific design features (e.g., membrane systems, bioactive agent(s), architecture, electronic design, power source, software, or the like) customized for the intended sensor life. Similarly, some embodiments provide sensor systems suitable for a variety of uses such as pediatrics, adults, geriatrics, persons with type-1 diabetes, persons with type-2 diabetes, intensive care (ICU), hospital use, home use, rugged wear, everyday wear, exercise, and the like, wherein the sensor systems include particular design features (e.g., membrane systems, bioactive agent(s), architecture, electronic design, power source, software, or the like) customized for an intended use. Accordingly, it can be advantageous to differentiate sensor systems that are substantially similar, for example, sensors wherein the electronics unit of a sensor system can releasably mate with different mounting units, or sensors wherein different electronics units designed for different functionality can mate with a specific mounting unit.

In some embodiments, the mechanical, electrical, and/or software design enables the differentiation (e.g., non-interchangeability) of these different sensor systems. In other words, the sensor systems can be "keyed" to ensure a proper match between an electronics unit and a mounting unit (housing including sensor) as described herein. The terms "key" and "keyed" as used herein are broad terms and are used in their ordinary sense, including, without limitation, to refer to systems and methods that control the operable connection or operable communication between the sensor, its associated electronics, the receiver, and/or its associated electronics. The terms are broad enough to include mechanical, electrical, and software "keys." For example, a mechanically designed key can include a mechanical design that allows an operable connection between two parts, for example, a mating between the electronics unit and the mounting unit wherein the contacts are keyed to mutually engage contacts of complementary parts. As another example, an electronically designed key can be embedded in a radio frequency identification chip (RFID chip) on the mounting unit, wherein the electronics unit is programmed to identify a predetermined identification number (e.g., key) from the RFID chip prior to operable connection or communication between the sensor and/or sensor electronics. Alternatively, the sensor's packaging can include an RFID chip with the key embedded therein and configured to provide key information to the electronics unit and/or receiver. As yet another example, a software key can include a code or serial number that identifies a sensor and/or electronics unit.

Accordingly, systems and methods are provided for measuring an analyte in a host, including: a sensor configured for transcutaneous insertion into a host's tissue; a housing adapted for placement external to the host's tissue and for supporting the sensor; and an electronics unit releasably attachable to said housing, wherein at least one of the housing and the electronics unit are keyed to provide a match between the sensor and the electronics unit.

In some embodiments, the housing (including a sensor) and its matching electronics unit(s) are keyed by a configuration of the one or more contacts thereon. FIGS. 4A to 4C illustrate three unique contact configurations, wherein the configurations are differentiated by a distance between the first and second contacts located within the housing. In this embodiment, a properly keyed electronics unit is configured with contacts that mate with the contacts on a mating housing (FIGS. 4A to 4C), for example a narrow contact configuration on a housing mates only with a narrow contact configuration on an electronics unit. Accordingly, in practice, only an electronics unit comprising a contact configuration that is designed for mutual engagement with a similarly "keyed" housing can be operably connected thereto.

In some embodiments, the electronics unit is programmed with an ID, hereinafter referred to as a "transmitter ID," that uniquely identifies a sensor system. In one exemplary embodiment, wherein a first sensor system is designed for 3 day use and a second sensor system is designed for 7 day use, the transmitter ID can be programmed to begin with a "3" or a "7" in order to differentiate the sensor systems. In practice, a 3 day sensor system is programmed for 3 day use (see enforcement of sensor expiration described in more detail below), and thus upon operable connection of a 3 day sensor system, the receiver can function for the appropriate duration according to the transmitter ID.

In some embodiments, each sensor system is associated with a unique or near-unique serial number, which is associated with one or a set of sensor systems. This serial number can include information such as intended duration, calibration information, and the like, so that upon sensor insertion, and operable connection of the sensor electronics, the serial number can be manually entered into the receiver (from the packaging, for example) or can be automatically transmitted from the sensor's electronics unit. In this way, the serial number can provide the necessary information to enable the sensor system to function for the intended duration.

Additionally or alternatively, the electronics unit and/or mounting unit can be labeled or coded, for example, alphanumerically, pictorially, or colorfully, to differentiate unique sensor systems. In this way, a user is less likely to confuse different sensor systems.

Enforcement of Sensor Expiration (Duration of Sensor Life)

In some embodiments, sensor systems are packaged as starter sets, which include at least one reusable (durable) receiver, at least one reusable (durable) electronics unit and one or more single-use sensors, each including an applicator and a mounting unit with the sensor. In some alternative embodiments, the electronics unit is designed for single-use and can optionally be integrally formed with the sensor and/or mounting unit. Preferably, a single receiver, and in some embodiments a single electronics unit, is configured for use (e.g., reusable) with a plurality of sensors. Additionally, single-use sensors can be packaged individually or as sets (e.g., 5-, 10-, or 15 sensor systems per package (e.g., sensor refill packs)). Preferably, each sensor is configured for a predetermined duration (e.g., 3-, 5-, 7-, 10-, 15-, 20-, 25-, or 30 days or more of operation). In alternative embodiments, the electronics unit can be configured for single-use; for example, the electronics unit may be integral with the sensor (e.g., mounting unit with sensor) described with this embodiment. Additionally, the applicator can be coupled to the mounting unit prior to packaging or configured to be coupled by the user prior to insertion.

Because in some embodiments, the receiver is intended to be reused with a plurality of sensor systems, which sensor systems are configured for a predetermined duration, systems and methods for enforcing the prescribed use of each sensor system can be advantageous to ensure that the user removes and reinserts the sensor systems within prescribed time periods. Accordingly, systems and methods are provided for limiting the use of each sensor system to its predetermined duration.

In general, transcutaneous sensor systems can be designed for a predetermined (prescribed) amount of time (e.g., a few hours to 30 days or more). Some embodiments provide sensors suitable for 1-, 3-, 5-, 7-, 10-, 15-, 20-, 25-, or 30 days or more of operation. One potential problem that can occur in practice is the continued use of the sensor beyond its intended life; for example, a host may not remove the sensor after its intended life and/or the host can detach and reattach the electronics unit into the mounting unit (which may cause a refresh of the sensor system and/or use beyond its intended life in some circumstances). Accordingly, systems and methods are needed for ensuring the sensor system is used for its proper duration and that accidental or intentional efforts to improperly extend or reuse the sensor system are avoided.

The preferred embodiments provide systems and methods for measuring an analyte in a host, the system including: a sensor adapted for transcutaneous insertion through the skin of a host; a housing adapted for placement adjacent to the host's skin and for supporting the sensor upon insertion through the skin; and an electronics unit operably connected to the housing, wherein the sensor system is configured to prevent use of the sensor (e.g., to render the sensor inoperative or disable display of sensor data) beyond a predetermined time period.

In some embodiments, the sensor system is configured to destroy the sensor when the electronics unit is removed and/or after a predetermined time period has expired. In one exemplary embodiment, a loop of material surrounds a portion of the sensor and is configured to retract the sensor (from the host) when the electronics unit is removed from the housing. In another embodiment, the sensor system is configured to cut, crimp, or otherwise destroy the sensor when the electronics unit is removed from the housing.

In some embodiments, the sensor system is programmed to determine whether to allow an initialization of a new sensor. For example, the receiver can be programmed to require the sensor be disconnected prior to initiation of the receiver for an additional sensor system. In one such exemplary embodiment, the receiver can be programmed to look for a zero from the electronics unit, indicating the sensor has been disconnected, prior to allowing a new sensor to be initiated. This can help to ensure that a user actually removes the electronics unit (and/or sensor) prior to initialization of a new sensor. In another such embodiment, sensor insertion information can be programmed into the sensor electronics, such that the sensor insertion information is transmitted to the receiver to allow initialization of a new sensor.

In some embodiments, the receiver software receives information from the electronics unit (e.g., intended duration, transmitter ID, expiration date, serial code, manufacture date, or the like) and is programmed to automatically shut down after a predetermined time period (intended duration) or sensor expiration, for example.

In some embodiments, the receiver is programmed to algorithmically identify a new sensor insertion by looking for change in signal characteristic (e.g., a spike indicating break-in period, no change in sensor count values during the first hour, or the like). If a user has not inserted a new sensor, then the continued use of an expired sensor can be detected and can be used to trigger a shut down of the sensor and/or receiver.

In some embodiments, each sensor system is associated with a unique or near-unique serial number, which is associated with one or a set of sensor systems as described in more detail above. In general, the serial number can include information such as calibration information, intended duration, manufacture date, expiration date, and the like. For example, the serial number can provide sensor life (intended duration) information, which can be used to shut down the sensor and/or receiver (e.g., display of sensor data and/or use of the sensor) after the intended sensor life.

In some embodiments, one or a set of sensors are packaged such that a serial number, which is associated with the one sensor and/or the set of sensors, also referred to as a key or license code, is provided to enable the use of the sensor system. In preferred embodiments, the license code includes one or more of the following: a unique number, a receiver ID, a sensor duration, and a number of sensors for which the license code is enabled. The unique number preferably includes an auto-generated number that increments each time a license is issued. However, one skilled in the art will appreciate that a variety of unique numbering techniques can be utilized; the unique number is designed to reduce or eliminate fraud, such as reuse of a license code. The receiver ID (receiver identification) preferably includes a unique number associated with an individual receiver, which ensures that the license code is used with a particular receiver. The sensor duration preferably includes a predetermined time period for which the sensor use is prescribed (e.g., sensor life such as 1-, 3-, 5-, 7-, 10-, 15-, 20-, 25-, or 30 days or more) after which the sensor is disabled. The number of sensor systems for which the license code is enabled preferably includes a number that represents how many sensor insertions (e.g., number of sensor initializations or how many iterations of the sensor duration) are allowed using the unique license code; in some embodiments, this is the number of sensors provided in a packaged set of sensors.

The license code is designed to be input, either manually or automatically, into the sensor system (e.g., receiver or on-skin device), after which the sensor system (e.g., receiver or on-skin device) controls the display of sensor data. In one embodiment, a user is instructed to obtain a license code and manually enter the code into the receiver. In one alternative embodiment, a sensor system (e.g., packaging, single-use portion of the sensor, mounting unit and/or electronics unit) includes an embedded license code, for example, within an embedded RFID chip. In one exemplary embodiment, the RFID chip is configured to transmit the license code information to the receiver (e.g., when requested by the receiver).

Preferably, the license code is configured control the amount of time over which information is obtained from the sensor. The phrase "information . . . obtained from the sensor" can refer without limitation to any sensor information obtained, including measured, processed, transmitted and/or displayed in any manner including: measurement of the analyte information (e.g., glucose concentration) by the sensor, digitalizing of the sensor information (e.g., raw or filtered data) by the electronics unit, transmission of the sensor information (e.g., sensor data) from the electronics unit, receiving of the sensor information by the receiver, storing or processing of the sensor information by the receiver, and/or displaying of the sensor information by the receiver or other device. Accordingly, when the licensed (or prescribed) sensor duration and/or number of sensor insertions has been met, the receiver is configured to disable the "obtaining of information" (e.g., disabling display of the sensor data and/or any other method such as described above). In some embodiments, the sensor can continue to collect and store data after the sensor system has disabled "obtaining of information." Additionally or alternatively, the prescribed sensor duration can be enforced using any of the mechanical (e.g., destruction of the sensor), electrical, or software techniques described elsewhere herein and as will be appreciated by one skilled in the art.

The above described systems and methods for differentiating sensor systems and enforcing sensor lifetimes can be used alone or in combination, and can be combined with any of the preferred embodiments.

Figure 23B:
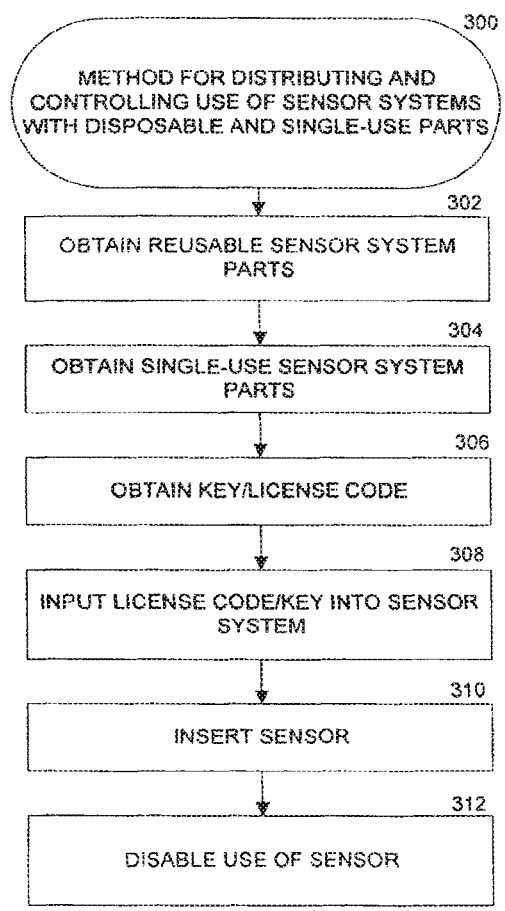
FIG. 23B is a flow chart that illustrates a method for distributing and controlling use of sensor systems with disposable and single-use parts.

Distributing and Controlling Use of Sensor Systems Including Single-Use (Disposable) and Reusable (Durable) Parts FIG. 23B is a flow diagram that illustrates a method for distributing and controlling use of sensor systems including disposable and reusable parts 300 in one embodiment.

At block 302, a user (doctor, patient, or other care provider) obtains reusable sensor system parts. Preferably sensor system is distributed with a starter pack including at least one of each reusable part. In general, the reusable sensor parts include at least the receiver, whereby a plurality of single-use sensors can be used with the receiver. In some embodiments the electronics unit is also reusable as shown and described in the illustrated embodiments; however, the sensor electronics can be integral with the single-use mounting unit/sensor in some embodiments as described elsewhere herein.

At block 304, the user obtains single-use sensor system parts. In some embodiments, the starter pack described above further includes one or more single-use sensors. Additionally or alternatively, one or a plurality of single-use sensors are packaged together.

At block 306, the user obtains a key, also referred to as a license code, configured to enable predefined (prescribed) use of the sensor system as described in more detail elsewhere herein. In some embodiments, the key is provided on or in the packaging. In some embodiments, the key is obtained by contacting the distributor electronically (e.g., via the Internet or e-mail), via telephone, written communication, or other communications protocol. In some embodiments, the key is embedded in a chip (e.g., RFID) on the single-use device or packaging. Although a few methods for obtaining a license key are described herein, numerous other methods for providing a key are possible as is appreciated by one skilled in the art.

At block 308, the key is input into the sensor system, for example, into the receiver. In some embodiments, the key is provided to the user via paper or other communication from the distributor, the key is input manually using buttons on the receiver, for example. In some alternative embodiments, the key is transmitted from a chip, for example, an RFID chip embedded in the single-use sensor and/or packaging associated with the single use device. Other methods for inputting the key are possible as is appreciated by one skilled in the art.

At block 310, the sensor is inserted into the user, as described in more detail elsewhere herein and/or as is known in the art. See also U.S. Pat. Nos. 6,974,437; 6,892,085; 6,809,507; 6,689,056; 6,666,821; 6,520,326; 6,512,939; 6,261,280; 6,572,542; 6,284,478; 6,565,509; 6,175,752; 6,329,161; 6,695,860; and 6,613,379. In some embodiments, the sensor is inserted into the host prior to inputting the license code into the receiver. Generally, it is preferred that the user be required to input the license code into the sensor system prior to obtaining information (i.e., sensor data) from the sensor.

At block 312, the sensor measures and displays the host's analyte values for the predetermined time period. As described in more detail elsewhere herein, the sensor is generally designed for a particular duration of use, for example a 3 day sensor is designed for a duration of 3 days. Some sensors may be designed for longer or shorter durations.

At block 314, the sensor system is disabled. Preferably, the disabling of the sensor includes at least discontinuing the display of sensor data. By discontinuing the display of sensor data, a host will be encouraged to remove the sensor at the appropriate time. However, further mechanical and software designs to disable the use of the device, such as destroying the sensor and shutting down all electronics can also be employed, as are described in more detail elsewhere herein. By utilizing the method of distributing and controlling use of sensor systems including disposable and reusable parts described herein, patients are more likely to use the sensor systems in a manner consistent with physician and/or prescriptive use.

EXAMPLES

The following examples serve to illustrate certain preferred embodiments and aspects and are not to be construed as limiting the scope thereof.

Transcutaneous Glucose Sensor with Cellulose Acetate Interference Domain

A short term (transcutaneous) sensor was built by providing a platinum wire, vapor-depositing the platinum with Parylene to form an insulating coating, helically winding a silver wire around the insulated platinum wire (to form a "twisted pair"), masking sections of electroactive surface of the silver wire, vapor-depositing Parylene on the twisted pair, chloridizing the silver electrode to form silver chloride reference electrode, and removing a radial window on the insulated platinum wire to expose a circumferential electroactive working electrode surface area thereon, this assembly also referred to as a "parylene-coated twisted pair assembly."

An interference domain was formed on the parylene-coated twisted pair assembly by dip coating in an interference domain solution comprising 7 weight percent, 50,000 molecular weight cellulose acetate (Sigma-Aldrich, St. Louis, Mo.) in a 2:1 acetone/ethanol solvent solution, followed by drying at room temperature for three minutes. This interference domain solution dip coating step was repeated three more times to form an interference domain comprised of four layers of cellulose acetate on the assembly. The dip length (insertion depth) was adjusted to ensure that the cellulose acetate covered from the tip of the working electrode, over the exposed electroactive working electrode window, to cover a distal portion of the exposed electroactive reference electrode.

An enzyme domain was formed over the interference domain by subsequently dip coating the assembly in an enzyme domain solution and drying in a vacuum oven for 20 minutes at 50° C. This dip coating process was repeated once more to form an enzyme domain comprised of two layers. A resistance domain was formed over the enzyme domain by subsequently spray coating the assembly with a resistance domain solution and dried in a vacuum oven for 60 minutes at 50° C. Both the enzyme domain and the resistance domain were formed as described in more detail in U.S. Publication No. US-2006-0020187-A1.

Additionally, selected sensors (test sensors) were exposed to electron beam radiation at a dose of 25 kGy, while others (control sensors) were not exposed to electron beam radiation.

Transcutaneous Glucose Sensor with Cellulose Acetate/Nafion® Interference Domain Transcutaneous glucose sensors with a cellulose acetate/Nafion® interference domain (CA/Naf sensors) were constructed as described with reference to the transcutaneous glucose sensors with a cellulose acetate interference domain above; however, after dip coating the parylene-coated twisted pair assembly in the cellulose acetate solution, the cellulose acetate coated assembly was further dip coated in a 5 weight percent Nafion® solution in low aliphatic alcohols (Sigma-Aldrich, St. Louis, Mo.) and allowed to dry at room temperature for 10 minutes. This Nafion® solution dip coating step was repeated twice to form three layers of Nafion® over the cellulose acetate layers. Enzyme and resistance domains were subsequently coated onto the cellulose acetate/Nafion® interference domain coated assembly, and selected test sensors were exposed to electron beam radiation, as described in more detail above.

In Vitro Testing

In vitro tests were run to evaluate the ability of the above-described sensors to resist uric acid, ascorbic acid, and acetaminophen. Namely, four CA sensors (two before and two after electron beam exposure) were immersed in 40, 200, and 400 mg/dL glucose while their electrical signal was monitored. Subsequently, the sensors were immersed into a solution containing 400 mg/dL glucose plus one of either 0.5 mM uric acid (FIG. 24A), 0.23 mM ascorbic acid (FIG. 24B), or 0.22 mM acetaminophen (FIG. 24C).

Figure 24A:
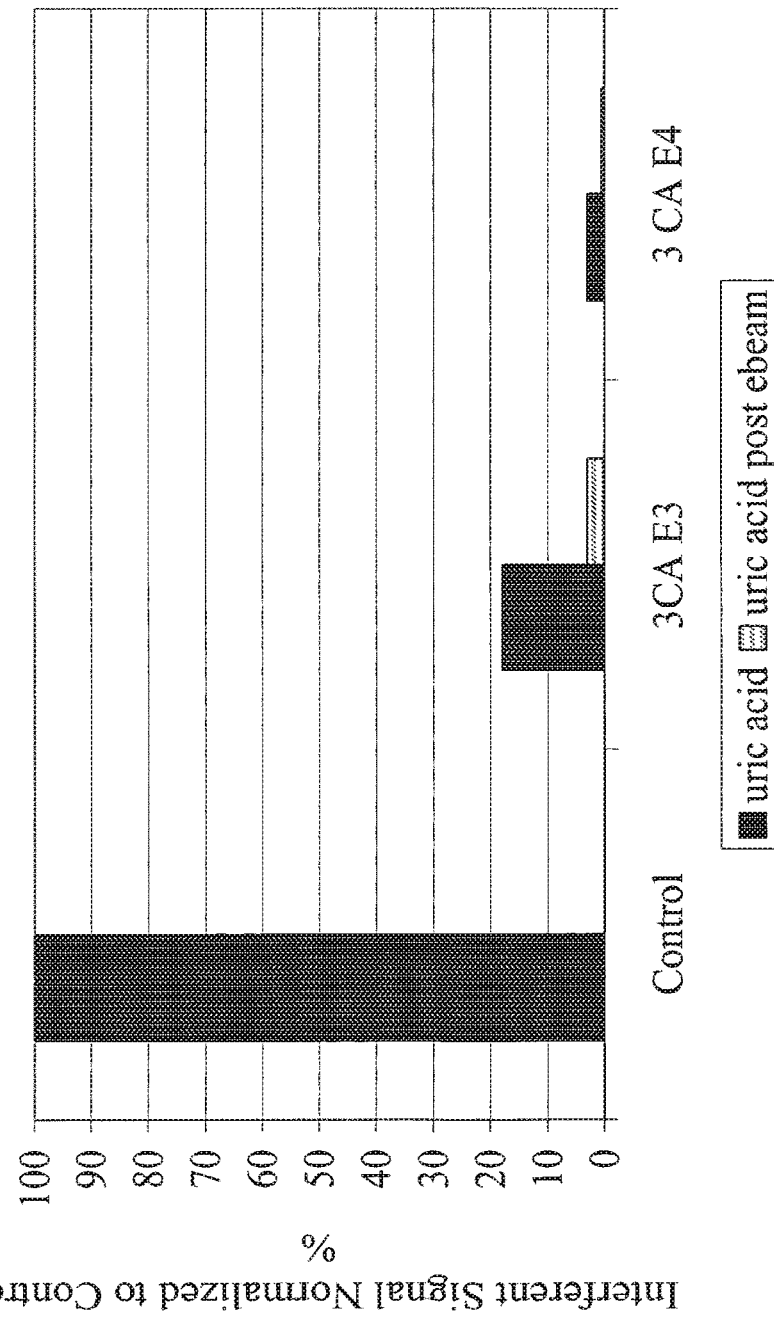
FIG. 24A is a bar graph that illustrates the ability of sensors to resist uric acid pre- and post-electron beam exposure in one in vitro experiment.

FIG. 24A is a bar graph that illustrates the ability of the CA sensors to resist uric acid pre- and post-electron beam exposure. The x-axis represents the sensors involved in the in vitro testing. Namely, 3CA represents an interference domain formed on sensors comprised of four dip coated layers of cellulose acetate as described above. Half of the CA sensors were tested pre-electron beam exposure and half of the sensors were tested post-electron beam exposure as indicated on the legend. The y-axis represents the percentage amount of signal due to the interferant (uric acid) as compared to a control sensor (i.e., sensor(s) without an interference domain).

The bar graph shows that in a first set CA sensors (E3), 3% of the control signal was produced by the electron beam treated sensor upon immersion into the uric acid containing solution (as compared to the control sensor); in contrast, the sensor that was not treated with electron beam produced an 18% signal increase when immersed in the uric acid containing solution. In a second set of CA sensors (E4), 0.5% of the the control signal was produced by the electron beam treated sensor upon immersion into the uric acid containing solution (as compared to the control sensor); in contrast, the sensor that was not treated with electron beam produced 3% of the control signal when immersed in the uric acid containing solution. Accordingly, it is believed that electron beam exposure provides improved ability to block uric acid in sensors in vitro as compared with sensors that have not been electron beam sterilized.

Figure 24B:
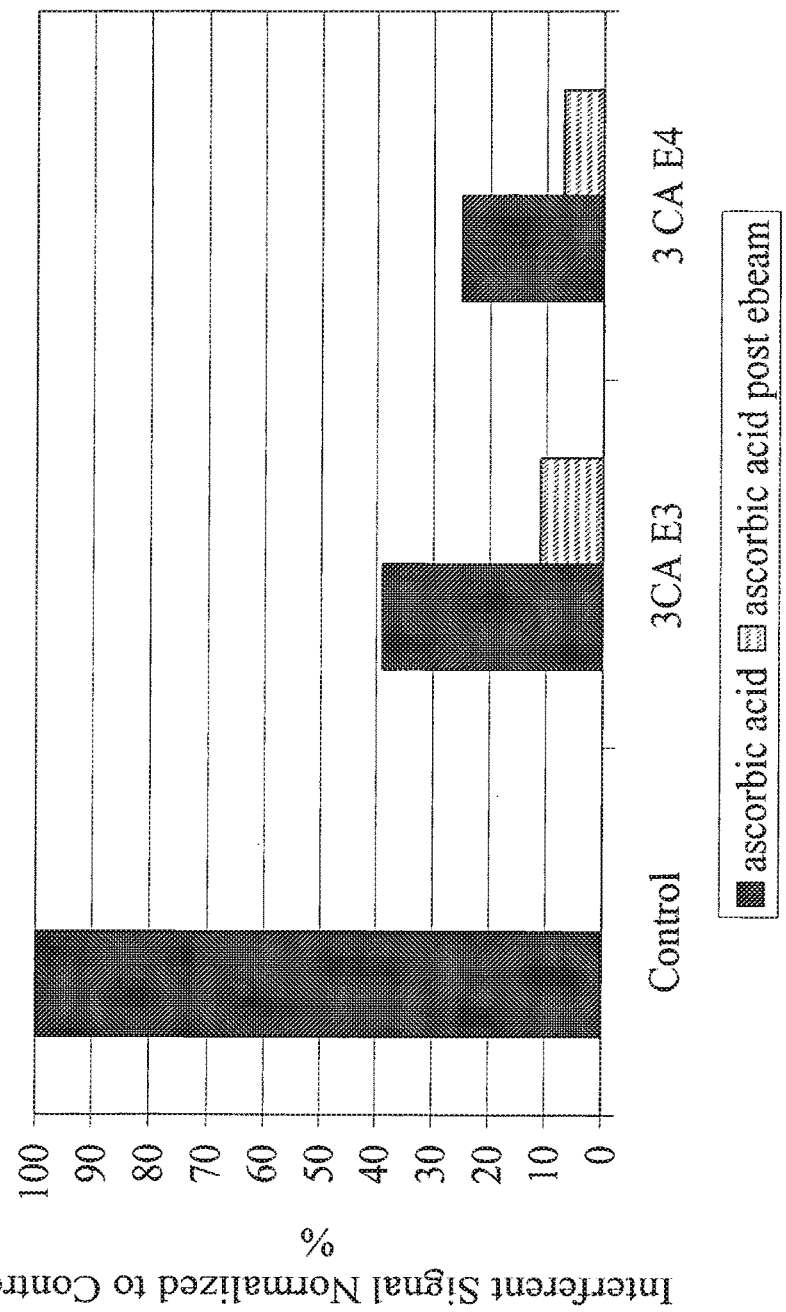
FIG. 24B is a bar graph that illustrates the ability of sensors to resist ascorbic acid pre- and post-electron beam exposure in one in vitro experiment.
Figure 24C:
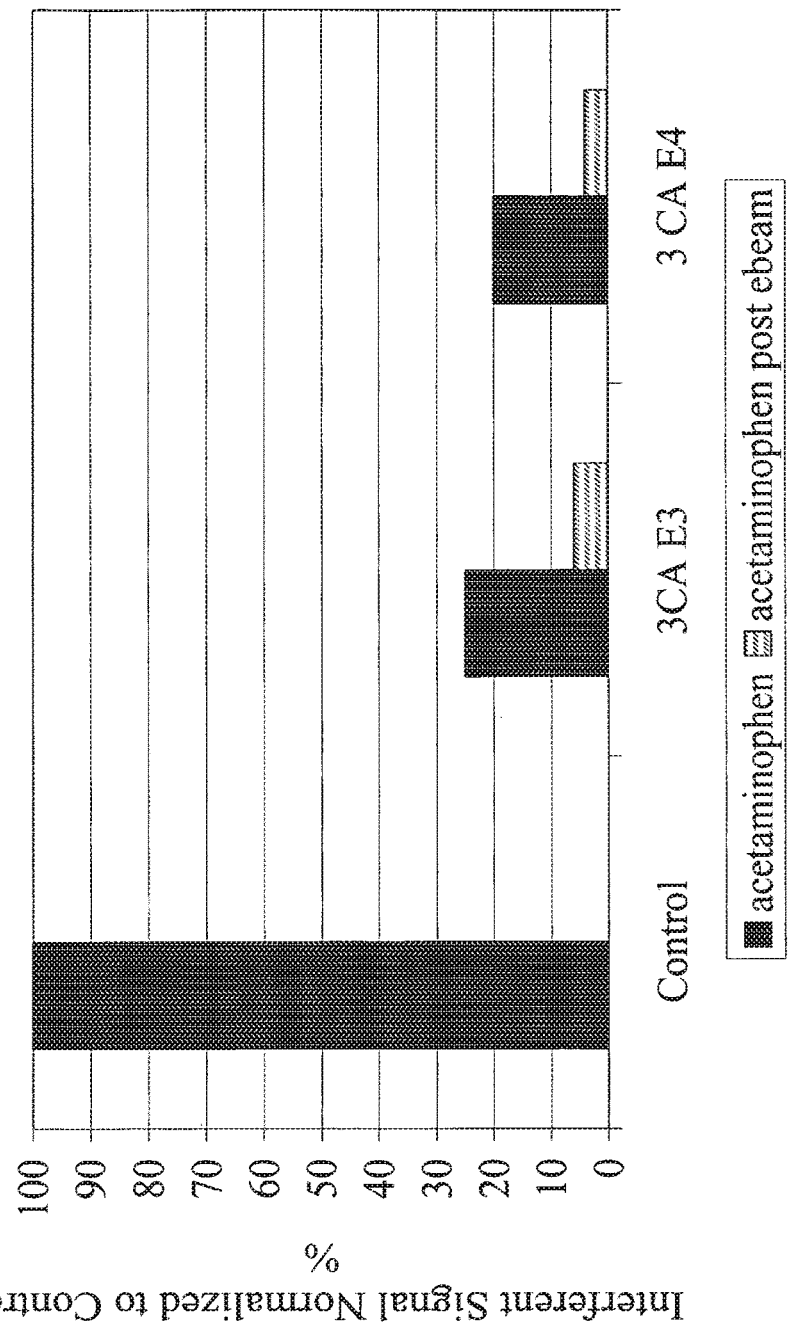
FIG. 24C is a bar graph that illustrates the ability of sensors to resist acetaminophen pre- and post-electron beam exposure in one in vitro experiment.

FIG. 24B is a bar graph that illustrates the ability of the CA sensors to resist ascorbic acid pre- and post-electron beam exposure. The x-axis represents the sensors involved in the in vitro testing. Namely, 3CA represents an interference domain formed on sensors comprised of four dip coated layers of cellulose acetate, as described above. Half of the sensors were tested pre-electron beam exposure and half of the sensors were tested post-electron beam exposure as indicated on the legend. The y-axis represents the amount of signal due to the interferant (ascorbic acid) as compared to a control sensor (i.e., sensor(s) without an interference domain).

The bar graph shows that in a first set CA sensors (E3), 11% of the control signal was produced by the electron beam treated sensor upon immersion into the ascorbic acid containing solution (as compared to the control sensor); in contrast, the sensor that was not treated with electron beam produced 39% of the control signal when immersed in the ascorbic acid containing solution. In a second set of CA sensors (E4), 7% of the control signal was produced by the electron beam treated sensor upon immersion into the ascorbic acid containing solution (as compared to the control sensor); in contrast, the sensor that was not treated with electron beam produced 35% of the control signal when immersed in the ascorbic acid containing solution.

FIG. 24C is a bar graph that illustrates the ability of the CA sensors to resist acetaminophen pre- and post-electron beam exposure. The x-axis represents the sensors involved in the in vitro testing. Namely, 3CA represents an interference domain formed on sensors comprised of four dip coated layers of cellulose acetate, as described above. Half of the sensors were tested pre-electron beam exposure and half of the sensors were tested post-electron beam exposure as indicated on the legend. The y-axis represents the amount of signal due to the interferant (acetaminophen) as compared to a control sensor (i.e., sensor(s) without an interference domain).

The bar graph shows that in a first set CA sensors (E3), 6% of the control signal was produced by the electron beam treated sensor upon immersion into the acetaminophen containing solution (as compared to the control sensor); in contrast, the sensor that was not treated with electron beam produced 25% of the control signal when immersed in the acetaminophen containing solution. In a second set of CA sensors (E4), 4% of the control signal was produced by the electron beam treated sensor upon immersion into the acetaminophen containing solution (as compared to the control sensor); in contrast, the sensor that was not treated with electron beam produced 20% of the control signal when immersed in the acetaminophen containing solution.

While not wishing to be bound by theory, it is believed that treatment of an interference domain comprising a cellulosic polymer, such as cellulose acetate, by ionizing radiation, such as electron beam radiation, crosslinks the domain and thereby improves the structure of the domain and its ability to block interfering species.

In Vivo Testing

Figure 25A:
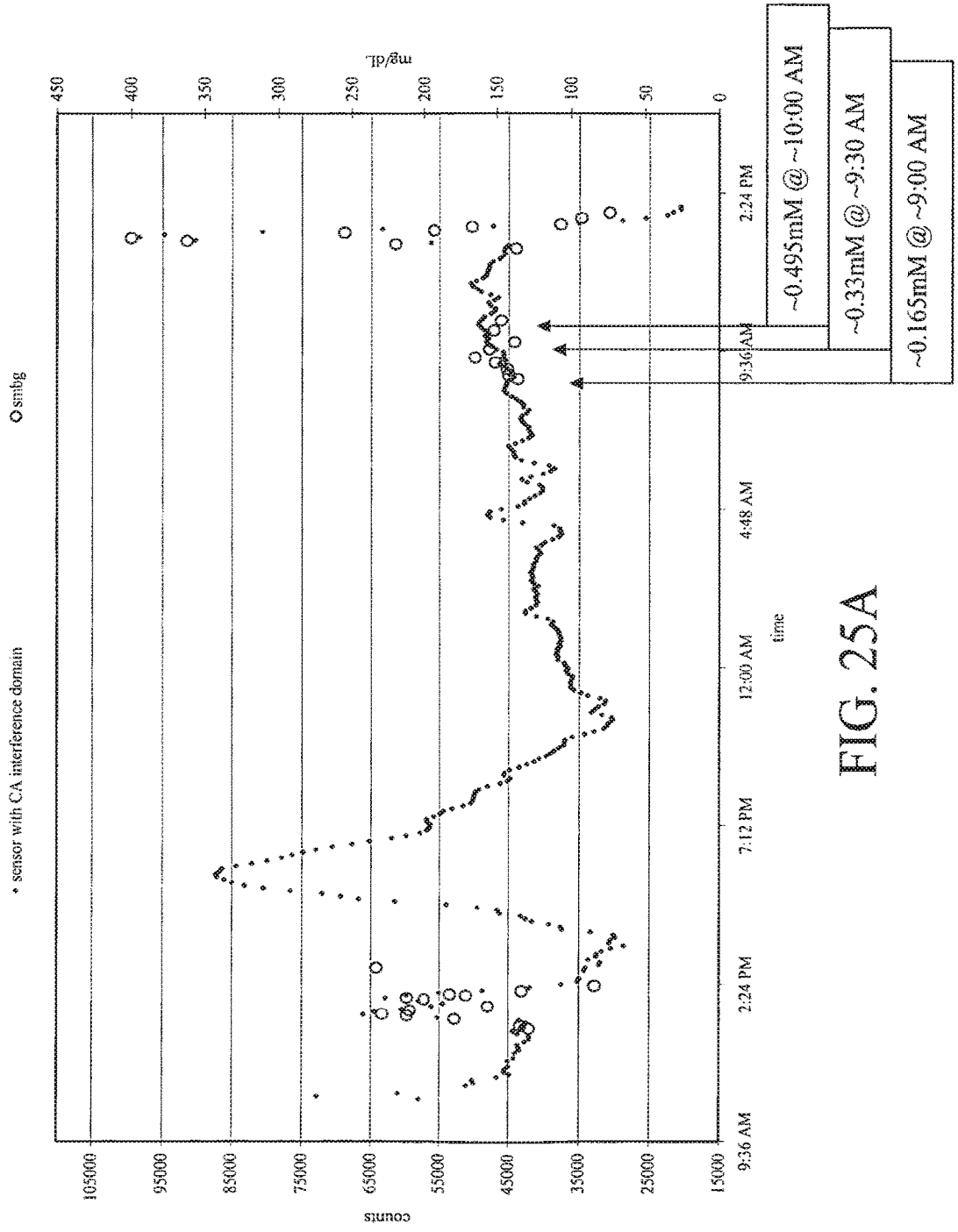
FIG. 25A is a graphical representation that illustrates the acetaminophen blocking ability of a glucose sensor including a cellulose acetate interference domain that has been treated using electron beam radiation and tested in vivo.

FIG. 25A is a graphical representation that shows the results of an experiment wherein a glucose sensor was implanted in a streptozocin-induced diabetic rat. Particularly, the glucose sensor was constructed with a cellulose acetate interference domain and was treated with electron beam exposure as described above. The x-axis represents time; the first y-axis represents counts from a raw data stream obtained from the glucose sensor (sensor with CA interference domain); and the second y-axis represents blood glucose in mg/dL obtained from tail sticks and measured on a reference self-monitoring blood glucose meter (smbg).

The rat was implanted with the CA sensor and was taken through a glucose excursion study on day 1 (see approximately 1 PM to 2 PM). On day 2 of the study, the rat was injected in the gut with 75%, 150%, and 225% of the maximum therapeutic dose of acetaminophen 0.22 mM (equal to approximately 0.165, 0.33 and 0.495 mM acetaminophen, respectively) at approximately 9 AM, 9:30 AM, and 10 AM, respectively as indicated by the arrows on the graph.

The graph illustrates the results of the glucose sensor as compared with a reference blood glucose meter during the glucose and acetaminophen tracking studies. During the glucose excursion study on day 1, one can see that the glucose sensor is indeed tracking glucose as shown by the sensor's increase and subsequent decrease in counts and corresponding smbg values. Furthermore, during the acetaminophen tracking study, the relative minimal change in sensor value (with corresponding reference blood glucose meter) indicates the sensor's ability to block signal due to acetaminophen similar to that of the reference blood glucose meter. Namely, if the sensor had been constructed without an interference domain, one would expect to see three step increases in the sensor's signal corresponding to the three bolus injections described above. Thus, it is believed that the incorporation of the CA interference domain that has been exposed to ionizing beam radiation as described above enables the glucose sensor to substantially resist acetaminophen in vivo.

Figure 25B:
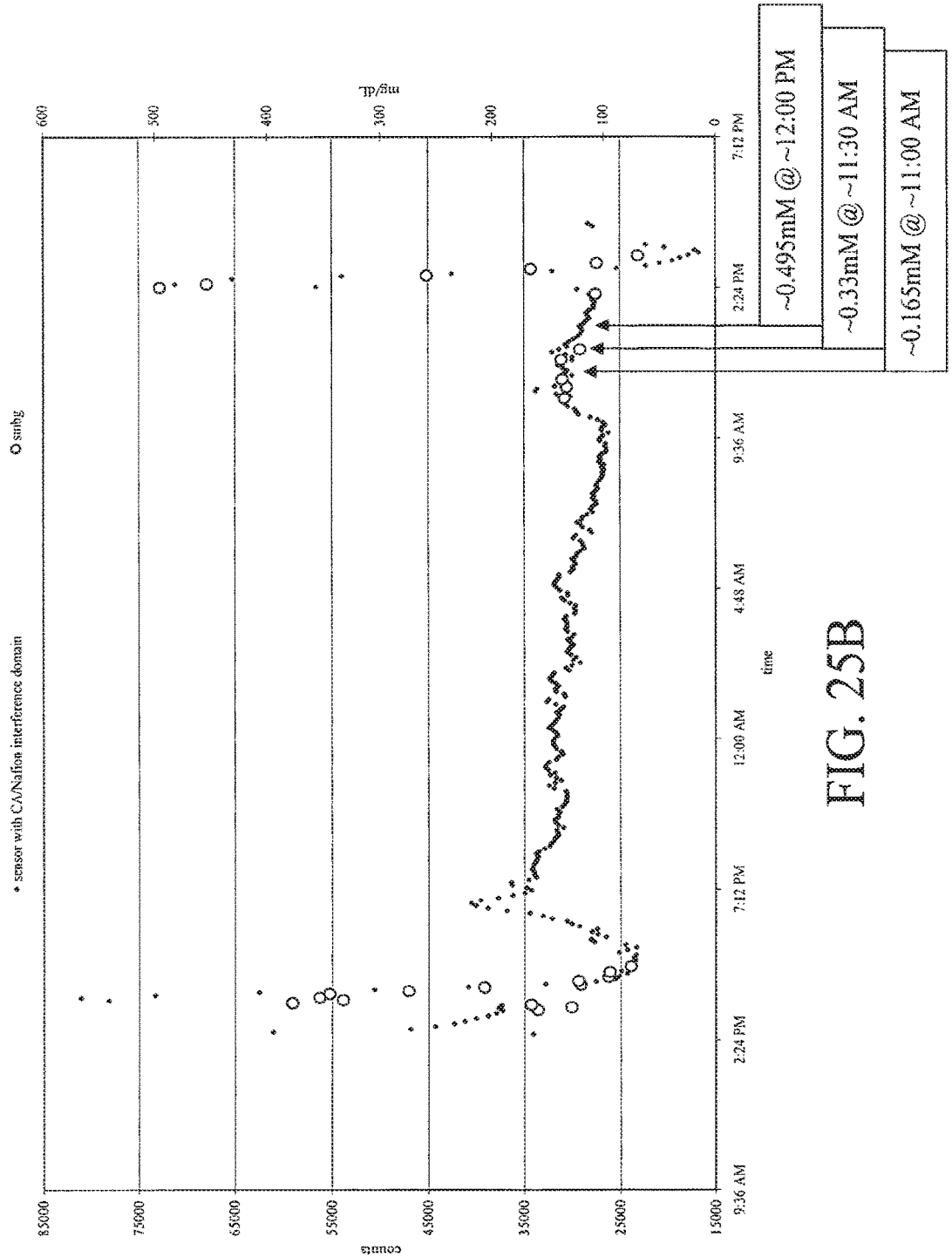
FIG. 25B is a graphical representation that illustrates the acetaminophen blocking ability of a glucose sensor including a cellulose acetate/Nafion® interference domain that has been treated using electron beam radiation and tested in vivo.

FIG. 25B is a graphical representation that shows the results of an experiment the wherein a glucose sensor was implanted in a streptozocin-induced diabetic rat. Particularly, the glucose sensor was constructed with a cellulose acetate/Nafion® interference domain and was treated with electron beam exposure as described above. The x-axis represents time; the first y-axis represents counts from a raw data stream obtained from the glucose sensor (sensor with CA/Nafion® interference domain); and the second y-axis represents blood glucose in mg/dL obtained from tail sticks and measured on a reference self-monitoring blood glucose meter (smbg).

The rat was implanted with the CA/Nafion® sensor and was taken through a glucose excursion study on day 1 (see approximately 3 PM to 4 PM). On day 2 of the study, the rat was injected in the gut with 75%, 150%, and 225% of the maximum therapeutic dose of acetaminophen 0.22 mM (equal to approximately 0.165, 0.33 and 0.495 mM acetaminophen, respectively) at approximately 11 AM, 11:30 AM, and 12 PM, respectively as indicated by the arrows on the graph.

The graph illustrates the results of the glucose sensor as compared with a reference blood glucose meter during the glucose and acetaminophen tracking studies. During the glucose excursion study on day 1, one can see that the glucose sensor is indeed tracking glucose as shown by the sensor's increase and subsequent decrease in counts and corresponding smbg values. Furthermore, during the acetaminophen tracking study, the relatively minimal change in sensor value (with corresponding reference blood glucose meter) indicates the sensor's ability to block signal due to acetaminophen similar to that of the reference blood glucose meter. Namely, if the sensor had been constructed without an interference domain, one would expect to see three step increases in the sensor's signal corresponding to the three bolus injections as shown in FIG. 24C. Thus, it is believed that incorporation of the CA/Nafion® interference domain that has been exposed to ionizing radiation as described above enables the glucose sensor to substantially resist acetaminophen in vivo.

Figure 25C:
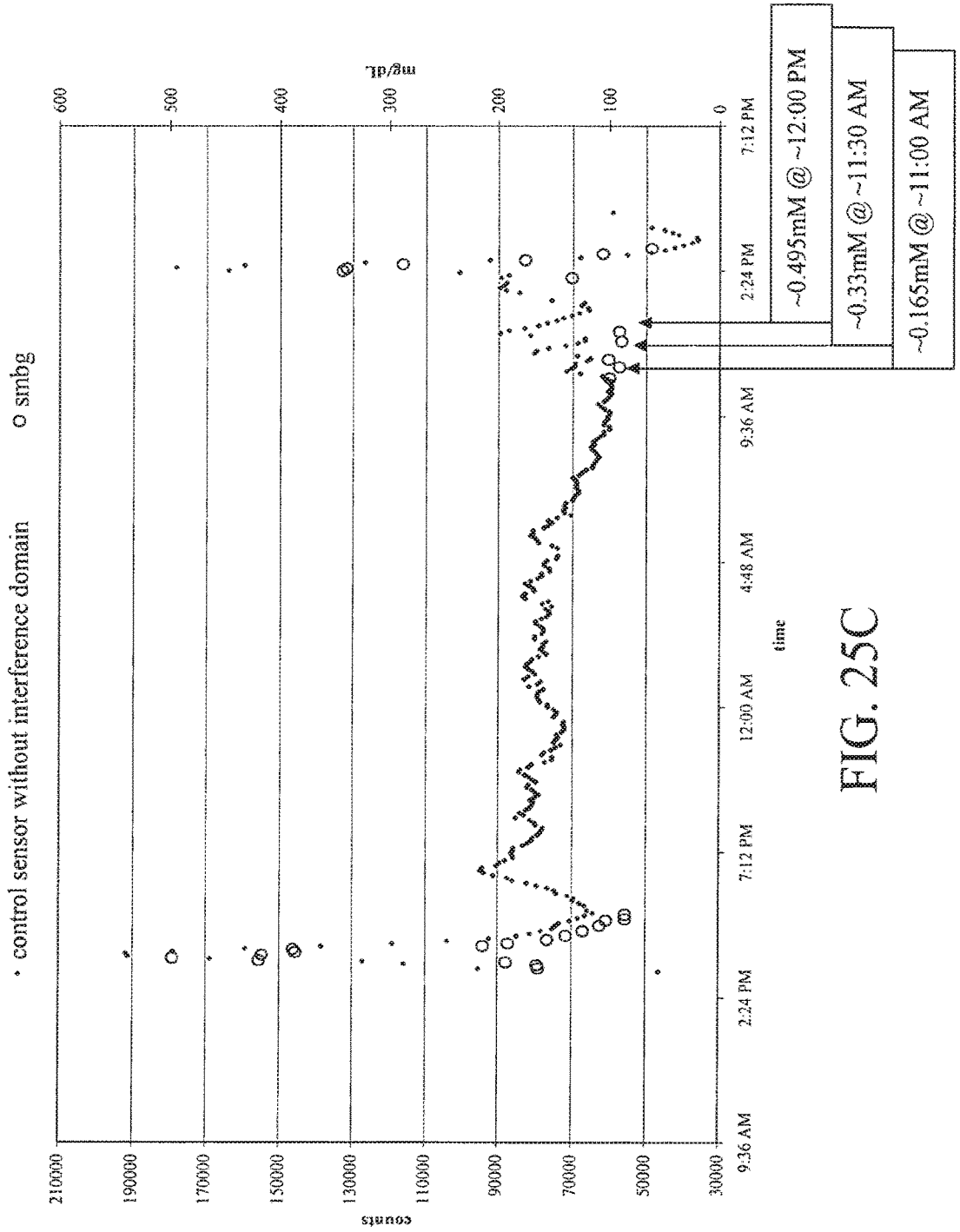
FIG. 25C is a graphical representation that illustrates the lack of acetaminophen blocking ability of a control glucose sensor without an interference domain and tested in vivo.

FIG. 25C is a graphical representation that illustrates the lack of acetaminophen blocking ability of a control glucose sensor without an interference domain in the study of FIG. 25B. Particularly, the glucose sensor was constructed without an interference domain The x-axis represents time; the first y-axis represents counts from a raw data stream obtained from the glucose sensor (without an interference domain); and the second y-axis represents blood glucose in mg/dL obtained from tail sticks and measured on a reference self-monitoring blood glucose meter (smbg).

The rat was implanted with the interference domain-free sensor and was taken through a glucose excursion study on day 1 (see approximately 3 PM to 4 PM). On day 2 of the study, the rat was injected in the gut with 75%, 150%, and 225% of the maximum therapeutic dose of acetaminophen 0.22 mM (equal to approximately 0.165, 0.33 and 0.495 mM acetaminophen, respectively) at approximately 11 AM, 11:30 AM, and 12 PM, respectively as indicated by the arrows on the graph.

The graph illustrates the results of the control glucose sensor as compared with a reference blood glucose meter during the glucose and acetaminophen tracking studies. During the glucose excursion study on day 1, one can see that the glucose sensor is indeed tracking glucose as shown by the sensor's increase and subsequent decrease in counts and corresponding smbg values. Furthermore, during the acetaminophen tracking study on day 2, three step increases in the sensor's signal can be seen, which correspond to the three bolus acetaminophen injections described above. These three signal increases indicate the affect of acetaminophen on the sensor signal as compared with corresponding reference blood glucose meter values (smbg) indicates the sensor's lack of ability to block signal due to acetaminophen as compared with that of the reference blood glucose meter, for example. Thus, it is believed that the incorporation of the CA and/or CA/Nafion® interference domain that has been exposed to ionizing radiation as described above enables the glucose sensor to substantially resist acetaminophen in vivo as compared to a glucose sensor without the interference domain of the preferred embodiments.

Transcutaneous Glucose Sensor with Cellulose Acetate Interference Domain and PVP Electrode Domain Transcutaneous glucose sensors with a cellulose acetate (CA) interference domain with and without a PVP electrode domain were each built as described with reference to the transcutaneous glucose sensors above. Namely, a first (control) set of parylene-coated twisted pair assemblies were dip-coated with a CA interference domain and subsequent enzyme and resistance domains as described in more detail. Additionally, a second (test) set of parylene-coated twisted pair assemblies were dip-coated one time with a 10 wt. % PVP (International Specialty Products PVP K-90) solution in DI water, prior to the application of a CA interference domain and subsequent enzyme and resistance domains.

Figure 26A:
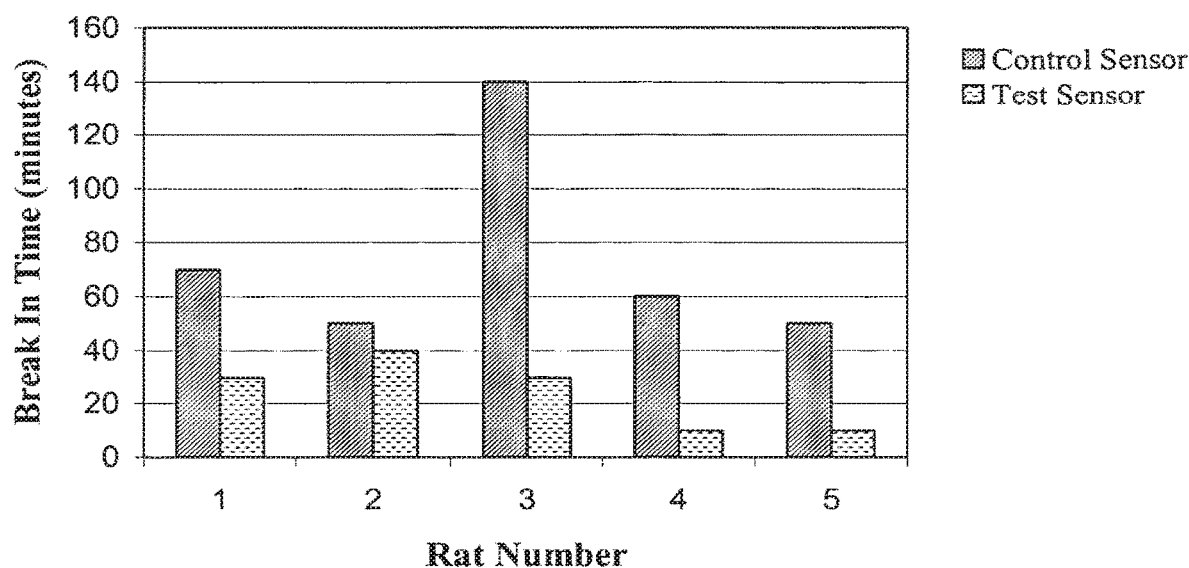
FIG. 26A is a bar graph that represents the break-in time of the test sensors vs. the control sensors.

FIG. 26A is a bar graph that represents the break-in time of the test sensors vs. the control sensors. Five test sensors and five control sensors were built as described above and inserted bi-laterally into a rat (each rat receiving one test sensor and one control sensor). After insertion, the sensors measured glucose for a time period at least beyond the electrochemical break-in time of each sensor. The data was analyzed to determine the electrochemical break-in of each sensor. Electrochemical break-in is well documented and is appreciated by one skilled in the art, however it can be stated that the time at which reference glucose data (e.g., from an SMBG meter) substantially correlates with sensor glucose data is an indicator of electrochemical break-in of the sensor. The y-axis represents the amount of time required for electrochemical break-in in minutes. The x-axis represents the 5 rats in this experiment showing the test and control sensors for each rat. It can be seen from the bar graph that the break-in time of the test sensors (with the PVP electrode domain) had faster break-in times than the control sensors (without PVP electrode domain). Namely, the control sensors had break-in time periods in the range of about 50 to about 130 minutes, while the test sensors had break-in time periods in the range of about 10 to about 40 minutes. Thus, a membrane system comprising a cellulosic derivative (e.g., cellulose acetate butyrate) and an electrode domain comprising a hydrophilic polymer (e.g., PVP) enables fast break-in times for a sensor, including not more than about 40 minutes, not more than about 30 minutes, preferably not more than about 20 minutes, and more preferably not more than about 10 minutes.

Transcutaneous Glucose Sensor with Cellulose Acetate Butyrate Interference Domain Transcutaneous glucose sensors with a cellulose acetate butyrate (CAB) interference domain were each constructed as described with reference to the transcutaneous glucose sensors above, namely, by dip-coating a parylene-coated twisted pair assembly with three coats of 17.7 wt. % cellulose acetate butyrate CAB (Eastman Chemical 553-0.4) solution in 2:1 acetone:ethanol. Enzyme and resistance domains were subsequently coated onto the cellulose acetate butyrate interference domain coated assembly as described in more detail above. Subsequent testing showed effective blocking of acetaminophen, a known interferant, at therapeutic levels. Additionally, at least some sensors (test sensors) were exposed to electron beam radiation at a dose of 25 kGy, while others (control sensors) were not exposed to electron beam radiation after electron beam sterilization at a dose of 25 kGy, all of which showed equivalent blocking ability of acetaminophen.

Transcutaneous Glucose Sensors with Cellulose Acetate Butyrate Interference Domain and PVP Electrode Domain In some circumstances, a cellulose acetate butyrate interference domain may alter or reduce the sensitivity of some glucose oxidase-based sensor assemblies. Accordingly, in some circumstances, it can be useful to apply an electrode domain (e.g., more proximal to the electroactive surface) of polyvinylpyrrolidone (PVP), or the like, on the electroactive surface(s) (e.g., working and/or reference electrodes) prior to application of the CAB interference domain. Accordingly, in addition the above described CAB interference-based sensors, some sensors were coated with 20 wt. % PVP (International Specialty Products PVP K-90) solution in DI water prior to the application of CAB and the subsequent coatings described above. These sensors showed that the addition of a PVP electrode domain beneath the CAB interference domain results in an increase in glucose sensitivity (e.g., slope) of the sensor and a reduction of slope variability (e.g., from sensor to sensor).

Figure 26B:
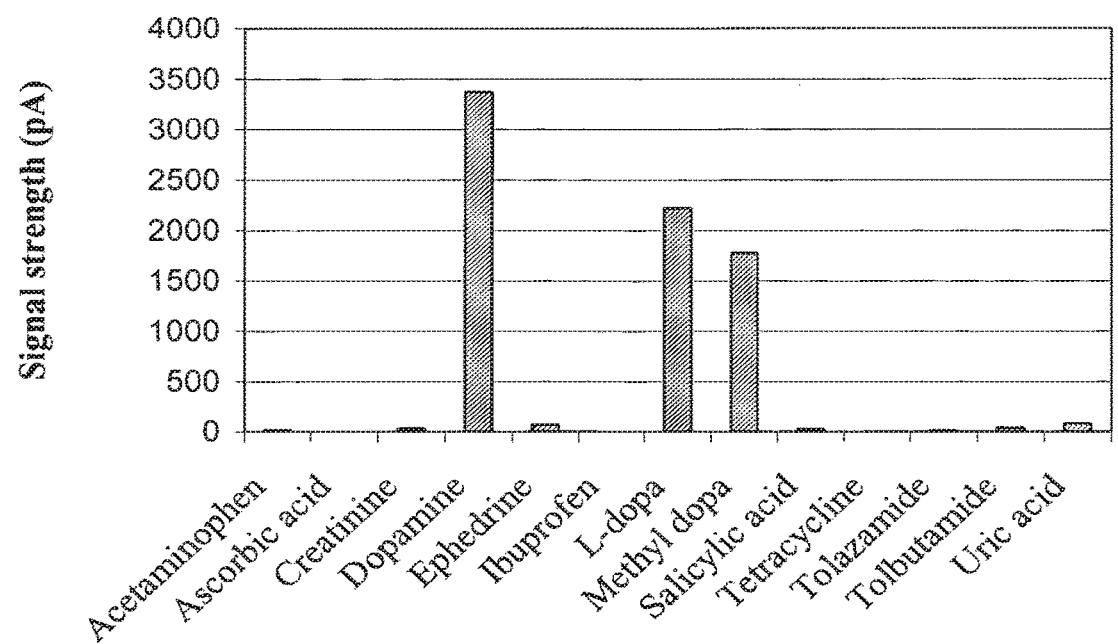
FIG. 26B is a graph that represents the response of glucose sensors to a variety of interferents.

FIG. 26B is a graph that represents the response of glucose sensors to a variety of interferents. Five sensors were built including a PVP electrode domain and CAB interference domain as described above and immersed for at least three minutes in a variety of heated (37° C.) PBS solutions each containing an interferent as shown in Table 1, below.

TABLE 1

| Interferent | Solution Concentration Tested, mg/dL | Therapeutic Concentration, mg/dL |
|---|---|---|
| acetaminophen | 6.5 | 1-2 |
| ascorbic acid | 3.8 | 0.8-1.2 |
| dopamine | 3.1 | 0.03-0.104 |
| ibuprofen | 40 | 0.5-2.04 |
| salicylic acid | 50 | 15-30 |
| tolbutamide | 70 | 5.3-10 |
| creatinine | 30 | 1.5 |
| uric acid | 9.5 | 7 |
| ephedrine | 0.94 | 0.005-0.01 |
| L-dopa | 1.82 | 0.02-0.3 |
| methyl dopa | 1.735 | 0.1-0.5 |
| tetracycline | 0.44 | 0.4 |

The graph of FIG. 26B represents data as an average of the five sensors tested in each of the interferent solutions at high concentrations (see column entitled, "Solution Concentration Tested" in Table 1). The y-axis represents signal strength in picoAmps after a three-minute immersion time in each solution. The x-axis represents the interferents tested. It is noted that at least three interferents showed substantially no response (Ascorbic acid, Ibuprofen and Tetracycline). Other interferents (Acetaminophen, Creatinine, Ephedrine, Salicylic acid, Tolazamide, Tolbutamide and Uric Acid) showed minimal response, which is believed to provide sufficient interferent blocking to enable functional (useful) sensor data even in the presence of these interferents at the tested concentrations (see FIG. 26C).

Figure 26C:
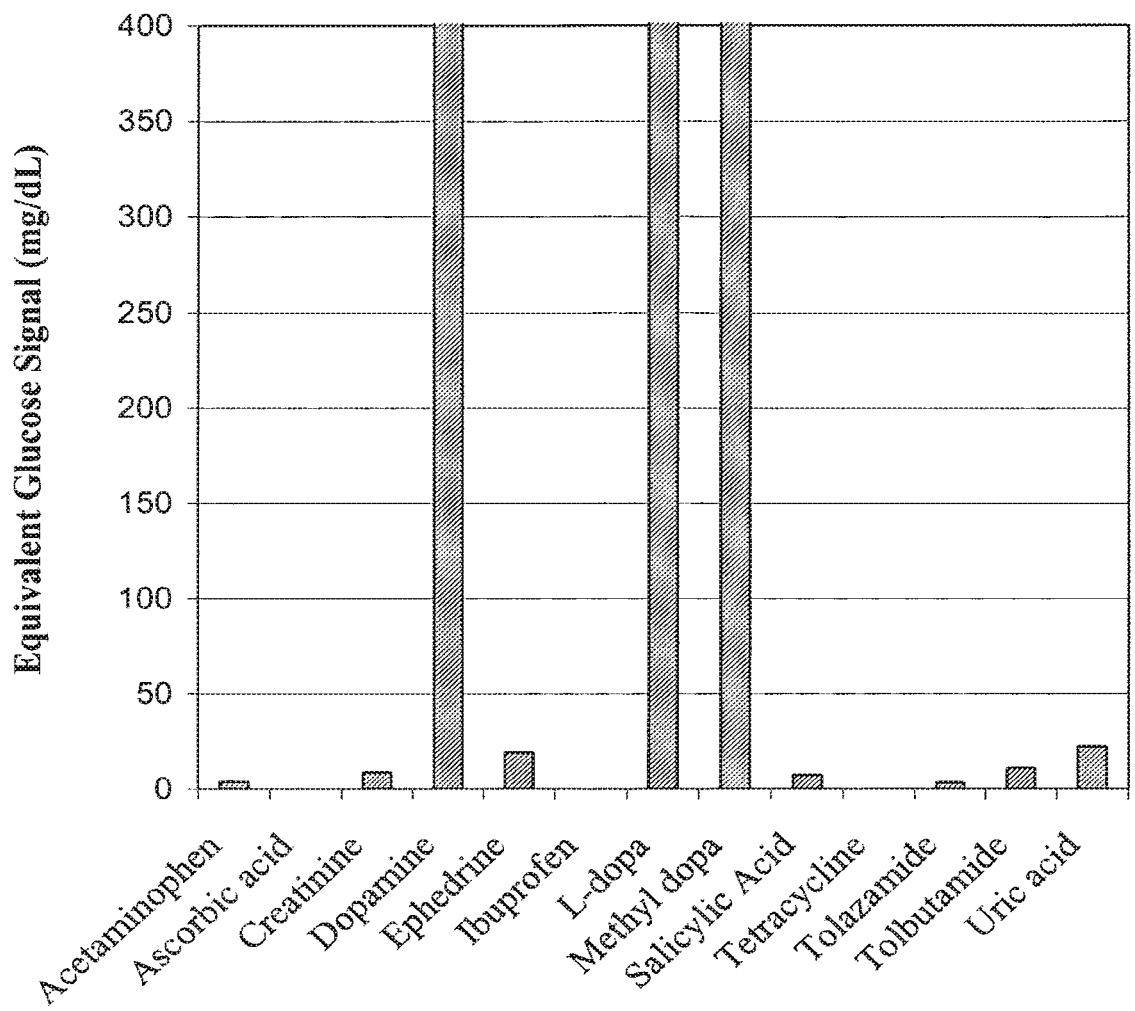
FIG. 26C is a graph that represents an "equivalent glucose signal" caused by the interferents tested.

FIG. 26C is a graph that represents an apparent glucose concentration or "equivalent glucose signal" caused by each of the interferent solutions at high concentrations (see column entitled, "Solution Concentration Tested" in Table 1). For the purposes of calculating the equivalent glucose signal, a sensitivity of 3.5 pA/mg/dL is assumed and the signal strength converted to an "equivalent glucose signal" (or apparent glucose concentration) in mg/dL. The y-axis represents the equivalent glucose signal in mg/dL. The x-axis represents the interferents tested. As discussed above, at least three interferents showed zero "equivalent glucose signal" (Ascorbic acid, Ibuprofen and Tetracycline). Other interferents (Acetaminophen, Creatinine, Salicylic acid, and Tolazamide, showed very minimal signal (or "equivalent glucose signal"); namely, less than about 10 mg/dL "equivalent glucose signal." An additional three of the interferants, (ephedrine, tolbutamide and uric acid) showed minimal signal; namely, less than 20 mg/dl equivalent) which is believed to provide sufficient interferent blocking (resistance) to enable functional (useful) sensor data even in the presence of these interferents at the tested concentrations. Although three of the interferents tested showed more response than other of the interferents, these three interferents were re-tested at their therapeutic concentrations (see column entitled, "Therapeutic Concentration" it Table 1.) After a three-minute immersion time in the therapeutic concentration, the "equivalent glucose signal" for Dopamine, L-dopa, and Methyldopa, respectively, was measured as 10, 14, and 52 mg/dL. Accordingly, the glucose sensors of the preferred embodiments effectively block a plurality of interfering species selected with an "equivalent glucose signal" of less than about 30 mg/dL, preferably less than about 20 mg/dL, and more preferably less than about 10 mg/dL or less at therapeutic doses of interfering species of the glucose sensor.

The glucose sensors of the preferred embodiments, constructed with a cellulose acetate butyrate interference domain, and including embodiments with a PVP electrode domain, have been shown to block a broad spectrum of exogeneous and endogeneous interferents in therapeutic concentrations, including, but not limited to, Acetaminophen, Ascorbic acid, Dopamine, Ibuprofen, Salicylic acid, Tolbutamide, Creatinine, Uric acid, Ephedrine, L-dopa, methyl dopa and Tetracycline. Additionally, while some prior art interference domains have been known to create altered sensitivity of the sensor to glucose (e.g., variability and/or unreliability of sensors in manufacture), the preferred glucose sensors built with a cellulose acetate butyrate interference domain, and including embodiments with a PVP electrode domain, provide excellent glucose sensitivity consistency for sensor manufacture. Furthermore, it was observed that the preferred embodiments described herein provide glucose sensors that reduce or eliminate breakthrough upon prolonged exposure to a solution containing an interferant.

Deposition of Resistance Domain Using Physical Vapor Deposition

Twenty nine (29) transcutaneous sensors were fabricated by providing a platinum wire, vapor-depositing the platinum with Parylene to form an insulating coating, helically winding a silver wire around the insulated platinum wire (to form a "twisted pair"), masking sections of electroactive surface of the silver wire, vapor depositing Parylene on the twisted pair, chloridizing the silver electrode to form a silver chloride reference electrode, and removing a radial window on the insulated platinum wire to expose a circumferential electroactive working electrode surface area thereon, this assembly also referred to as a "parylene-coated twisted pair assembly." The electroactive surface of the radial window of each Parylene-coated twisted pair was then cleaned by surface treatment.

An electrode domain was formed over the electroactive surface areas of the working and reference electrodes by dip coating the assembly in an electrode solution (comprising BAYHYDROL® 123, an aliphatic polycarbonate urethane resin) and drying. An enzyme domain was formed over the electrode domain by subsequently dip coating the assembly in an enzyme solution (comprising BAYHYDROL® 140AQ, an aliphatic polyester urethane resin, and glucose oxidase) and drying. A resistance domain was formed over the enzyme domain using a physical vapor deposition process as described above; namely, by placing twenty nine of the assemblies coated with the electrode and enzyme domains into a vacuum chamber and using an ultrasonic nozzle to produce a mist of micro-droplets of the resistance domain solution (comprising a blend of CHRONOTHANE®-1020 (a polyetherurethaneurea based on polytetramethylene glycol, methylene diisocyanate and organic amines) and CHRONOTHANE®-H (a polyetherurethaneurea based on polytetramethylene glycol, polyethylene glycol, methylene diisocyanate, and organic amines)) within the vacuum chamber (solution feed rate 1.5 ml/minute; nozzle power 1.5 watts; solution temperature ambient room temp.; chamber temperature 30° C.; nozzle frequency 120 kHz; chamber gas argon; purge gas pressure 3 psi; solvent physical properties: tetrahydrofuran (boiling point 65-67° C., vapor pressure 143 mm Hg @ 20° C.) and dimethylacetamide (boiling point 164.5° C., vapor pressure 2 mm Hg @ 25° C.)). The contact time with the mist within the vacuum chamber was about 36 minutes in duration and included 12 spray cycles lasting three minutes each. The resistance domain was then dried for 1 hr at 50° C., 26" vacuum. After drying, the twenty nine sensors were tested in vitro to determine their slope (i.e., glucose sensitivity). The twenty nine sensors had an average slope of 4.97 pA/mg/dL, with a standard deviation of 0.55 pA/mg/dL, showing the use of vapor deposition methods, as described herein, to produce functional sensors with good consistency and uniformity. Specifically, the manufacturing lot consisted of sensors having in vitro sensitivities with a standard deviation of about 11%. Methods for producing manufacturing lots of sensors can be employed to produce sensors typically with a standard deviation of less than about 20%, preferably less than about 18%, more preferably a standard deviation of less than about 16%, more preferably still a standard deviation of less than about 12%, and most preferably a standard deviation of less than about 8%.

In the above-described method, the morphology of the resistance domain was controlled by adjusting the solvent evaporation rate of the coating liquid through chamber temperature and chamber vacuum control to yield a surface with the preferred morphology (e.g., non-smoothness). Namely, in contrast to prior art devices which are fabricated using methods specifically adapted to depositing a smooth surface (see, for example, WO/2003-072269-A1 to Leiby et al.), devices of the preferred embodiment fabricated using the above-described method have a resistance domain including a substantially non-smooth surface (e.g., a roughness on the surface that varies in appearance under magnification from a super-positioning of disc shaped objects, such as coins, to a beadlike surface) A variety of parameters of the vapor deposition apparatus/process can be adjusted to produce the desired non-smooth membrane surface; namely, parameters including: feed rate, nozzle power, chamber vacuum, liquid solution temperature (to be sprayed), chamber temperature, purge gas pressure or flow rate, identity of the purge gas, total cycle time, number of cycles, and solvent physical properties can be altered, and are dependent on one another, to produce desired membrane surface properties.

Figure 27:
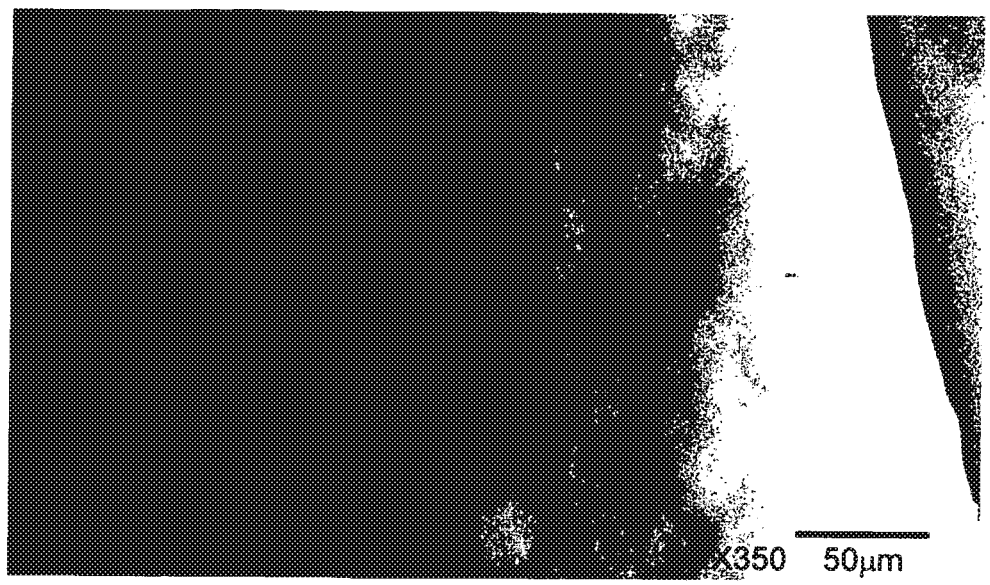
FIG. 27 is a photomicrograph obtained by Scanning Electron Microscopy (SEM) at 350× magnification of a sensor including a vapor deposited resistance domain on an outer surface.

FIG. 27 is a photomicrograph obtained by Scanning Electron Microscopy (SEM) at 350× magnification of a sensor formed as described in the example above, including vapor depositing the resistance domain onto the sensor. FIG. 27 shows the substantially non-smooth surface of the sensor after deposition of the resistance domain; namely, FIG. 27 shows a plurality of super-positioned disc-shaped objects, wherein the disc-shaped objects are a result of the deposition of the resistance domain. Preferably, the disc-shaped objects are rounded, for example, circular, oval or tear drop-shaped. In this example, the average diameter of the disc-shaped objects (by either the shortest or longest dimension) is preferably from about 5 to about 250 microns, more preferably from about 10 to about 100 microns, and more preferably still from about 30 to about 80 microns; however, larger or smaller average diameters can be desirable in certain embodiments. For example, in one alternative embodiment, certain parameters of the vapor deposition process were modified (e.g., temperature), which resulted in smaller diameter beads (e.g., a speckled appearance) than shown in FIG. 27.

Methods and devices that are suitable for use in conjunction with aspects of the preferred embodiments are disclosed in U.S. Pat. Nos. 4,994,167; 4,757,022; 6,001,067; 6,741,877; 6,702,857; 6,558,321; 6,931,327; and 6,862,465.

Methods and devices that are suitable for use in conjunction with aspects of the preferred embodiments are disclosed in U.S. Publication No. US-2005-0176136-A1; U.S. Publication No. US-2005-0251083-A1; U.S. Publication No. US-2005-0143635-A1; U.S. Publication No. US-2005-0181012-A1; U.S. Publication No. US-2005-0177036-A1; U.S. Publication No. US-2005-0124873-A1; U.S. Publication No. US-2005-0051440-A1; U.S. Publication No. US-2005-0115832-A1; U.S. Publication No. US-2005-0245799-A1; U.S. Publication No. US-2005-0245795-A1; U.S. Publication No. US-2005-0242479-A1; U.S. Publication No. US-2005-0182451-A1; U.S. Publication No. US-2005-0056552-A1; U.S. Publication No. US-2005-0192557-A1; U.S. Publication No. US-2005-0154271-A1; U.S. Publication No. US-2004-0199059-A1; U.S. Publication No. US-2005-0054909-A1; U.S. Publication No. US-2005-0112169-A1; U.S. Publication No. US-2005-0051427-A1; U.S. Publication No. US-2003-0032874; U.S. Publication No. US-2005-0103625-A1; U.S. Publication No. US-2005-0203360-A1; U.S. Publication No. US-2005-0090607-A1; U.S. Publication No. US-2005-0187720-A1; U.S. Publication No. US-2005-0161346-A1; U.S. Publication No. US-2006-0015020-A1; U.S. Publication No. US-2005-0043598-A1; U.S. Publication No. US-2003-0217966-A1; U.S. Publication No. US-2005-0033132-A1; U.S. Publication No. US-2005-0031689-A1; U.S. Publication No. US-2004-0045879-A1; U.S. Publication No. US-2004-0186362-A1; U.S. Publication No. US-2005-0027463-A1; U.S. Publication No. US-2005-0027181-A1; U.S. Publication No. US-2005-0027180-A1; U.S. Publication No. US-2006-0020187-A1; U.S. Publication No. US-2006-0036142-A1; U.S. Publication No. US-2006-0020192-A1; U.S. Publication No. US-2006-0036143-A1; U.S. Publication No. US-2006-0036140-A1; U.S. Publication No. US-2006-0019327-A1; U.S. Publication No. US-2006-0020186-A1; U.S. Publication No. US-2006-0020189-A1; U.S. Publication No. US-2006-0036139-A1; U.S. Publication No. US-2006-0020191-A1; U.S. Publication No. US-2006-0020188-A1; U.S. Publication No. US-2006-0036141-A1; U.S. Publication No. US-2006-0020190-A1; U.S. Publication No. US-2006-0036145-A1;

U.S. Publication No. US-2006-0036144-A1; and U.S. Publication No. US-2006-0016700A1.

Methods and devices that are suitable for use in conjunction with aspects of the preferred embodiments are disclosed in U.S. application Ser. No. 09/447,227 filed Nov. 22, 1999 and entitled "DEVICE AND METHOD FOR DETERMINING ANALYTE LEVELS"; U.S. application Ser. No. 11/280,672 filed Nov. 16, 2005, and entitled "TECHNIQUES TO IMPROVE POLYURETHANE MEMBRANES FOR IMPLANTABLE GLUCOSE SENSORS"; U.S. application Ser. No. 11/280,102 filed Nov. 16, 2005, and entitled "TECHNIQUES TO IMPROVE POLYURETHANE MEMBRANES FOR IMPLANTABLE GLUCOSE SENSORS"; U.S. application Ser. No. 11/201,445 filed Aug. 10, 2005 and entitled "SYSTEM AND METHODS FOR PROCESSING ANALYTE SENSOR DATA"; U.S. application Ser. No. 11/335,879 filed Jan. 18, 2006 and entitled "CELLULOSIC-BASED INTERFERENCE DOMAIN FOR AN ANALYTE SENSOR"; U.S. application Ser. No. 11/334,876 filed Jan. 18, 2006 and entitled "TRANSCUTANEOUS ANALYTE SENSOR"; U.S. application Ser. No. 11/333,837 filed Jan. 17, 2006 and entitled "LOW OXYGEN IN VIVO ANALYTE SENSOR".

All references cited herein, including but not limited to published and unpublished applications, patents, and literature references, and also including but not limited to the references listed in the Appendix, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A system for measuring an analyte concentration in a host, the system comprising:
    a transcutaneous analyte sensor;
    sensor electronics configured to operatively connect to the transcutaneous analyte sensor;
    an electrical contact comprising a first material, wherein the first material is associated with a first durometer hardness, wherein the electrical contact is configured to operably connect the transcutaneous analyte sensor to the sensor electronics;
    a sealing member comprising a second material, wherein the second material is associated with a second durometer hardness, wherein the sealing member at least partially surrounds the electrical contact and at least a portion of the transcutaneous analyte sensor when the transcutaneous analyte sensor is operably connected to the sensor electronics, wherein the sealing member substantially seals at least a portion of the electrical contact from moisture;
    a contact holder over which the sealing member and the transcutaneous analyte sensor are at least partially located; and
    wherein the first durometer hardness is higher than the second durometer hardness.

2. The system of claim 1, wherein the first durometer hardness is from about 5 Shore A to about 80 Shore A.

3. The system of claim 2, wherein the second durometer hardness is from about 5 Shore A to about 80 Shore A.

4. The system of claim 2, wherein the second durometer hardness is from about 20 Shore A to about 50 shore A.

5. The system of claim 1, wherein the first durometer hardness is from about 5 Shore A to about 80 Shore A and the second durometer hardness is from about 5 Shore A to about 80 Shore A.

6. The system of claim 1, wherein the first durometer hardness is from about 5 Shore A to about 80 Shore A and the second durometer hardness is from about 10 Shore A to about 50 Shore A.

7. The system of claim 1, wherein the contact holder is connected to a mounting unit.

8. The system of claim 1, wherein the contact holder comprises means for maintaining the sealing member on the contact holder.

9. The system of claim 1, wherein the contact holder and sealing member comprises means for maintaining the sealing member substantially in place on the contact holder.

10. The system of claim 1, wherein the sealing member is held at least in part on the contact holder by mating male-female mechanical structures on the contact holder and on the sealing member.

11. The system of claim 1, wherein the sealing member comprises a raised ridge to improve a seal around the electrical contact.

12. The system of claim 1, wherein the sealing member is held on the contact holder at least in part by protrusions on the contact holder that are configured to mate with recesses on the sealing member.

13. The system of claim 1, wherein the sealing member is held on the contact holder at least in part by a chemical to maintain the sealing member substantially stationary without substantial translation or deformation during sensor insertion.

14. The system of claim 1, wherein the sealing member comprises an upper portion and a lower portion, wherein an ex vivo portion of the transcutaneous analyte sensor is sandwiched between the upper portion and the lower portion.

15. The assembly of claim 14, wherein the upper portion is connected to the lower portion.

16. The system of claim 1, wherein the sealing member comprises an upper portion and a lower portion, wherein the upper portion comprises an inner face and an outer face, wherein the lower portion comprises an inner face and an outer face, wherein an ex vivo portion of the transcutaneous analyte sensor is positioned between the inner face of the upper portion and the inner face of the lower portion.

17. The assembly of claim 16, wherein the upper portion is connected to the lower portion.

18. The system of claim 1, further comprising a memory storing calibration information for the transcutaneous analyte sensor, wherein the calibration information is derived at least in part from a predictive relationship between in vitro sensor sensitivity to the analyte and in vivo sensor sensitivity to the analyte.

19. A system for measuring a glucose concentration in a host, the system comprising:
   a transcutaneous glucose sensor;
   sensor electronics configured to operably connect to the transcutaneous glucose sensor;
   an electrical contact configured to operably connect the transcutaneous glucose sensor to the sensor electronics;
   a sealing member comprising a sealing member upper portion and a sealing member lower portion, wherein the sealing member at least partially surrounds the electrical contact and at least a portion of the transcutaneous glucose sensor when the transcutaneous glucose sensor is operably connected to the sensor electronics, wherein the sealing member substantially seals at least a portion of the electrical contact from moisture, and wherein an ex vivo portion of the transcutaneous glucose sensor is sandwiched between the sealing member upper portion and the sealing member lower portion; and
   a contact holder over which the sealing member and the transcutaneous glucose sensor are at least partially located.

20. The system of claim 19, wherein the electrical contact is formed from a material associated with a durometer hardness of from about 5 Shore A to about 80 Shore A.

21. The system of claim 20, wherein the sealing member is formed from a material associated with a durometer hardness of from about 5 Shore A to about 80 Shore A.

22. The system of claim 20, wherein the sealing member is formed from a material associated with a durometer hardness of from about 20 Shore A to about 50 shore A.

23. The system of claim 19, wherein the contact holder is connected to a mounting unit.

24. The system of claim 19, wherein the contact holder comprises means for maintaining the sealing member on the contact holder.

25. The system of claim 19, wherein the contact holder and sealing member comprises means for maintaining the sealing member substantially in place on the contact holder.

26. The system of claim 19, wherein the sealing member is held at least in part on the contact holder by mating male-female mechanical structures on the contact holder and on the sealing member.

27. The system of claim 19, wherein the sealing member comprises a raised ridge to improve a seal around the electrical contact.

28. The system of claim 19, wherein the sealing member is held on the contact holder at least in part by protrusions on the contact holder that are configured to mate with recesses on the sealing member.

29. The system of claim 19, wherein the sealing member is held on the contact holder at least in part by a chemical to maintain the sealing member substantially stationary without substantial translation or deformation during sensor insertion.

30. A system for measuring a glucose concentration in a host, the system comprising:
   a transcutaneous glucose sensor;
   sensor electronics configured to operably connect to the transcutaneous glucose sensor;
   an electrical contact configured to operably connect the transcutaneous glucose sensor to the sensor electronics;
   a sealing member comprising a sealing member upper portion and a sealing member lower portion;
   wherein the sealing member upper portion comprises an inner face and an outer face, wherein the sealing member lower portion comprises an inner face and an outer face;
   wherein the sealing member at least partially surrounds the electrical contact and at least a portion of the transcutaneous glucose sensor when the transcutaneous glucose sensor is operably connected to the sensor electronics;
   wherein the sealing member substantially seals at least a portion of the electrical contact from moisture;
   wherein an ex vivo portion of the transcutaneous glucose sensor is positioned between the sealing member upper portion inner face and the sealing member lower portion inner face; and
   a contact holder over which the sealing member and the transcutaneous glucose sensor are at least partially located.

31. The system of claim 30, wherein the electrical contact is formed from a material associated with a durometer hardness of from about 5 Shore A to about 80 Shore A.

32. The system of claim 31, wherein the sealing member is formed from a material associated with a durometer hardness of from about 5 Shore A to about 80 Shore A.

33. The system of claim 31, wherein the sealing member is formed from a material associated with a durometer hardness of from about 20 Shore A to about 50 shore A.

34. The system of claim 30, wherein the contact holder is connected to a mounting unit.

35. The system of claim 30, wherein the contact holder comprises means for maintaining the sealing member on the contact holder.

36. The system of claim 30, wherein the contact holder and sealing member comprises means for maintaining the sealing member substantially in place on the contact holder.

37. The system of claim 30, wherein the sealing member is held at least in part on the contact holder by mating male-female mechanical structures on the contact holder and on the sealing member.

38. The system of claim 30, wherein the sealing member comprises a raised ridge to improve a seal around the electrical contact.

39. The system of claim 30, wherein the sealing member is held on the contact holder at least in part by protrusions on the contact holder that are configured to mate with recesses on the sealing member.

40. The system of claim 30, wherein the sealing member is held on the contact holder at least in part by a chemical to maintain the sealing member substantially stationary without substantial translation or deformation during sensor insertion.

41. A system for measuring a glucose concentration in a host, the system comprising:
   a transcutaneous glucose sensor;
   sensor electronics configured to operably connect to the transcutaneous glucose sensor;
   an electrical contact configured to operably connect the transcutaneous glucose sensor to the sensor electronics;

a sealing member comprising a sealing member upper portion and a sealing member lower portion;

wherein the sealing member upper portion comprises an inner face and an outer face, wherein the sealing member lower portion comprises an inner face and an outer face;

wherein the sealing member upper portion comprises one or more holes therethrough, wherein each of the one or more holes extends from a respective opening in the outer face of the sealing member upper portion to a respective opening in the inner face of the sealing member upper portion;

wherein the sealing member at least partially surrounds the electrical contact and at least a portion of the transcutaneous glucose sensor when the transcutaneous glucose sensor is operably connected to the sensor electronics;

wherein the sealing member substantially seals at least a portion of the electrical contact from moisture;

wherein an ex vivo portion of the transcutaneous glucose sensor is positioned between the sealing member upper portion inner face and the sealing member lower portion inner face;

wherein the electrical contact is exposed for connection to the sensor electronics by the opening in the outer face of the sealing member upper portion;

wherein the electrical contact is exposed to the transcutaneous glucose sensor by the opening in the inner face of the sealing member upper portion; and a contact holder over which the sealing member and the transcutaneous glucose sensor are at least partially located.

42. The system of claim 41, wherein the electrical contact is formed from a material associated with a durometer hardness of from about 5 Shore A to about 80 Shore A.

43. The system of claim 42, wherein the sealing member is formed from a material associated with a durometer hardness of from about 5 Shore A to about 80 Shore A.

44. The system of claim 42, wherein the sealing member is formed from a material associated with a durometer hardness of from about 20 Shore A to about 50 shore A.

45. The system of claim 41, wherein the contact holder is connected to a mounting unit.

46. The system of claim 41, wherein the contact holder comprises means for maintaining the sealing member on the contact holder.

47. The system of claim 41, wherein the contact holder and sealing member comprises means for maintaining the sealing member substantially in place on the contact holder.

48. The system of claim 41, wherein the sealing member is held at least in part on the contact holder by mating male-female mechanical structures on the contact holder and on the sealing member.

49. The system of claim 41, wherein the sealing member comprises a raised ridge to improve a seal around the electrical contact.

50. The system of claim 41, wherein the sealing member is held on the contact holder at least in part by protrusions on the contact holder that are configured to mate with recesses on the sealing member.

51. The system of claim 41, wherein the sealing member is held on the contact holder at least in part by a chemical to maintain the sealing member substantially stationary without substantial translation or deformation during sensor insertion.

52. An assembly for glucose monitoring in a host, the assembly comprising:

a transcutaneous glucose sensor having an in vivo portion and an ex vivo portion, wherein the transcutaneous glucose sensor is operably connectable to sensor electronics configured for detecting a signal from the transcutaneous glucose sensor, wherein the signal is indicative of a glucose concentration in the host;

at least one electrical contact configured to operably connect the ex vivo portion of the sensor to the sensor electronics;

a base configured for placement over the host's skin;

an elastomeric sealing member in contact with the ex vivo portion of the sensor and at least partially surrounding the at least one electrical contact, wherein the elastomeric sealing member is configured to seal the at least one electrical contact from moisture, wherein the elastomeric sealing member is located over the base by mating mechanical structures on the base and on the elastomeric sealing member.

53. The assembly of claim 52, wherein the base comprises at least one protrusion, and wherein the mating mechanical structures comprise the at least one protrusion.

54. The assembly of claim 52, wherein the elastomeric sealing member comprises at least one recess, and wherein the mating mechanical structures comprise the at least one recess.

55. The assembly of claim 52, wherein the base comprises at least one protrusion, wherein the sealing member comprises at least one recess, and wherein the at least one protrusion and the at least one recess mate with one another.

56. The assembly of claim 52, wherein the base comprises reinforcing mechanical supports configured to hold the sealing member.

57. An assembly for glucose monitoring in a host, the assembly comprising:

a transcutaneous glucose sensor having an in vivo portion and an ex vivo portion, wherein the transcutaneous glucose e sensor is operably connectable to sensor electronics configured for detecting a signal from the transcutaneous glucose sensor, wherein the signal is indicative of a glucose concentration in the host;

at least one electrical contact configured to operably connect the ex vivo portion of the sensor to the sensor electronics;

a base configured for placement over the host's skin;

an elastomeric sealing member in contact with the ex vivo portion of the sensor and to at least partially surrounding the at least one electrical contact, wherein the elastomeric sealing member is configured to seal the at least one electrical contact from moisture, wherein the elastomeric sealing member is held over the base by mechanical structures and/or chemical adhesives without substantial translation or deformation during sensor insertion.

58. The assembly of claim 57, wherein the base comprises at least one protrusion, and wherein the mechanical structures comprise the at least one protrusion.

59. The assembly of claim 57, wherein the sealing member comprises at least one recess, and wherein the mechanical structures comprise the at least one recess.

60. The assembly of claim 57, wherein the base comprises at least one protrusion, wherein the sealing member comprises at least one recess, and wherein the at least one protrusion and the at least one recess mate with one another.

61. The assembly of claim 57, wherein the base comprises reinforcing mechanical supports configured to hold the sealing member.

62. An assembly for glucose monitoring in a host, the assembly comprising:
- a transcutaneous glucose sensor having an in vivo portion and an ex vivo portion, wherein the transcutaneous glucose sensor is operably connectable to sensor electronics configured for detecting a signal from the transcutaneous glucose sensor, wherein the signal is indicative of a glucose concentration in the host;
- an electrical contact configured to operably connect the ex vivo portion of the transcutaneous glucose sensor to the sensor electronics;
- a contact holder configured for placement over a skin of the host;
- an elastomeric sealing member at least partially located over the contact holder, wherein the elastomeric sealing member is in contact with the ex vivo portion of the transcutaneous glucose sensor, wherein the elastomeric sealing member at least partially surrounds the electrical contact, wherein the elastomeric sealing member is configured to substantially seal at least a portion of the electrical contact from moisture, wherein the elastomeric sealing member is held on the contact holder by mating male-female mechanical structures on the contact holder and on the elastomeric sealing member.

63. The assembly of claim 62, wherein a durometer of the electrical contact is higher than a durometer hardness of the elastomeric sealing member.

64. The assembly of claim 62, wherein the electrical contact is formed from a material associated with a durometer hardness of from about 5 Shore A to about 80 Shore A.

65. The assembly of claim 64, wherein the elastomeric sealing member is formed from a material associated with a durometer hardness of from about 5 Shore A to about 80 Shore A.

66. The assembly of claim 64, wherein the elastomeric sealing member is formed from a material associated with a durometer hardness of from about 20 Shore A to about 50 shore A.

67. The assembly of claim 62, wherein the contact holder is connected to a mounting unit.

68. The assembly of claim 62, wherein the elastomeric sealing member comprises an upper portion and a lower portion, wherein the ex vivo portion of the transcutaneous glucose sensor is sandwiched between the upper portion and the lower portion.

69. The assembly of claim 62, wherein the elastomeric sealing member comprises an upper portion and a lower portion, wherein the upper portion comprises an inner face and an outer face, wherein the lower portion comprises an inner face and an outer face, wherein the ex vivo portion of the transcutaneous glucose sensor is positioned between the inner face of the upper portion and the inner face of the lower portion.

70. The assembly of claim 62, wherein the elastomeric sealing member comprises an upper portion and a lower portion, wherein the upper portion comprises an inner face and an outer face, wherein the lower portion comprises an inner face and an outer face, wherein the upper portion comprises one or more holes therethrough, wherein each of the one or more holes extends from a respective opening in the outer face of the upper portion to a respective opening in the inner face of the upper portion, wherein the ex vivo portion of the transcutaneous glucose sensor is positioned between the inner face of the upper portion and the inner face of the lower portion.

71. The assembly of claim 68, wherein the upper portion is connected to the lower portion.

72. The assembly of claim 69, wherein the upper portion is connected to the lower portion.

73. The assembly of claim 70, wherein the upper portion is connected to the lower portion.

74. An assembly for glucose monitoring in a host, the assembly comprising:
- a transcutaneous glucose sensor having an in vivo portion and an ex vivo portion, wherein the transcutaneous glucose sensor is operably connectable to sensor electronics configured for detecting a signal from the transcutaneous glucose sensor, wherein the signal is indicative of a glucose concentration in the host;
- an electrical contact configured to operably connect the ex vivo portion of the transcutaneous glucose sensor to the sensor electronics;
- a contact holder configured for placement over the skin of the host;
- an elastomeric sealing member at least partially located over the contact holder, wherein the elastomeric sealing member is in contact with the ex vivo portion of the transcutaneous glucose sensor, wherein the elastomeric sealing member at least partially surrounds the electrical contact, wherein the elastomeric sealing member is configured to substantially seal at least a portion of the electrical contact from moisture, wherein the elastomeric sealing member is held on the contact holder by protrusions on the contact holder that are configured to mate with recesses on the elastomeric sealing member.

75. The assembly of claim 74, wherein a durometer of the electrical contact is higher than a durometer hardness of the elastomeric sealing member.

76. The assembly of claim 74, wherein the electrical contact is formed from a material associated with a durometer hardness of from about 5 Shore A to about 80 Shore A.

77. The assembly of claim 76, wherein the elastomeric sealing member is formed from a material associated with a durometer hardness of from about 5 Shore A to about 80 Shore A.

78. The assembly of claim 76, wherein the elastomeric sealing member is formed from a material associated with a durometer hardness of from about 20 Shore A to about 50 shore A.

79. The assembly of claim 74, wherein the contact holder is connected to a mounting unit.

80. The assembly of claim 74, wherein the elastomeric sealing member comprises an upper portion and a lower portion, wherein the ex vivo portion of the transcutaneous analyte sensor is sandwiched between the upper portion and the lower portion.

81. The assembly of claim 74, wherein the elastomeric sealing member comprises an upper portion and a lower portion, wherein the upper portion comprises an inner face and an outer face, wherein the lower portion comprises an inner face and an outer face, wherein the ex vivo portion of the transcutaneous analyte sensor is positioned between the inner face of the upper portion and the inner face of the lower portion.

82. The assembly of claim 74, wherein the elastomeric sealing member comprises an upper portion and a lower portion, wherein the upper portion comprises an inner face and an outer face, wherein the lower portion comprises an inner face and an outer face, wherein the upper portion comprises one or more holes therethrough, wherein each of the one or more holes extends from a respective opening in the outer face of the upper portion to a respective opening in the inner face of the upper portion, wherein the ex vivo portion of the transcutaneous analyte sensor is positioned between the inner face of the upper portion and the inner face of the lower portion.

83. The assembly of claim 80, wherein the upper portion is connected to the lower portion.

84. The assembly of claim 81, wherein the upper portion is connected to the lower portion.

85. The assembly of claim 82, wherein the upper portion is connected to the lower portion.

86. An assembly for glucose monitoring in a host, the assembly comprising:
- a transcutaneous glucose sensor having an in vivo portion and an ex vivo portion, wherein the transcutaneous glucose sensor is operably connectable to sensor electronics configured for detecting a signal from the transcutaneous glucose sensor, wherein the signal is indicative of a glucose concentration in the host;
- an electrical contact configured to operably connect the ex vivo portion of the sensor to the sensor electronics;
- a contact holder configured for placement over a skin of the host;
- an elastomeric sealing member in contact with the ex vivo portion of the sensor and at least partially surrounding the electrical contact, wherein the elastomeric sealing member is configured to seal the electrical contact from moisture, wherein the elastomeric sealing member is held on the contact holder by a chemical implemented to maintain the elastomeric sealing member substantially stationary without substantial translation or deformation during sensor insertion.

* * * * *